United States Patent
Terstiege et al.

(10) Patent No.: US 11,866,405 B2
(45) Date of Patent: Jan. 9, 2024

(54) SUBSTITUTED INDAZOLES AS IRAK4 INHIBITORS

(71) Applicant: AstraZeneca AB, Södertälje (SE)

(72) Inventors: Ina Terstiege, Gothenburg (SE); Stefan Schiesser, Göthenburg (SE); Yafeng Xue, Göthenburg (SE); Hui-Fang Chang, Göthenburg (SE); Anna Ingrid Kristina Berggren, Göthenburg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 17/457,249

(22) Filed: Dec. 1, 2021

(65) Prior Publication Data

US 2022/0185817 A1 Jun. 16, 2022

Related U.S. Application Data

(60) Provisional application No. 63/199,160, filed on Dec. 10, 2020.

(51) Int. Cl.
| | | |
|---|---|---|
| A61K 31/416 | (2006.01) | |
| C07D 231/56 | (2006.01) | |
| C07D 487/04 | (2006.01) | |
| A61P 11/06 | (2006.01) | |
| A61P 37/06 | (2006.01) | |

(52) U.S. Cl.
CPC ............ C07D 487/04 (2013.01); A61P 11/06 (2018.01); A61P 37/06 (2018.01)

(58) Field of Classification Search
CPC ............................ A61K 31/416; C07D 231/56
USPC ........................................ 514/403; 548/361.1
See application file for complete search history.

(56) References Cited

U.S. PATENT DOCUMENTS

2017/0305901 A1  10/2017  Shilatifard et al.

FOREIGN PATENT DOCUMENTS

| WO | 2012007375 A1 | 1/2012 |
|---|---|---|
| WO | 2012084704 A1 | 6/2012 |
| WO | 2014143666 A1 | 9/2014 |
| WO | 2015104662 A1 | 7/2015 |
| WO | 2016083433 A1 | 6/2016 |
| WO | 2017009798 A1 | 1/2017 |
| WO | 2017148902 A1 | 9/2017 |
| WO | 2018234343 A1 | 12/2018 |
| WO | 2020263967 A1 | 12/2020 |
| WO | 2020263980 A1 | 12/2020 |

OTHER PUBLICATIONS

Jordan, V. C. Nature Reviews: Drug Discovery, 2, 2003, 205.*
Hackam, et al. JAMA, 296(14), 2006, 1731-1732.*
Zhai Wenqiang et al. "Discovery and optimization of a potent and selective indazolamine series of IRAK4 inhibitors", Bioorganic & Medicinal Chemistry Letters, Elsevier, Amsterdam, NL, vol. 31, Nov. 24, 2020 (Nov. 24, 2020), XP086408220, ISSN: 0960-894X, DOI: 10.1016/J.BMCL.2020.127686.
Chen Yun et al., "Design and synthesis of Imidazo[1,2-b]pyridazine IRAK4 inhibitors for the treatment of mutant MYD88 L265P diffuse large B-cell lymphoma", European Journal of Medicinal Chemistry, Elsevier, Amsterdam, NL, vol. 190, Jan. 25, 2020 (Jan. 25, 2020), XP086065710, ISSN: 0223-5234, DOI: 10.1016/J.EJMECH.2020.112092.
Marian C. Bryan et al., "Development of Potent and Selective Pyrazolopyrimidine IRAK4 Inhibitors", Journal of Medicinal Chemistry, vol. 62, No. 13, May 13, 2019 (May 13, 2019), pp. 6223-6240, XP055683011, US ISSN: 0022-2623, DOI: 10.1021/acs.jmedchem.9b00439.
Mcelroy, "Interleukin-1 receptor-associated kinase 4 (IRAK4) inhibitors: an updated patent review (2016-2018)", Expert Opinion on Therapeutic Patents, 2019, 29:4, 243-259, DOI: 10.1080/13543776.2019.1597850.

* cited by examiner

*Primary Examiner* — Douglas M Willis

(57) ABSTRACT

The present application relates to chemical compounds of Formula (A):

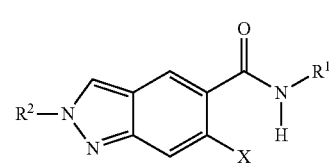

(A)

and pharmaceutically acceptable salts thereof, wherein X, $R^1$, and $R^2$ are as defined herein. The chemical compounds of Formula (A) inhibit IRAK4 and consequently have potential utility in medicine.

17 Claims, 1 Drawing Sheet

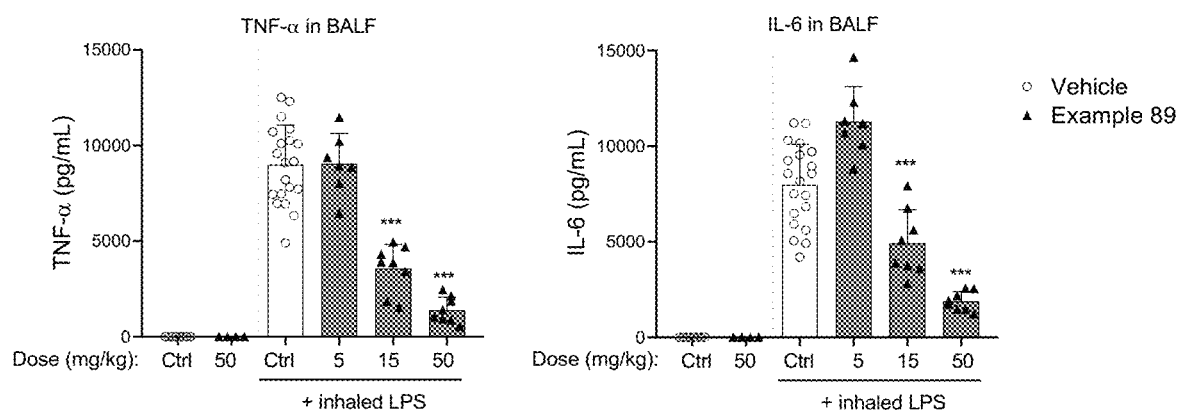

SUBSTITUTED INDAZOLES AS IRAK4 INHIBITORS

CROSS-REFERENCE TO RELATED APPLICATIONS

This application claims the benefit of priority under 35 USC 119(e) to U.S. Provisional Application No. 63/199,160 filed on Dec. 10, 2020. The entire contents of the foregoing are hereby incorporated by reference.

BACKGROUND OF THE DISCLOSURE

The specification relates to chemical compounds, and pharmaceutically acceptable salts thereof, that inhibit IRAK4 and consequently have potential utility in medicine. The specification also relates to the use of these IRAK4 inhibitors in the treatment of respiratory diseases such as asthma and chronic obstructive pulmonary disease (COPD), of cancer, of inflammatory diseases and of autoinflammatory/autoimmune diseases such as systemic lupus erythematosus, rheumatoid arthritis, myositis, Sjögren's syndrome, systemic sclerosis, gout, endometriosis, atopic dermatitis and psoriasis. The specification also relates to processes and intermediate compounds involved in the preparation of said IRAK4 inhibitors and to pharmaceutical compositions containing them.

Interleukin-1 receptor (IL-1R)-associated kinase 4 (IRAK4) is a key regulator of immune signaling. IRAK4 is expressed by multiple cell types and mediates signal transduction from Toll-like receptors (TLRs) and receptors of the interleukin-1 (IL-1) family, including IL-1R, IL-18R and the IL-33 receptor ST2. TLRs recognize and respond to ligands derived from microbes, such as lipopolysaccharide (LPS) or microbial RNA or DNA, while receptors of the IL-1 family can be activated by endogenous ligands produced by TLR-activated cells (IL-1β and IL-18) or by tissue damage (IL-la and IL-33). Upon activation of TLRs or IL-1 receptors by their ligands, the adaptor protein myeloid differentiation primary response 88 (MyD88) is recruited to the receptor and forms a multimeric protein complex, called the "Myddosome", together with proteins of the IRAK family (IRAK1, IRAK2 and IRAK4). The Myddosome serves as a signaling platform to induce nuclear factor κB (NF-κB) and mitogen-activated protein kinase (MAPK) signal transduction pathways, culminating in the activation of transcription factors NF-κB, activator protein 1 (AP1), c-AMP response element-binding protein (CREB) and interferon regulatory factor 5 (IRF5), driving transcription of inflammatory cytokines and chemokines. Mice lacking IRAK4 are viable but lack inflammatory cytokine response to IL-1β, IL-18 and LPS. Humans presenting loss-of-function mutations in IRAK4 display an immunocompromised phenotype and their immune cells show an abrogated cytokine response to TLR agonists and IL-1 receptor ligands.

IRAK4 is characterized by an N-terminal death domain that mediates the interaction with MyD88 and a centrally located kinase domain. Myddosome formation promotes IRAK4 auto-phosphorylation which modulates the stability and downstream signaling of the Myddosome. The kinase activity of IRAK4 is required for cytokine induction by TLRs and IL-1R, as shown by studies in knock-in mice expressing a kinase-dead IRAK4, as well as in studies using small molecule IRAK4 kinase inhibitors. Given its critical role in eliciting an inflammatory response, IRAK4 constitutes a target for drugs that exert an anti-inflammatory effect.

Asthma and COPD (chronic obstructive pulmonary disease) are chronic lung diseases constituting a major unmet medical need around the world. Asthma and COPD are characterized by chronic airway inflammation, involving abnormal cytokine release, dysregulated immune cell activation and airway remodeling. In asthma, insults to the airways such as allergenic, viral and bacterial insults activate the TLR receptors via pathogen associated molecular patterns (PAMPs), and the IL-1R and ST2 receptors via the release of alarmins, including IL-33 and IL-1α, as well as by IL-1β released upon inflammasome activation. TLRs and receptors of the IL-1 family are present in multiple cell types in the airways, including macrophages, dendritic cells, mast cells, monocytes and epithelial cells, and respond to their ligands by releasing inflammatory cytokines (TNF-α, IL-6, IL-8, GM-CSF, IL-5) leading to airway inflammation, recruitment of inflammatory cells such as neutrophils and eosinophils, airway hyperresponsiveness and mucus production. IRAK4 inhibition has the potential to suppress these inflammatory pathways in the airways. Gene expression analysis of lung samples from asthma and COPD patients, have revealed an upregulated expression of genes associated with the IL-1R and TLR2/4 inflammatory pathways in subsets of severe patients. Although IRAK4 inhibitors have not, to the best of our knowledge, been explored in the clinic for the treatment of respiratory diseases, pre-clinical data from several research groups indicates that interfering with IRAK4-regulated pathways attenuates airway inflammation in animal models of both asthma and COPD. For instance, mice lacking MyD88, the central component of the myddosome, are protected against airway inflammation induced by allergens or IL-33, as are mice treated with a small molecule mimetics blocking the interaction between IRAK2 and IRAK4. Blocking IL-1β with a monoclonal antibody has also been found to suppress airway inflammation induced by allergens and bacteria in a steroid-resistant mouse model of asthma. Moreover, the treatment of mice with the IL-1R antagonist anakinra at the time of allergen challenge ameliorates asthma-like symptoms in a mouse model of allergic asthma. Chronic exposure to cigarette smoke is a major contributing factor to the development of COPD. In mice exposed to cigarette smoke, IL-1 signaling is central in mediating neutrophilic airway inflammation, and blocking IL-1 signaling with antibodies against IL-1α, IL-1β or the IL-1R can ameliorate the neutrophilic inflammation in the lung and reduce bacteria- or virus-induced exacerbations in cigarette smoke-exposed mice. Taken together, IRAK4 inhibition has potential to provide a broad anti-inflammatory effect in inflammatory respiratory diseases by simultaneously blocking several disease-relevant signaling pathways.

As a central regulator of the Myddosome, IRAK4 is also a promising therapeutic target in other inflammatory diseases driven by IL-1R-, TLR- or ST2-mediated mechanisms. As previously disclosed, IRAK4 plays a role in autoimmune disorders such as rheumatoid arthritis and systemic lupus erythematosus (SLE) (see e.g. WO2017207386 & WO2015150995). In SLE, immunocomplexes composed by autoantibodies and self-antigens, can drive TLR-dependent pathological signaling. In SLE pathogenesis, IRAK4 inhibition reportedly blocks the release of type I interferons and proinflammatory cytokines mediated by TLR7 and TLR9 activation in plasmacytoid dendritic cells. Mice expressing a kinase-dead mutant of IRAK4 or treated with IRAK4 kinase inhibitor compounds, are resistant to experimentally induced arthritis and lupus (see e.g. WO2017207386). The approved use of anakinra (an IL-1 receptor antagonist) for the treatment of rheumatoid arthritis, also support the role of pathogenic IL-1R signaling in this disease. In Sjögren's syndrome, TLRs are upregulated in PBMCs (peripheral blood mononuclear cells) and salivary glands and TLR activation can stimulate release of interferon and other inflammatory cytokines, suggested to be implicated in Sjögren's pathogenesis. MyD88 knockout mice also display reduced disease manifestations in an experimental mouse model of Sjögren's syndrome. Systemic sclerosis is a severe autoimmune disorder where IL-1R, TLR4, TLR8 and ST2-signaling can drive pathogenic mechanisms, including microvascular damage and fibrosis. Inhibition of IRAK4 as a treatment in systemic sclerosis would thus block multiple disease-relevant pathways simultaneously. In myositis, elevated levels of IL-la and IL-113 can contribute to muscle tissue inflammation. Myositis patients have also been characterized with high type I interferon gene signature, that may be partly driven by TLR7/9 activation, and the relevance of IL-1R signaling was supported by an improved clinical outcome in myositis patients treated with anakinra in a smaller mechanistic clinical trial. As a central regulator of the IL-1R pathway, IRAK4 is also a promising target in the treatment of gout. Monosodium urate crystals, characteristically formed in gout sufferers, can trigger the activation of the inflammasome and release of IL-113. The use of both canakinumab, an anti IL-113 monoclonal antibody or anakinra has demonstrated clinical efficacy in the treatment of gout flares. Elevated levels of IL-113 and IL-33 have also been found in patients with endometriosis. The importance of IRAK4 in the disease process of endometriosis was shown in a mouse model where oral administration of an IRAK4 inhibitor suppressed lesion formation. MyD88 knockout mice were also protected against the development of endometriosis in the same mouse model. IL-33/5T2 signaling is a key mechanism in atopic dermatitis, involved in the regulation of skin inflammation, epithelial barrier integrity and eosinophil recruitment. IL-33 can trigger eczema and dermatitis in mice in a MyD88-dependent manner. As a regulator of ST2 signaling and a central component of the myddosome, IRAK4 inhibition has the potential to inhibit pathogenic IL-33/5T2 signaling in atopic dermatitis. Both TLR7 and IL-1R mediated mechanisms have been suggested to be involved in psoriasis. Imiquimod (TLR/8 agonist) can induce psoriasis-like disease in mice in a MyD88-dependent manner. IL-113 is upregulated in psoriatic skin lesions and the IL-1β/IL-1R axis has been suggested to contribute to skin inflammation and regulate the production of IL-17, a critical cytokine released from TH17 cells in psoriasis pathogenesis. IRAK4 kinase activity has further been shown to be required for the regulation of TH17 differentiation and TH17-mediated diseases in vivo.

A number of IRAK4 kinase inhibitors are known and have been developed principally for use in oncology or inflammatory disease (see e.g. WO2015150995, WO2017207386, WO2017009806, WO2016174183, WO2018234342). Of the known IRAK4 kinase inhibitors PF-06650833 has recently completed a phase II clinical trial for the treatment of rheumatoid arthritis (see clinicaltrials.gov entry for NCT02996500).

Taken together, IRAK4 inhibitors have potential for the treatment of a number of diseases and conditions albeit to date no such inhibitor has been approved for clinical use. It is an object of the present specification to provide new IRAK4 inhibitors with physicochemical and selectivity profiles that render them suitable for clinical use, for example in the treatment of inflammatory diseases associated with activation of IRAK4-mediated pathways, such as asthma, COPD and chronic autoimmune/autoinflammatory diseases.

BRIEF SUMMARY OF THE DISCLOSURE

In a first aspect, the present specification provides a compound of Formula (A), or a pharmaceutically acceptable salt thereof, (A)

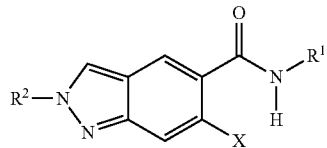

wherein:
$R^1$ is selected from

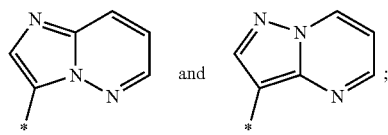 [SMILES: *c1cnc2cccnn12 ; *c1cnn2cccnc12]

$R^2$ is selected from

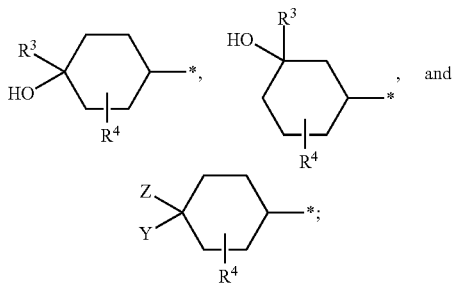

$R^3$ and $R^4$ are each independently selected from H, Me, Et, optionally substituted $C_1$-$C_6$ alkyl and optionally substituted $C_3$-$C_6$ cycloalkyl;
Y is N(Me)COMe, N($R^5$)COMe, N(Me)CO$R^6$, N($R^5$)CO$R^6$, CONMe$_2$ or a 5-membered N-heterocycle such as 1,2,3-triazole and Z is H, Me, Et and optionally substituted $C_1$-$C_6$ alkyl; or
Y and Z combine to form an optionally substituted 4-, 5- or 6-membered ring;
X is selected from O$R^7$ and N$R^8R^9$;
$R^5$ is selected from H, optionally substituted $C_1$-$C_6$ alkyl and optionally substituted $C_3$-$C_6$ cycloalkyl;
$R^6$ is selected from optionally substituted $C_1$-$C_6$ alkyl, optionally substituted $C_3$-$C_6$ cycloalkyl and optionally substituted 5- or 6-membered saturated N-heterocycle;
$R^7$ is Me, Et, i-propyl, n-propyl, cyclopropyl, cyclobutyl, an optionally substituted $C_1$-$C_6$ alkyl, $C_3$-$C_6$ cycloalkyl group or 4-, 5- or 6-membered ring containing an heteroatom selected from O and N;
$R^8$ and $R^9$ are independently selected from H, Me and optionally substituted $C_1$-$C_6$ alkyl or together form an optionally substituted $C_3$-$C_6$ cycloalkyl or an optionally substituted 4-, 5- or 6-membered ring containing a further heteroatom selected from O and N;
wherein the optional substituents of Z, $R^3$, $R^4$, $R^5$, $R^6$, $R^7$, le and $R^9$, when present, are independently selected from OH, $C_1$-$C_3$ alkyl, $C_1$-$C_3$alkoxy, C(O)Me, amino, NHMe, NMe$_2$, F or Cl.

In a second aspect the present specification provides a compound of Formula (I), or a pharmaceutically acceptable salt thereof,

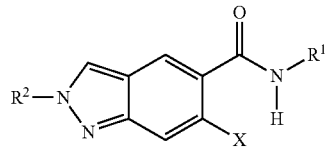

wherein:
R¹ is selected from

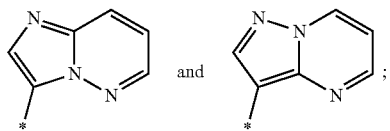 [SMILES: *c1cnc2cccnn12 ; *c1cnn2cccnc12]

R² is selected from

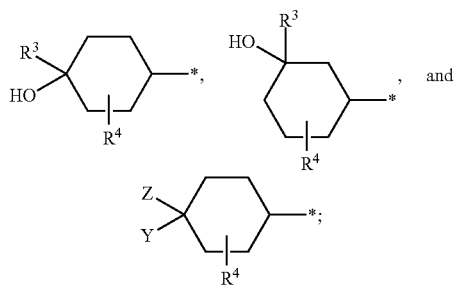

R³ and R⁴ are each independently selected from H, Me, Et, optionally substituted $C_1$-$C_6$ alkyl and optionally substituted $C_3$-$C_6$ cycloalkyl;
Y is N(Me)COMe, N(R⁵)COMe, N(Me)COR⁶, N(R⁵)COR⁶, CONMe₂ or a 5-membered N-heterocycle such as 1,2,3-triazole and Z is H, Me, Et and optionally substituted $C_1$-$C_6$ alkyl; or
Y and Z combine to form an optionally substituted 4-, 5- or 6-membered ring;
X is selected from OR⁷ and NR⁸R⁹;
R⁵ is selected from H, optionally substituted $C_1$-$C_6$ alkyl and optionally substituted $C_3$-$C_6$ cycloalkyl;
R⁶ is selected from optionally substituted $C_1$-$C_6$ alkyl and optionally substituted $C_3$-$C_6$ cycloalkyl;
R⁷ is Me, Et, i-propyl, n-propyl, cyclopropyl, cyclobutyl, an optionally substituted $C_1$-$C_6$ alkyl, $C_3$-$C_6$ cycloalkyl group or 4-, 5- or 6-membered ring containing an heteroatom selected from O and N;
R⁸ and R⁹ are independently selected from H, Me and optionally substituted $C_1$-$C_6$ alkyl or together form an optionally substituted $C_3$-$C_6$ cycloalkyl or an optionally substituted 4-, 5- or 6-membered ring containing a further heteroatom selected from O and N;
wherein the optional substituents of Z, R³, R⁴, R⁵, R⁶, R⁷, le and R⁹, when present, are independently selected from OH, $C_1$-$C_3$ alkyl, $C_1$-$C_3$ alkoxy, C(O)Me, amino, N H Me, NMe₂, F or Cl.

References to a compound of Formula (I) herein below should be read to include reference to a compound of Formula (A) as well as to refer to a compound of Formula (I).

The specification also describes a pharmaceutical composition that comprises a compound of Formula (I), or a pharmaceutically acceptable salt thereof, and at least one pharmaceutically acceptable excipient.

The specification also describes a compound of Formula (I), or a pharmaceutically acceptable salt thereof, for use as a medicament.

The specification also describes a compound of Formula (I), or a pharmaceutically acceptable salt thereof, for use in the treatment of respiratory diseases such as asthma and chronic obstructive pulmonary disease (COPD).

The specification also describes a compound of Formula (I), or a pharmaceutically acceptable salt thereof, for use in the treatment of inflammatory diseases.

The specification also describes a compound of Formula (I), or a pharmaceutically acceptable salt thereof, for use in the treatment of autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

The specification also describes a compound of Formula (I), or a pharmaceutically acceptable salt thereof, for use in the treatment of cancer, for example for use in combination with a BTK inhibitor.

The specification also describes a compound of Formula (I), or a pharmaceutically acceptable salt thereof, for use in the treatment of cancer. In such uses the compound of Formula (I) may be used as a monotherapy, or in combination with a further therapeutic agent, for example for the treatment of a haematologic malignancy. The haematologic malignancy to be treated may be selected from Waldenstrom's macroglobulinemia (WM), non-Hodgkin lymphoma (NHL), diffuse large B-cell lymphoma (DLBCL), primary central nervous system lymphoma (PCNSL), Splenic Marginal Zone Lymphoma (SMZL), small lymphocytic lymphoma (SLL), leukaemias (chronic lymphocytic leukaemia (CLL)) and monoclonal gammopathy of undetermined significance (MGUS-IgM+). Furthermore, the use may be for the treatment of haematologic malignancies that has MYD88 mutation, B-cell receptor (BCR) mutation or both MYD88 and BCR mutations. When the compound is used in combination with a further therapeutic agent the second agent may be selected from group comprising BCR inhibitors such as BTK inhibitors (examples include ibrutinib, acalabrutinib, zanubrutinib or tirabrutinib), PI3Kδ inhibitors and SYK inhibitors or immunotherapies.

The specification also describes the use of a compound of Formula (I) for the manufacture of a medicament, for example wherein the medicament is for use in the treatment of respiratory diseases such as asthma and chronic obstructive pulmonary disease (COPD) or for use in the treatment of cancer or for use in the treatment of autoinflammatory/autoimmune diseases such as systemic lupus erythematosus, rheumatoid arthritis, myositis, Sjögren's syndrome, systemic sclerosis, gout, endometriosis, atopic dermatitis and psoriasis or for use in the treatment of inflammatory disease.

The specification also describes methods of treatment comprising administration of an effective amount of a compound of Formula (I) to a patient in need thereof, wherein the patient in need has a respiratory diseases such as asthma and chronic obstructive pulmonary disease (COPD), cancer, an autoinflammatory/autoimmune disease such as systemic lupus erythematosus, rheumatoid arthritis, myositis, Sjögren's syndrome, systemic sclerosis, gout, endometriosis, atopic dermatitis and psoriasis or an inflammatory disease.

The present specification also relates to processes for the manufacture of a compound of Formula (I).

Further aspects of the specification will be apparent to one skilled in the art from reading this specification.

BRIEF DESCRIPTION OF THE DRAWING

The specification make reference to the following FIGURE.

FIG. 1. In vivo dose response of Example 89 in an acute mouse model of LPS-induced lung inflammation. Example 89 compound was dosed orally to mice 1 h prior to inhaled LPS challenge (1 mg/mL). 4 h after the challenge, the animals were terminated and the levels of IL-6 and TNF-α released in the bronchoalveolar lavage fluid were measured. Example 89 reduced the levels of IL-6 and TNF-α in a dose-dependent manner. Individual data points represent individual animals, and bars represent the mean value of each group. Statistical differences between groups were calculated with a one-way ANOVA test comparing treatment groups to the vehicle group. p<0.01, *p<0.001. The ability of IRAK4 inhibitors according to the specification to reduce inflammatory cytokines and TNF-α in vivo is thus established.

DETAILED DESCRIPTION OF THE DISCLOSURE

As noted above, it has been found that compounds of Formula (I), or pharmaceutically acceptable salts thereof, are potent inhibitors of IRAK4 kinase. In addition, preferred compounds of Formula (I) exhibit excellent selectivity over other kinases thus providing a profile that avoids off target effects and toxicities. This desirable combination of IRAK4 inhibitory activity and lack of detrimental off target effect indicates the suitability of compounds of the specification for use in medicine.

Unless defined otherwise, all technical and scientific terms used herein have the same meaning as that commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

So that the present specification may be more readily understood, certain terms are explicitly defined below. In addition, definitions are set forth as appropriate throughout the detailed description.

Units, prefixes, and symbols are denoted in their Systéme International de Unites (SI) accepted form. Numeric ranges are inclusive of the numbers defining the range.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition according to the present specification will comprise a compound of Formula (I), or a pharmaceutical acceptable salt thereof, and at least one pharmaceutically acceptable excipient.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have or develop the disorder; and those in whom the disorder is to be prevented. In certain aspects, a subject is successfully "treated" for respiratory disease according to the methods of the present disclosure if the patient shows, e.g., total, partial, or transient relief from the symptoms of that respiratory disease.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein and above the symbol * is used to indicate the site of connection of a component of the compound of Formula (I) to other components of the compound. To illustrate this by example, when the compound of Formula (I) has the $R^1$ motif specified below the compound will be a compound of structure A. Similarly, when the compound of Formula (I) has the $R^2$ motif below, the compound will be a compound of structure B.

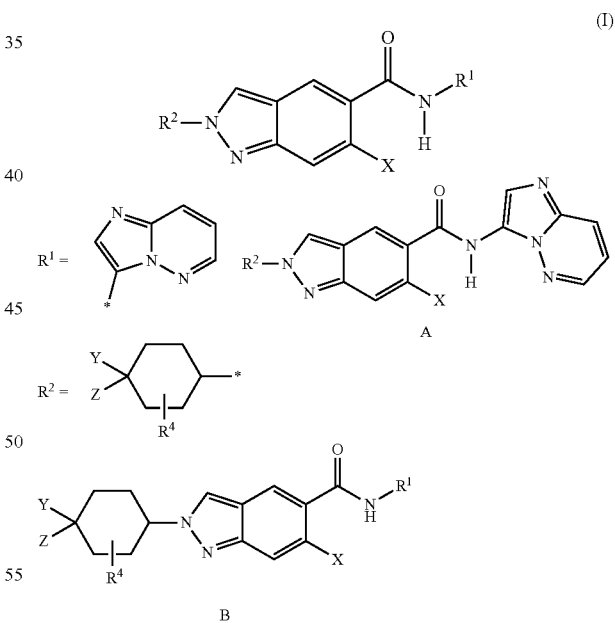

As used herein the term "alkyl" refers to both straight and branched chain saturated hydrocarbon radicals having the specified number of carbon atoms. As used herein the term deuteroalkyl refers to an alkyl groups in which one or more, optionally all, hydrogens are replaced with deuterium atoms. The term cycloalkyl refers to a saturated cyclic hydrocarbon.

In this specification the prefix $C_x$-$C_y$, as used in terms such as $C_x$-$C_y$ alkyl and the like where x and y are integers, indicates the numerical range of carbon atoms that are present in the group. For example, $C_1$-$C_4$ alkyl includes methyl, ethyl, n-propyl, i-propyl, n-butyl, s-butyl, i-butyl and t-butyl, while examples of $C_1$-$C_3$ alkyl groups include methyl, ethyl, n-propyl, and i-propyl. $C_1$-$C_4$ alkoxy groups include methoxy, ethoxy, n-propoxy, i-propoxy, n-butoxy, s-butoxy and t-butoxy. Examples of $C_1$-$C_3$ alkoxy groups include methoxy, ethoxy, n-propoxy and i-propoxy.

Unless specifically stated, the bonding of an atom or group may be any suitable atom of that group; for example, propyl includes prop-1-yl and prop-2-yl.

As used herein the term cycloalkyl refers to cyclic saturated hydrocarbon radicals having the specified number of carbon atoms. Thus $C_3$-$C_6$ cycloalkyl refers to cyclopropyl, cyclobutyl, cyclopentyl and cyclohexyl groups.

As used herein the term alkoxy refers to a group with an oxygen atom connected to an alkyl chain wherein, as defined above the alkyl chain is a straight and branched chain saturated hydrocarbon radicals having the specified number of carbon atoms. Thus $C_1$-$C_3$ alkoxy refers to methoxy, ethoxy, O"Pr and O'Pr groups.

As described herein and above the group $R^2$ may be substituted with a group $R^4$. In such cases the group $R^4$ may be attached to any available ring carbon, albeit it is preferred that $R^4$ is attached to the carbon atom adjacent the carbon atom attached to the indazole ring as shown below.

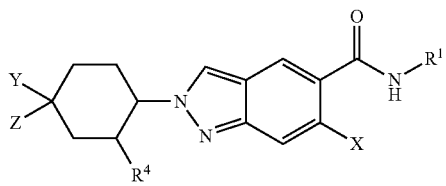

As used herein and above the term acetyl refers to a group of formula —C(O)Me. Reference to a N-acylated group herein is used to refer to amides with a small alkyl side chain i.e. an optionally substituted $C_1$-$C_6$ alkyl side chain or an optionally substituted $C_3$-$C_6$ cycloalkyl, in each instance the optional substituents are selected from OH, $C_1$-$C_3$ alkoxy, C(O)Me, amino, NHMe, $NMe_2$, F or Cl, with a preferred N-acylated group being an N-acetyl group i.e. a group —NRC(O)Me.

As described herein and above the compounds of Formula (I) comprise a group $R^2$ that can be a cyclohexyl ring substituted with two groups Y and Z that combine to form a 4-, 5- or 6-membered ring. In such cases the 4-, 5- or 6-membered ring is a saturated hydrocarbon ring system optionally wherein one or two ring carbons are replaced with a heteroatom selected from O and N. In the case wherein two ring carbons are replaced with heteroatoms, the heteroatoms are not directly bound, i.e. the heteroatoms replace non-adjacent ring carbons, nor are they separated in the ring by a $CH_2$ group but may for example be joined by a carbonyl group to deliver e.g. a carbonate or carbamate motif. The hydrocarbon ring may incorporate a carbonyl group as is the case when Y and Z combine to form a cyclic amide. In preferred instances, the 4-, 5- or 6-membered ring is a cyclic amide or carbamate such as a pyrrolidin-2-one, oxazolidin-2-one, piperidin-2-one and 1,3-oxazinan-2-one. Alternatively, the groups Y and Z may combine to form an azetidine substituted with an acyl group at nitrogen. In addition, the 4-, 5- or 6-membered ring may be substituted with a group selected from OH, $C_1$-$C_3$ alkyl, $C_1$-$C_3$ alkoxy, C(O)Me, amino, NHMe, $NMe_2$, F or Cl. These optional substituents may advantageously be used to modulate physicochemical properties of the molecule, such as solubility, or further optimize the interaction with IRAK4 kinase, for example relative to other kinases, thus delivering more potent and selective IRAK4 kinase inhibitors.

As described herein compounds of Formula (A) comprise a group Y that can be selected from $N(R^5)COMe$, $N(Me)COR^6$ and $N(R^5)COR^6$. In such cases, the group $R^6$ may be an optionally substituted 5- or 6-membered saturated N-heterocycle, for instance a pyrrolidine or piperidine connected to the carbonyl group of Y via the nitrogen atom of the heterocycle to provide a urea moiety. For example, Y may be a group $N(Me)COR^6$ in which $R^6$ is 3-hydroxypyrrolidine as shown below.

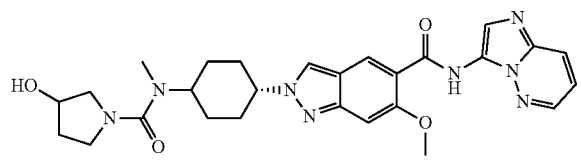

As described herein and above the group Fe may be an optionally substituted 4-, 5- or 6-membered ring containing a heteroatom selected from O and N. For the avoidance of doubt "containing an heteroatom" means that one of the atoms of the ring will be a heteroatom selected from O or N. In such instances saturated 4-, 5- or 6-membered rings containing a heteroatom selected from O and N are preferred. Examples of preferred 4-, 5- or 6-membered rings containing a heteroatom selected from O and N are azetidine, oxetane, tetra hydrofuran, pyrrolidine, tetra hydropyran and piperidine. As described herein and above the substituents $R^8$ and $R^9$ may combine to form an optionally substituted 4-, 5- or 6-membered ring containing a further heteroatom selected from O and N. In the case wherein a further heteroatom is present, the heteroatom is not directly bound to N, i.e. the heteroatoms in the ring are non-adjacent, nor are they separated by a $CH_2$ group. In such instances it is preferred that the resultant ring is saturated, for example the resultant ring may be a morpholine or piperazine ring.

As will be apparent to the skilled reader, the compounds of Formula (I) and in particular the groups $R^2$ can exist in various stereochemical forms. It will be understood that the claims encompass all stereochemical forms of the compounds of Formula (I), albeit the compounds with highest activity as inhibitors of IRAK4 are preferred. It will be recognised that the compounds of Formula (I), may be prepared, isolated and/or supplied with or without the presence, of one or more of the other possible stereoisomeric forms of the compound of Formula (I) in any relative proportions. The preparation of stereoenriched or stereopure compounds may be carried out by standard techniques of organic chemistry that are well known in the art, for example by synthesis from stereoenriched or stereopure starting materials, use of an appropriate stereoenriched or stereopure catalysts during synthesis, and/or by resolution of a racemic or partially enriched mixture of stereoisomers, for example via chiral chromatography.

As an example, in the case below the substituent $R^2$ is a 1,3-substituted cyclohexanol group. In this system the relative (rel) stereochemistry of the alcohol and the indazole group on the ring may be cis or trans and each of the cis and trans isomers will in turn exist in two enantiomeric forms reflecting the (R) or (S) configuration of the chiral centres (i.e. of the carbons attached to the hydroxyl group and indazole group). In certain cases described herein the compounds will be referred to as Isomers 1 and 2 of compounds having the relative (rel) stereochemical arrangement, thus in the case of a compound referred to as rel-(1S,3R) it will be understood that the two possible isomers are the (1S,3R) isomer and the (1R,3S) isomer that have the same relative stereochemistry, but that are enantiomers of each other. Thus reference to a compound below that has cis relative stereochemistry refers to the two possible compounds with this relative stereochemistry. Structures of known relative stereochemistry and undetermined absolute stereochemistry herein are drawn as a single enantiomer with the qualifier "or enantiomer".

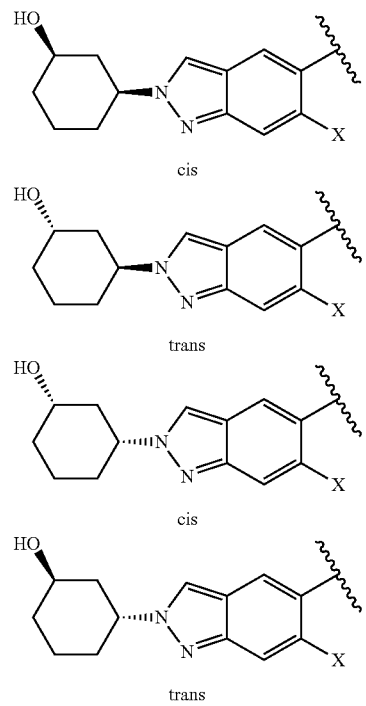

As described herein and above, certain components of the compounds of Formula (I) are optionally substituted. As used herein the term optionally substituted means that the structural element of the compound may or may not be substituted with one or more of the specified optional substituents. In instances wherein an optional substituent is present in one or more of the groups Z, $R^3$, $R^4$, $R^5$, $R^6$, $R^7$, $R^8$ and $R^9$ it is general preferred that zero, one or two substituents are present per each substituted group, for example zero or one substituent is present. In the case wherein the two hydroxyl substituents are present it will be understood that the two hydroxyl groups are not attached to the same carbon atom. In the case where the optional substituent is F it is preferred that one, two or three F substituents are present and, in addition, where two or three substituents are present they are directly bound to the same carbon atom. These optional substituents may be used to modulate physicochemical properties of the molecule, such as solubility, modulate metabolism, or further optimize the interaction with IRAK4 kinase, for example relative to other kinases, thus delivering more potent and selective IRAK4 kinase inhibitors.

As noted above, in a first embodiment the specification provides a compound of Formula (A), or a pharmaceutically acceptable salt thereof,

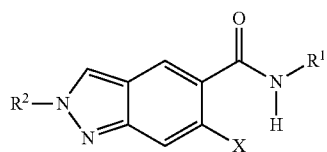

(A)

wherein:
$R^1$ is selected from

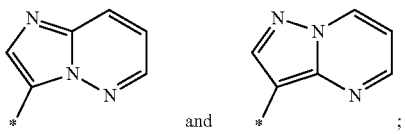 [SMILES: *c1cnc2cccnn12 ; *c1cnn2cccnc12]

$R^2$ is selected from

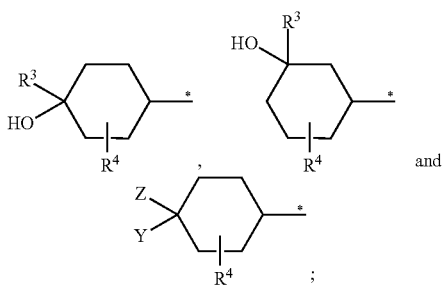

$R^3$ and $R^4$ are each independently selected from H, Me, Et, optionally substituted $C_1$-$C_6$ alkyl and optionally substituted $C_3$-$C_6$ cycloalkyl;
Y is N(Me)COMe, N($R^5$)COMe, N(Me)COR$^6$, N($R^5$)COR$^6$, CONMe$_2$ or a 5-membered N-heterocycle such as 1,2,3-triazole and Z is H, Me, Et and optionally substituted $C_1$-$C_6$ alkyl; or
Y and Z combine to form an optionally substituted 4-, 5- or 6-membered ring;
X is selected from OR' and NR$^8$R$^9$;
$R^5$ is selected from H, optionally substituted $C_1$-$C_6$ alkyl and optionally substituted $C_3$-$C_6$ cycloalkyl;
$R^6$ is selected from optionally substituted $C_1$-$C_6$ alkyl, optionally substituted $C_3$-$C_6$ cycloalkyl and optionally substituted 5- or 6-membered saturated N-heterocycle;
$R^7$ is Me, Et, i-propyl, n-propyl, cyclopropyl, cyclobutyl, an optionally substituted $C_1$-$C_6$ alkyl, $C_3$-$C_6$ cycloalkyl group or 4-, 5- or 6-membered ring containing an heteroatom selected from O and N;
$R^8$ and $R^9$ are independently selected from H, Me and optionally substituted $C_1$-$C_6$ alkyl or together form an optionally substituted $C_3$-$C_6$ cycloalkyl or an optionally substituted 4-, 5- or 6-membered ring containing a further heteroatom selected from O and N;
wherein the optional substituents of Z, $R^3$, $R^4$, $R^5$, $R^6$, $R^7$, $R^8$ and $R^9$, when present, are independently selected from OH, $C_1$-$C_3$ alkyl, $C_1$-$C_3$ alkoxy, C(O)Me, amino, NHMe, NMe$_2$, F or Cl.

In embodiments, the compound of Formula (A) is a compound of Formula (I), or a pharmaceutically acceptable salt thereof,

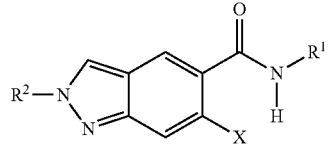
(I)

wherein:
R¹ is selected from

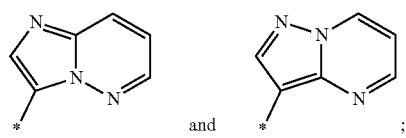 [SMILES: *c1cnc2cccnn12 ; *c1cnn2cccnc12]

R² is selected from

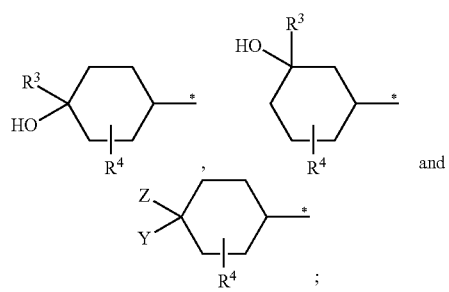

R³ and R⁴ are each independently selected from H, Me, Et, optionally substituted $C_1$-$C_6$ alkyl and optionally substituted $C_3$-$C_6$ cycloalkyl;
Y is N(Me)COMe, N(R⁵)COMe, N(Me)COR⁶, N(R⁵)COR⁶, CONMe₂ or a 5-membered N-heterocycle such as 1,2,3-triazole and Z is H, Me, Et and optionally substituted $C_1$-$C_6$ alkyl; or
Y and Z combine to form an optionally substituted 4-, 5- or 6-membered ring;
X is selected from OR⁷ and NR⁸R⁹;
R⁵ is selected from H, optionally substituted $C_1$-$C_6$ alkyl and optionally substituted $C_3$-$C_6$ cycloalkyl;
R⁶ is selected from optionally substituted $C_1$-$C_6$ alkyl and optionally substituted $C_3$-$C_6$ cycloalkyl;
R⁷ is Me, Et, i-propyl, n-propyl, cyclopropyl, cyclobutyl, an optionally substituted $C_1$-$C_6$ alkyl, $C_3$-$C_6$ cycloalkyl group or 4-, 5- or 6-membered ring containing an heteroatom selected from O and N;
R⁸ and R⁹ are independently selected from H, Me and optionally substituted $C_1$-$C_6$ alkyl or together form an optionally substituted $C_3$-$C_6$ cycloalkyl or an optionally substituted 4-, 5- or 6-membered ring containing a further heteroatom selected from O and N;
wherein the optional substituents of Z, R³, R⁴, R⁵, R⁶, R⁷, R⁸ and R⁹, when present, are independently selected from OH, $C_1$-$C_3$ alkyl, $C_1$-$C_3$ alkoxy, C(O)Me, amino, NHMe, NMe₂, F or Cl.

In embodiments, the compound of Formula (I) or Formula (A) is a compound of Formula (Ia) wherein the group R² is

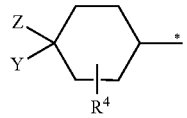

and the groups Y and Z combine to form a 4-, 5- or 6-membered ring that is an optionally substituted 3-hydroxycyclobutyl, N-acylated azetidine, pyrrolidin-2-one, 1-alkylpyrrolidin-2-one, 3-alkyloxazolidin-2-one, 1-alkylpiperidin-2-one or 3-alkyl-1,3-oxazinan-2-one ring.

In embodiments, the compound of Formula (I) or Formula (A) is a compound of Formula (Ib) wherein the group R² is

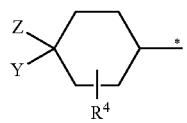

and the groups Y and Z combine to form a 4-, 5- or 6-membered ring that is selected from 3-hydroxycyclobutyl, N-acetyl azetidine, 1-methylpyrrolidin-2-one, 3-methyloxazolidin-2-one, 1-methylpiperidin-2-one and 3-methyl-1,3-oxazinan-2-one.

In embodiments, the compound of Formula (I) or Formula (A) is a compound of Formula (Ic) wherein the group R² is

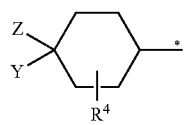

and the groups Y and Z combine to form a 4-, 5- or 6-membered ring that is selected from

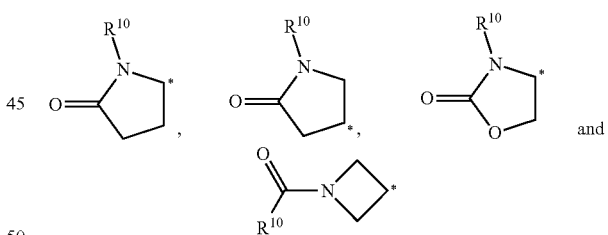

wherein * denotes the site of attachment to the cyclohexyl group and R¹⁰ is Me or a $C_1$-$C_6$ alkyl group optionally substituted with OH, $C_1$-$C_3$ alkoxy, C(O)Me, NH₂, NHMe, NMe₂, F or Cl.

In embodiments, the compound of Formula (A) is a compound of Formula (Ac) wherein the group R² is

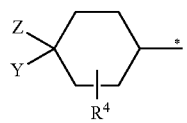

and the groups Y and Z combine to form a 4-, 5- or 6-membered ring that is

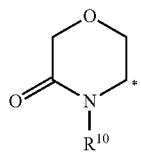

wherein * denotes the site of attachment to the cyclohexyl group and $R^{10}$ is Me or a $C_1$-$C_6$ alkyl group optionally substituted with OH, $C_1$-$C_3$ alkoxy, C(O)Me, $NH_2$, NHMe, $NMe_2$, F or Cl.

In embodiments, the compound of Formula (I) or Formula (A) is a compound of Formula (Id) wherein the group $R^2$ is

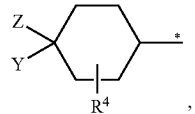

Y is selected from N(Me)COMe, $N(R^5)$COMe, N(Me)$COR^6$, $N(R^5)COR^6$ and $CONMe_2$ and Z is H.

In embodiments, the compound of Formula (I) or Formula (A) is a compound of Formula (Ie) wherein the group $R^2$ is

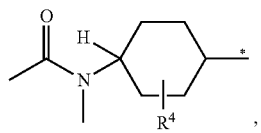

optionally wherein $R^4$ is H.

In embodiments, the compound of Formula (I) or Formula (A) is a compound of Formula (If) wherein the group $R^2$ is

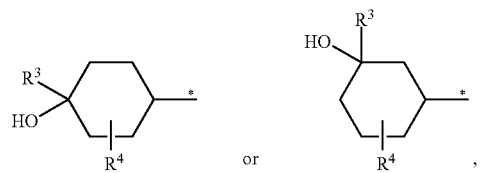

optionally wherein $R^3$ and $R^4$ are methyl.

In embodiments, the compound of Formula (If) is a compound of Formula (Ig) wherein the group $R^2$ is selected from

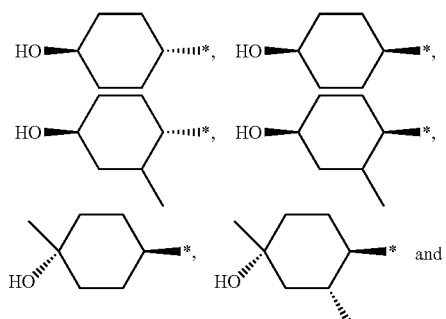

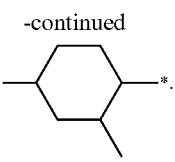

In embodiments, the compound of Formula (If) is a compound of Formula (Ih) wherein the group $R^2$ is selected from

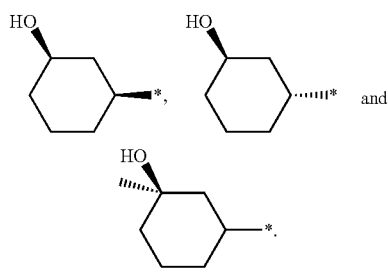

In embodiments, the compound of Formula (If) is a compound of Formula (Ah) wherein the group $R^2$ is selected from

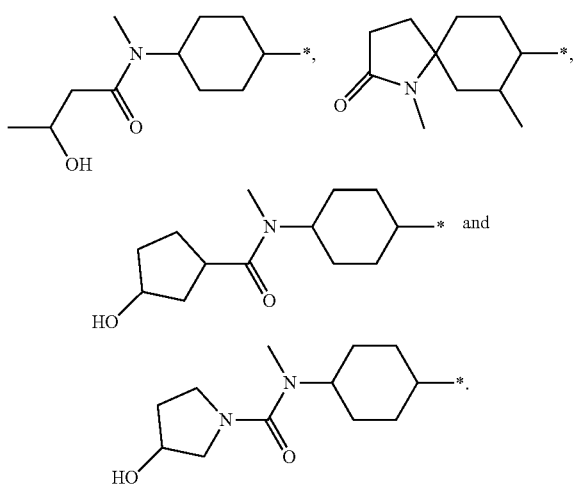

In embodiments, the compound of Formula (I), for example a compound of any of Formula (Ia), (Ib), (Ic), (Id), (Ie), (If), (Ig), or (Ih), is a compound of Formula (Ii) wherein the $R^1$ is

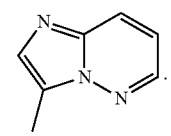

In embodiments, the compound of Formula (I), for example a compound of any of Formula (Ac) or (Ah) is a compound of Formula (Ai) wherein the $R^1$ is

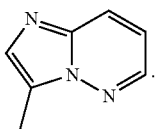

In embodiments, the compound of Formula (I), for example a compound of any of Formula (Ac) or (Ah) is a compound of Formula (Aj) wherein the $R^1$ is

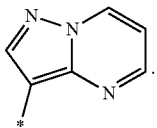

In embodiments, the compound of Formula (I), for example a compound of Formula (Ia), (Ib), (Ic), (Id), (Ie), (If), (Ig), or (Ih), is a compound of Formula (Ij) wherein the $R^1$ is

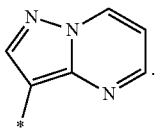

In embodiments, the compound of Formula (I), for example a compound of Formula (Ia), (Ib), (Ic), (Id), (Ie), (If), (Ig), (Ih), (Ii) or (Ij), is a compound of Formula (Ik) in which X is $OR^7$, optionally wherein $R^7$ is OMe.

In embodiments, the compound of Formula (I), for example a compound of any of Formula (Ac) or (Ah) is a compound of Formula (Ak) in which X is $OR^7$, optionally wherein $R^7$ is OMe. In embodiments, the compound of Formula (I), for example a compound of Formula (Ia), (Ib), (Ic), (Id), (Ie), (If), (Ig), (Ih), (Ii) or (Ij), is a compound of Formula (II) in which X is $NR^8R^9$.

In embodiments, the compound of Formula (I), for example a compound of any of Formula (Ac) or (Ah) is a compound of Formula (A) in which in which X is $NR^8R^9$.

In embodiments, the compound of Formula (A) is selected from:
N-(Imidazo[1,2-b]pyridazin-3-yl)-6-methoxy-2-((5r,8r)-1-methyl-2-oxo-1-azaspiro[4.5]decan-8-yl)-2H-indazole-5-carboxamide;
N-(Imidazo[1,2-b]pyridazin-3-yl)-6-methoxy-2-((5s,8s)-1-methyl-2-oxo-1-azaspiro[4.5]decan-8-yl)-2H-indazole-5-carboxamide;
2-((1s,4s)-4-(Dimethylcarbamoyl)cyclohexyl)-N-(imidazo[1,2-b]pyridazin-3-yl)-6-methoxy-2H-indazole-5-carboxamide;
2-((1r,4r)-4-(Dimethylcarbamoyl)cyclohexyl)-N-(imidazo[1,2-b]pyridazin-3-yl)-6-methoxy-2H-indazole-5-carboxamide;
2-(2-Hydroxy-2-methylspiro[3.5]nonan-7-yl)-N-(imidazo[1,2-b]pyridazin-3-yl)-6-methoxy-2H-indazole-5-carboxamide—Isomer 1 or Isomer 2;
2-((1s,4s)-4-Hydroxycyclohexyl)-N-(imidazo[1,2-b]pyridazin-3-yl)-6-methoxy-2H-indazole-5-carboxamide;
2-((1r,4r)-4-Hydroxycyclohexyl)-N-(imidazo[1,2-b]pyridazin-3-yl)-6-methoxy-2H-indazole-5-carboxamide;
rel-2-((1S,3R)-3-Hydroxycyclohexyl)-N-(imidazo[1,2-b]pyridazin-3-yl)-6-methoxy-2H-indazole-5-carboxamide—Isomer 1 or Isomer 2;
6-Methoxy-2-(1-methyl-2-oxo-1-azaspiro[4.5]decan-8-yl)-N-(pyrazolo[1,5-a]pyrimidin-3-yl)-2H-indazole-5-carboxamide—Isomer 1 or Isomer 2;
rel-2-((1S,3R)-3-Hydroxycyclohexyl)-6-methoxy-N-(pyrazolo[1,5-a]pyrimidin-3-yl)-2H-indazole-5-carboxamide—Isomer 1 or Isomer 2;
6-Cyclopropoxy-2-(2-hydroxy-2-methylspiro[3.5]nonan-7-yl)-N-(pyrazolo[1,5-a]pyrimidin-3-yl)-2H-indazole-5-carboxamide—Isomer 1 or Isomer 2;
6-Cyclopropoxy-2-((1R,3S)-3-hydroxycyclohexyl)-N-(pyrazolo[1,5-a]pyrimidin-3-yl)-2H-indazole-5-carboxamide;
6-Cyclopropoxy-2-((1S,3R)-3-hydroxycyclohexyl)-N-(pyrazolo[1,5-a]pyrimidin-3-yl)-2H-indazole-5-carboxamide;
rel-6-Cyclopropoxy-2-((1S,3S)-3-hydroxycyclohexyl)-N-(pyrazolo[1,5-a]pyrimidin-3-yl)-2H-indazole-5-carboxamide—Isomer 1 or Isomer 2;
2-(2-Acetyl-2-azaspiro[3.5]nonan-7-yl)-N-(imidazo[1,2-b]pyridazin-3-yl)-6-methoxy-2H-indazole-5-carboxamide;
N-(Imidazo[1,2-b]pyridazin-3-yl)-6-methoxy-2-((1s,4s)-4-(N-methylacetamido)cyclohexyl)-2H-indazole-5-carboxamide;
N-(Imidazo[1,2-b]pyridazin-3-yl)-6-methoxy-2-((1r,4r)-4-(N-methylacetamido)cyclohexyl)-2H-indazole-5-carboxamide;
6-Methoxy-2-((1s,4s)-4-(N-methylacetamido)cyclohexyl)-N-(pyrazolo[1,5-a]pyrimidin-3-yl)-2H-indazole-5-carboxamide;
6-Methoxy-2-((1r,4r)-4-(N-methylacetamido)cyclohexyl)-N-(pyrazolo[1,5-a]pyrimidin-3-yl)-2H-indazole-5-carboxamide;
2-((1r,4r)-4-(Cyclopropanecarboxamido)cyclohexyl)-6-methoxy-N-(pyrazolo[1,5-a]pyrimidin-3-yl)-2H-indazole-5-carboxamide;
2-((1s,4s)-4-(Cyclopropanecarboxamido)cyclohexyl)-6-methoxy-N-(pyrazolo[1,5-a]pyrimidin-3-yl)-2H-indazole-5-carboxamide;
rel-2-((6R,7R)-2-Acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 1 or Isomer 2;
rel-2-((6S,7R)-2-Acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 1 or Isomer 2;
6-Cyclopropoxy-2-((1s,4s)-4-(N-methylacetamido)cyclohexyl)-N-(pyrazolo[1,5-a]pyrimidin-3-yl)-2H-indazole-5-carboxamide;
6-Cyclopropoxy-2-((1r,4r)-4-(N-methylacetamido)cyclohexyl)-N-(pyrazolo[1,5-a]pyrimidin-3-yl)-2H-indazole-5-carboxamide;
N-(Imidazo[1,2-b]pyridazin-3-yl)-6-methoxy-2-((1S,2S,4R*)-2-methyl-4-(N-methylacetamido) cyclohexyl)-2H-indazole-5-carboxamide—Isomer 1 or Isomer 2;
N-(Imidazo[1,2-b]pyridazin-3-yl)-6-methoxy-2-((1R,2R,4R*)-2-methyl-4-(N-methylacetamido) cyclohexyl)-2H-indazole-5-carboxamide—Isomer 1 or Isomer 2;
rel-2-((1S,2S,4S)-4-Hydroxy-2-methylcyclohexyl)-6-methoxy-N-(pyrazolo[1,5-a]pyrimidin-3-yl)-2H-indazole-5-carboxamide—Isomer 1 or Isomer 2;
rel-2-((1S,2S,4R)-4-Hydroxy-2-methylcyclohexyl)-6-methoxy-N-(pyrazolo[1,5-a]pyrimidin-3-yl)-2H-indazole-5-carboxamide—Isomer 1 or Isomer 2;

rel-6-Cyclopropoxy-2-((1S,2S,4R)-4-hydroxy-2-methylcyclohexyl)-N-(pyrazolo[1,5-c]pyrimidin-3-yl)-2H-indazole-5-carboxamide—Isomer 1 or Isomer 2;

rel-6-Cyclopropoxy-2-((1S,2S,4S)-4-hydroxy-2-methylcyclohexyl)-N-(pyrazolo[1,5-c]pyrimidin-3-yl)-2H-indazole-5-carboxamide—Isomer 1 or Isomer 2;

6-Cyclopropoxy-2-(2-hydroxyspiro[3.5]nonan-7-yl)-N-(pyrazolo[1,5-a]pyrimidin-3-yl)-2H-indazole-5-carboxamide—Isomer 1 or Isomer 2;

2-(4-Hydroxy-4-methylcyclohexyl)-N-(imidazo[1,2-b]pyridazin-3-yl)-6-methoxy-2H-indazole-5-carboxamide—Isomer 1 or Isomer 2;

rel-2-((1S,3R)-3-Hydroxy-3-methylcyclohexyl)-6-methoxy-N-(pyrazolo[1,5-a]pyrimidin-3-yl)-2H-indazole-5-carboxamide—Isomer 1 or Isomer 2;

rel-2-((1S,3S)-3-Hydroxy-3-methylcyclohexyl)-6-methoxy-N-(pyrazolo[1,5-a]pyrimidin-3-yl)-2H-indazole-5-carboxamide—Isomer 1 or Isomer 2;

rel-6-Cyclopropoxy-2-((1S,3R)-3-hydroxy-3-methylcyclohexyl)-N-(pyrazolo[1,5-c]pyrimidin-3-yl)-2H-indazole-5-carboxamide—Isomer 1 or Isomer 2;

6-Cyclopropoxy-2-((1s,4s)-4-hydroxycyclohexyl)-N-(pyrazolo[1,5-c]pyrimidin-3-yl)-2H-indazole-5-carboxamide;

6-Cyclopropoxy-2-((1r,4r)-4-hydroxycyclohexyl)-N-(pyrazolo[1,5-c]pyrimidin-3-yl)-2H-indazole-5-carboxamide;

2-((1R,4r)-4-((R)-2-Hydroxy-N-methylpropanamido)cyclohexyl)-6-methoxy-N-(pyrazolo[1,5-a]pyrimidin-3-yl)-2H-indazole-5-carboxamide;

2-((1S,4r)-4-((S)-2-Hydroxy-N-methylpropanamido)cyclohexyl)-6-methoxy-N-(pyrazolo[1,5-c]pyrimidin-3-yl)-2H-indazole-5-carboxamide;

6-Methoxy-2-((1R,2R,4R*)-2-methyl-4-(N-methylacetamido)cyclohexyl)-N-(pyrazolo[1,5-c]pyrimidin-3-yl)-2H-indazole-5-carboxamide—Isomer 1 or Isomer 2;

6-Methoxy-2-((1S,2S,4R*)-2-methyl-4-(N-methylacetamido)cyclohexyl)-N-(pyrazolo[1,5-c]pyrimidin-3-yl)-2H-indazole-5-carboxamide—Isomer 1 or Isomer 2;

rel-2-((6S,7R)-2-Acetyl-6-methyl-2-azaspiro[3.5]nonan-7-yl)-N-(imidazo[1,2-b]pyridazin-3-yl)-6-methoxy-2H-indazole-5-carboxamide—Isomer 1 or Isomer 2;

rel-2-((6R,7R)-2-Acetyl-6-methyl-2-azaspiro[3.5]nonan-7-yl)-N-(imidazo[1,2-b]pyridazin-3-yl)-6-methoxy-2H-indazole-5-carboxamide—Isomer 1 or Isomer 2;

N-(Imidazo[1,2-b]pyridazin-3-yl)-6-methoxy-2-((5s,8s)-2-methyl-3-oxo-2-azaspiro[4.5]decan-8-yl)-2H-indazole-5-carboxamide;

N-(Imidazo[1,2-b]pyridazin-3-yl)-6-methoxy-2-((5r,8r)-2-methyl-3-oxo-2-azaspiro[4.5]decan-8-yl)-2H-indazole-5-carboxamide;

rel-2-((7R,8R)-2,7-Dimethyl-3-oxo-2-azaspiro[4.5]decan-8-yl)-N-(imidazo[1,2-b]pyridazin-3-yl)-6-methoxy-2H-indazole-5-carboxamide or rel-2-((7S,8S)-2,7-Dimethyl-3-oxo-2-azaspiro[4.5]decan-8-yl)-N-(imidazo[1,2-b]pyridazin-3-yl)-6-methoxy-2H-indazole-5-carboxamide—Isomers 1, 2, 3 or 4;

N-(Imidazo[1,2-b]pyridazin-3-yl)-6-methoxy-2-(1-methyl-2-oxo-3-oxa-1-azaspiro[4.5]decan-8-yl)-2H-indazole-5-carboxamide—Isomer 1 or Isomer 2;

rel-2-((1R,3R,4S)-4-Hydroxy-3-methylcyclohexyl)-N-(imidazo[1,2-b]pyridazin-3-yl)-6-methoxy-2H-indazole-5-carboxamide—Isomer 1 or Isomer 2;

rel-2-((1S,3R,4S)-4-Hydroxy-3-methylcyclohexyl)-N-(imidazo[1,2-b]pyridazin-3-yl)-6-methoxy-2H-indazole-5-carboxamide—Isomer 1 or Isomer 2;

rel-2-((1S,3S,4S)-4-Hydroxy-3-methylcyclohexyl)-N-(imidazo[1,2-b]pyridazin-3-yl)-6-methoxy-2H-indazole-5-carboxamide—Isomer 1 or Isomer 2;

rel-2-((1R,3S,4S)-4-Hydroxy-3-methylcyclohexyl)-N-(imidazo[1,2-b]pyridazin-3-yl)-6-methoxy-2H-indazole-5-carboxamide—Isomer 1 or Isomer 2;

6-Cyclopropoxy-2-((1r,4r)-4-hydroxycyclohexyl)-N-(imidazo[1,2-b]pyridazin-3-yl)-2H-indazole-5-carboxamide;

6-Cyclopropoxy-2-((1s,4s)-4-hydroxycyclohexyl)-N-(imidazo[1,2-b]pyridazin-3-yl)-2H-indazole-5-carboxamide;

6-Methoxy-2-((5r,8r)-2-methyl-3-oxo-2-azaspiro[4.5]decan-8-yl)-N-(pyrazolo[1,5-a]pyrimidin-3-yl)-2H-indazole-5-carboxamide;

6-Methoxy-2-((5s,8s)-2-methyl-3-oxo-2-azaspiro[4.5]decan-8-yl)-N-(pyrazolo[1,5-a]pyrimidin-3-yl)-2H-indazole-5-carboxamide;

2-((1R,2R,4S)-4-Hydroxy-2-methylcyclohexyl)-N-(imidazo[1,2-b]pyridazin-3-yl)-6-methoxy-2H-indazole-5-carboxamide;

2-((1R,2R,4R)-4-Hydroxy-2-methylcyclohexyl)-N-(imidazo[1,2-b]pyridazin-3-yl)-6-methoxy-2H-indazole-5-carboxamide;

2-((1S,2S,4R)-4-Hydroxy-2-methylcyclohexyl)-N-(imidazo[1,2-b]pyridazin-3-yl)-6-methoxy-2H-indazole-5-carboxamide;

2-((1S,2S,4S)-4-Hydroxy-2-methylcyclohexyl)-N-(imidazo[1,2-b]pyridazin-3-yl)-6-methoxy-2H-indazole-5-carboxamide;

2-((1R,2R,4S)-4-Hydroxy-2,4-dimethylcyclohexyl)-N-(imidazo[1,2-b]pyridazin-3-yl)-6-methoxy-2H-indazole-5-carboxamide;

2-((1R,2R,4R)-4-Hydroxy-2,4-dimethylcyclohexyl)-N-(imidazo[1,2-b]pyridazin-3-yl)-6-methoxy-2H-indazole-5-carboxamide;

2-((1S,4r)-4-((S)-2-Hydroxy-N-methylpropanamido)cyclohexyl)-N-(imidazo[1,2-b]pyridazin-3-yl)-6-methoxy-2H-indazole-5-carboxamide;

2-((1R,4r)-4-((R)-2-Hydroxy-N-methylpropanamido)cyclohexyl)-N-(imidazo[1,2-b]pyridazin-3-yl)-6-methoxy-2H-indazole-5-carboxamide;

6-Methoxy-2-((1r,4r)-4-(N-methylcyclopropanecarboxamido)cyclohexyl)-N-(pyrazolo[1,5-c]pyrimidin-3-yl)-2H-indazole-5-carboxamide;

2-((1R,4r)-4-((1r,3R)-3-Hydroxy-N-methylcyclobutane-1-carboxamido)cyclohexyl)-6-methoxy-N-(pyrazolo[1,5-c]pyrimidin-3-yl)-2H-indazole-5-carboxamide;

2-((1R,4r)-4-((1s,3S)-3-Hydroxy-N-methylcyclobutane-1-carboxamido)cyclohexyl)-6-methoxy-N-(pyrazolo[1,5-a]pyrimidin-3-yl)-2H-indazole-5-carboxamide;

2-((1r,4r)-4-(2-Hydroxy-N,2-dimethylpropanamido)cyclohexyl)-6-methoxy-N-(pyrazolo[1,5-a]pyrimidin-3-yl)-2H-indazole-5-carboxamide;

2-(2-Acetyl-2-azaspiro[3.5]nonan-7-yl)-N-(imidazo[1,2-b]pyridazin-3-yl)-6-((1r,3r)-3-methoxycyclobutoxy)-2H-indazole-5-carboxamide;

2-(2-Acetyl-2-azaspiro[3.5]nonan-7-yl)-N-(imidazo[1,2-b]pyridazin-3-yl)-6-((1s,3s)-3-methoxycyclobutoxy)-2H-indazole-5-carboxamide;

2-((1r,4r)-4-(1H-1,2,3-triazol-1-yl)cyclohexyl)-N-(imidazo[1,2-b]pyridazin-3-yl)-6-methoxy-2H-indazole-5-carboxamide;

2-((1r,4r)-4-(2H-1,2,3-triazol-2-yl)cyclohexyl)-N-(imidazo[1,2-b]pyridazin-3-yl)-6-methoxy-2H-indazole-5-carboxamide rel-2-((1S,2S,3R)-3-Hydroxy-2-methylcyclohexyl)-N-(imidazo[1,2-b]pyridazin-3-yl)-6-methoxy-2H-indazole-5-carboxamide—Isomer 1 or Isomer 2;

rel-2-((1S,2R,3S)-3-Hydroxy-2-methylcyclohexyl)-N-(imidazo[1,2-b]pyridazin-3-yl)-6-methoxy-2H-indazole-5-carboxamide—Isomer 1 or Isomer 2;

rel-2-((1S,2R,3R)-3-Hydroxy-2-methylcyclohexyl)-N-(imidazo[1,2-b]pyridazin-3-yl)-6-methoxy-2H-indazole-5-carboxamide—Isomer 1 or Isomer 2;

2-((1S,4r)-4-((S)-3-Hydroxy-N-methylbutanamido)cyclohexyl)-6-methoxy-N-(pyrazolo[1,5-a]pyrimidin-3-yl)-2H-indazole-5-carboxamide;

2-((1R,4r)-4-((R)-3-Hydroxy-N-methylbutanamido)cyclohexyl)-6-methoxy-N-(pyrazolo[1,5-a]pyrimidin-3-yl)-2H-indazole-5-carboxamide;

rel-2-((1R,4r)-4-((1R,3R)-3-Hydroxy-N-methylcyclopentane-1-carboxamido)cyclohexyl)-6-methoxy-N-(pyrazolo[1,5-a]pyrimidin-3-yl)-2H-indazole-5-carboxamide—Isomer 1 or Isomer 2;

rel-2-((1R,4r)-4-((1R,3S)-3-hydroxy-N-methylcyclopentane-1-carboxamido)cyclohexyl)-6-methoxy-N-(pyrazolo[1,5-a]pyrimidin-3-yl)-2H-indazole-5-carboxamide—Isomer 1 or Isomer 2;

2-((1S,4r)-4-((S)-3-Hydroxy-N-methylpyrrolidine-1-carboxamido)cyclohexyl)-N-(imidazo[1,2-b]pyridazin-3-yl)-6-methoxy-2H-indazole-5-carboxamide;

2-((1R,4r)-4-((R)-3-Hydroxy-N-methylpyrrolidine-1-carboxamido)cyclohexyl)-N-(imidazo[1,2-b]pyridazin-3-yl)-6-methoxy-2H-indazole-5-carboxamide;

6-Methoxy-2-(1-methyl-2-oxo-4-oxa-1-azaspiro[5.5]undecan-9-yl)-N-(pyrazolo[1,5-a]pyrimidin-3-yl)-2H-indazole-5-carboxamide—Isomer 1 or Isomer 2;

rel-2-((5R,7R,8R)-1,7-dimethyl-2-oxo-1-azaspiro[4.5]decan-8-yl)-N-(imidazo[1,2-b]pyridazin-3-yl)-6-methoxy-2H-indazole-5-carboxamide—Isomer 1 or Isomer 2 and rel-2-((5S,7R,8R)-1,7-Dimethyl-2-oxo-1-azaspiro[4.5]decan-8-yl)-N-(imidazo[1,2-b]pyridazin-3-yl)-6-methoxy-2H-indazole-5-carboxamide—Isomer 1 or Isomer 2 or a pharmaceutically acceptable salt thereof.

The IRAK4 inhibitors of the present invention can be prepared from readily available starting materials, either available from commercial suppliers, such as Merck KGaA or by methods comprised in the common general knowledge of those skilled in the art. The reaction schemes below describe a variety of methods for the synthesis of the IRAK4 inhibitors. Typical or preferred reaction conditions might be given for the synthesis but those skilled in the art will be able to suggest modifications of these conditions to obtain analogues not described herein. Schemes presented below are therefore representative methods for the synthesis of the compounds of this specification and they should not be construed as constraining the scope of the specification in any way. In addition, the order of reactions can be modified to change the overall synthesis to allow for variations at different positions of the molecule at different stages of the synthesis.

The informed reader will recognize that the compounds described in the schemes below might in some cases be obtained as mixtures of regioisomers and stereoisomers, which can be separated at different stages of the synthesis using techniques such as silica/C18 chromatography, HPLC, SFC, crystallization etc. that are well known to those skilled in the art.

General Synthesis of Scaffolds/Building Blocks:

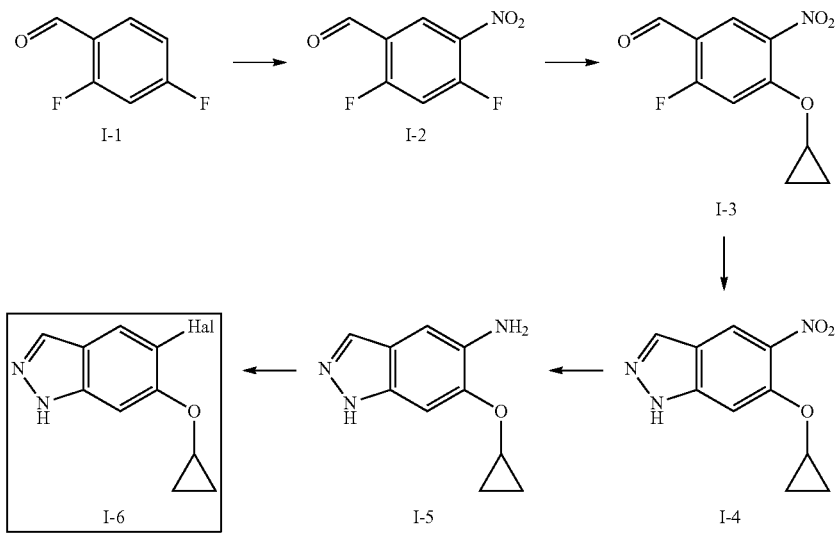

Scheme 1: Synthesis of scaffold I-6 with Hal = halide.

Scaffold I-6 as shown in Scheme 1 can be prepared from commercially available 2,4-difluorobenzaldehyde (I-1). I-1 can be nitrated using standard nitrating conditions, e.g. using a mixture of concentrated sulfuric acid and concentrated nitric acid or, as described in e.g. WO2017/009798, using a mixture of concentrated sulfuric acid and potassium nitrate, to give nitro compound I-2. Treatment of I-2 with cyclopropanol, in the presence of a base (e.g. DIPEA) and a suitable solvent (e.g. DMF) under elevated temperature forms the isopropyl ether I-3. The indazole I-4 can be obtained from I-3 by its reaction with hydrazine in a suitable solvent at elevated temperature (e.g. 80° C.). Subsequently, the aromatic amine I-5 can be obtained by reducing the nitro compound I-4 e.g. by treatment with Fe and ammonium chloride in an ethanol/water mixture (alternatively Pd on carbon (or Pd(OH)$_2$ on carbon) in MeOH under an H$_2$ atmosphere can be used). Amine I-5 can be converted into the corresponding bromide I-6 (Hal=Br) by e.g. treatment with tert-butyl nitrite and copper (I) bromide in a suitable solvent (e.g. acetonitrile). Protection of the indazole NH of I-4, with e.g. a PMB-protecting group, before the reduction of the nitro group followed by deprotection after the introduction of the bromide increases the yield of these transformations. Amine I-5 can be converted into the corresponding iodide I-6 (Hal=I) by e.g. treatment with sodium nitrite and potassium iodide in water/acetic acid.

Scheme 2: General synthesis of building block II-4 with R¹ as defined in the claims and R⁷ = -Me or -cyclopropyl.

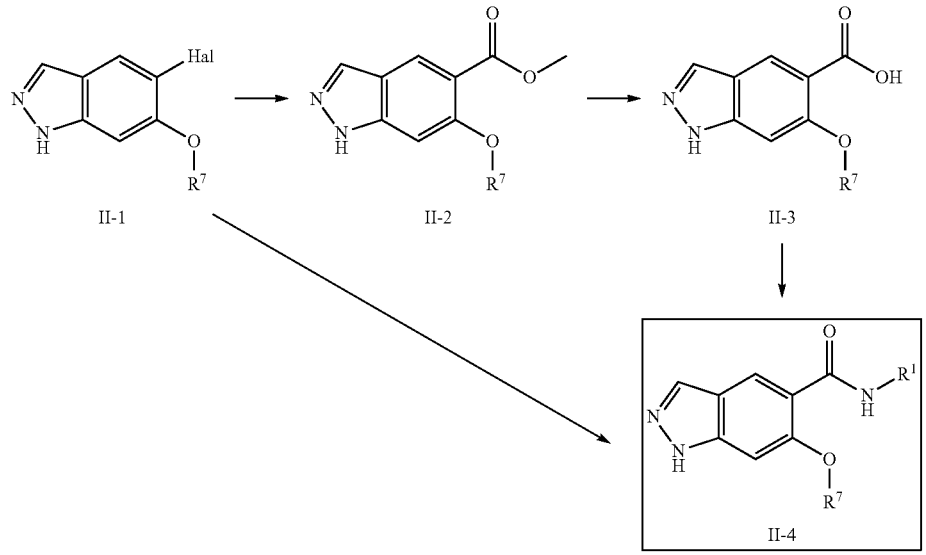

The halide II-1 (Hal=Br or I) can be used as the starting material for the synthesis of building block II-4, as depicted in Scheme 2. The halide II-1 is either commercially available or can be obtained using the steps described in Scheme 1 above. Treatment of II-1 with a Pd-catalyst (e.g. Pd(dppf)Cl$_2$) under an atmosphere of CO (optionally generated in situ with the help of COware® and SilaCOgen®) in the presence of an alcohol as the solvent yields the ester II-2 (here shown as the methyl ester, when using MeOH as the solvent). Subsequent cleavage of the ester with e.g. lithium hydroxide or potassium hydroxide in a suitable solvent (e.g. water) yields carboxylic acid II-3. Amide formation of this acid II-3 with amines R¹—NH$_2$ can be performed with a variety of amide coupling reagents (e.g. HATU) in the presence of a base (e.g. DIPEA) and DMF and/or THF as the solvent to yield the desired building block II-4.

The conversion of halide II-1 into amide II-4 can also be performed in a one step fashion using an aminocarbonylation reaction. Stirring II-1 (Hal=Br or I) with a Pd-source (e.g. Pd(OAc)$_2$) and a suitable ligand (e.g. 1,3-bis(diphenylphosphino)propane) in a solvent (e.g. CH$_3$CN) in the presence of a base (e.g. TEA) and amine R¹—NH$_2$ under an atmosphere of CO (optionally generated in situ) affords amide II-4 in one step.

Scheme 3: General synthesis of building block III-2 with Hal = halide (Br, I); R = R² (as defined in the claims) or a protected precursor of R² as defined below; R⁷ = -Me or -cyclopropyl etc.

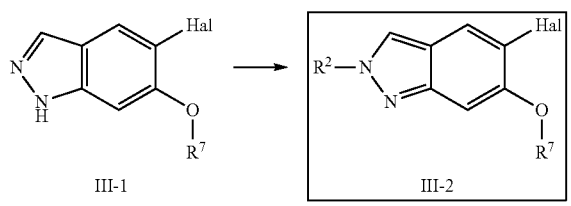

Indazole III-2, shown in Scheme 3, can be obtained from compound III-1 (commercially available or obtained by the synthesis shown in Scheme 1 above) by treating with a base (e.g. K$_2$CO$_3$, Cs$_2$CO$_3$, NaHCO$_3$, NaOH, KOH, Na$^t$OBu, K$^t$OBu, KOEt, KHMDS, DIPEA, pyridine, TEA) in a suitable solvent (e.g. DMF, THF, dioxane, xylene, MeCN) and an alkylating reagent R-Y, e.g. the mesylate, tosylate or halide of R² at elevated temperature. Alternatively, the alkylation can be performed by Michael reaction of compound III-1 and an (1,13-unsaturated carbonyl precursor of R². In case R² contains a functionality which requires to be protected by a suitable protection group for this synthetic step a suitable protected precursor of R² should be used. In addition, the alkylation reaction as shown in Scheme 3, can be performed with a suitable precursor of R² which can be converted into R² later in the synthesis towards the target compound. For example, if R² contains an amine or amide functionality, the amine can be protected in the alkylating agent with a suitable protecting group (e.g. Boc), which is cleaved after the alkylation reaction. Subsequently, the amine can be alkylated or converted into an amide. If R² contains an alcohol functionality, this functionality can be protected with a suitable alcohol protection group, which withstands the reaction conditions of the alkylation reaction and is cleaved at a later stage in the synthesis of the target compound. Protecting groups are well known in the art (see e.g. Greene's Protective Groups in Organic Synthesis, Ed P.G.M. Wuts, Wiley, NY 2014, 5$^{th}$ Edition). Alternatively, the alkylating agent could contain a precursor of the amine/amide/alcohol functionality in form of a suitable protected carbonyl functionality which can be deprotected and converted to the desired amine/amide/alcohol functionality of the target compound in a later stage in the synthesis by synthetic methods known to the one skilled in the art.

Depending on the reaction conditions used in the alkylation reaction described above, a mixture of N1 and N2-regioisomers can be obtained. The N1 isomer can be separated from the N2 isomer by e.g. column chromatography either directly after the alkylation reaction described above or at a later stage in the synthesis of the target compound.

Scheme 4: General synthesis of building blocks IV-2 and IV-7 with R = R² (as defined in the claims or a suitably protected precursor thereof as described under Scheme 3; R⁷ = -Me, -cyclopropyl, etc.

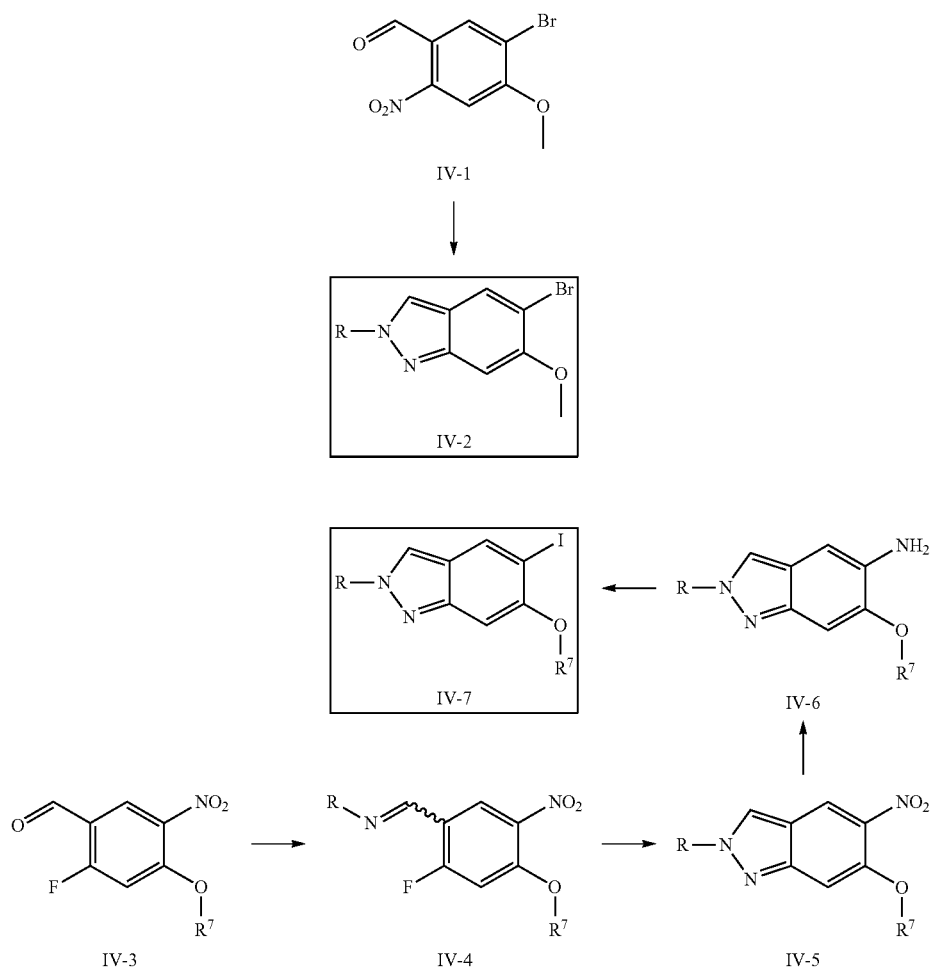

Scheme 4 describes the regioselective synthesis of the N-2 indazole isomers IV-2 and IV-7. Treatment of the commercially available starting material IV-1 for the synthesis of IV-2 with an amine R—NH₂ in a suitable solvent (e.g. iPrOH) at elevated temperature, followed by addition of tri-n-butylphosphine results in the formation of IV-2. The starting material IV-3 for the synthesis of IV-7 is commercially available (IV-3, R⁷=Me, CAS 586412-86-4) or can be obtained as shown in the synthesis sequence outlined in Scheme 1 (for R⁷=cyclopropyl). Treatment of benzaldehyde IV-3 with an amine R—NH₂ in a suitable solvent (e.g. EtOH) to form the corresponding imine, followed by stirring of the crude imine IV-4 with sodium azide in a suitable solvent (e.g. DMF) yields the bicyclic intermediate IV-5. Reduction of the nitro group of IV-5 (with e.g. Pd(OH)₂ on carbon under H₂ atmosphere) yields the aromatic amine IV-6. Subsequent treatment of IV-6 with e.g. sodium nitrite and potassium iodide in acetic acid leads to the corresponding iodo compound IV-7.

General Synthesis of Compounds of Formula (I):

Scheme 5: General synthesis of compounds of formula (I), Method 1

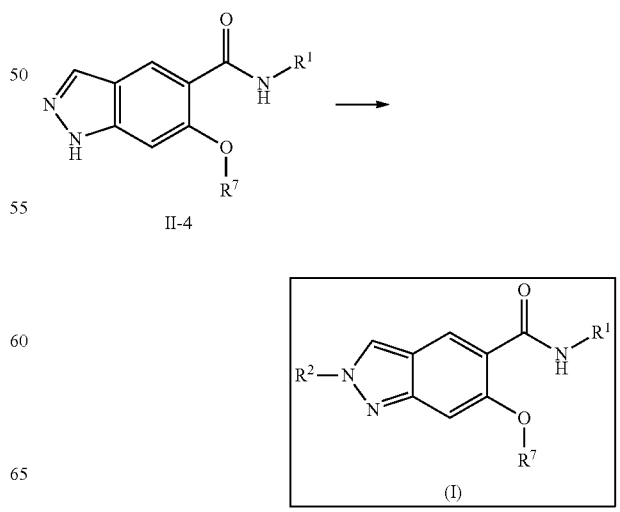

The compounds of Formula (I) can be prepared as shown in Scheme 5 from compound II-4 ($R^7$=-Me, -cyclopropyl, etc.; $R^1$ as defined in the claims). A reaction sequence to prepare compound II-4 is shown in Scheme 2.

Indazole II-4 can be alkylated by treatment with a base (e.g. KOH, KHMDS, $Cs_2CO_3$) and a suitable alkylating reagent R-Y (Y=mesylate, tosylate, halide, R=$R^2$ or a suitable protected precursor of $R^2$ as defined above under Scheme 3) in a solvent compatible with the base. In case an R-Y with R=a suitable precursor of $R^2$ is used in the alkylation reaction the steps described under Scheme 3 can be performed after the alkylation to covert R into $R^2$ of the target compound.

Depending on the reaction conditions used in the alkylation reaction described above, a mixture of N1 and N2-regioisomers can be obtained. The N1 isomer can be separated from the N2 isomer by e.g. column chromatography to obtain the compound of formula (I).

If the reaction sequence shown in Scheme 6 starts with compound III-2 (R=a protected precursor of $R^2$), the transformations to convert R into $R^2$ (as described under Scheme 3) can be performed at different stages of the synthesis sequence shown in Scheme 6, depending on the nature of the transformation and the compatibility of the functional groups present in the sequence intermediates with the reaction conditions (a person skilled in the art will be able to decide the order of steps).

The conversion of halide III-2 (R=$R^2$) into the compound of Formula (I) can also be performed in a one pot aminocarbonylation protocol. Stirring III-2 (R=$R^2$) with a Pd-source (e.g. $Pd(OAc)_2$) and a suitable ligand (e.g. 1,3-bis(diphenylphosphino)propane or di(adamantan-1-yl)butylphosphane) in a solvent (e.g. $CH_3CN$) in the presence of a base (e.g. TEA) and the coupling amine $R^1$—$NH_2$ under an atmosphere of CO (at elevated pressure) yields the compound of formula (I) in one step.

If the aminocarbonylation reaction is performed with compound III-2 (R=a suitable protected precursor of $R^2$), the Scheme 6: General synthesis of compounds of formula (I), Method 2

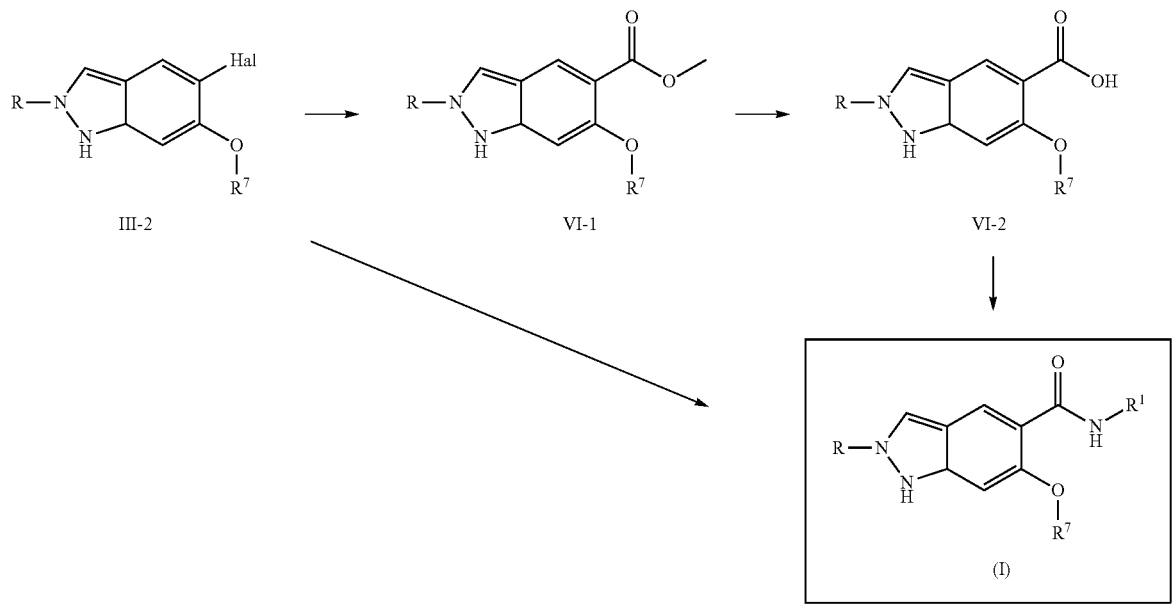

Another method to prepare compounds of Formula (I) is shown in Scheme 6. A suitable starting material for this route is indazole III-2 (Hal=halide (Br, I); R=$R^2$ as defined in the claims or a suitable precursor of thereof as described under Scheme 3; $R^7$=-Me, -cyclopropyl, etc). Halide III-2 can be obtained as described in Schemes 3 and 4 and can be first treated with a Pd-catalyst (e.g. $Pd(dppf)Cl_2$) under an atmosphere of CO (at elevated pressure) in the presence of an alcohol as the solvent to yield ester VI-1 (if MeOH is used as the solvent the Me-ester VI-1 is formed). Subsequent cleavage of the ester by e.g. lithium hydroxide or potassium hydroxide in a suitable solvent (e.g. water) yields the carboxylic acid VI-2. Amide formation of this acid VI-2 with an amine $R^1$—$NH_2$ ($R^1$ as defined in the claims) can be performed with a variety of amide coupling reagents (e.g. HATU, T3P) to yield the desired compound of Formula (I).

transformations to convert R into $R^2$ (as described under Scheme 3) can be performed after the aminocarbonylation reaction shown in Scheme 6, to afford the compound of Formula (I).

Scheme 7: General synthesis of compounds of formula (I), Method 3

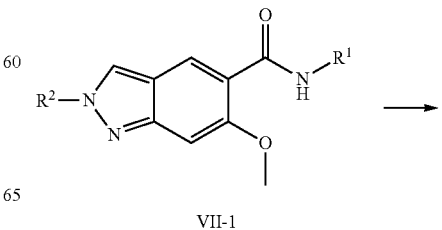

VII-1

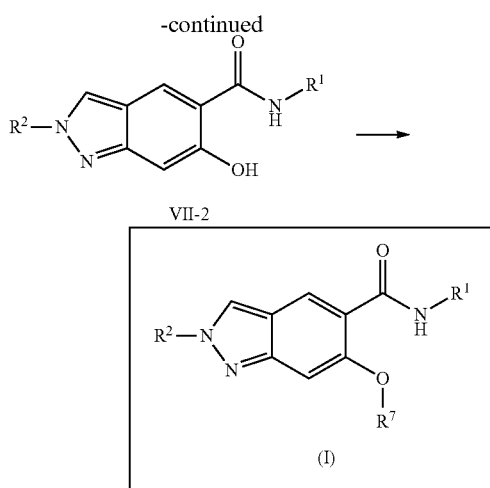

Scheme 7 shows a method to change the substituent $R^7$ late in the synthesis to obtain the compound of Formula (I). Starting with compound VII-1 the methoxy ether can be cleaved with e.g. $BBr_3$ in DCM to yield phenol VII-2. Subsequent reaction of VII-2 with an alkylating reagent $R^7$—Y, e.g. the mesylate, tosylate or halide or an alcohol $R^7$—OH in either an alkylation reaction or a Mitsunobu coupling yields compounds of formula (I).

In embodiments of the specification there are provided methods of synthesizing compounds of Formula (I) or pharmaceutically acceptable salts thereof, intermediates in the synthesis of the compounds of Formula (I), for example methods and intermediates described herein and above.

In embodiments there is provided a pharmaceutical composition which comprises a compound of Formula (I) or a pharmaceutically acceptable salt thereof, in association with a pharmaceutically acceptable excipient. In such embodiments the compound of Formula (i) is preferably used as a single enantiomeric form. Minor impurities, for example up to 1% by mass of other stereoisomeric forms may be optionally be present. The pharmaceutical compositions can be used for the treatment of conditions in which IRAK4 kinase inhibition can be beneficial as described in more detail herein and above.

In embodiments there is provided a compound of Formula (I) for use in the production of a medicine, optionally wherein the medicines is for use in the treatment or prevention of a condition in which IRAK4 kinase inhibition can be beneficial as described in more detail herein and above.

The compounds of Formula (I) and pharmaceutically acceptable salts thereof may be prepared, used or supplied in amorphous form, crystalline form, or semi-crystalline form and any given compound of Formula (I) or pharmaceutically acceptable salt thereof may be capable of being formed into more than one crystalline and/or polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I) and pharmaceutically acceptable salts thereof.

In further embodiments of the present specification there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopically labelled compounds of Formula (I) can generally be prepared by conventional techniques known to those skilled in the art or by processes analogous to those described in the accompanying Examples using appropriate isotopically labelled reagents in place of the non-labelled reagents previously employed.

A suitable pharmaceutically acceptable salt of a compound of the Formula (I) may be, for example, an acid addition salt. A suitable pharmaceutically acceptable salt of a compound of the Formula (I) may be, for example, an acid addition salt of a compound of the Formula (I), for example an acid-addition salt with an inorganic or organic acid. The compounds of the specification may be provided as the free base compound, i.e. in the non-salified state.

A further suitable pharmaceutically acceptable salt of a compound of the Formula (I) may be, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

For use in a pharmaceutical context it may be preferable to provide a compound of Formula (I) or a pharmaceutically acceptable salt thereof without large amounts of the other stereoisomeric forms being present.

The compound of Formula (I), or a pharmaceutically acceptable salt thereof, will normally be administered via the oral route though parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form may be possible. Depending upon the disorder and patient to be treated and the route of administration, the compositions may be administered at varying doses, for example in an oral dose of from 1 mg to 1,000 mg or from 100 mg to 2,000 mg.

The pharmaceutical formulations of the compound of Formula (I) described above may be prepared e.g. for parenteral, subcutaneous, intramuscular or intravenous administration.

The pharmaceutical formulations of the compound of Formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives Liquid compositions may be encapsulated in, for example, gelatin to provide a unit dosage form. Solid oral dosage forms include tablets, two-piece hard shell capsules and soft elastic gelatin (SEG) capsules. An exemplary oral composition according to the specification comprises a compound of Formula (I) and at least one pharmaceutically acceptable excipient filled into a two-piece hard shell capsule or a soft elastic gelatin (SEG) capsule.

According to a further embodiment there is provided a compound of the Formula (I), or a pharmaceutically acceptable salt thereof, as defined hereinbefore, for use as a medicament in a warm-blooded animal such as man.

According to a further embodiment, there is provided a compound of the Formula (I), or a pharmaceutically acceptable salt thereof, as defined hereinbefore for use in the production of an anti-proliferative effect in a warm-blooded animal such as man.

According to a further embodiment, there is provided a compound of the Formula (I), or a pharmaceutically acceptable salt thereof, as defined hereinbefore for use in a warm-blooded animal such as man as an anti-invasive agent in the containment and/or treatment of solid tumour disease.

According to a further embodiment, there is provided the use of a compound of the Formula (I), or a pharmaceutically acceptable salt thereof, as defined hereinbefore, for the production of an anti-proliferative effect in a warm-blooded animal such as man.

According to a further embodiment, there is provided the use of a compound of the Formula (I), or a pharmaceutically acceptable salt thereof, as defined hereinbefore, in the manufacture of a medicament for use in a warm-blooded animal such as man as an anti-invasive agent in the containment and/or treatment of solid tumour disease.

In embodiments where the compound of Formula (I) is for use in the treatment of conditions characterized by hyperproliferative diseases or solid tumour disease, and related methods of treatment and use in the manufacture of a medicament intended for the treatment of such diseases it will be understood that in preferred embodiments the disease is melanoma and, furthermore, that the use in combination with a Bruton's Tyrosine Kinase inhibitor is preferred.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. The effective amount will generally be in the range of 0.1 mg to 1,000 mg.

According to a further embodiment, there is provided a compound of the Formula (I), or a pharmaceutically acceptable salt thereof, as defined hereinbefore for use in providing an inhibitory effect on IRAK4 kinase.

According to a further embodiment, there is provided the use of a compound of the Formula (I), or a pharmaceutically acceptable salt thereof, as defined hereinbefore in the manufacture of a medicament for use in providing an inhibitory effect on IRAK4 kinase.

According to a further embodiment, there is also provided a method for providing an inhibitory effect on IRAK4 kinase which comprises administering an effective amount of a compound of the Formula (I), or a pharmaceutically acceptable salt thereof, as defined hereinbefore, to a patient in need thereof.

According to a further embodiment, there is provided a compound of the Formula (I), or a pharmaceutically acceptable salt thereof, as defined hereinbefore, for use in providing a selective inhibitory effect on IRAK4 kinase. In such cases the selective inhibitory effect indicates that the concentration of the compound of Formula (I) required to effect 50% inhibition in IRAK4 kinase activity in vitro is 10-fold, 100-fold or 1000-fold or more lower than that required to effect 50% inhibition of another kinase, for example another kinase that if inhibited gives rise to a toxic side effect.

According to a further embodiment, there is provided the use of a compound of the Formula (I), or a pharmaceutically acceptable salt thereof, as defined hereinbefore, in the manufacture of a medicament for use in providing a selective inhibitory effect on IRAK4 kinase.

According to a further embodiment, there is also provided a method for providing a selective inhibitory effect on IRAK4 kinase which comprises administering an effective amount of a compound of the Formula (I), or a pharmaceutically acceptable salt thereof, to a patient in need thereof.

Described herein are compounds that can inhibit IRAK4 kinase. In biochemical and cell based assays the compounds of the present specification are shown to be potent IRAK4 kinase inhibitors and may therefore be useful in the treatment of disorders mediated by IRAK4 kinase activity, in particular in the treatment of respiratory diseases such as asthma and chronic obstructive pulmonary disease (COPD), of inflammatory diseases and of autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

In embodiments there is provided the use of a compound Formula (I) for the treatment of respiratory disease, optionally wherein the respiratory disease is asthma and chronic obstructive pulmonary disease (COPD).

In embodiments there is provided the use of a compound Formula (I) for the treatment of inflammatory diseases or autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

In embodiments there is provided a method of treatment comprising administration of an effective amount of a compound of Formula (I) to a patient in need thereof, wherein the patient has a respiratory diseases, optionally wherein the respiratory disease is asthma and chronic obstructive pulmonary disease (COPD).

In embodiments there is provided a method of treatment comprising administration of an effective amount of a compound of Formula (I) to a patient in need thereof, wherein the patient has an inflammatory diseases or autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

According to a further aspect of the specification, there is provided the use of a compound of the Formula (I), or a pharmaceutically acceptable salt thereof, as defined hereinbefore, in the manufacture of a medicament for use in the treatment of disorders mediated by IRAK4 kinase activity, in particular in the treatment of respiratory diseases such as asthma and chronic obstructive pulmonary disease (COPD), of inflammatory diseases and of autoinflammatory/autoimmune diseases such as systemic lupus erythematosus, rheumatoid arthritis, myositis, Sjögren's syndrome, systemic sclerosis, gout, endometriosis, atopic dermatitis and psoriasis.

It will be appreciated that the following examples are provided so that the nature of the invention may be fully understood. It will also be appreciated that the following examples are not intended to limit the scope of the description in any way.

EXAMPLES

The following abbreviations are used:

| | |
|---|---|
| atm | Standard Atmosphere Pressure Unit |
| aq. | Aqueous |
| BOC | tert-Butyloxycarbonyl |
| CO | Carbon monoxide |
| $Cs_2CO_3$ | Cesium carbonate |
| DCE | 1,2-Dichloroethane |
| DCM | Dichloromethane |
| DIAD | Di-iso-propyl azodicarboxylate |
| DIPEA | N,N-Di-iso-propylethylamine |
| DMAP | 4-(Dimethylamino)pyridine |
| DMF | N,N-Dimethylformamide |
| DMSO | Dimethyl sulfoxide |
| dppf | 1,1'-Bis(diphenylphosphanyl)ferrocene |
| dppp | 1,3-Bis(diphenylphosphino)propane |
| EtOAc | Ethyl acetate |
| EtOH | Ethanol |
| FA | Formic acid |
| g | Gram(s) |
| h | Hour(s) |
| HATU | N-[(Dimethylamino)-1H-1,2,3-triazolo-[4,5-b]pyridin-1-ylmethylene]-N-methylmethanaminium hexafluorophosphate N-oxide |
| HCl | Hydrochloric acid |
| HPLC | High performance liquid chromatography |
| $K_2CO_3$ | Potassium carbonate |
| KF | Potassium fluoride |
| KOH | Potassium hydroxide |
| L | Liter(s) |
| LiOH | Lithium hydroxide |
| LiHMDS | Lithium bis(trimethylsilyl)amide |
| MeCN | Acetonitrile |
| MeOH | Methanol |
| min | Minute(s) |
| mL | Milliliter(s) |
| MsCl | Methanesulfonyl chloride |
| MTBE | Methyl tert-butyl ether |
| $NaBH_4$ | Sodium tetrahydridoborate |
| NaH | Sodium hydride |
| NaOH | Sodium hydroxide |
| $NH_3$ | Ammonia |
| $NH_4HCO_3$ | Ammonium bicarbonate |
| $NH_4Cl$ | Ammonium chloride |
| $NH_4OH$ | Ammonium hydroxide |
| nm | Nanometer |
| $N_2$ | Nitrogen |
| $Pd(dppf)Cl_2$ | [1,1'-Bis(diphenylphosphino)ferrocene]palladium(II) dichloride |
| $Pd(dppf)Cl_2$-$CH_2Cl_2$ | [1,1'-Bis(diphenylphosphino)ferrocene]palladium(II) dichloride dichloromethane complex |
| $Pd(OAc)_2$ | Palladium(II) acetate |
| $Pd(OH)_2$ | Palladium(II) hydroxide |
| PE | petroleum ether |
| PMB | p-Methoxybenzyl |
| prep. | Preparative |
| i-PrOH | 2-Propanol |
| rt | Room temperature |
| SFC | Supercritical fluid chromatography |
| T3P | Propanephosphonic acid anhydride |
| TFA | Trifluoroacetic acid |
| TEA | Triethylamine |
| TsCl | 4-Methylbenzenesulfonyl chloride |

Abbreviations used for analytical data, if not defined above, are consistent with the common usage in the field (see J Med Chem Standard Abbreviations and Acronyms http://pubsapp.acs.org/paragonplus/submission/imcmar.imcmar.abbreviations.pdf!).

The compound names provided below are generated using PerkinElmer ChemDraw Professional, Version 20.0.2.51. In instances where there is uncertainty as to the absolute stereochemistry, relative stereochemistry is specified as far as possible.

Preparation of Intermediates

Synthesis of Intermediate Int I-1:
5-Bromo-4-methoxy-2-nitrobenzaldehyde

5-Bromo-4-fluoro-2-nitrobenzaldehyde

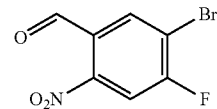

A solution of fuming nitric acid (12.0 mL, 0.3 mol) in concentrated sulfuric acid (25 mL) was added dropwise to 3-bromo-4-fluorobenzaldehyde (19.3 g, 95.1 mmol) in concentrated sulfuric acid (75 mL) at 0° C. The resulting yellow solution was slowly warmed to rt and stirred for 4 d. Then the reaction mixture was poured on crushed ice and the resulting precipitation was collected by filtration to afford 5-bromo-4-fluoro-2-nitrobenzaldehyde (22.6 g, 96%) as a yellow solid. m/z (ESI−), [M−H]⁻=245/247.

5-Bromo-4-methoxy-2-nitrobenzaldehyde (Int I-1)

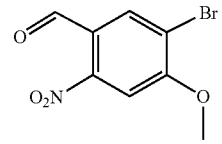

Sodium methoxide (10.9 g, 60.6 mmol) in MeOH (46 mL) was added to 5-bromo-4-fluoro-2-nitrobenzaldehyde (10.0 g, 40.3 mmol) in MeOH (150 mL) at rt. After stirring for 16 h the reaction was quenched with water (300 mL), the formed solid was filtered off and washed with water (100 mL) to afford 5-bromo-4-methoxy-2-nitrobenzaldehyde (6.6 g, 63%) as a pale-yellow solid. ¹H NMR (300 MHz, DMSO-d₆) δ 10.03 (s, 1H), 8.15 (s, 1H), 7.78 (s, 1H), 4.04 (s, 3H).

Synthesis of Intermediate Int I-2:
6-Cyclopropoxy-5-nitro-1H-indazole 2,4-Difluoro-5-nitrobenzaldehyde

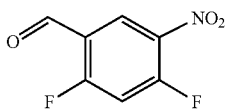 [SMILES: O=Cc1cc([N+](=O)[O-])c(F)cc1F]

To a solution of 2,4-difluorobenzaldehyde (50.0 g, 351.9 mmol) in sulfuric acid (180 mL) was slowly added a mixture of nitric acid (15 M) (30.5 mL, 457.4 mmol) and sulfuric acid (900 mL) over a period of 1 h at 0° C. under N₂ atmosphere. The reaction mixture was stirred at rt for additional 3 h before the mixture was poured on ice/water and extracted with EtOAc (400 mL×3). The combined organic layers were dried over Na₂SO₄, filtered and concentrated under reduced pressure to afford 2,4-difluoro-5-nitrobenzaldehyde (50.0 g, 76%) as a yellow oil.

4-Cyclopropoxy-2-fluoro-5-nitrobenzaldehyde

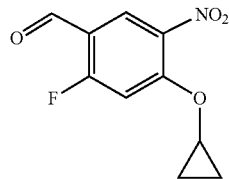 [SMILES: O=Cc1cc([N+](=O)[O-])c(OC2CC2)cc1F]

2,4-Difluoro-5-nitrobenzaldehyde (20.0 g, 106.9 mmol), cyclopropanol (6.2 g, 106.9 mmol) and DIPEA (37.3 mL, 213.8 mmol) in DMF (25 mL) were stirred at 100° C. for 2 h. The reaction mixture was allowed to cool to rt, poured into ice/water (750 mL) and extracted with EtOAc (350 mL). The organic layer was dried over Na₂SO₄, filtered and concentrated under reduced pressure. The residue was purified by silica gel chromatography (eluting with PE/EtOAc (6:1)) to afford crude 4-cyclopropoxy-2-fluoro-5-nitrobenzaldehyde (12.0 g) as a yellow solid. MS ESI, m/z=226 [M+H]⁺.

6-Cyclopropoxy-5-nitro-1H-indazole (Int I-2)

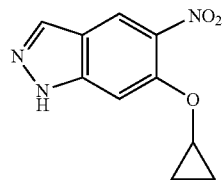 [SMILES: O=[N+]([O-])c1cc2cn[nH]c2cc1OC1CC1]

4-Cyclopropoxy-2-fluoro-5-nitrobenzaldehyde (37.0 g, 164.3 mmol) was slowly added into hydrazine hydrate (80% in water) (32.9 g, 525.8 mmol) in EtOH (100 mL). The resulting mixture was stirred at rt for 15 min, and then stirred at 80° C. for 2 h. The reaction mixture was allowed to cool to rt and concentrated under reduced pressure to afford 6-cyclopropoxy-5-nitro-1H-indazole (34.0 g, 94%) as a red solid. MS ESI, m/z=220 [M+H]⁺.

Synthesis of Intermediate Int I-3:
6-Cyclopropoxy-5-iodo-1H-indazole

6-Cyclopropoxy-1H-indazol-5-amine

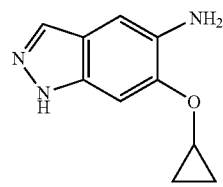 [SMILES: Nc1cc2cn[nH]c2cc1OC1CC1]

To a suspension of 6-cyclopropoxy-5-nitro-1H-indazole (Int I-2) (35.0 g, 159.7 mmol) and NH₄Cl (42.7 g, 798.4 mmol) in EtOH (100 mL)/water (100 mL) was added iron (44.6 g, 798.4 mmol). The resulting mixture was stirred at 80° C. for 2 h, cooled to rt, filtered, and the filtrate was concentrated under reduced pressure. The residue was purified by silica gel chromatography (eluting with PE/EtOAc (2:1)) to afford 6-cyclopropoxy-1H-indazol-5-amine (15.3 g, 51%) as a red solid. MS ESI, m/z=190 [M+H]⁺.

6-Cyclopropoxy-5-iodo-1H-indazole (Int I-3)

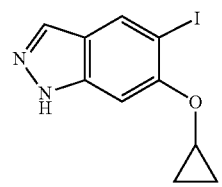 [SMILES: Ic1cc2cn[nH]c2cc1OC1CC1]

To a solution of 6-cyclopropoxy-1H-indazol-5-amine (5.0 g, 26.4 mmol) in acetic acid (100 mL) was slowly added a solution of sodium nitrite (2.7 g, 39.6 mmol) in water (10 mL) at 0° C. The resulting mixture was stirred at rt for 1 h. Then a solution of potassium iodide (8.8 g, 52.9 mmol) in water (10 mL) was added dropwise and the mixture was stirred at 60° C. for 4 h. The reaction mixture was cooled to rt, poured into water (400 mL) and extracted with EtOAc (500 mL). The organic layer was dried over Na₂SO₄, filtered and concentrated under reduced pressure. The residue was purified by silica gel chromatography (eluting with PE/EtOAc (2:1)) to afford 6-cyclopropoxy-5-iodo-1H-indazole (4.0 g, 50%) as a red solid. ¹H NMR (300 MHz, DMSO-d₆) δ 12.95 (s, 1H), 8.16 (s, 1H), 7.89 (s, 1H), 7.28 (s, 1H), 3.94-4.02 (m, 1H), 0.61-0.95 (m, 4H). MS ESI, m/z=301 [M+H]⁺.

Synthesis of Intermediate Int
I-4:5-Bromo-6-cyclopropoxy-1H-indazole

6-Cyclopropoxy-1-(4-methoxybenzyl)-5-nitro-1H-indazole

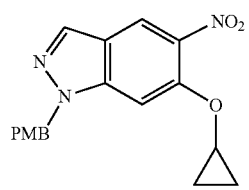

NaH (60 wt %) (2.6 g, 63.9 mmol) was slowly added to 1-(chloromethyl)-4-methoxybenzene (7.5 g, 47.9 mmol) and 6-cyclopropoxy-5-nitro-1H-indazole (Int I-2) (7.0 g, 31.9 mmol) in DMF (20 mL). The resulting mixture was stirred at rt for 2 h. The mixture was poured into water (750 mL) and extracted with EtOAc (1×400 mL). The organic layer was dried over Na₂SO₄, filtered and concentrated to yield the crude product, which was purified by silica gel chromatography (eluting with PE/EtOAc 2/1) to afford 6-cyclopropoxy-1-(4-methoxybenzyl)-5-nitro-1H-indazole (6.0 g, 55%) as a red solid. MS ESI, m/z=340 [M+H]⁺.

6-Cyclopropoxy-1-(4-methoxybenzyl)-1H-indazol-5-amine

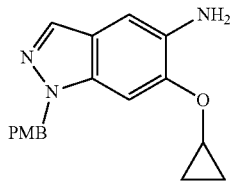

Iron (4.9 g, 88.4 mmol) was added to NH$_4$Cl (4.7 g, 88.4 mmol) and 6-cyclopropoxy-1-(4-methoxybenzyl)-5-nitro-1H-indazole (6.0 g, 17.7 mmol) in EtOH (20 mL) and water (20.00 mL). The resulting mixture was stirred at 80° C. for 2 h, cooled to rt and then filtered and concentrated. The crude product was purified by silica gel chromatography (eluting with PE/EtOAc 2/1) to afford 6-cyclopropoxy-1-(4-methoxybenzyl)-1H-indazol-5-amine (4.8 g, 88%) as a red gum. MS ESI, m/z=310 [M+H]$^+$.

5-Bromo-6-cyclopropoxy-1-(4-methoxybenzyl)-1H-indazole

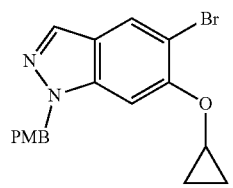

Copper bromide (464 mg, 3.2 mmol) was added to tert-butylnitrite (333 mg, 3.2 mmol) and 6-cyclopropoxy-1-(4-methoxybenzyl)-1H-indazol-5-amine (500 mg, 1.6 mmol) in MeCN (5 mL) at 16° C. over a period of 20 min under N$_2$ atmosphere. The resulting mixture was stirred at 50° C. for 0.5 h. The mixture was cooled to rt, then poured into water (400 mL) and extracted with EtOAc (2×400 mL). The organic phase was dried over Na$_2$SO$_4$, filtered and concentrated. The crude product was purified by silica gel chromatography (eluting with EtOAc/PE (1:3)) to afford 5-bromo-6-cyclopropoxy-1-(4-methoxybenzyl)-1H-indazole (68 mg, 11%) as a pale-yellow solid. MS ESI, m/z=373/375 [M+H]$^+$.

5-Bromo-6-cyclopropoxy-1H-indazole (Int I-4)

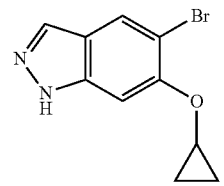 [SMILES: Brc1cc2cn[nH]c2cc1OC1CC1]

TFA (3.0 mL, 39.0 mmol) was added to 5-bromo-6-cyclopropoxy-1-(4-methoxybenzyl)-1H-indazole (400 mg, 1.1 mmol) in DCE (1 mL). The resulting mixture was stirred at 100° C. for 12 h, cooled to rt and then concentrated. The crude product was purified by flash C18-flash chromatography (eluting with 0 to 100% MeCN in water (5% NH$_4$OH)) to afford 5-bromo-6-cyclopropoxy-1H-indazole (156 mg, 58%) as a grey solid. $^1$H NMR (300 MHz, DMSO-d$_6$) δ 13.00 (s, 1H), 7.99 (s, 1H), 7.94 (s, 1H), 7.36 (s, 1H), 4.00 (tt, 1H), 0.83-0.92 (m, 2H), 0.70-0.80 (m, 2H). MS ESI, m/z=253/255 [M+H]$^+$.

Synthesis of Intermediate Int I-5: Pyrazolo[1,5-a]pyrimidin-3-amine

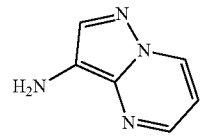

An aq. NH$_3$ solution (25%) (34.9 mL, 403.0 mmol) was added to a solution of the TFA salt of pyrazolo[1,5-a]pyrimidin-3-amine (20.0 g, 80.6 mmol) in EtOH (300 mL). The resulting mixture was stirred at rt for 2 h before the mixture was concentrated under reduced pressure. The residue was purified by silica gel chromatography (eluting with 50-90% EtOAc in PE) to afford pyrazolo[1,5-a]pyrimidin-3-amine (9.9 g, 92%) as an orange solid. MS ESI, m/z=135 [M+H]$^+$.

Synthesis of Intermediate Int II-1: N-(Imidazo[1,2-b]pyridazin-3-yl)-6-methoxy-1H-indazole-5-carboxamide

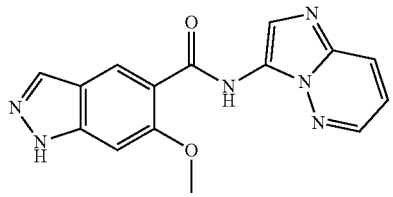 [SMILES: COc1cc2[nH]ncc2cc1C(=O)Nc1cnc2cccnn12]

Pd(OAc)$_2$ (89 mg, 0.4 mmol) was added to TEA (3.7 mL, 26.4 mmol), dppp (165 mg, 0.4 mmol), 5-bromo-6-methoxy-1H-indazole (2.0 g, 8.8 mmol) and imidazo[1,2-b]pyridazin-3-amine (1.3 g, 9.7 mmol) in degassed MeCN (30 mL). The resulting mixture was stirred under CO atmosphere at 4 bar at 100° C. for 23 h. After cooling of the mixture to rt, the formed precipitate was collected by filtration, washed with MeCN (2 mL) and dried under vacuum to afford N-(imidazo[1,2-b]pyridazin-3-yl)-6-methoxy-1H-indazole-5-carboxamide (2.4 g, 87%) as a grey solid, which was used without further purification. $^1$H NMR (500 MHz, DMSO-d$_6$) δ 12.86 (s, 1H), 10.79 (s, 1H), 8.50-8.65 (m, 2H), 8.15 (s, 1H), 8.01-8.12 (m, 2H), 7.23 (s, 1H), 7.18 (dd, 1H), 4.18 (s, 3H). m/z (ESI+) [M+H]$^+$=309.

Synthesis of Intermediate Int II-2: 6-Methoxy-N-(pyrazolo[1,5-c]pyrimidin-3-yl)-1H-indazole-5-carboxamide Methyl 6-methoxy-1H-indazole-5-carboxylate

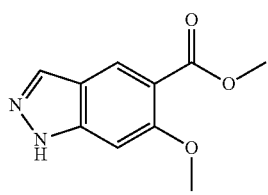

A solution of Pd(dppf)Cl$_2$ (9.7 g, 13.2 mmol), DIPEA (77 mL, 440.4 mmol) and 5-bromo-6-methoxy-1H-indazole (20.0 g, 88 mmol) in MeOH (500 mL) was stirred under CO atmosphere at 15 atm and 110° C. for 12 h. After cooling of the mixture to rt, the reaction mixture was filtered through silica and the solvent was removed under reduced pressure. The crude was purified by silica gel chromatography (eluting with 0 to 30% EtOAc in PE) to afford methyl 6-methoxy-1H-indazole-5-carboxylate (8.0 g, 44%) as a brown solid. m/z (ESI+), [M+H]$^+$=207.

6-Methoxy-1H-indazole-5-carboxylic Acid

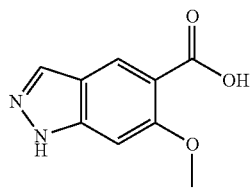

LiOH (732 mg, 30.5 mmol) in water (5 mL) was added to methyl 6-methoxy-1H-indazole-5-carboxylate (2.1 g, 10.2 mmol) in MeOH (5 mL) at rt under N$_2$ atmosphere. The reaction mixture was stirred at rt for 3 h and then acidified with aq. HCl (0.1 M). The formed precipitate was collected by filtration, washed with MeOH and dried under vacuum to afford 6-methoxy-1H-indazole-5-carboxylic acid (1.6 g, 80%) as a grey solid, which was used without further purification. m/z (ESI+), [M+H]$^+$=193.

6-Methoxy-N-(pyrazolo[1,5-c]pyrimidin-3-yl)-1H-indazole-5-carboxamide (Int II-2)

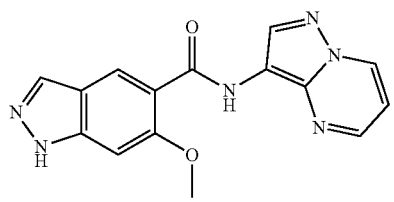 [SMILES: COc1cc2[nH]ncc2cc1C(=O)Nc1cnn2cccnc12]

Pyrazolo[1,5-a]pyrimidin-3-amine (Int I-5) (7.3 g, 54.0 mmol) was added to HATU (20.6 g, 54.0 mmol), DIPEA (36 mL, 208.0 mmol) and 6-methoxy-1H-indazole-5-carboxylic acid (8.0 g, 42.0 mmol) in THF (20 mL) at rt under N$_2$ atmosphere. The resulting solution was stirred for 2 h. The reaction mixture was poured into water (20 mL) and the formed solid was collected via filtration, washed with water (100 mL) and dried under vacuum to afford 6-methoxy-N-(pyrazolo[1,5-a]pyrimidin-3-yl)-1H-indazole-5-carboxamide (10.0 g) as a yellow solid, which was used without further purification. $^1$H NMR (300 MHz, DMSO-d$_6$) δ 13.13 (s, 1H), 10.32 (s, 1H), 9.01-9.12 (m, 1H), 8.74 (s, 1H), 8.53-8.56 (m, 1H), 8.48 (s, 1H), 8.16 (s, 1H), 7.18 (s, 1H), 7.00-7.11 (m, 1H), 4.10 (s, 3H). m/z (ESI+), [M+H]$^+$=309.

Synthesis of Intermediate Int II-3: 6-Cyclopropoxy-N-(pyrazolo[1,5-c]pyrimidin-3-yl)-1H-indazole-5-carboxamide Methyl 6-cyclopropoxy-1H-indazole-5-carboxylate

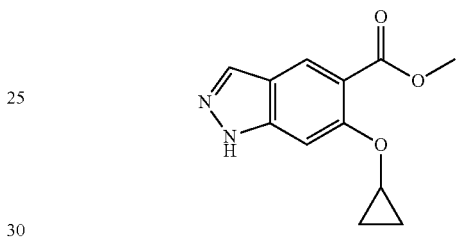

A suspension of 5-bromo-6-cyclopropoxy-1H-indazole (Int I-4) (5.5 g, 21.7 mmol), DIPEA (2.1 g, 16.6 mmol) and Pd(dppf)Cl$_2$ (15.9 g, 21.7 mmol) in MeOH (30 mL) was stirred under CO atmosphere at 15 atm and 110° C. for 12 h. The mixture was cooled to rt, concentrated and was purified by silica gel chromatography (eluting with 0-50% EtOAc in PE) to afford methyl 6-cyclopropoxy-1H-indazole-5-carboxylate (4.4 g, 87%) as a yellow solid. MS ESI, m/z=233 [M+H]$^+$.

6-Cyclopropoxy-1H-indazole-5-carboxylic acid

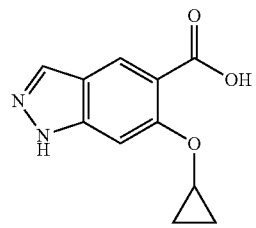 [SMILES: O=C(O)c1cc2cn[nH]c2cc1OC1CC1]

To a solution of methyl 6-cyclopropoxy-1H-indazole-5-carboxylate (4.4 g, 19.0 mmol) in MeOH (5 mL) at rt was added a solution of LiOH (1.4 g, 56.8 mmol) in water (5 mL). The resulting solution was stirred at 30° C. for 12 h. The reaction mixture was cooled to rt, diluted with water (25 mL) and washed with EtOAc (10 mL×3). The aq. layer was acidified to pH 4-5 with 0.1N HCl and the formed precipitate was collected by filtration to obtain 6-cyclopropoxy-1H-indazole-5-carboxylic acid (2.7 g, 65%). MS ESI, m/z=219 [M+H]$^+$.

6-Cyclopropoxy-N-(pyrazolo[1,5-c]pyrimidin-3-yl)-1H-indazole-5-carboxamide (Int II-3)

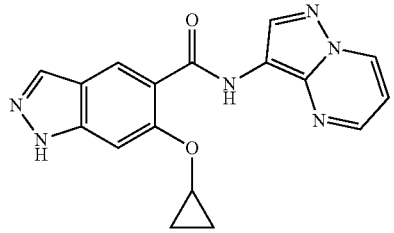 [SMILES: O=C(Nc1cnn2cccnc12)c1cc2cn[nH]c2cc1OC1CC1]

To a solution of 6-cyclopropoxy-1H-indazole-5-carboxylic acid (5.5 g, 25.2 mmol), HATU (14.4 g, 37.8 mmol) and DIPEA (22.0 mL, 126.0 mmol) in DMF (6 mL) and THF (54 mL) at rt was added pyrazolo[1,5-a]pyrimidin-3-amine (Int I-5) (5.1 g, 37.8 mmol) was added. The resulting solution was stirred at rt for 12 h. The reaction mixture was poured into water (1 L) and the formed precipitate was collected by filtration. The solid was suspended in MeOH (150 mL), followed by the addition of K$_2$CO$_3$ (15 g) and the resulting mixture was stirred at rt for 2 h. Subsequently, the suspension was poured into water (1 L) and filtered to give 6-cyclopropoxy-N-(pyrazolo[1,5-c]pyrimidin-3-yl)-1H-indazole-5-carboxamide (6.9 g, 81%) as a yellow solid. $^1$H NMR (300 MHz, DMSO-d$_6$) δ 13.14 (s, 1H), 10.26 (s, 1H), 8.97-9.17 (m, 1H), 8.76 (s, 1H), 8.42-8.64 (m, 2H), 8.18 (s, 1H), 7.48 (s, 1H), 6.95-7.10 (m, 1H), 4.17-4.39 (m, 1H), 1.06-0.90 (m, 2H), 0.90-1.20 (m, 2H). MS ESI, m/z=335 [M+H]$^+$.

Synthesis of Intermediate Int III-1: 1-Methyl-2-oxo-1-azaspiro[4.5]decan-8-yl 4-methylbenzenesulfonate 8-Hydroxy-1-azaspiro[4.5]decan-2-one

To 1-azaspiro[4.5]decane-2,8-dione (4.5 g, 26.9 mmol) in MeOH (100 mL) at 0° C. was added NaBH$_4$ (2.0 g, 53.8 mmol) in one portion and the resulting solution was stirred at rt. After 14 h the reaction mixture was quenched with EtOAc (50 mL), the solvent was removed in vacuo, and the resulting residue was purified using silica gel chromatography (eluting with EtOAc) to afford 8-hydroxy-1-azaspiro[4.5]decan-2-one (2.5 g, 55%) as a colourless oil. m/z (ESI+), [M+H]$^+$=170.

2-Oxo-1-azaspiro[4.5]decan-8-yl 4-methylbenzenesulfonate

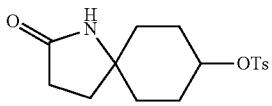 [SMILES: Cc1ccc(S(=O)(=O)OC2CCC3(CCC(=O)N3)CC2)cc1]

TsCl (6.8 g, 35.8 mmol) was slowly added to a solution of 8-hydroxy-1-azaspiro[4.5]decan-2-one (2.8 g, 16.3 mmol), DMAP (199 mg, 1.6 mmol) and TEA (9.1 mL, 65.0 mmol) in DCM (15 mL) at rt under N$_2$ atmosphere. The resulting mixture was stirred at rt for 3 h. The reaction mixture was quenched with water (100 mL), extracted with DCM (15 mL×3), dried over Na$_2$SO$_4$, filtered and concentrated under reduced pressure. The residue was purified by silica gel chromatography (eluting with 30-60% EtOAc in PE) to afford 2-oxo-1-azaspiro[4.5]decan-8-yl 4-methylbenzenesulfonate (2.00 g, 38%) as a colorless solid. $^1$H NMR (300 MHz, DMSO-d$_6$) δ 7.79 (d, 2H), 7.47 (d, 2H), 4.39-4.59 (m, 1H), 2.42 (s, 3H), 2.07-2.19 (m, 2H), 1.48-1.83 (m, 8H), 1.35-1.48 (m, 2H). m/z (ESI+), [M+H]$^+$=324.

1-Methyl-2-oxo-1-azaspiro[4.5]decan-8-yl 4-methylbenzenesulfonate (Int III-1)

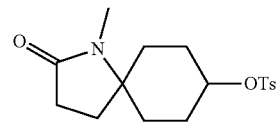 [SMILES: Cc1ccc(S(=O)(=O)OC2CCC3(CCC(=O)N3C)CC2)cc1]

To a solution of 2-oxo-1-azaspiro[4.5]decan-8-yl 4-methylbenzenesulfonate (1.9 g, 5.9 mmol) in DMF (8 mL) at 0° C. under N$_2$ atmosphere was added NaH (60 wt. %) (352 mg, 8.8 mmol). The resulting suspension was stirred at 0° C. for 30 min, followed by the addition of iodomethane (1.5 mL, 23.5 mmol). The reaction mixture was stirred at rt for another 6 h and then quenched with water (10 mL). The mixture was purified directly by C18-flash chromatography (eluting with 0-60% MeCN in water (0.5% NH$_4$OH)) to afford 1-methyl-2-oxo-1-azaspiro[4.5]decan-8-yl 4-methylbenzenesulfonate (1.8 g, 91%) as a colorless solid. $^1$H NMR (400 MHz, DMSO-d$_6$) (3:1 mixture of isomers) δ 7.78-7.86 (m, 2H), 7.48 (d, 2H), 4.61-4.70/4.43-4.53 (m, 1H) (isomers), 2.59/2.55 (s, 3H) (isomers), 2.42 (s, 3H), 2.13-2.23 (m, 2H), 1.54-1.89 (m, 8H), 1.15-1.26/1.26-1.37 (m, 2H) (isomers). m/z (ESI+), [M+H]$^+$=338.

Synthesis of Intermediate Int III-2: tert-Butyl 7-((methylsulfonyl)oxy)-2-azaspiro[3.5]nonane-2-carboxylate

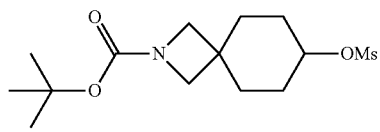 [SMILES: CC(C)(C)OC(=O)N1CC2(CCC(OS(C)(=O)=O)CC2)C1]

To tert-butyl 7-hydroxy-2-azaspiro[3.5]nonane-2-carboxylate (2.0 g, 8.3 mmol) and TEA (2.3 mL, 16.6 mmol) in DCM (15 mL) was added MsCl (839 μLa, 10.8 mmol) at 0° C. under N$_2$ atmosphere and the resulting solution was stirred at rt. After 15 h the reaction mixture was poured into water (150 mL) and extracted with DCM (3×100 mL). The combined organic layers were dried over Na$_2$SO$_4$, filtered, and the solvent was removed in vacuo to afford crude tert-butyl 7-((methylsulfonyl)oxy)-2-azaspiro[3.5]nonane-2-carboxylate (2.70 g) as an orange solid. $^1$H NMR (300 MHz, DMSO-d$_6$) δ 4.57-4.70 (m, 1H), 3.53 (s, 2H), 3.50 (s, 2H), 3.16 (s, 3H), 1.71-1.90 (m, 4H), 1.51-1.66 (m, 4H), 1.38 (s, 9H). m/z (ESI+), [M−tBu+H]⁺=264.

Synthesis of Intermediate Int III-3: 2-Hydroxy-2-methylspiro[3.5]nonan-7-yl 4-methylbenzenesulfonate 2-Methyl-8,11-dioxadispiro[3.2.4⁷.2⁴]tridecan-2-ol

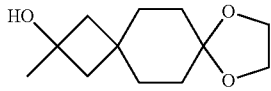

A solution of methylmagnesium bromide in THF (3N, 10.0 mL, 30.0 mmol) was slowly added to 8,11-dioxadispiro[3.2.4⁷.2⁴]tridecan-2-one (2.0 g, 10.2 mmol) in THF (50 mL) at −78° C. under N₂ atmosphere. The resulting mixture was stirred for 1 h at −65° C. and for 2 h at −40° C. The reaction mixture was quenched at −40° C. with an aq. saturated NH₄Cl solution (50 mL), allowed to warm to rt and extracted with EtOAc (3×50 mL). The combined organic layers were dried over Na₂SO₄, filtered, and the solvent was removed in vacuo. The resulting residue was purified using silica gel chromatography (eluting with 30% to 40% EtOAc in PE) to afford 2-methyl-8,11-dioxadispiro[3.2.4⁷.2⁴]tridecan-2-ol (2.1 g, 97%) as a colourless oil.

2-Hydroxy-2-methylspiro[3.5]nonan-7-one

An aq. HCl solution (2N, 20 mL, 40 mmol) was slowly added to 2-methyl-8,11-dioxadispiro[3.2.4⁷.2⁴]tridecan-2-ol (2.1 g, 9.9 mmol) in THF (20 mL) at rt under N₂ atmosphere and stirring was continued for 2 h. The mixture was neutralised to pH 7 with an aq. NaOH solution (2 M) and extracted with EtOAc (3×100 mL). The combined organic layers were washed with brine (1×50 mL), dried over Na₂SO₄ and concentrated in vacuo to afford crude 2-hydroxy-2-methylspiro[3.5]nonan-7-one (1.7 g) as a colourless oil. m/z (ESI+), [M+H]⁺=169.

2-Methylspiro[3.5]nonane-2,7-diol

NaBH₄ (37.8 mg, 1.0 mmol) was slowly added to crude 2-hydroxy-2-methylspiro[3.5]nonan-7-one (84 mg) in MeOH (3 mL) at rt under N₂ atmosphere and the resulting mixture was stirred for 30 min. Then, the solvent was removed in vacuo and the resulting residue was purified using silica gel chromatography (eluting with 50% to 70% EtOAc in PE) to afford 2-methylspiro[3.5]nonane-2,7-diol (78 mg, 92%) as a colorless solid.

2-Hydroxy-2-methylspiro[3.5]nonan-7-yl 4-methylbenzenesulfonate (Int III-3)

TsCl (4.0 g, 21.0 mmol) was slowly added to 2-methylspiro[3.5]nonane-2,7-diol (1.2 g, 7.1 mmol), DMAP (172 mg, 1.4 mmol) and TEA (4.9 mL, 35.2 mmol) in DCM (50 mL) at rt under N₂ atmosphere and the resulting mixture was stirred at 50° C. After 16 h the reaction mixture was allowed to cool to rt, quenched with water (50 mL) and extracted with DCM (2×50 mL). The combined organic layers were washed with brine (20 mL), dried over Na₂SO₄ and concentrated in vacuo. The resulting residue was purified using silica gel chromatography (eluting with 10% to 50% EtOAc in PE) to afford 2-hydroxy-2-methylspiro[3.5]nonan-7-yl 4-methylbenzenesulfonate (1.7 g, 74%) as a pale-yellow oil. ¹H NMR (300 MHz, DMSO-d₆) δ 7.77 (d, 2H), 7.46 (d, 2H), 4.38-4.51 (m, 1H), 2.41 (s, 3H), 1.21-1.81 (m, 12H), 1.18 (s, 3H).

Synthesis of Intermediate Int III-4: tert-Butyl 6-methyl-7-oxo-2-azaspiro[3.5]nonane-2-carboxylate

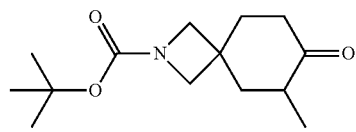 [SMILES: CC1CC2(CCC1=O)CN(C(=O)OC(C)(C)C)C2]

1M LiHMDS in THF (157.0 mL, 157.0 mmol) was added to THF (100 mL) at −78° C., followed by the dropwise addition of a solution of tert-butyl 7-oxo-2-azaspiro[3.5] nonane-2-carboxylate (18.8 g, 78.6 mmol) in THF (300 mL) over a period of 30 min under N₂ atmosphere. The resulting mixture was stirred at −78° C. for 1 h. Subsequently, iodomethane (22.3 g, 157.1 mmol) was added dropwise. The reaction mixture was stirred at −78° C. for another 30 min, followed by stirring at rt for 15 h. The mixture was quenched with ice water (150 mL) and extracted with EtOAc (500 mL×3). The organic layer was dried over Na₂SO₄, filtered and concentrated under reduced pressure. The residue was purified by silica gel chromatography (eluting with 16-20% EtOAc in PE) to afford tert-butyl 6-methyl-7-oxo-2-azaspiro[3.5]nonane-2-carboxylate (9.5 g, 48%) as a pale-yellow solid. ¹H NMR (400 MHz, DMSO-d₆) δ 3.83 (br. s, 2H), 3.53 (br. s, 2H), 2.40-2.49 (m, 2H), 2.06-2.22 (m, 3H), 1.72-1.83 (m, 1H), 1.47-1.57 (m, 1H), 1.39 (s, 9H), 0.88 (d, 3H). MS ESI, m/z=239 [M−tBu+CH₃CN+2H]⁺.

Synthesis of Intermediates Int III-5 & Int III-6:
rac-tert-Butyl (6R,7S)-6-methyl-7-((methylsulfonyl)oxy)-2-azaspiro[3.5]nonane-2-carboxylate & rac-tert-Butyl (6S,7S)-6-methyl-7-((methylsulfonyl)oxy)-2-azaspiro[3.5]nonane-2-carboxylate rac-tert-Butyl (6R,7S)-7-hydroxy-6-methyl-2-azaspiro[3.5]nonane-2-carboxylate & rac-tert-Butyl (6S,7S)-7-hydroxy-6-methyl-2-azaspiro[3.5]nonane-2-carboxylate

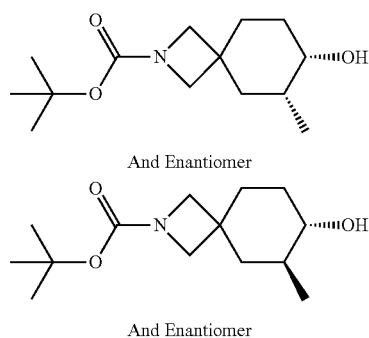

And Enantiomer

To a solution of tert-butyl 6-methyl-7-oxo-2-azaspiro[3.5]nonane-2-carboxylate (Int III-4) (19.5 g, 77.0 mmol) in MeOH (300 mL) at 0° C. was added NaBH₄ (5.8 g, 153.9 mmol) portionwise over a period of 40 min under N₂ atmosphere. The resulting mixture was warmed to rt for 5 h. The reaction was quenched with brine (300 mL) and extracted with EtOAc (500 mL×3). The combined organic layers were dried over Na₂SO₄, filtered and evaporated under reduced pressure. The residue was purified twice by silica gel chromatography ((1.): eluting with 25-30% EtOAc in PE; (2.): eluting with 25% EtOAc in PE) to afford rac-tert-butyl (6R,7S)-7-hydroxy-6-methyl-2-azaspiro[3.5]nonane-2-carboxylate (13.6 g, 69%) and rac-tert-butyl (6S,7S)-7-hydroxy-6-methyl-2-azaspiro[3.5]nonane-2-carboxylate (1.8 g, 9%) as colorless solids. (6R,7S)—Isomer: MS ESI, m/z=200 [M−tBu+2H]⁺; (6S,7S)—Isomer: MS ESI, m/z=200 [M−tBu+2H]⁺.

rac-tert-Butyl (6R,7S)-6-methyl-7-((methylsulfonyl)oxy)-2-azaspiro[3.5]nonane-2-carboxylate (Int III-5)

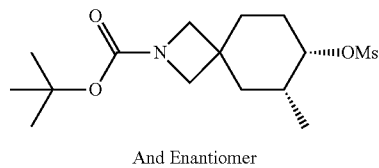 [SMILES: C[C@@H]1CC2(CC[C@@H]1OS(C)(=O)=O)CN(C(=O)OC(C)(C)C)C2]

And Enantiomer

MsCl (7.7 mL, 98.7 mmol) was added dropwise to a solution of rac-tert-butyl (6R,7S)-7-hydroxy-6-methyl-2-azaspiro[3.5]nonane-2-carboxylate (4.2 g, 16.5 mmol) and TEA (22.9 mL, 165 mmol) in DCM (20 mL) at rt over 15 min. The resulting mixture was stirred at rt for 12 h. The mixture was washed with water (25 mL×2). The organic layer was dried over Na₂SO₄, filtered and concentrated. The residue was purified by silica gel chromatography (eluting with 50 to 100% EtOAc in PE) to afford rac-tert-butyl (6R,7S)-6-methyl-7-((methylsulfonyl)oxy)-2-azaspiro[3.5]nonane-2-carboxylate (3.5 g, 64%) as a yellow oil. ¹H NMR (300 MHz, DMSO-d₆) δ 4.64-4.68 (m, 1H), 3.41-3.61 (m, 4H), 3.16 (s, 3H), 1.94-2.02 (m, 1H), 1.52-1.82 (m, 5H), 1.38 (s, 10H), 0.88-0.97 (m, 3H).

rac-tert-Butyl (6S,7S)-6-methyl-7-((methylsulfonyl)oxy)-2-azaspiro[3.5]nonane-2-carboxylate (Int III-6)

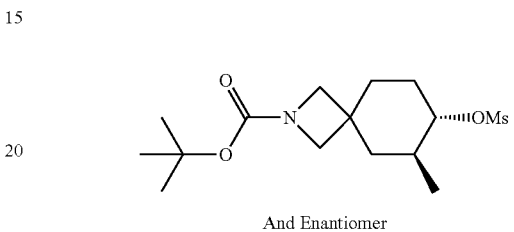

And Enantiomer

MsCl (0.55 mL, 7.1 mmol) was added dropwise to a solution of rac-tert-butyl (6S,7S)-7-hydroxy-6-methyl-2-azaspiro[3.5]nonane-2-carboxylate (1.8 g, 7.1 mmol) and TEA (983 μL, 7.1 mmol) in DCM (8 mL) at 0° C. under N₂ atmosphere. The resulting solution was stirred at rt for 3 h. The reaction mixture was quenched with water (10 mL) and extracted with DCM (15 mL×3). The combined organic layers were dried over Na₂SO₄, filtered, and concentrated under reduced pressure. The residue was purified by silica gel chromatography (eluting with 0-60% EtOAc in PE) to afford rac-tert-butyl (6S,7S)-6-methyl-7-((methylsulfonyl)oxy)-2-azaspiro[3.5]nonane-2-carboxylate (1.4 g, 60%) as a yellow solid. MS ESI, m/z=667 [2M+H]⁺.

Synthesis of Intermediate Int III-7:
rac-(1R,3R)-3-Hydroxycyclohexyl 4-methylbenzenesulfonate

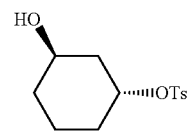

And Enantiomer

TsCl (8.2 g, 42.0 mmol) was added to TEA (12.0 mL, 86.1 mmol), DMAP (526 mg, 4.3 mmol) and rac-(1R,3R)-cyclohexane-1,3-diol (5 mg, 43.0 mmol) in DCM (300 mL) at 0° C. and the resulting mixture was stirred at rt. After 2 h the reaction mixture was quenched with water (200 mL) and extracted with DCM (2×300 mL). The combined organic layers were washed with brine (1×200 mL), dried over Na₂SO₄ and concentrated in vacuo. The resulting residue was purified using silica gel chromatography (eluting with 0% to 40% EtOAc in DCM) to afford rac-(1R,3R)-3-hydroxycyclohexyl 4-methylbenzenesulfonate (5.0 g, 43%) as a pale-yellow oil. ¹H NMR (300 MHz, DMSO-d₆) δ 7.77

(d, 2H), 7.47 (d, 2H), 4.68-4.80 (m, 1H), 4.59 (br. s, 1H), 3.70-3.81 (m, 1H), 2.42 (s, 3H), 1.20-1.73 (m, 8H).

Synthesis of Intermediate Int III-8: (1s,4s)-4-((tert-Butoxycarbonyl)amino)cyclohexyl 4-methylbenzenesulfonate

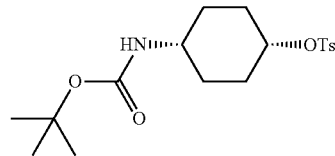 [SMILES: Cc1ccc(S(=O)(=O)O[C@H]2CC[C@@H](NC(=O)OC(C)(C)C)CC2)cc1]

TsCl (33.2 g, 174.2 mmol) was added to a solution of tert-butyl ((1s,4s)-4-hydroxycyclohexyl)carbamate (15.0 g, 69.7 mmol), DMAP (851 mg, 7.0 mmol) and TEA (29.1 mL, 209.0 mmol) in DCM (300 mL) over a period of 5 min at rt under $N_2$ atmosphere. The resulting mixture was stirred at 50° C. for 20 h. The reaction mixture was allowed to cool to rt, diluted with DCM (500 mL), washed with brine (150 mL), dried over $Na_2SO_4$ and concentrated under reduced pressure. The residue was purified by silica gel chromatography (eluting with 10-50% EtOAc in PE) to afford (1s,4s)-4-((tert-butoxycarbonyl)amino)cyclohexyl 4-methylbenzenesulfonate (15.5 g, 60%) as a colorless solid.
$^1$H NMR (300 MHz, DMSO-$d_6$) δ 7.70-7.85 (m, 2H), 7.41-7.54 (m, 2H), 6.80 (d, 1H), 4.58 (s, 1H), 3.14-3.34 (m, 1H), 2.42 (s, 3H), 1.61-1.79 (m, 2H), 1.32-1.60 (m, 15H).

Synthesis of Intermediate Int III-9: 4-((tert-Butoxycarbonyl)amino)cyclohexyl 4-methylbenzenesulfonate

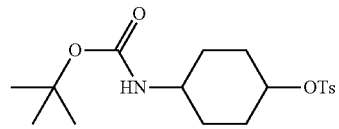 [SMILES: Cc1ccc(S(=O)(=O)OC2CCC(NC(=O)OC(C)(C)C)CC2)cc1]

TsCl (21.3 g, 111.5 mmol) was added dropwise to a solution of tert-butyl (4-hydroxycyclohexyl)carbamate (cis/trans ratio 1:5) (20.0 g, 92.9 mmol) and TEA (25.9 mL, 185.8 mmol) in DCM (400 mL) over a period of 5 min at rt under $N_2$ atmosphere. The resulting mixture was stirred at rt for 20 h. The reaction mixture was diluted with DCM (400 mL), washed with water (150 mL×2) and concentrated under reduced pressure. The residue was purified by silica gel chromatography (eluting with 10-25% EtOAc in PE) to afford 4-((tert-butoxycarbonyl)amino)cyclohexyl 4-methylbenzenesulfonate (cis/trans ratio 1:5) (26.0 g, 76%) as a colorless solid. $^1$H NMR (300 MHz, DMSO-$d_6$) (1:5 mixture of cis/trans-isomers) δ 7.75-7.85 (m, 2H), 7.47 (d, 2H), 6.81/6.71 (d, 1H) (isomers), 4.54-4.62/4.27-4.42 (m, 1H) (isomers), 3.10-3.28 (m, 1H), 2.42 (s, 3H), 1.62-1.83 (m, 4H), 1.39-1.58 (m, 2H), 1.30-1.38 (m, 9H) (isomers), 1.09-1.27 (m, 2H). MS ESI, m/z=270 [M−Boc+2H]$^+$.

Synthesis of Intermediate Int III-10: 4-((tert-Butoxycarbonyl)(methyl)amino)cyclohexyl 4-methylbenzenesulfonate

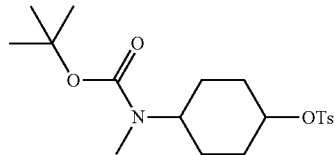 [SMILES: Cc1ccc(S(=O)(=O)OC2CCC(N(C)C(=O)OC(C)(C)C)CC2)cc1]

Iodomethane (3.8 g, 27.1 mmol) was added dropwise to a suspension of NaH (60 wt. %) (812 mg, 20.3 mmol) and (4-((tert-butoxycarbonyl)amino)cyclohexyl 4-methylbenzenesulfonate (cis/trans ratio 1:5) (Int III-9) (5.0 g, 13.5 mmol) in DMF (50 mL) at rt. The resulting mixture was stirred at 60° C. for 4 h. The mixture was allowed to cool to rt, the reaction was quenched with water (100 mL) and extracted with EtOAc (100 mL×2). The combined organic layers were washed with brine (100 mL×4), dried over $Na_2SO_4$, filtered and concentrated under reduced pressure to give a pale-yellow solid. The solid was purified by silica gel chromatography (eluting with 10-25% EtOAc in PE) to afford 4-((tert-butoxycarbonyl)(methyl)amino)cyclohexyl 4-methylbenzenesulfonate (cis/trans ratio 1:5) (2.5 g, 48%) as a colorless solid. $^1$H NMR (300 MHz, DMSO-$d_6$) δ 7.80 (d, 2H), 7.48 (d, 2H), 4.32-4.45 (m, 1H), 3.57-3.89 (m, 1H), 2.60 (s, 3H), 2.43 (s, 3H), 1.67-1.91 (m, 2H), 1.42-1.67 (m, 6H), 1.38 (s, 9H). MS ESI, m/z=284 [M−Boc+2H]$^+$.

Synthesis of Intermediates Int III-11 and Int III-12: rac-(7R,8S)-7-Methyl-1,4-dioxaspiro[4.5]decan-8-ol & rac-(7S,8S)-7-Methyl-1,4-dioxaspiro[4.5]decan-8-ol

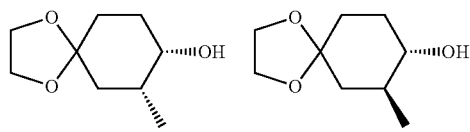

and Enantiomer        and Enantiomer

To a solution of 7-methyl-1,4-dioxaspiro[4.5]decan-8-one (50.0 g, 293.8 mmol) in MeOH (500 mL) at 0° C. under $N_2$ atmosphere was added NaBH$_4$ (22.3 g, 587.5 mmol) portionwise over a period of 20 min. The resulting mixture was stirred at rt for 1 h and then concentrated under reduced pressure. The residue was purified directly by silica gel chromatography (eluting with 16% EtOAc in PE) to afford rac-(7R,8S)-7-methyl-1,4-dioxaspiro[4.5]decan-8-ol (3.18 g, 6%) and rac-(7S,8S)-7-methyl-1,4-dioxaspiro[4.5]decan-8-ol (19.00 g, 38%). rac-(7R,8S)—Isomers: $^1$H NMR (300 MHz, DMSO-$d_6$) δ 4.27 (d, 1H), 3.75-3.9 (m, 4H), 3.51-3.6 (m, 1H), 1.44-1.78 (m, 5H), 1.25-1.44 (m, 2H), 0.86 (d, 3H). rac-(7S,8S)—Isomers: $^1$H NMR (300 MHz, DMSO-$d_6$) δ 4.45 (d, 1H), 3.75-3.89 (m, 4H), 2.89-3.05 (m, 1H), 1.27-1.77 (m, 6H), 1.19 (t, 1H), 0.90 (d, 3H).

Synthesis of Intermediate Int III-13: rac-(7R,8S)-7-Methyl-1,4-dioxaspiro[4.5]decan-8-yl methanesulfonate

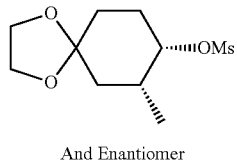 [SMILES: C[C@@H]1CC2(CC[C@@H]1OS(C)(=O)=O)OCCO2]

And Enantiomer

MsCl (1.4 mL, 17.4 mmol) was added dropwise to a solution of rac-(7R,8S)-7-methyl-1,4-dioxaspiro[4.5]decan-8-ol (Int III-11) (2.5 g, 14.5 mmol) and TEA (6.1 mL, 43.6 mmol) in DCM (50 mL) over a period of 30 min at 0° C. under $N_2$ atmosphere. The resulting mixture was stirred at rt for 2 h.

The reaction mixture was quenched with brine (100 mL) and extracted with DCM (100 mL×3). The combined organic layers were dried over $Na_2SO_4$, filtered, and concentrated under reduced pressure. The residue was purified by silica gel chromatography (eluting with 0-20% EtOAc in PE) to afford rac-(7R,8S)-7-Methyl-1,4-dioxaspiro[4.5]decan-8-yl methanesulfonate (2.1 g, 58%) as a brown oil. $^1$H NMR (300 MHz, DMSO-$d_6$) δ 4.71 (br. s, 1H), 3.80-3.92 (m, 4H), 3.17 (s, 3H), 2.02-2.13 (m, 1H), 1.85-2.02 (m, 1H), 1.32-1.83 (m, 5H), 0.94 (d, 3H).

Synthesis of Intermediate Int IV-1: (1s,4s)-4-(6-Cyclopropoxy-5-iodo-2H-indazol-2-yl)cyclohexan-1-ol (1r,4r)-4-Hydroxycyclohexyl 4-methylbenzenesulfonate

To a solution of TsCl (8.2 g, 43.0 mmol), TEA (8.7 g, 86.1 mmol), and DMAP (591 mg, 4.8 mmol) in DCM (100 mL) was added (1r,4r)-cyclohexane-1,4-diol (5.0 g, 43.0 mmol). The resulting mixture was stirred at rt for 14 h. The reaction mixture was concentrated under reduced pressure and the residue was purified by silica gel chromatography (eluting with 20-50% EtOAc in PE) to afford (1R,4R)-4-hydroxycyclohexyl 4-methylbenzenesulfonate (2.1 g, 18%) as a colorless solid. $^1$H NMR (300 MHz, DMSO-$d_6$) δ 7.78 (d, 2H), 7.47 (d, 2H), 4.40-4.53 (m, 1H), 3.39-3.54 (m, 1H), 2.42 (s, 3H), 1.60-1.83 (m, 4H), 1.32-1.60 (m, 2H), 1.13-1.32 (m, 2H).

(1s,4s)-4-(6-Cyclopropoxy-5-iodo-2H-indazol-2-yl)cyclohexan-1-ol (Int IV-1)

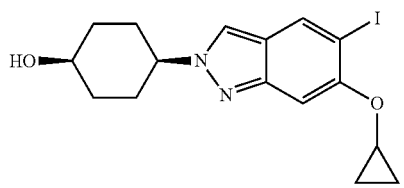 [SMILES: O[C@H]1CC[C@@H](n2cc3cc(I)c(OC4CC4)cc3n2)CC1]

To a solution of 6-cyclopropoxy-5-iodo-1H-indazole (Int I-3) (300 mg, 1.0 mmol) and KOH (224 mg, 4.0 mmol) in DMF (30 mL) at rt was added (1r,4r)-4-hydroxycyclohexyl 4-methylbenzenesulfonate (946 mg, 3.5 mmol). The resulting mixture was stirred at 80° C. for 14 h. The mixture was cooled to rt, diluted with EtOAc (50 mL) and washed with water (50 mL). The organic layer was dried over $Na_2SO_4$, filtered, and concentrated under reduced pressure. The residue was purified by C18-flash chromatography (eluting with 0-100% MeCN in water (0.1% FA)) to afford (1s,4s)-4-(6-cyclopropoxy-5-iodo-2H-indazol-2-yl)cyclohexan-1-ol (115 mg, 25%) as a yellow solid. MS ESI, m/z=399 [M+H]$^+$.

Synthesis of Intermediate Int IV-2: (1r,4r)-4-(6-Cyclopropoxy-5-iodo-2H-indazol-2-yl)cyclohexan-1-ol (1s,4s)-4-Hydroxycyclohexyl 4-methylbenzenesulfonate

To a solution of (1s,4s)-cyclohexane-1,4-diol (3.0 g, 25.8 mmol), TEA (5.2 g, 51.7 mmol) and DMAP (316 mg, 2.6 mmol) in DCM (50 mL) at 0° C. was added TsCl (5.2 g, 27.1 mmol). The resulting mixture was stirred at rt for 1 h. The reaction mixture was diluted with DCM (50 mL) and washed sequentially with 0.1N HCl (50 mL) and water (50 mL). The organic layer was dried over $Na_2SO_4$, filtered and concentrated under reduced pressure. The residue was purified by silica gel chromatography (eluting with 0-60% EtOAc in PE) to afford (1s,4s)-4-hydroxycyclohexyl 4-methylbenzenesulfonate (2.2 g, 32%) as a colorless liquid. $^1$H NMR (300 MHz, DMSO-$d_6$) δ 7.78 (d, 2H), 7.47 (d, 2H), 4.47-4.55 (m, 1H), 3.43-3.53 (m, 1H), 2.42 (s, 3H), 1.60-1.78 (m, 2H), 1.35-1.60 (m, 6H).

(1r,4r)-4-(6-Cyclopropoxy-5-iodo-2H-indazol-2-yl)cyclohexan-1-ol (Int IV-2)

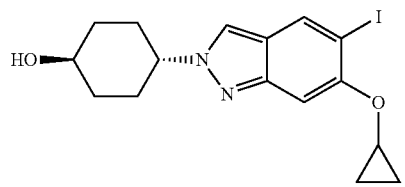 [SMILES: O[C@H]1CC[C@H](n2cc3cc(I)c(OC4CC4)cc3n2)CC1]

To a solution of (1s,4s)-4-hydroxycyclohexyl 4-methylbenzenesulfonate (1.3 g, 4.7 mmol) and 6-cyclopropoxy-5-iodo-1H-indazole (Int I-3) (350 mg, 1.2 mmol) in DMF (20 mL) was added KOH (196 mg, 3.5 mmol). The resulting mixture was stirred at 70° C. for 13 h. The reaction mixture was cooled to rt, diluted with EtOAc (50 mL) and washed with water (50 mL). The organic layer was dried over $Na_2SO_4$, filtered and concentrated under reduced pressure. The residue was purified by C18-flash chromatography (eluting with 0-100% MeCN in water (0.1% FA)) to afford (1r,4r)-4-(6-cyclopropoxy-5-iodo-2H-indazol-2-yl)cyclohexan-1-ol (110 mg, 24%) as a yellow solid. $^1$H NMR (300 MHz, DMSO-$d_6$) δ 8.23 (s, 1H), 8.16 (s, 1H), 7.30 (s, 1H), 4.66 (br. s, 1H), 4.32-4.47 (m, 1H), 3.87-3.99 (m, 1H), 3.43-3.59 (m, 1H), 1.82-2.12 (m, 6H), 1.35-1.47 (m, 2H), 0.82-0.91 (m, 2H), 0.66-0.75 (m, 2H). MS ESI, m/z=399 [M+H]+.

Synthesis of Intermediate Int IV-3: rac-5-Bromo-6-methoxy-2-(7R,8R)-7-methyl-1,4-dioxaspiro[4.5]decan-8-yl)-2H-indazole

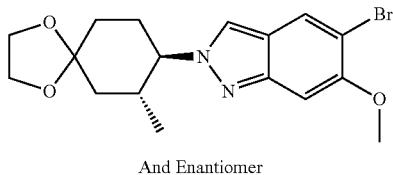 [SMILES: COc1cc2nn([C@@H]3CCC4(C[C@H]3C)OCCO4)cc2cc1Br]

And Enantiomer

To a solution of 5-bromo-6-methoxy-1H-indazole (1.5 g, 6.6 mmol) and KOH (1.5 g, 26.4 mmol) in DMF (40 mL) at rt was added rac-(7R,8S)-7-methyl-1,4-dioxaspiro[4.5]decan-8-yl methanesulfonate (Int III-13) (2.0 g, 8.0 mmol). The resulting mixture was stirred overnight at 80° C. The reaction mixture was diluted with EtOAc (300 mL) and washed with brine (150 mL×4). The organic layer was dried over Na₂SO₄, filtered and concentrated under reduced pressure. The residue was purified by C18-flash chromatography (eluting with 0-80% MeCN in water (0.1% FA)) to afford rac-5-bromo-6-methoxy-2-((7R,8R)-7-methyl-1,4-dioxaspiro[4.5]decan-8-yl)-2H-indazole (600 mg, 22%) as a brown solid. MS ESI, m/z=381/383 [M+H]+.

Synthesis of Intermediates Int IV-4 & Int IV-5: 5-Bromo-6-methoxy-2-(7R,8R)-7-methyl-1,4-dioxaspiro[4.5]decan-8-O-2H-indazole & 5-Bromo-6-methoxy-2-(7S,8S)-7-methyl-1,4-dioxaspiro[4.5]decan-8-O-2H-indazole

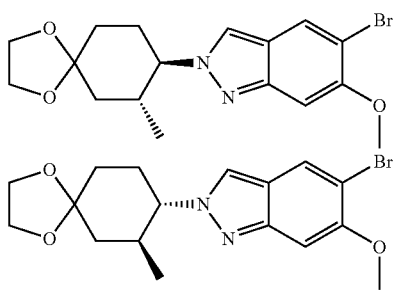

rac-5-Bromo-6-methoxy-2-((7R,8R)-7-methyl-1,4-dioxaspiro[4.5]decan-8-yl)-2H-indazole (Int IV-3) (7.3 g, 19.2 mmol) was separated by prep. SFC (Chiralpak® IG, 5 μm 50×250 mm; isocratic with 50% MeOH (0.1% 2N NH₃-MeOH) in CO₂ (35° C., 100 bar); 200 mL/min) to afford 5-bromo-6-methoxy-2-((7R,8R)-7-methyl-1,4-dioxaspiro[4.5]decan-8-yl)-2H-indazole (3.1 g, 43%, 100% ee) and 5-bromo-6-methoxy-2-((7S,8S)-7-methyl-1,4-dioxaspiro[4.5]decan-8-yl)-2H-indazole (3.0 g, 41%, 100% ee), both as grey solids. The ¹H NMR and MS obtained for both products were identical. ¹H NMR (300 MHz, DMSO-d₆) δ 8.25 (d, 1H), 7.96 (s, 1H), 7.12 (s, 1H), 4.13 (td, 1H), 3.87-3.99 (m, 4H), 3.87 (s, 3H), 2.26-2.43 (m, 1H), 2.19 (td, 1H), 1.75-1.99 (m, 3H), 1.68 (td, 1H), 1.46 (t, 1H), 0.52 (d, 3H). MS ESI, m/z=381/383 [M+H]+.

Synthesis of Intermediates Int IV-6 & Int IV-7: (5s, 8s)-8-(5-Bromo-6-methoxy-2H-indazol-2-yl)-2-methyl-2-azaspiro[4.5]decan-3-one & (5r,8r)-8-(5-Bromo-6-methoxy-2H-indazol-2-yl)-2-methyl-2-azaspiro[4.5]decan-3-one 2-Methyl-3-oxo-2-azaspiro[4.5]decan-8-yl methanesulfonate

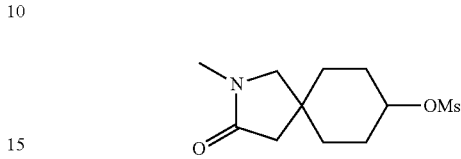

MsCl (2.0 g, 17.6 mmol) was added dropwise to a solution of 8-hydroxy-2-methyl-2-azaspiro[4.5]decan-3-one (1.9 g, 10.4 mmol) and DIPEA (4.7 g, 36.3 mmol) in DCM (25 mL) at 0° C. The resulting mixture was warmed to rt and stirred for 48 h. The reaction mixture was quenched with ice cold aq. half-saturated NaHCO₃ (30 mL) and extracted with DCM (50 mL×2). The combined organic layers were dried over Na₂SO₄, filtered and concentrated under reduced pressure. The residue was purified by silica gel chromatography (eluting with DCM) to give as 2-methyl-3-oxo-2-azaspiro[4.5]decan-8-yl methanesulfonate (3.1 g, 96%) as an orange oil.

(5s,8s)-8-(5-Bromo-6-methoxy-2H-indazol-2-yl)-2-methyl-2-azaspiro[4.5]decan-3-one (Int IV-6) & (5r,8r)-8-(5-Bromo-6-methoxy-2H-indazol-2-yl)-2-methyl-2-azaspiro[4.5]decan-3-one (Int IV-7)

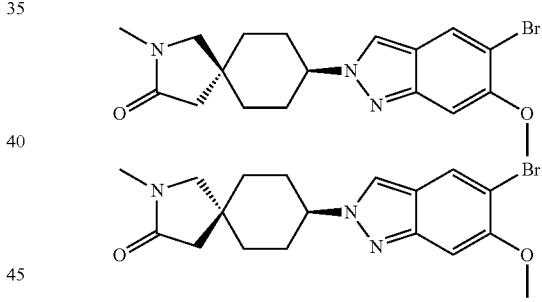

To a solution of 5-bromo-6-methoxy-1H-indazole (775 mg, 3.4 mmol) and KOH (434 mg, 7.0 mmol) in THF (15 mL) at 75° C. was added 2-methyl-3-oxo-2-azaspiro[4.5]decan-8-yl methanesulfonate (1.3 g, 5.0 mmol). The resulting mixture was stirred at 75° C. overnight. The reaction was cooled to rt, quenched with water, extracted with DCM (40 mL×4), dried and concentrated under reduced pressure. The residue was loaded onto a 10 g Isolute®SCX2 exchange cartridge. The cartridge was washed with DCM/MeOH (1:1) (150 mL) to remove the unwanted 1H-indazole isomer and then eluted with 100 mL 2N NH₃-MeOH solution/DCM (1:1) to give the crude product after evaporation of the solvent. The brown residue was further purified by silica gel chromatography (eluting with EtOAc and then with 0-2% 2N NH₃-MeOH solution in DCM) to give 8-(5-bromo-6-methoxy-2H-indazol-2-yl)-2-methyl-2-azaspiro[4.5]decan-3-one. This material was further separated by chiral prep. SFC (Lux® Cellulose-3, 5 μm 30 mm×250 mm; isocratic with 20% EtOH (20 mM diethylamine) in CO₂ (40° C., 130 bar); 120 mL/min) to give as first eluting isomer (5s,8s)-8-

(5-bromo-6-methoxy-2H-indazol-2-yl)-2-methyl-2-azaspiro [4.5]decan-3-one (153 mg, 3%, 100% ee) and as second eluting isomer (5r,8r)-8-(5-bromo-6-methoxy-2H-indazol-2-yl)-2-methyl-2-azaspiro[4.5]decan-3-one (153 mg, 3%, 99.2% ee). (5s,8s)—Isomer: $^1$H NMR (500 MHz, CDCl$_3$) δ 7.83 (s, 1H), 7.80 (s, 1H), 7.03 (s, 1H), 4.26-4.36 (m, 1H), 3.91 (s, 3H), 3.34 (s, 2H), 2.85 (s, 3H), 2.28 (s, 2H), 2.12-2.20 (m, 2H), 2.01-2.12 (m, 2H), 1.87-1.96 (m, 2H), 1.57-1.68 (m, 2H). MS ESI, m/z=392/394 [M+H]$^+$. (5r,8r)—Isomer: $^1$H NMR (500 MHz, CDCl$_3$) δ 7.85 (s, 1H), 7.82 (s, 1H), 7.03 (s, 1H), 4.29-4.41 (m, 1H), 3.92 (s, 3H), 3.18 (s, 2H), 2.85 (s, 3H), 2.41 (s, 2H), 2.18-2.26 (m, 2H), 1.96-2.09 (m, 2H), 1.85-1.95 (m, 2H), 1.57-1.69 (m, 2H). MS ESI, m/z=392/394 [M+H]$^+$.

Synthesis of Intermediate Int IV-8: tert-Butyl ((1r, 4r)-4-(5-bromo-6-methoxy-2H-indazol-2-yl)cyclohexyl)carbamate

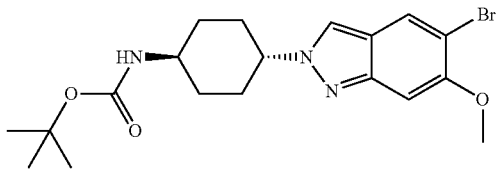 [SMILES: COc1cc2nn([C@H]3CC[C@H](NC(=O)OC(C)(C)C)CC3)cc2cc1Br]

To a solution of tert-butyl ((1r,4r)-4-aminocyclohexyl) carbamate (10.5 g, 49.0 mmol) in i-PrOH (200 mL) at rt was added 5-bromo-4-methoxy-2-nitrobenzaldehyde (Int I-1) (12.7 g, 49.0 mmol) under N$_2$ atmosphere. The resulting mixture was stirred at 80° C. for 1 h, followed by the addition of tri-n-butylphosphine (29.7 g, 147.0 mmol). The reaction mixture was stirred at 80° C. for 13 h. The mixture was cooled to rt and concentrated under reduced pressure. The residue was purified by silica gel chromatography (eluting with 9-50% EtOAc in PE) to afford tert-butyl ((1r,4r)-4-(5-bromo-6-methoxy-2H-indazol-2-yl)cyclohexyl)carbamate (14.2 g, 68%) as a colorless solid. MS ESI, m/z=424/426 [M+H]$^+$.

Synthesis of Intermediates Int V-1 & Int V-2: N-(Imidazo[1,2-b]pyridazin-3-yl)-6-methoxy-2-((1S, 2S)-2-methyl-4-oxocyclohexyl)-2H-indazole-5-carboxamide & N-(Imidazo[1,2-b]pyridazin-3-O-6-methoxy-2-((1R,2R)-2-methyl-4-oxocyclohexyl)-2H-indazole-5-carboxamide rac-(3R,4R)-4-(5-Bromo-6-methoxy-2H-indazol-2-yl)-3-methylcyclohexan-1-one

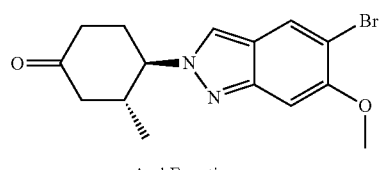

And Enantiomer rac-5-Bromo-6-methoxy-2-((7R,8R)-7-methyl-1,4-dioxaspiro[4.5]decan-8-yl)-2H-indazole (Int IV-3) (400 mg, 1.1 mmol) was added to a 1.2N HCl solution in THF (5 mL)/water (5 mL) at rt under N$_2$ atmosphere. The resulting mixture was stirred at rt overnight. The reaction mixture was purified by C18-flash chromatography (eluting with 0-60% MeCN in water (0.05% TFA)) to afford rac-(3R,4R)-4-(5-bromo-6-methoxy-2H-indazol-2-yl)-3-methylcyclohexan-1-one (330 mg, 93%) as a yellow solid. MS ESI, m/z=337/339 [M+H]$^+$.

N-(Imidazo[1,2-b]pyridazin-3-yl)-6-methoxy-2-(1S, 2S)-2-methyl-4-oxocyclohexyl)-2H-indazole-5-carboxamide (Int V-1) & N-(Imidazo[1,2-b]pyridazin-3-yl)-6-methoxy-2-(1R,2R)-2-methyl-4-oxocyclohexyl)-2H-indazole-5-carboxamide (Int V-2)

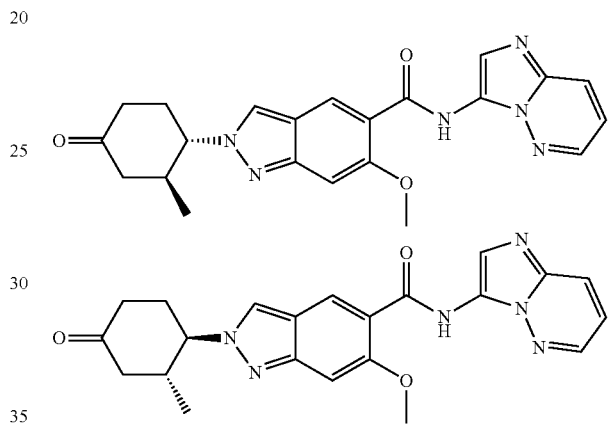

A suspension of rac-(3R,4R)-4-(5-bromo-6-methoxy-2H-indazol-2-yl)-3-methylcyclohexan-1-one (330 mg, 1.0 mmol), imidazo[1,2-b]pyridazin-3-amine (201 mg, 1.5 mmol), Pd(OAc)$_2$ (22 mg, 0.1 mmol), dppp (81 mg, 0.2 mmol) and TEA (409 µL, 2.9 mmol) in MeCN (15 mL) was stirred under CO atmosphere at 15 atm and 90° C. for 15 h. The mixture was cooled to rt, concentrated and purified by C18-flash chromatography (eluting with 0-80% MeCN in water (0.1% NH$_4$OH)) to afford rac-N-(imidazo[1,2-b] pyridazin-3-yl)-6-methoxy-2-((1R,2R)-2-methyl-4-oxocyclohexyl)-2H-indazole-5-carboxamide as a yellow solid. This material was separated by prep. chiral SFC (Chiralpak® AS-H, 5 µm 20 mm×250 mm; isocratic with 45% i-PrOH (2 mM NH$_3$-MeOH) in CO$_2$ (40° C., 70 bar); 40 mL/min) to afford as first eluting isomer N-(imidazo[1,2-b] pyridazin-3-yl)-6-methoxy-2-((1S,2S)-2-methyl-4-oxocyclohexyl)-2H-indazole-5-carboxamide (220 mg, 34%, 71.2% ee) and as second eluting isomer N-(imidazo[1,2-b] pyridazin-3-yl)-6-methoxy-2-((1R,2R)-2-methyl-4-oxocyclohexyl)-2H-indazole-5-carboxamide (200 mg, 31%, 83.3% ee), both as a yellow solids. The $^1$H NMR and MS obtained for both products were identical. $^1$H NMR (400 MHz, DMSO-d$_6$) δ 11.05 (s, 1H), 8.67 (s, 1H), 8.65 (dd, 1H), 8.60 (s, 1H), 8.16 (dd, 1H), 8.06 (s, 1H), 7.30 (s, 1H), 7.23 (dd, 1H), 4.61-4.76 (m, 1H), 4.13 (s, 3H), 2.64-2.79 (m, 1H), 2.52-2.60 (m, 1H), 2.23-2.49 (m, 5H), 0.65 (d, 3H). MS ESI, m/z=419 [M+H]$^+$.

Synthesis of Intermediate Int V-3: N-(imidazo[1,2-b]pyridazin-3-yl)-6-methoxy-2-((1r,4r)-4-(methylamino)cyclohexyl)-2H-indazole-5-carboxamide tert-Butyl ((1r,4r)-4-(5-bromo-6-methoxy-2H-indazol-2-yl)cyclohexyl)(methyl)carbamate

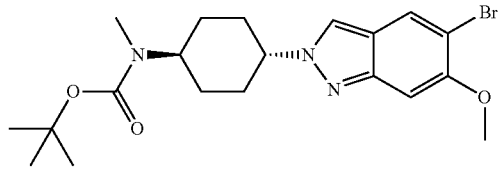 [SMILES: COc1cc2nn([C@H]3CC[C@H](N(C)C(=O)OC(C)(C)C)CC3)cc2cc1Br]

To a solution of tert-butyl ((1r,4r)-4-(5-bromo-6-methoxy-2H-indazol-2-yl)cyclohexyl)carbamate (Int IV-8) (990 mg, 2.3 mmol) in DMF (10 mL) at 0° C. was added NaH (60 wt. %) (1.1 g, 28.0 mmol). The resulting mixture was stirred at 0° C. for 30 min followed by the addition of iodomethane (662 mg, 4.7 mmol). The reaction mixture was stirred at rt for 15 h, then quenched with water (10 mL) and purified directly by C18-flash chromatography (eluting with 0-100% MeCN in water (0.05% NH$_4$OH)) to afford tert-butyl ((1r,4r)-4-(5-bromo-6-methoxy-2H-indazol-2-yl)cyclohexyl)(methyl)carbamate (600 mg, 59%) as a black solid, which was used without further purification. MS ESI, m/z=438/440 [M+H]$^+$.

tert-Butyl ((1r,4r)-4-(5-(imidazo[1,2-b]pyridazin-3-ylcarbamoyl)-6-methoxy-2H-indazol-2-yl)cyclohexyl)(methyl)carbamate

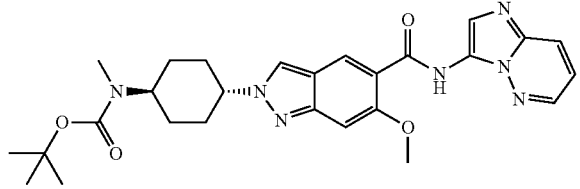 [SMILES: COc1cc2nn([C@H]3CC[C@H](N(C)C(=O)OC(C)(C)C)CC3)cc2cc1C(=O)Nc1cnc2cccnn12]

A suspension of tert-butyl ((1r,4r)-4-(5-bromo-6-methoxy-2H-indazol-2-yl)cyclohexyl) (methyl)carbamate (380 mg, 0.9 mmol), imidazo[1,2-b]pyridazin-3-amine (134 mg, 1.0 mmol), Pd(OAc)$_2$ (44 mg, 0.2 mmol), dppp (165 mg, 0.4 mmol) and TEA (604 μL, 4.3 mmol) in MeCN (20 mL) was stirred under CO atmosphere at 15 atm and 100° C. for 15 h. Then, the mixture was cooled to rt and concentrated under reduced pressure. The residue was purified by C18-flash chromatography (eluting with 0-100% acetonitrile in water (0.05% NH$_4$OH)) to afford tert-butyl ((1r,4r)-4-(5-(imidazo[1,2-b]pyridazin-3-ylcarbamoyl)-6-methoxy-2H-indazol-2-yl)cyclohexyl)(methyl)carbamate (430 mg, 95%) as a red solid. $^1$H NMR (300 MHz, DMSO-d$_6$) δ 11.04 (s, 1H), 8.63 (d, 1H), 8.60 (s, 1H), 8.56 (s, 1H), 8.14 (dd, 1H), 8.05 (s, 1H), 7.26 (s, 1H), 7.21 (dd, 1H), 4.34-4.61 (m, 1H), 4.11 (s, 3H), 3.79-4.04 (m, 1H), 2.73 (s, 3H), 2.12-2.33 (m, 2H), 1.92-2.12 (m, 2H), 1.62-1.92 (m, 4H), 1.42 (s, 9H). MS ESI, m/z=520 [M+H]$^+$.

N-(imidazo[1,2-b]pyridazin-3-yl)-6-methoxy-2-((1r,4r)-4-(methylamino)cyclohexyl)-2H-indazole-5-carboxamide (Int V-3)

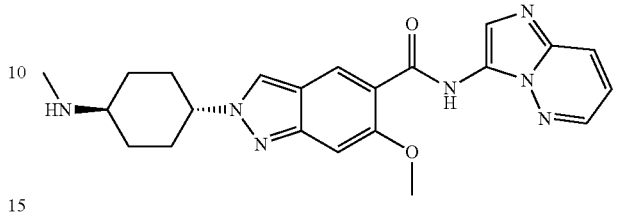

tert-Butyl ((1r,4r)-4-(5-(imidazo[1,2-b]pyridazin-3-ylcarbamoyl)-6-methoxy-2H-indazol-2-yl) cyclohexyl)(methyl)carbamate (430 mg, 0.8 mmol) was added into 2N HCl in dioxane (12 mL, 24.0 mmol) at rt under N$_2$ atmosphere. The resulting mixture was stirred at rt for 2 h and then concentrated under reduced pressure to afford the crude HCl salt of N-(imidazo[1,2-b]pyridazin-3-yl)-6-methoxy-2-((1r,4r)-4-(methylamino)cyclohexyl)-2H-indazole-5-carboxamide (300 mg), which was used directly without further purification. $^1$H NMR (300 MHz, DMSO-d$_6$) δ 11.26 (s, 1H), 8.97 (dd, 1H), 8.63 (s, 1H), 8.60 (s, 1H), 8.43 (dd, 1H), 8.37 (s, 1H), 7.67 (dd, 1H), 7.28 (s, 1H), 4.48-4.64 (m, 1H), 4.13 (s, 3H), 3.01-3.22 (m, 1H), 2.54-2.59 (m, 3H), 2.12-2.29 (m, 4H), 1.85-2.12 (m, 2H), 1.47-1.73 (m, 2H). MS ESI, m/z=420 [M+H]$^+$.

Synthesis of Intermediate Int V-4: 6-Methoxy-2-((1r,4r)-4-(methylamino)cyclohexyl)-N-(pyrazolo[1,5-a]pyrimidin-3-yl)-2H-indazole-5-carboxamide tert-Butyl ((1r,4r)-4-(5-bromo-6-methoxy-2H-indazol-2-yl)cyclohexyl)(methyl)carbamate

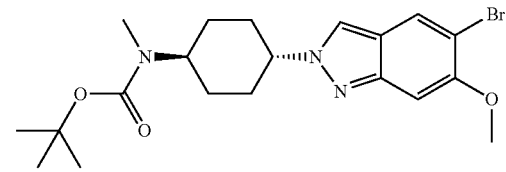 [SMILES: COc1cc2nn([C@H]3CC[C@H](N(C)C(=O)OC(C)(C)C)CC3)cc2cc1Br]

To a solution of tert-butyl ((1r,4r)-4-(5-bromo-6-methoxy-2H-indazol-2-yl)cyclohexyl)carbamate (Int IV-8) (4.2 g, 9.9 mmol) in DMF (50 mL) at 0° C. under N$_2$ atmosphere was added NaH (60 wt. %) (792 mg, 19.8 mmol). The resulting suspension was stirred at rt for 30 min, followed by the addition of iodomethane (1.2 mL, 19.8 mmol). After stirring for 13 h, the reaction was quenched with water (150 mL). The precipitate was filtered, washed with water (150 mL) and dried in vacuo to afford tert-butyl ((1r,4r)-4-(5-bromo-6-methoxy-2H-indazol-2-yl)cyclohexyl)(methyl)carbamate (4.4 g, 100%) as a colorless solid. MS ESI, m/z=438/440 [M+H]$^+$.

Methyl 2-((1r,4r)-4-((tert-butoxycarbonyl)(methyl)amino)cyclohexyl)-6-methoxy-2H-indazole-5-carboxylate

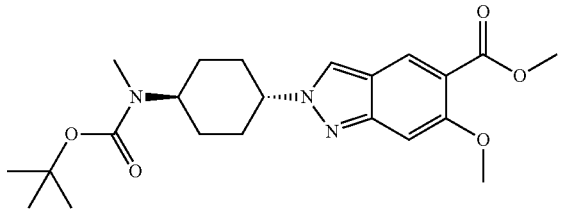 [SMILES: COC(=O)c1cc2cn([C@H]3CC[C@H](N(C)C(=O)OC(C)(C)C)CC3)nc2cc1OC]

A suspension of tert-butyl ((1r,4r)-4-(5-bromo-6-methoxy-2H-indazol-2-yl)cyclohexyl) (methyl)carbamate (4.3 g, 9.8 mmol), Pd(dppf)Cl$_2$ (714 mg, 1.0 mmol) and TEA (13.6 mL, 97.6 mmol) in MeOH (125 mL) was stirred under CO atmosphere at 15 atm and 100° C. for 15 h. The reaction mixture was cooled to rt and concentrated under reduced pressure. The residue was purified by silica gel chromatography (eluting with 30-50% EtOAc in PE) to afford methyl 2-((1r,4r)-4-((tert-butoxycarbonyl)(methyl)amino)cyclohexyl)-6-methoxy-2H-indazole-5-carboxylate (3.8 g, 93%) as a yellow solid. MS ESI, m/z=418 [M+H]$^+$.

2-((1r,4r)-4-((tert-Butoxycarbonyl)(methyl)amino)cyclohexyl)-6-methoxy-2H-indazole-5-carboxylic acid

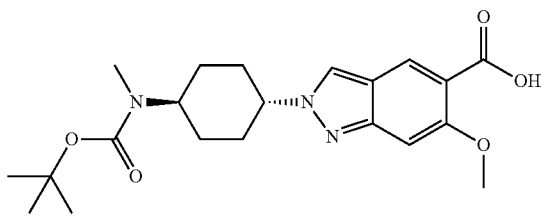 [SMILES: COc1cc2nn([C@H]3CC[C@H](N(C)C(=O)OC(C)(C)C)CC3)cc2cc1C(=O)O]

To a solution of methyl 2-((1r,4r)-4-((tert-butoxycarbonyl)(methyl)amino)cyclohexyl)-6-methoxy-2H-indazole-5-carboxylate (2.9 g, 6.9 mmol) in MeOH (50 mL)/water (25 mL) at rt was added NaOH (556 mg, 13.9 mmol). The resulting solution was stirred at 30° C. for 12 h. The reaction mixture was cooled to rt and acidified to pH ~6 with 4N HCl. The precipitate was filtered, washed with water (200 mL) and dried in vacuo to afford 2-((1r,4r)-4-((tert-butoxycarbonyl)(methyl)amino)cyclohexyl)-6-methoxy-2H-indazole-5-carboxylic acid (2.7 g, 95%) as a pale-yellow solid. MS ESI, m/z=404 [M+H]$^+$.

tert-Butyl ((1r,4r)-4-(6-methoxy-5-(pyrazolo[1,5-c]pyrimidin-3-ylcarbamoyl)-2H-indazol-2-yl)cyclohexyl)(methyl)carbamate

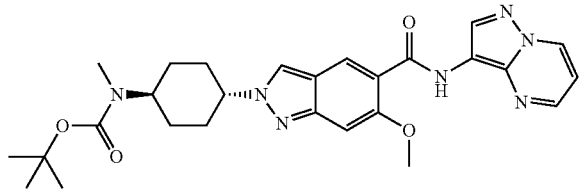 [SMILES: COc1cc2nn([C@H]3CC[C@H](N(C)C(=O)OC(C)(C)C)CC3)cc2cc1C(=O)Nc1cnn2cccnc12]

To a solution of 2-((1r,4r)-4-((tert-butoxycarbonyl)(methyl)amino)cyclohexyl)-6-methoxy-2H-indazole-5-carboxylic acid (2.6 g, 6.4 mmol) and DIPEA (3.4 mL, 19.3 mmol) in DMF (50 mL) at rt under N$_2$ atmosphere was added HATU (2.9 g, 7.7 mmol). The resulting mixture was stirred at rt for 15 min, followed by the addition of the HCl salt of pyrazolo[1,5-a]pyrimidin-3-amine (1.4 g, 8.4 mmol). The reaction mixture was stirred at rt for 13 h. The mixture was diluted with water (100 mL) and filtered to obtained the crude solid. The solid was washed with water (100 mL) and then purified by silica gel chromatography (eluting with 0-5% MeOH in DCM) to afford tert-butyl ((1r,4r)-4-(6-methoxy-5-(pyrazolo[1,5-c]pyrimidin-3-ylcarbamoyl)-2H-indazol-2-yl)cyclohexyl)(methyl)carbamate (3.3 g, 99%) as a yellow solid. MS ESI, m/z=520 [M+H]$^+$.

6-Methoxy-2-((1r,4r)-4-(methylamino)cyclohexyl)-N-(pyrazolo[1,5-c]pyrimidin-3-yl)-2H-indazole-5-carboxamide (Int V-4)

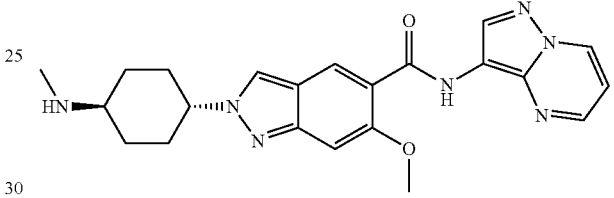

To a solution of tert-butyl ((1r,4r)-4-(6-methoxy-5-(pyrazolo[1,5-a]pyrimidin-3-ylcarbamoyl)-2H-indazol-2-yl)cyclohexyl)(methyl)carbamate (3.3 g, 6.4 mmol) in DCM (40 mL) at rt under N$_2$ atmosphere was added 4N HCl in dioxane (15.9 mL, 63.5 mmol) and the resulting solution was stirred at rt for 12 h. The mixture was concentrated under reduced pressure to afford the HCl salt of 6-methoxy-2-((1r,4r)-4-(methylamino)cyclohexyl)-N-(pyrazolo[1,5-c]pyrimidin-3-yl)-2H-indazole-5-carboxamide (2.9 g) as a pale-yellow solid, which was used directly without further purification. MS ESI, m/z=420 [M+H]$^+$.

Synthesis of Intermediate Int V-5: 2-(2-Acetyl-2-azaspiro[3.5]nonan-7-yl)-6-hydroxy-N-(imidazo[1,2-b]pyridazin-3-yl)-2H-indazole-5-carboxamide

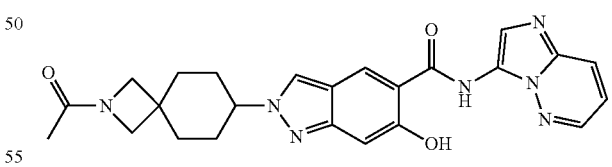

BBr$_3$ (8.0 mL, 8.3 mmol) was added dropwise to 2-(2-acetyl-2-azaspiro[3.5]nonan-7-yl)-N-(imidazo[1,2-b]pyridazin-3-yl)-6-methoxy-2H-indazole-5-carboxamide (Example 21, see below)(380 mg, 0.8 mmol) in DCM (15 mL) over a period of 5 min at 0° C. under N$_2$ atmosphere and the resulting mixture stirred at 40° C. After 6 h the reaction mixture was allowed to cool to rt, quenched with an aq. saturated NaHCO$_3$ solution (10 mL) and diluted with brine (50 mL). The mixture was extracted with EtOAc (2×50 mL). The combined organic layers were dried over Na$_2$SO$_4$, filtered and concentrated under reduced pressure. The resulting residue was purified using C18-flash chromatography (eluting with 0% to 25% MeCN in water) followed by silica gel chromatography (eluting with 9% to 10% MeOH in DCM) to afford 2-(2-acetyl-2-azaspiro[3.5]nonan-7-yl)-6-hydroxy-N-(imidazo[1,2-b]pyridazin-3-yl)-2H-indazole-5-carboxamide (170 mg, 46%) as a light brown solid. $^1$H NMR (300 MHz, DMSO-d$_6$) (1:1 mixture of rotamers) δ 11.69 (s, 1H), 11.62 (s, 1H), 8.62 (s, 1H), 8.60 (dd, 1H), 8.57 (s, 1H), 8.15 (dd, 1H), 8.10 (s, 1H), 7.21 (dd, 1H), 7.00 (s, 1H), 4.33-4.53 (m, 1H), 3.92 (s, 1H), 3.80 (s, 1H), 3.63 (s, 1H), 3.52 (s, 1H), 1.83-2.12 (m, 6H), 1.76/1.78 (s, 3H) (rotamers), 1.61-1.74 (m, 2H). m/z (ESI+), [M+H]$^+$=460.

EXAMPLES

N-(Imidazo[1,2-b]pyridazin-3-yl)-6-methoxy-2-((5r,8r)-1-methyl-2-oxo-1-azaspiro[4.5]decan-8-yl)-2H-indazole-5-carboxamide (Example 1)

8-Amino-1-azaspiro[4.5]decan-2-one

1-azaspiro[4.5]decane-2,8-dione (1.0 g, 6.0 mmol) was mixed with 4N NH$_3$ in MeOH (46.0 mL, 0.18 mol) and stirred at rt. After 1 h the resulting solution was added to a suspension of NaBH$_4$ (256 mg, 6.8 mmol) in THF (20 mL) at −50° C. and allowed to warm to rt. The reaction was quenched with water (10 mL) and the organic solvents were removed in vacuo. Then, an aq. 4M NaOH solution (40 mL) and sodium chloride (10 g) was added. The resulting suspension was extracted with DCM (4×70 mL), the combined organic phases were dried over MgSO$_4$ and the solvent was removed in vacuo to give crude 8-amino-1-azaspiro[4.5]decan-2-one (0.9 g), which was used without further purification.

(5r,8r)-8-(5-Bromo-6-methoxy-2H-indazol-2-yl)-1-azaspiro[4.5]decan-2-one

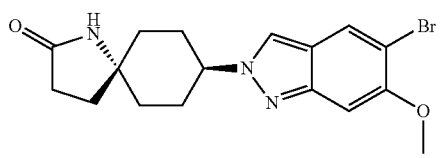 [SMILES: COc1cc2nn([C@H]3CC[C@@]4(CCC(=O)N4)CC3)cc2cc1Br]

To crude 8-amino-1-azaspiro[4.5]decan-2-one (600 mg) in i-PrOH (25 mL) was added 5-bromo-4-methoxy-2-nitrobenzaldehyde (Int I-1) (1.1 g, 2.2 mmol) and the resulting mixture was stirred at 80° C. After 4 h, tri-n-butylphosphine (1.6 mL, 6.5 mmol) was added and the mixture was stirred overnight at 80° C. Then the reaction mixture was allowed to cool to rt and filtered. The collected solid was washed with heptane (3×10 mL) and purified using ion exchange chromatography, washing with 250 mL DCM/MeOH (1:1) and eluting with DCM/4N NH$_3$-MeOH solution (1/1). The isolated solid was then recrystallized using i-PrOH to remove undesired (5s,8s)-8-(5-bromo-6-methoxy-2H-indazol-2-yl)-1-azaspiro[4.5]decan-2-one. The filtrate was further purified by silica gel chromatography (eluting with 50-100% EtOAc in heptane, then EtOAc, followed by 0-3% NH$_3$-MeOH in DCM) to afford (5r,8r)-8-(5-bromo-6-methoxy-2H-indazol-2-yl)-1-azaspiro[4.5]decan-2-one (320 mg, 39%). m/z (ESI+), [M+H]$^+$=378/380.

(5r,8r)-8-(5-Bromo-6-methoxy-2H-indazol-2-yl)-1-methyl-1-azaspiro[4.5]decan-2-one

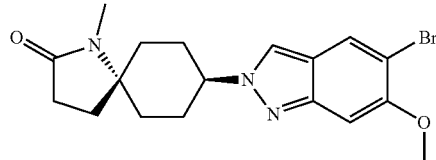

To a stirred solution of (5r,8r)-8-(5-bromo-6-methoxy-2H-indazol-2-yl)-1-azaspiro[4.5]decan-2-one (310 mg, 0.7 mmol) in DMF (5 mL)/THF (5 mL) was added NaH (60 wt. %) (93 mg, 2.1 mmol) at 0° C. After 20 min, methyl iodide (130 μL, 2.1 mmol) was slowly added at 0° C. The resulting mixture was warmed to rt and stirred overnight. The reaction mixture was then quenched with ice water (250 mL) and extracted with DCM (4×25 mL). The combined organic phases were concentrated in vacuo and the resulting residue was purified using silica gel chromatography (eluting with DCM (300 mL), EtOAc (2 L), then with 2% NH$_3$-MeOH in DCM (150 mL)) to give (5r,8r)-8-(5-bromo-6-methoxy-2H-indazol-2-yl)-1-methyl-1-azaspiro[4.5]decan-2-one (225 mg, 78%) as a beige solid. m/z (ESI+), [M+H]$^+$=392/394.

N-(Imidazo[1,2-b]pyridazin-3-yl)-6-methoxy-2-((5r,8r)-1-methyl-2-oxo-1-azaspiro[4.5]decan-8-yl)-2H-indazole-5-carboxamide (Example 1)

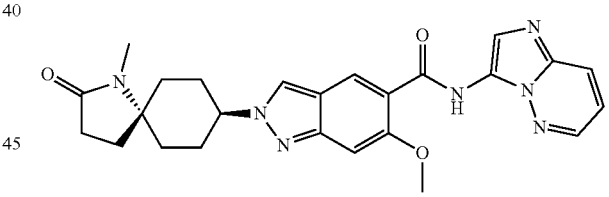

Methyldiphenylsilanecarboxylic acid (193 mg, 0.8 mmol) and KF (46 mg, 0.8 mmol) were added to chamber A of a dried and N$_2$-flushed COware gas reactor. (5r,8r)-8-(5-Bromo-6-methoxy-2H-indazol-2-yl)-1-methyl-1-azaspiro[4.5]decan-2-one (116 mg, 0.3 mmol), imidazo[1,2-b]pyridazin-3-amine (121 mg, 0.9 mmol), dppp (41 mg, 0.1 mmol), Pd(OAc)$_2$ (27 mg, 0.1 mmol) and TEA (223 μL, 1.6 mmol) in degassed anhydrous MeCN (2 mL) were added to chamber B. Then, DMSO (350 μL) was added to chamber A and chamber B was stirred at 85° C. overnight. The reaction mixture was allowed to cool to rt. The reaction in chamber B was quenched with saturated NaHCO$_3$, the solvent was removed in vacuo, and the resulting residue was purified using ion exchange chromatography, washing with DCM/MeOH (1/1; 200 mL), and eluting with 4N NH$_3$ in MeOH (200 mL). The resulting dark-brown solid was further purified using silica gel chromatography (eluting with EtOAc (2 L) and then with 0-3% NH$_3$-MeOH in DCM) to give an orange-yellow solid. The orange-yellow solid was triturated with EtOAc (20 mL) to give a bright-yellow solid, which was slurried in i-PrOH (3 mL) overnight. The slurry solution was filtered, and the collected precipitate was washed with i-PrOH (4×500 4) and pentane (3×1 mL) to give N-(imidazo[1,2-b]pyridazin-3-yl)-6-methoxy-2-((5r,8r)-1-methyl-2-oxo-1-azaspiro[4.5]decan-8-yl)-2H-indazole-5-carboxamide (93 mg, 74%) as a light-yellow solid. $^1$H NMR (500 MHz, DMSO-d$_6$) δ 11.05 (s, 1H), 8.65 (dd, 1H), 8.64 (d, 1H), 8.59 (s, 1H), 8.16 (dd, 1H), 8.05 (s, 1H), 7.29 (s, 1H), 7.23 (dd, 1H), 4.49-4.61 (m, 1H), 4.12 (s, 3H), 2.68 (s, 3H), 2.28 (t, 2H), 2.07-2.18 (m, 4H), 1.94-2.03 (m, 4H), 1.53-1.59 (m, 2H). m/z (ESI+), [M+H]$^+$=474.

N-(Imidazo[1,2-b]pyridazin-3-yl)-6-methoxy-2-((5s,8s)-1-methyl-2-oxo-1-azaspiro[4.5]decan-8-yl)-2H-indazole-5-carboxamide (Example 2)

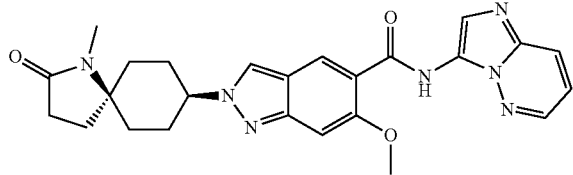 [SMILES: COc1cc2nn([C@H]3CC[C@]4(CCC(=O)N4C)CC3)cc2cc1C(=O)Nc1cnc2cccnn12]

To 1-methyl-2-oxo-1-azaspiro[4.5]decan-8-yl 4-methylbenzenesulfonate (Int III-1) (1.4 g, 4.2 mmol) was added DMF (15 mL), N-(imidazo[1,2-b]pyridazin-3-yl)-6-methoxy-1H-indazole-5-carboxamide (Int II-1) (1.3 g, 4.2 mmol) and KOH (466 mg, 8.3 mmol). The resulting solution was stirred at 100° C. After 12 h the reaction mixture was allowed to cool to rt and directly purified using C18-flash chromatography (eluting with 0% to 100% MeCN in water (0.05% FA)) followed by chiral HPLC (CHIRAL ART Cellulose-SB, 2×25 mm, 5 μm; mobile Phase A: MTBE (2 mm NH$_3$ in MeOH); mobile Phase B: i-PrOH; gradient: isocratic 50% B for 21.5 min; flow rate: 20 mL/min) to afford N-(imidazo[1,2-b]pyridazin-3-yl)-6-methoxy-2-((5s,8s)-1-methyl-2-oxo-1-azaspiro[4.5]decan-8-yl)-2H-indazole-5-carboxamide (28.0 mg, 1%) as a yellow solid. $^1$H NMR (300 MHz, CD$_3$OD) δ 8.75 (d, 1H), 8.62 (s, 1H), 8.59 (d, 1H), 8.15 (s, 1H), 8.04 (dd, 1H), 7.21-7.28 (m, 2H), 4.71-4.79 (m, 1H), 4.23 (s, 3H), 2.68 (s, 3H), 2.59-2.69 (m, 2H), 2.44 (t, 2H), 2.07-2.33 (m, 6H), 1.45-1.55 (m, 2H). m/z (ESI+), [M+H]$^+$=474.

2-((1s,4s)-4-(Dimethylcarbamoyl)cyclohexyl)-N-(imidazo[1,2-b]pyridazin-3-yl)-6-methoxy-2H-indazole-5-carboxamide (Example 3)

(1r,4r)-4-Hydroxy-N,N-dimethylcyclohexane-1-carboxamide

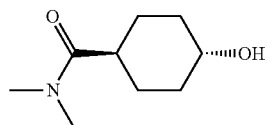

HATU (9.5 g, 25.0 mmol) was added to (1r,4r)-4-hydroxycyclohexane-1-carboxylic acid (3.0 g, 20.8 mmol), dimethylamine hydrochloride (5.1 g, 62.5 mmol) and DIPEA (14.5 mL, 83.0 mmol) in DCM (30 mL) over a period of 3 h at rt under N$_2$ atmosphere. After stirring of the resulting mixture for 3 h, the reaction mixture was poured into water (20 mL) and extracted with DCM (3×20 mL). The combined organic layers were dried over Na$_2$SO$_4$, filtered, and the solvent was removed in vacuo. The crude product was subjected to silica gel chromatography (eluting with 0% to 50% EtOAc in PE) to afford crude (1r,4r)-4-hydroxy-N,N-dimethylcyclohexane-1-carboxamide (2.1 g), which was used without further purification. m/z (ESI+), [M+H]$^+$=172.

(1r,4r)-4-(Dimethylcarbamoyl)cyclohexyl 4-methylbenzenesulfonate

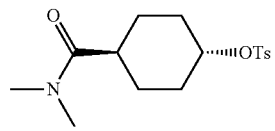

TsCl (8.4 g, 44.1 mmol) was added dropwise to TEA (7.3 mL, 52.4 mmol), DMAP (214 mg, 1.8 mmol) and crude (1r,4r)-4-hydroxy-N,N-dimethylcyclohexane-1-carboxamide (2 g) in DCM (20 mL) at 0° C. under N$_2$ atmosphere and the resulting solution was stirred at rt. After 11 h the reaction mixture was poured into water (20 mL), extracted with DCM (3×10 mL), the combined organic layers were dried over Na$_2$SO$_4$, filtered, and the solvent was removed in vacuo. The resulting residue was subjected to silica gel chromatography (eluting with 10% to 20% EtOAc in PE) to afford crude (1r,4r)-4-(dimethylcarbamoyl)cyclohexyl 4-methylbenzenesulfonate (2.1 g), which was used without further purification. m/z (ESI+), [M+H]$^+$=326.

2-((1s,4s)-4-(Dimethylcarbamoyl)cyclohexyl)-N-(imidazo[1,2-b]pyridazin-3-yl)-6-methoxy-2H-indazole-5-carboxamide (Example 3)

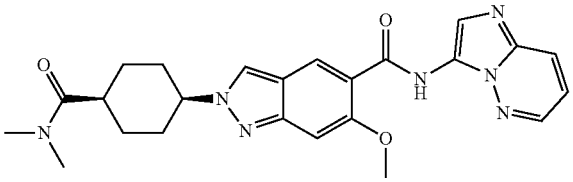 [SMILES: COc1cc2nn([C@H]3CC[C@@H](C(=O)N(C)C)CC3)cc2cc1C(=O)Nc1cnc2cccnn12]

KOH (218 mg, 3.9 mmol) was added to N-(imidazo[1,2-b]pyridazin-3-yl)-6-methoxy-1H-indazole-5-carboxamide (Int II-1) (300 mg, 1.0 mmol) and crude (1r,4r)-4-(dimethylcarbamoyl)cyclohexyl 4-methylbenzenesulfonate (950 mg) in DMF (6 mL) at rt under N$_2$ atmosphere and the resulting solution was stirred at 100° C. After 12 h the reaction mixture was allowed to cool to rt and directly subjected to C18-flash chromatography (eluting with 10% to 60% MeCN in water (0.5% FA)), followed by prep. HPLC (XSelect CSH Prep C18 OBD column, 5 μm, 19 mm×150 mm; mobile phase A: water (0.1% FA); mobile phase B: MeCN; gradient: 15% to 27% B in 7 min, then 27% B for 2 min, flow rate: 60 mL/min) to afford 2-((1s,4s)-4-(dimethylcarbamoyl)cyclohexyl)-N-(imidazo[1,2-b]pyridazin-3- yl)-6-methoxy-2H-indazole-5-carboxamide (40 mg, 9%) as a yellow solid. $^1$H NMR (400 MHz, DMSO-d$_6$) δ 11.05 (s, 1H), 8.64 (t, 2H), 8.59 (s, 1H), 8.15 (dd, 1H), 8.05 (s, 1H), 7.29 (s, 1H), 7.22 (dd, 1H), 4.56-4.65 (m, 1H), 4.12 (s, 3H), 3.03 (s, 3H), 2.85-2.97 (m, 1H), 2.80 (s, 3H), 1.94-2.04 (m, 3H), 1.59-1.81 (m, 6H). m/z (ESI+), [M+H]$^+$=462.

2-((1r,4r)-4-(Dimethylcarbamoyl)cyclohexyl)-N-(imidazo[1,2-b]pyridazin-3-yl)-6-methoxy-2H-indazole-5-carboxamide (Example 4)

(1s,4s)-4-Hydroxy-N,N-dimethylcyclohexanecarboxamide

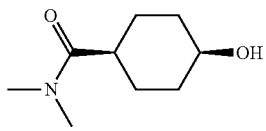

HATU (9.5 g, 24.9 mmol) was added to a solution of DIPEA (14.5 mL, 83.2 mmol), dimethylamine×HCl (5.1 g, 62.4 mmol) and (1s,4s)-4-hydroxycyclohexanecarboxylic acid (3.0 g, 20.8 mmol) in DCM (30 mL) at rt under N$_2$ atmosphere. The resulting mixture was stirred at rt for 3 h. The reaction mixture was poured into water (20 mL) and extracted with DCM (2×20 mL). The combined organic layers were dried over Na$_2$SO$_4$, filtered and concentrated. The crude product was purified by silica gel chromatography (eluting with 0 to 80% EtOAc in PE) to afford crude (1s,4s)-4-hydroxy-N,N-dimethylcyclohexanecarboxamide (3.5 g) as a yellow oil.

(1s,4s)-4-(Dimethylcarbamoyl)cyclohexyl 4-methylbenzenesulfonate

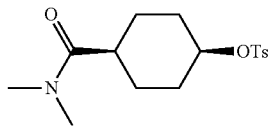 [SMILES: Cc1ccc(S(=O)(=O)O[C@H]2CC[C@@H](C(=O)N(C)C)CC2)cc1]

TEA (7.3 mL, 52.6 mmol) was added to DMAP (214 mg, 1.8 mmol), (1s,4s)-4-hydroxy-N,N-dimethylcyclohexanecarboxamide (3.0 g, 17.0 mmol) and TsCl (6.7 g, 35 mmol) in DCM (30 mL) over a period of 3 h at rt under N$_2$ atmosphere. The resulting mixture was stirred at rt for 3 h. The reaction mixture was poured into water (20 mL) and extracted with DCM (3×25 mL). The combined organic layers were dried over Na$_2$SO$_4$, filtered and concentrated. The crude product was purified by silica gel chromatography (eluting with 0 to 20% EtOAc in PE) to afford (1s,4s)-4-(dimethylcarbamoyl)cyclohexyl 4-methylbenzenesulfonate (2.1 g, 37%) as a yellow oil. m/z (ESI+) [M+H]$^+$=326.

2-((1r,4r)-4-(Dimethylcarbamoyl)cyclohexyl)-N-(imidazo[1,2-b]pyridazin-3-yl)-6-methoxy-2H-indazole-5-carboxamide (Example 4)

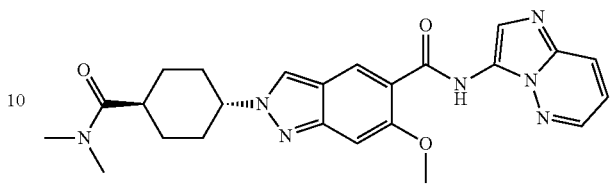

KOH (80 mg, 1.4 mmol) was added to a solution of (1s,4s)-4-(dimethylcarbamoyl)cyclohexyl 4-methylbenzenesulfonate (348 mg, 1.1 mmol) and N-(imidazo[1,2-b]pyridazin-3-yl)-6-methoxy-1H-indazole-5-carboxamide (Int II-1) (110 mg, 0.4 mmol) in DMF (10 mL) at rt under N$_2$ atmosphere. The resulting solution was stirred at 100° C. for 12 h and cooled to rt before the mixture was poured into water (10 mL). The aqueous phase was extracted with EtOAc (3×20 mL), the combined organic layers were dried over Na$_2$SO$_4$, filtered and concentrated to afford a yellow oil. The crude product was purified by silica gel chromatography (eluting with 0% to 30% EtOAc in PE), followed by prep. HPLC (Xselect CSH Fluoro phenyl OBD column, 5 μm silica, 30×150 mm, mobile Phase A: Water (0.1% FA), mobile Phase B: MeCN; flow rate: 60 mL/min; gradient: 20% B to 30% B in 7 min) to afford 2-((1r,4r)-4-(dimethylcarbamoyl)cyclohexyl)-N-(imidazo[1,2-b]pyridazin-3-yl)-6-methoxy-2H-indazole-5-carboxamide (10 mg, 17%) as a yellow solid. $^1$H NMR (400 MHz, DMSO-d$_6$) δ 11.05 (s, 1H), 8.61-8.67 (m, 1H), 8.59 (s, 2H), 8.14-8.18 (m, 1H), 8.05 (s, 1H), 7.18-7.27 (m, 2H), 4.48-4.54 (m, 1H), 4.13 (s, 3H), 3.07 (s, 3H), 2.83 (s, 3H), 2.70-2.80 (m, 1H), 2.16-2.20 (m, 2H), 1.99-2.05 (m, 2H), 1.84-1.88 (m, 2H), 1.58-1.65 (m, 2H). m/z (ESI+) [M+H]$^+$=462.

2-(2-Hydroxy-2-methylspiro[3.5]nonan-7-yl)-N-(imidazo[1,2-b]pyridazin-3-yl)-6-methoxy-2H-indazole-5-carboxamide—Isomer 1 (Example 5) & Isomer 2 (Example 6)

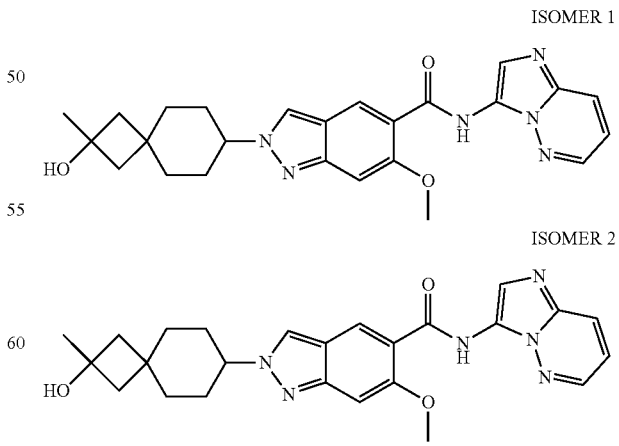

Cs$_2$CO$_3$ (793 mg, 2.4 mmol) was added to N-(imidazo[1,2-b]pyridazin-3-yl)-6-methoxy-1H-indazole-5-carboxamide (Int II-1) (300 mg, 1.0 mmol) and 2-hydroxy-2-methylspiro

[3.5]nonan-7-yl 4-methylbenzenesulfonate (Int III-3) (631 mg, 2.0 mmol) in DMF (15 mL) and the resulting mixture was stirred at 85° C. under N₂ atmosphere. After 5 h, the reaction mixture was allowed to cool to rt and directly subjected to C18-flash chromatography (eluting with 0% to 100% MeCN in water (0.5% FA)) followed by two prep. HPLC purifications ((1' prep. HPLC: XBridge Prep OBD C18, 30×150 mm 5 μm; mobile Phase A: water (10 mM NH₄HCO₃+0.1% NH₄OH); mobile Phase B: MeCN; gradient: 28% B to 48% B in 7 min; flow rate: 60 mL/min.) ($2^{nd}$ prep. HPLC: Chiralpak ID-2, 2×25 cm, 5 μm; mobile Phase A: MTBE (0.1% 2N NH₃-MeOH); mobile Phase B: MeOH; gradient: isocratic 50% B in 14 min; flow rate: 16 mL/min.)) to afford 2-(2-hydroxy-2-methylspiro[3.5]nonan-7-yl)-N-(imidazo[1,2-b]pyridazin-3-yl)-6-methoxy-2H-indazole-5-carboxamide—Isomer 1 (25 mg, 6%, 100% ee) and 2-(2-hydroxy-2-methylspiro[3.5]nonan-7-yl)-N-(imidazo[1,2-b]pyridazin-3-yl)-6-methoxy-2H-indazole-5-carboxamide—Isomer 2 (23 mg, 5%, 99.5% ee), both as a yellow solids. The ¹H NMR and MS obtained for both products were identical. ¹H NMR (300 MHz, DMSO-d₆) δ 11.04 (s, 1H), 8.63 (dd, 1H), 8.58 (s, 1H), 8.57 (s, 1H), 8.15 (dd, 1H), 8.05 (s, 1H), 7.28 (s, 1H), 7.21 (dd, 1H), 4.75 (s, 1H), 4.33-4.52 (m, 1H), 4.12 (s, 3H), 1.71-2.05 (m, 10H), 1.43-1.61 (m, 2H), 1.26 (s, 3H). m/z (ESI+), [M+H]⁺=461.

2-((1s,4s)-4-Hydroxycyclohexyl)-N-(imidazo[1,2-b]pyridazin-3-yl)-6-methoxy-2H-indazole-5-carboxamide (Example 7) & 2-((1r,4r)-4-Hydroxycyclohexyl)-N-(imidazo[1,2-b]pyridazin-3-yl)-6-methoxy-2H-indazole-5-carboxamide (Example 8)

(1s,4s)-4-Hydroxycyclohexyl methanesulfonate

MsCl (1.9 mL, 23.7 mmol) was added to a solution of (1s,4s)-cyclohexane-1,4-diol (2.5 g, 21.5 mmol) and TEA (6.0 mL, 43.0 mmol) in DCM (200 mL) at 0° C. The resulting mixture was stirred at rt for 12 h. The mixture was poured into water (20 mL), the aqueous layer was extracted with DCM (1×20 mL) and the organic layer was dried over Na₂SO₄, filtered and concentrated. The crude product was purified by silica gel chromatography (eluting with PE:EtOAc 50% to 100%) to afford crude (1s,4s)-4-hydroxycyclohexyl methanesulfonate (2.9 g) as a colorless solid.

2-((1s,4s)-4-Hydroxycyclohexyl)-N-(imidazo[1,2-b]pyridazin-3-yl)-6-methoxy-2H-indazole-5-carboxamide (Example 7) & 2-((1r,4r)-4-Hydroxycyclohexyl)-N-(imidazo[1,2-b]pyridazin-3-yl)-6-methoxy-2H-indazole-5-carboxamide (Example 8)

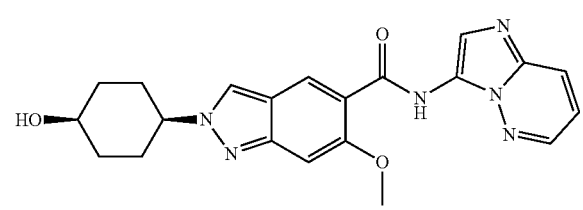

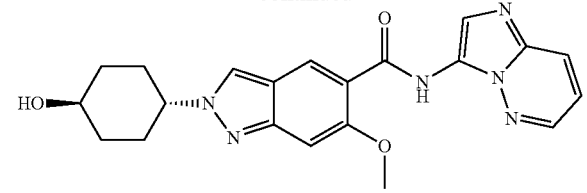

Cs₂CO₃ (1.8 g, 5.7 mmol) was added to a solution of N-(imidazo[1,2-b]pyridazin-3-yl)-6-methoxy-1H-indazole-5-carboxamide (Int II-1) (350 mg, 1.1 mmol) and crude (1s,4s)-4-hydroxycyclohexyl methanesulfonate (1.3 g) in DMF (20 mL). The resulting mixture was stirred at 100° C. for 15 h. The mixture was cooled to rt, concentrated and purified by C18-flash chromatography (eluting with 0 to 100% MeCN in water (0.1% FA)) to afford a mixture of trans- and cis-isomers of 2-(4-hydroxycyclohexyl)-N-(imidazo[1,2-b]pyridazin-3-yl)-6-methoxy-2H-indazole-5-carboxamide as a pale-yellow solid. This material was separated by prep. SFC (CHIRALPAK IH, 2.0×25 cm, 5 μm; mobile phase A: CO2, mobile phase B: EtOH (8 mmol/L NH₃-MeOH); flow rate: 40 mL/min; gradient: 40% B) to afford the first eluting 2-((1s,4s)-4-hydroxycyclohexyl)-N-(imidazo[1,2-b]pyridazin-3-yl)-6-methoxy-2H-indazole-5-carboxamide (4 mg, 1%), and the second eluting 2-((1r,4r)-4-hydroxycyclohexyl)-N-(imidazo[1,2-b]pyridazin-3-yl)-6-methoxy-2H-indazole-5-carboxamide (12 mg, 3%), both as light yellow solids. (1s,4s)—Isomer: ¹H NMR (300 MHz, DMSO-d₆) δ 11.06 (s, 1H), 8.49-8.70 (m, 3H), 8.13-8.20 (m, 1H), 8.06 (s, 1H), 7.17-7.31 (m, 2H), 4.39-4.62 (m, 2H), 4.13 (s, 3H), 3.85-3.92 (m, 1H), 2.21-2.38 (m, 2H), 1.56-1.98 (m, 6H). m/z (ESI+) [M+H]⁺=407. (1r,4r)—Isomer: ¹H NMR (300 MHz, DMSO-d₆) δ 11.05 (s, 1H), 8.61-8.67 (m, 1H), 8.55-8.60 (m, 2H), 8.12-8.19 (m, 1H), 8.06 (s, 1H), 7.18-7.29 (m, 2H), 4.70-4.78 (m, 1H), 4.41-4.53 (m, 1H), 4.13 (s, 3H), 3.72-3.47 (m, 1H), 1.88-2.18 (m, 6H), 1.39-1.49 (m, 2H). m/z (ESI+) [M+H]⁺=407.

rel-2-(1S,3R)-3-Hydroxycyclohexyl)-N-(imidazo[1,2-b]pyridazin-3-yl)-6-methoxy-2H-indazole-5-carboxamide—Isomer 1 (Example 9) & Isomer 2 (Example 10)

ISOMER 1

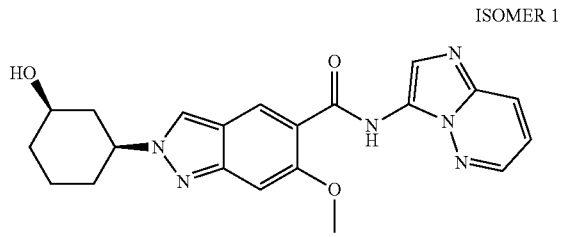

Or Enantiomer

ISOMER 2

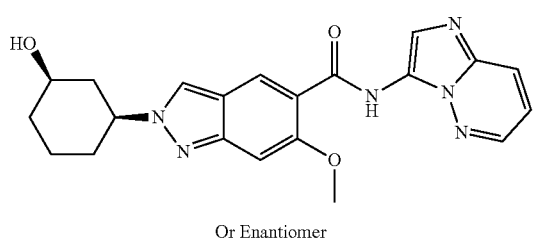

Or Enantiomer

To rac-(1R,3R)-3-hydroxycyclohexyl 4-methylbenzenesulfonate (Int III-7) (351 mg, 1.3 mmol) and Cs$_2$CO$_3$ (423 mg, 1.3 mmol) in DMF (10 mL) was added N-(imidazo[1,2-b]pyridazin-3-yl)-6-methoxy-1H-indazole-5-carboxamide (Int II-1) (400 mg, 1.3 mmol) under N$_2$ atmosphere and the resulting mixture was stirred at 90° C. After 5 h, the reaction mixture was allowed to cool to rt and directly subjected to C18-flash chromatography (eluting with 0% to 100% MeCN in water (0.05% FA)) followed by prep. HPLC (XBridge Prep OBD C18, 30×150 mm 5 µm; mobile phase A: water (10 mM NH$_4$HCO$_3$+0.1% NH$_4$OH); mobile Phase B: MeCN; gradient: 16% B to 36% B in 7 min; flow rate: 60 mL/min) and chiral prep. HPLC (CHIRAL ART Cellulose-SB, 4.6×100 mm, 3 µm; mobile Phase A: (MTBE+0.5% 2N NH$_3$ in MeOH), mobile Phase B: i-PrOH; gradient: isocratic 30% B in 25 min; flow rate: 18 mL/min) to afford rel-2-((1S,3R)-3-hydroxycyclohexyl)-N-(imidazo[1,2-b]pyridazin-3-yl)-6-methoxy-2H-indazole-5-carboxamide—Isomer 1 (16 mg, 3%, 99% ee) and rel-2-((1S,3R)-3-hydroxycyclohexyl)-N-(imidazo[1,2-b]pyridazin-3-yl)-6-methoxy-2H-indazole-5-carboxamide—Isomer 2 (17 mg, 3%, 98.7% ee), both as a yellow solids. Isomer 1: $^1$H NMR (400 MHz, DMSO-d$_6$) δ 11.04 (s, 1H), 8.64 (dd, 1H), 8.59 (d, 1H), 8.58 (s, 1H), 8.15 (dd, 1H), 8.05 (s, 1H), 7.26 (s, 1H), 7.22 (dd, 1H), 4.86 (d, 1H), 4.46-4.57 (m, 1H), 4.12 (s, 3H), 3.56-3.67 (m, 1H), 2.27-2.37 (m, 1H), 2.01-2.09 (m, 1H), 1.67-1.95 (m, 4H), 1.39-1.48 (m, 1H), 1.12-1.26 (m, 1H). m/z (ESI+), [M+H]$^+$=407. Isomer 2: $^1$H NMR (400 MHz, DMSO-d$_6$) δ 11.04 (s, 1H), 8.64 (dd, 1H), 8.59 (d, 1H), 8.58 (s, 1H), 8.15 (dd, 1H), 8.05 (s, 1H), 7.26 (s, 1H), 7.22 (dd, 1H), 4.86 (d, 1H), 4.46-4.57 (m, 1H), 4.12 (s, 3H), 3.55-3.67 (m, 1H), 2.25-2.37 (m, 1H), 2.02-2.12 (m, 1H), 1.65-1.95 (m, 4H), 1.32-1.53 (m, 1H), 1.12-1.26 (m, 1H). m/z (ESI+), [M+H]$^+$=407.

6-Methoxy-2-(1-methyl-2-oxo-1-azaspiro[4.5]decan-8-yl)-N-(pyrazolo[1,5-a]pyrimidin-3-yl)-2H-indazole-5-carboxamide—Isomer 1 (Example 11) & Isomer 2 (Example 12)

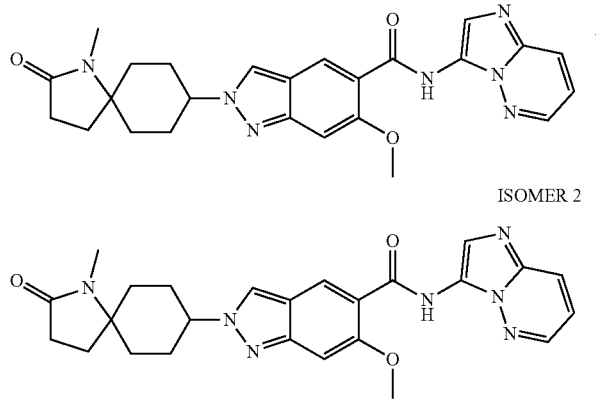

To a solution of 6-methoxy-N-(pyrazolo[1,5-a]pyrimidin-3-yl)-1H-indazole-5-carboxamide (Int II-2) (450 mg, 1.5 mmol) and 1-methyl-2-oxo-1-azaspiro[4.5]decan-8-yl 4-methylbenzenesulfonate (Int III-1) (985 mg, 2.9 mmol) in DMF (8 mL) at rt under N$_2$ atmosphere was added Cs$_2$CO$_3$ (1.4 g, 4.4 mmol). The reaction mixture was stirred at 90° C. for 12 h. The mixture was cooled to rt and purified directly by C18-flash chromatography (eluting with 0-40% MeCN in water (0.5% FA)) and further by prep. HPLC (Waters Xbridge® Shield RP18 OBD, 5 µm 30×150 mm; elution gradient with 22-32% MeCN in water (0.1% FA) in 9 min; 60 mL/min) to afford 6-methoxy-2-(1-methyl-2-oxo-1-azaspiro[4.5]decan-8-yl)-N-(pyrazolo[1,5-a]pyrimidin-3-yl)-2H-indazole-5-carboxamide as a yellow solid. The solid was separated by chiral prep. HPLC (YMC Chiral ART Cellulose-SB 5 µm 20 mm×250 mm; isocratic with 50% hexane/DCM (75/25, 0.5% 2M NH$_3$-MeOH) in MeOH in 9 min; 20 mL/min) to afford 6-methoxy-2-(1-methyl-2-oxo-1-azaspiro[4.5]decan-8-yl)-N-(pyrazolo[1,5-a]pyrimidin-3-yl)-2H-indazole-5-carboxamide—Isomer 1 (55 mg, 8%, 100% ee) and 6-methoxy-2-(1-methyl-2-oxo-1-azaspiro[4.5]decan-8-yl)-N-(pyrazolo[1,5-a]pyrimidin-3-yl)-2H-indazole-5-carboxamide—Isomer 2 (32 mg, 5%, 99.8% ee). Isomer 1: $^1$H NMR (400 MHz, DMSO-d$_6$) (3:7 mixture of rotamers) δ 10.32 (s, 1H), 9.08 (dd, 1H), 8.73 (br. s, 1H), 8.54 (dd, 1H), 8.46/8.45 (s, 1H) (rotamers), 8.16 (s, 1H), 7.44 (s, 1H), 7.06 (dd, 1H), 4.70-4.80 (m, 1H), 4.15 (s, 3H), 2.72 (s, 3H), 2.29 (t, 2H), 1.92-2.21 (m, 8H), 1.51-1.61 (m, 2H). m/z (ESI+), [M+H]$^+$=474. Isomer 2: $^1$H NMR (400 MHz, DMSO-d$_6$) (1:7 mixture of rotamers) δ 10.35 (s, 1H), 9.08 (dd, 1H), 8.73 (s, 1H), 8.59 (s, 1H), 8.54 (dd, 1H), 8.49/8.48 (s, 1H) (rotamers), 7.25 (s, 1H), 7.05 (dd, 1H), 4.48-4.60 (m, 1H), 4.06 (s, 3H), 2.68 (s, 3H), 2.28 (t, 2H), 2.08-2.18 (m, 4H), 1.93-2.04 (m, 4H), 1.52-1.60 (m, 2H). m/z (ESI+), [M+H]$^+$=474.

rel-2-(1S,3R)-3-Hydroxycyclohexyl)-6-methoxy-N-(pyrazolo[1,5-a]pyrimidin-3-yl)-2H-indazole-5-carboxamide—Isomer 1 (Example 13) & Isomer 2 (Example 14)

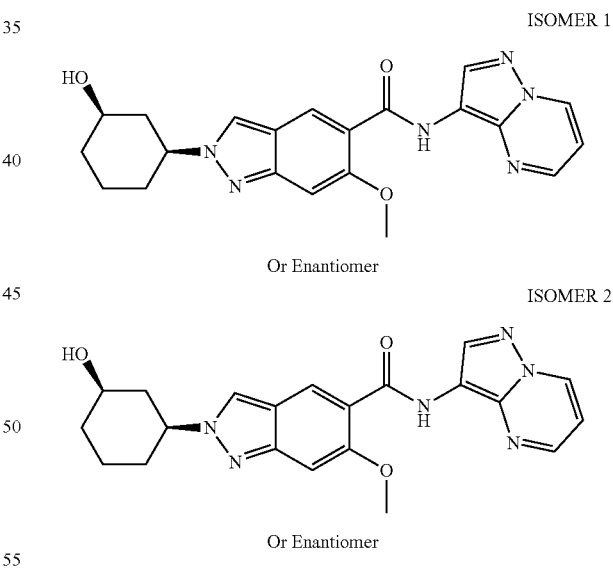

6-Methoxy-N-(pyrazolo[1,5-a]pyrimidin-3-yl)-1H-indazole-5-carboxamide (Int II-2) (400 mg, 1.3 mmol) was added to a slurry of Cs$_2$CO$_3$ (1.3 g, 3.9 mmol) and rac-(1R,3R)-3-hydroxycyclohexyl 4-methylbenzenesulfonate (Int III-7) (702 mg, 2.6 mmol) in DMF (15 mL) at rt under N$_2$ atmosphere. The resulting mixture was stirred at 90° C. for 12 h. The reaction mixture was allowed to cool to rt, concentrated and purified directly first by C18-flash chromatography (eluting with 0 to 100% MeCN in water (0.05% NH$_4$OH)), then by prep. HPLC (XBridge Prep OBD C18, 30×150 mm, 5 µm; mobile Phase A: Water (10 mM NH$_4$HCO$_3$+0.1% NH$_4$OH) mobile Phase B: MeCN; flow rate: 60 mL/min; gradient: 21% B to 30% B in 7 min) to afford the desired regioisomers rac-2-((1S,3R)-3-hydroxycyclohexyl)-6-methoxy-N-(pyrazolo[1,5-c]pyrimidin-3-yl)-2H-indazole-5-carboxamide as a yellow solid. This material was separated by chiral prep. HPLC (CHIRAL ART Cellulose-SB column, 2×25 cm, 5 μm; mobile Phase A: MTBE (0.5% 2N NH$_3$-MeOH), mobile Phase B: i-PrOH; flow rate: 20 mL/min; isocratic 50% B in 14 min) to afford rel-2-((1S, 3R)-3-hydroxycyclohexyl)-6-methoxy-N-(pyrazolo[1,5-a]pyrimidin-3-yl)-2H-indazole-5-carboxamide—Isomer 1 (26 mg, 5%, 99% ee) and rel-2-((1S,3R)-3-hydroxycyclohexyl)-6-methoxy-N-(pyrazolo[1,5-c]pyrimidin-3-yl)-2H-indazole-5-carboxamide—Isomer 2 (26 mg, 5%, 99% ee), both as yellow solids. Isomer 1: $^1$H NMR (400 MHz, DMSO-d$_6$) δ 10.35 (s, 1H), 9.05-9.12 (m, 1H), 8.73 (s, 1H), 8.51-8.57 (m, 2H), 8.47 (s, 1H), 7.22 (s, 1H), 7.00-7.10 (m, 1H), 4.82-4.86 (m, 1H), 4.45-4.55 (m, 1H), 4.06 (s, 3H), 3.55-3.67 (m, 1H), 2.25-2.34 (m, 1H), 2.00-2.11 (m, 1H), 1.68-1.95 (m, 4H), 1.40-1.51 (m, 1H), 1.13-1.26 (m, 1H). m/z (ES+), [M+H]$^+$=407. Isomer 2: $^1$H NMR (400 MHz, DMSO-d$_6$) δ 10.35 (s, 1H), 9.05-9.10 (m, 1H), 8.73 (s, 1H), 8.51-8.56 (m, 2H), 8.47 (s, 1H), 7.22 (s, 1H), 7.01-7.10 (m, 1H), 4.45-4.55 (m, 1H), 4.06 (s, 3H), 3.56-3.67 (m, 1H), 2.28-2.32 (m, 1H), 2.00-2.10 (m, 1H), 1.87-1.92 (m, 1H), 1.67-1.87 (m, 3H), 1.36-1.50 (m, 1H), 1.12-1.26 (m, 1H). m/z (ES+), [M+H]$^+$=407.

6-Cyclopropoxy-2-(2-hydroxy-2-methylspiro[3.5]nonan-7-yl)-N-(pyrazolo[1,5-a]pyrimidin-3-yl)-2H-indazole-5-carboxamide—Isomer 1 (Example 15) & Isomer 2 (Example 16)

ISOMER 1

ISOMER 2

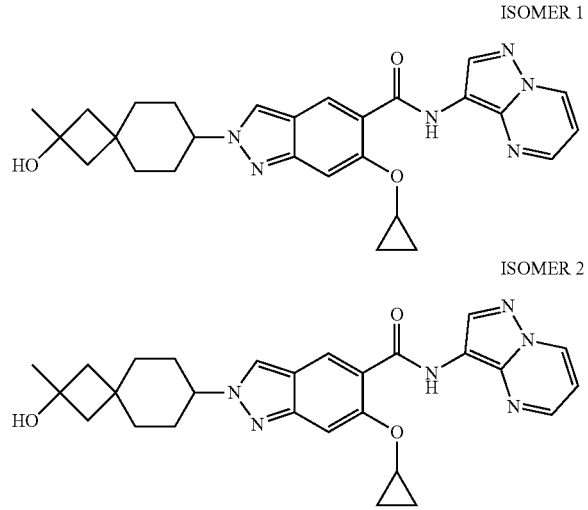

To a solution of 6-cyclopropoxy-N-(pyrazolo[1,5-c]pyrimidin-3-yl)-1H-indazole-5-carboxamide (Int II-3) (330 mg, 1.0 mmol) and 2-hydroxy-2-methylspiro[3.5]nonan-7-yl 4-methylbenzenesulfonate (Int III-3) (480 mg, 1.5 mmol) in DMF (15 mL) at rt was added Cs$_2$CO$_3$ (643 mg, 2.0 mmol). The reaction mixture was stirred at 85° C. for 5 h under N$_2$ atmosphere. The mixture was cooled to rt and purified directly by C18-flash chromatography (eluting with 0-100% MeCN in water (0.5% FA)) and further by prep. HPLC (Waters XBridge BEH C18 OBD, 5 μm, 30×150 mm; elution gradient with 35-55% MeCN in water (10 mM NH$_4$HCO$_3$+0.1% NH$_4$OH) in 7 min; 60 mL/min) to afford 6-cyclopropoxy-2-(2-hydroxy-2-methylspiro[3.5]nonan-7-yl)-N-(pyrazolo[1,5-a]pyrimidin-3-yl)-2H-indazole-5-carboxamide as a yellow solid. This material was separated by prep. chiral-HPLC (Chiralpak® IE 5 μm 20 mm×250 mm; isocratic with 50% hexane/DCM (75/25, 10 mM NH$_3$-MeOH) in MeOH; 20 mL/min) to afford 6-cyclopropoxy-2-(2-hydroxy-2-methylspiro[3.5]nonan-7-yl)-N-(pyrazolo[1,5-a]pyrimidin-3-yl)-2H-indazole-5-carboxamide—Isomer 1 (37 mg, 9%, 100% ee) and 6-cyclopropoxy-2-(2-hydroxy-2-methylspiro[3.5]nonan-7-yl)-N-(pyrazolo[1,5-a]pyrimidin-3-yl)-2H-indazole-5-carboxamide—Isomer 2 (38 mg, 9%, 95.8% ee), both as yellow solids. The $^1$H NMR and MS obtained for both products were identical. $^1$H NMR (300 MHz, DMSO-d$_6$) δ 10.31 (s, 1H), 9.07 (dd, 1H), 8.75 (s, 1H), 8.46-8.63 (m, 3H), 7.53 (s, 1H), 7.05 (dd, 1H), 4.76 (s, 1H), 4.34-4.49 (m, 1H), 4.15-4.26 (m, 1H), 1.67-2.08 (m, 10H), 1.37-1.67 (m, 2H), 1.27 (s, 3H), 1.03-1.12 (m, 2H). 0.92-1.03 (m, 2H). MS ESI, m/z=487 [M+H]$^+$.

6-Cyclopropoxy-2-(1R,3S)-3-hydroxycyclohexyl)-N-(pyrazolo[1,5-c]pyrimidin-3-yl)-2H-indazole-5-carboxamide (Example 17) & 6-Cyclopropoxy-2-(1S,3R)-3-hydroxycyclohexyl)-N-(pyrazolo[1,5-a]pyrimidin-3-yl)-2H-indazole-5-carboxamide (Example 18) rel-6-Cyclopropoxy-2-(1S,3S)-3-hydroxycyclohexyl)-N-(pyrazolo[1,5-a]pyrimidin-3-yl)-2H-indazole-5-carboxamide—Isomer 1 (Example 19) & Isomer 2 (Example 20) 3-Hydroxycyclohexyl 4-methylbenzenesulfonate

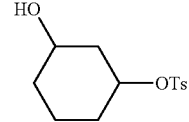

TsCl (17.2 g, 90.4 mmol) was slowly added to a solution of cyclohexane-1,3-diol (10.0 g, 86.1 mmol), DMAP (1.1 g, 8.6 mmol) and TEA (36.0 mL, 258.3 mmol) in DCM (100 mL) over a period of 5 min at 0° C. under N$_2$ atmosphere. The resulting mixture was stirred at rt for 15 h. The mixture was quenched with brine (100 mL), extracted with DCM (100 mL×2), dried over Na$_2$SO$_4$, filtered and concentrated under reduced pressure. The residue was purified by silica gel chromatography (eluting with 25-30% EtOAc in PE) to afford 3-hydroxycyclohexyl 4-methylbenzenesulfonate (8.0 g, 34%) as a yellow oil. MS ESI, m/z=271 [M+H]$^+$.

rac-6-Cyclopropoxy-2-(1S,3R)-3-hydroxycyclohexyl)-N-(pyrazolo[1,5-c]pyrimidin-3-yl)-2H-indazole-5-carboxamide & rac-6-Cyclopropoxy-2-(1S,3S)-3-hydroxycyclohexyl)-N-(pyrazolo[1,5-c]pyrimidin-3-yl)-2H-indazole-5-carboxamide

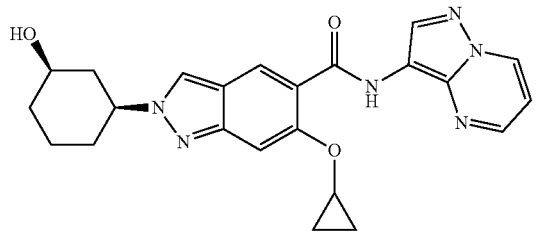

And Enantiomer

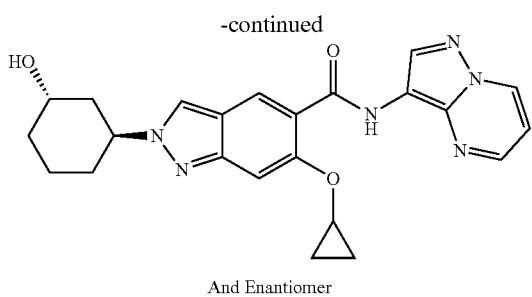

And Enantiomer

To a solution of 6-cyclopropoxy-N-(pyrazolo[1,5-c]pyrimidin-3-yl)-1H-indazole-5-carboxamide (Int II-3) (500 mg, 1.5 mmol) and 3-hydroxycyclohexyl 4-methylbenzenesulfonate (1.2 g, 4.5 mmol) in DMF (20 mL) at rt was added $Cs_2CO_3$ (1.5 g, 4.5 mmol). The reaction mixture was stirred at 100° C. for 5 h. The reaction mixture was cooled to rt and purified directly by C18-flash chromatography (eluting with 0-100% MeCN in water (0.5% FA)) followed by prep. HPLC (Waters XBridge BEH OBD C18, 5 μm 30 mm×150 mm; elution gradient with 24-34% MeCN in water (10 mM $NH_4HCO_3$+0.1% $NH_4OH$); 60 m L/m in) to afford rac-6-cyclopropoxy-2-((1S,3R)-3-hydroxycyclohexyl)-N-(pyrazolo[1,5-a]pyrimidin-3-yl)-2H-indazole-5-carboxamide (31 mg, 5%) and rac-6-cyclopropoxy-2-((1S,3S)-3-hydroxycyclohexyl)-N-(pyrazolo[1,5-c]pyrimidin-3-yl)-2H-indazole-5-carboxamide (110 mg, 17%), both as yellow solids.

6-Cyclopropoxy-2-(1R,3S)-3-hydroxycyclohexyl)-N-(pyrazolo[1,5-c]pyrimidin-3-yl)-2H-indazole-5-carboxamide (Example 17) & 6-Cyclopropoxy-2-(1S,3R)-3-hydroxycyclohexyl)-N-(pyrazolo[1,5-c]pyrimidin-3-yl)-2H-indazole-5-carboxamide (Example 18)

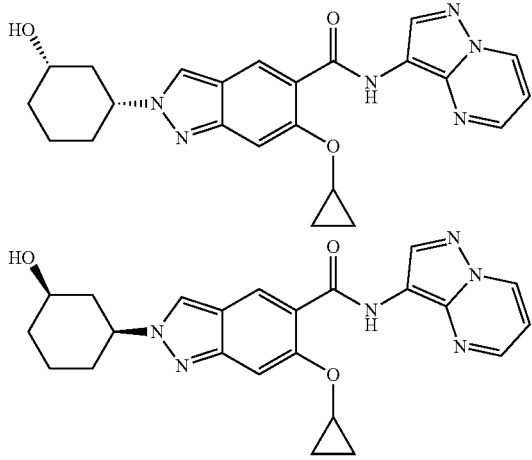

rac-6-Cyclopropoxy-2-((1S,3R)-3-hydroxycyclohexyl)-N-(pyrazolo[1,5-a]pyrimidin-3-yl)-2H-indazole-5-carboxamide (31 mg, 0.1 mmol) was separated by prep. chiral HPLC (Chiralpak® ID, 5 μm 30×250 mm; isocratic with 80% hexane/DCM (75/25, 10 mM $NH_3$-MeOH) in EtOH in 30 min; 45 mL/min) to afford 6-cyclopropoxy-2-((1R,3S)-3-hydroxycyclohexyl)-N-(pyrazolo[1,5-a]pyrimidin-3-yl)-2H-indazole-5-carboxamide (6 mg, 20%, 99.9% ee) and 6-cyclopropoxy-2-(1S,3R)-3-hydroxycyclohexyl)-N-(pyrazolo[1,5-c]pyrimidin-3-yl)-2H-indazole-5-carboxamide (10 mg, 33%, 99.5% ee), both as yellow solids. (1R,3S)—Isomer: $^1$H NMR (300 MHz, DMSO-$d_6$) δ 10.31 (s, 1H), 9.07 (dd, 1H), 8.75 (s, 1H), 8.57 (s, 1H), 8.55 (dd, 1H), 8.53 (s, 1H), 7.51 (s, 1H), 7.05 (dd, 1H), 4.85 (d, 1H), 4.45-4.62 (m, 1H), 4.18-4.28 (m, 1H), 3.53-3.69 (m, 1H), 2.24-2.29 (m, 1H), 1.98-2.12 (m, 1H), 1.69-1.96 (m, 4H), 1.31-1.53 (m, 1H), 1.10-1.31 (m, 1H), 0.93-1.10 (m, 4H). MS ESI, m/z=433 [M+H]$^+$. (1S,3R)—Isomer: $^1$H NMR (300 MHz, DMSO-$d_6$) δ 10.31 (s, 1H), 9.07 (dd, 1H), 8.75 (s, 1H), 8.49-8.58 (m, 3H), 7.51 (s, 1H), 7.05 (dd, 1H), 4.85 (d, 1H), 4.43-4.60 (m, 1H), 4.16-4.28 (m, 1H), 3.54-3.68 (m, 1H), 2.24-2.38 (m, 1H), 1.98-2.14 (m, 1H), 1.64-1.98 (m, 4H), 1.30-1.54 (m, 1H), 1.12-1.30 (m, 1H), 0.89-1.12 (m, 4H). MS ESI, m/z=433 [M+H]$^+$.

rel-6-Cyclopropoxy-2-(1S,3S)-3-hydroxycyclohexyl)-N-(pyrazolo[1,5-a]pyrimidin-3-yl)-2H-indazole-5-carboxamide—Isomer 1 (Example 19) & Isomer 2 (Example 20)

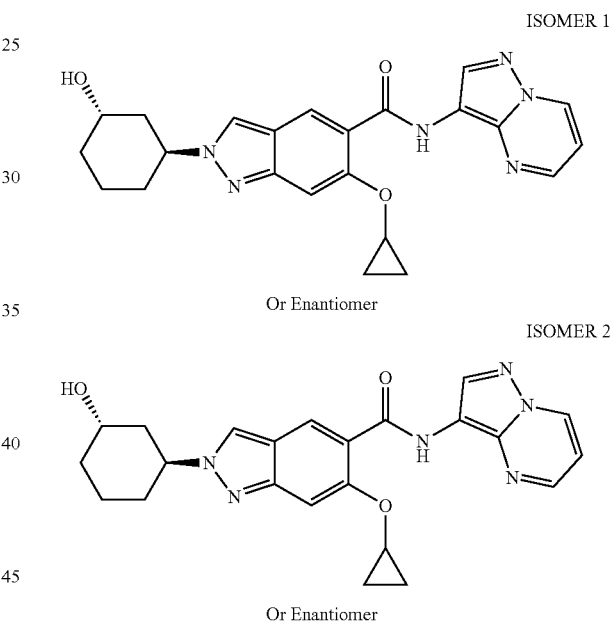

rac-6-Cyclopropoxy-2-((1S,3S)-3-hydroxycyclohexyl)-N-(pyrazolo[1,5-a]pyrimidin-3-yl)-2H-indazole-5-carboxamide (110 mg, 0.3 mmol) was separated by prep. chiral HPLC (YMC Chiral ART Cellulose-SB 5 μm 20 mm×250 mm; isocratic with 90% hexane/DCM (75/25, 10 mM $NH_3$-MeOH) in EtOH within 17 min; 20 mL/min) to afford rel-6-cyclopropoxy-2-((1S,3S)-3-hydroxycyclohexyl)-N-(pyrazolo[1,5-a]pyrimidin-3-yl)-2H-indazole-5-carboxamide—Isomer 1 (37 mg, 34%, 100% ee) and rel-6-cyclopropoxy-2-((1S,3S)-3-hydroxycyclohexyl)-N-(pyrazolo[1,5-c]pyrimidin-3-yl)-2H-indazole-5-carboxamide (22 mg, 20%, 98% ee)—Isomer 2, both as yellow solids. Isomer 1: $^1$H NMR (300 MHz, DMSO-$d_6$) δ 10.31 (s, 1H), 9.07 (dd, 1H), 8.75 (s, 1H), 8.59 (s, 1H), 8.55 (dd, 1H), 8.52 (s, 1H), 7.51 (s, 1H), 7.05 (dd, 1H), 4.74-4.88 (m, 1H), 4.71 (d, 1H), 4.17-4.27 (m, 1H), 4.10-4.17 (m, 1H), 2.00-2.16 (m, 3H), 1.75-2.00 (m, 2H), 1.53-1.75 (m, 2H), 1.42-1.53 (m, 1H), 0.94-1.12 (m, 4H). MS ESI, m/z=433 [M+H]$^+$. Isomer 2: $^1$H NMR (300 MHz, DMSO-$d_6$) δ 10.31 (s, 1H), 9.07 (dd, 1H), 8.75 (s, 1H), 8.59 (s, 1H), 8.55 (dd, 1H), 8.52 (s, 1H), 7.52 (s, 1H), 7.05 (dd, 1H), 4.70-4.88 (m, 1H), 4.16-4.26 (m, 1H), 4.08-4.16 (m, 1H), 1.99-2.17 (m, 3H), 1.76-1.99 (m, 2H), 1.56-1.76 (m, 2H), 1.38-1.56 (m, 1H), 0.93-1.12 (m, 4H). MS ESI, m/z=433 [M+H]$^+$.

2-(2-Acetyl-2-azaspiro[3.5]nonan-7-yl)-N-(imidazo [1,2-b]pyridazin-3-yl)-6-methoxy-2H-indazole-5-carboxamide (Example 21)

tert-Butyl 7-(5-(imidazo[1,2-b]pyridazin-3-ylcarbamoyl)-6-methoxy-2H-indazol-2-yl)-2-azaspiro [3.5]nonane-2-carboxylate

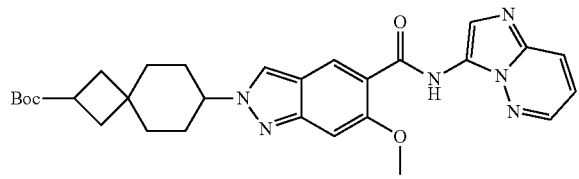 [SMILES: COc1cc2nn(C3CCC4(CC3)CC(C(=O)OC(C)(C)C)C4)cc2cc1C(=O)Nc1cnc2cccnn12]

To crude tert-butyl 7-((methylsulfonyl)oxy)-2-azaspiro [3.5]nonane-2-carboxylate (Int III-2) (1.5 g, 4.5 mmol) and N-(imidazo[1,2-b]pyridazin-3-yl)-6-methoxy-1H-indazole-5-carboxamide (Int II-1) (700 mg, 2.3 mmol) in DMF (20 mL) was added KOH (255 mg, 4.5 mmol) over a period of 2 min at rt and the resulting mixture was stirred at 100° C. overnight. Then, the reaction mixture was allowed to cool to rt, poured into water (150 mL) and extracted with EtOAc (3×100 mL). The combined organic layers were dried over Na$_2$SO$_4$, filtered and the solvent was removed in vacuo to afford a yellow solid. The residue was purified using C18-flash chromatography (eluting with 0 to 80% MeCN in water (0.05% FA)) to yield crude tert-butyl 7-(5-(imidazo[1,2-b] pyridazin-3-ylcarbamoyl)-6-methoxy-2H-indazol-2-yl)-2-azaspiro[3.5]nonane-2-carboxylate (280 mg), which was used without further purification.

N-(Imidazo[1,2-b]pyridazin-3-yl)-6-methoxy-2-(2-azaspiro[3.5]nonan-7-yl)-2H-indazole-5-carboxamide

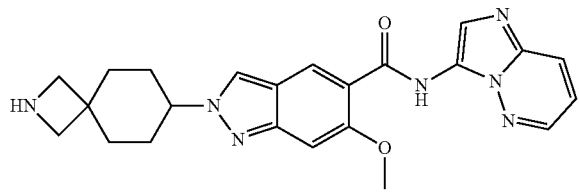 [SMILES: COc1cc2nn(C3CCC4(CC3)CNC4)cc2cc1C(=O)Nc1cnc2cccnn12]

To crude tert-butyl 7-(5-(imidazo[1,2-b]pyridazin-3-ylcarbamoyl)-6-methoxy-2H-indazol-2-yl)-2-azaspiro[3.5] nonane-2-carboxylate (280 mg) in DCM (4 mL) was added TFA (1.0 mL, 13.0 mmol) and the resulting mixture was stirred at rt. After 2 h, the solvent was removed in vacuo and the resulting residue was purified using C18-flash chromatography (eluting with 0 to 80% MeCN in water (5% NH$_4$OH)) to afford N-(imidazo[1,2-b]pyridazin-3-yl)-6-methoxy-2-(2-azaspiro[3.5]nonan-7-yl)-2H-indazole-5-carboxamide (60 mg, 26%) as a yellow solid. m/z (ESI+), [M+H]$^+$=432.

2-(2-Acetyl-2-azaspiro[3.5]nonan-7-yl)-N-(imidazo [1,2-b]pyridazin-3-yl)-6-methoxy-2H-indazole-5-carboxamide (Example 21)

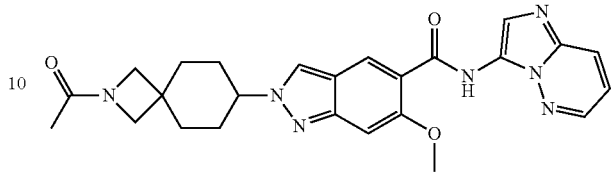

To N-(imidazo[1,2-b]pyridazin-3-yl)-6-methoxy-2-(2-azaspiro[3.5]nonan-7-yl)-2H-indazole-5-carboxamide (350 mg, 0.8 mmol) and TEA (452 µL, 3.2 mmol) in DCM (1 mL) was added acetic anhydride (0.2 mL, 1.6 mmol) at rt under N$_2$ atmosphere. The resulting solution was stirred for 1 h before the solvent was removed in vacuo to afford a yellow solid. The residue was purified using C18-flash chromatography (eluting with 60% to 70% MeCN in water (0.1% FA)) to afford 2-(2-acetyl-2-azaspiro[3.5]nonan-7-yl)-N-(imidazo[1,2-b]pyridazin-3-yl)-6-methoxy-2H-indazole-5-carboxamide (400 mg, 99%) as a yellow solid. $^1$H NMR (300 MHz, CD$_3$OD) (1:1 mixture of rotamers) δ 8.69 (s, 1H), 8.55-8.58 (m, 1H), 8.45 (s, 1H), 8.12 (s, 1H), 8.01 (d, 1H), 7.22 (dd, 1H), 7.18 (s, 1H), 4.52-4.55 (m, 1H), 4.21 (s, 3H), 4.06 (s, 1H), 3.93 (s, 1H), 3.83 (s, 1H), 3.69 (s, 1H), 1.95-2.28 (m, 6H), 1.89/1.91 (s, 3H) (rotamers), 1.74-1.87 (m, 2H). m/z (ESI+), [M+H]$^+$=474.

N-(Imidazo[1,2-b]pyridazin-3-yl)-6-methoxy-2-((1s, 4s)-4-(N-methylacetamido)cyclohexyl)-2H-indazole-5-carboxamide (Example 22)

(1r,4r)-4-((tert-Butoxycarbonyl)amino)cyclohexyl 4-methylbenzenesulfonate

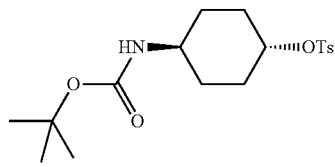 [SMILES: Cc1ccc(S(=O)(=O)O[C@H]2CC[C@H](NC(=O)OC(C)(C)C)CC2)cc1]

TsCl (5.3 g, 27.8 mmol) was added to tert-butyl ((1r,4r)-4-hydroxycyclohexyl)carbamate (5.0 g, 23.2 mmol) and TEA (6.5 mL, 46.6 mmol) in DCM (30 mL) over a period of 5 min at rt under N$_2$ atmosphere. After 2 h, the reaction mixture was poured into water (50 mL) and extracted with DCM (2×75 mL). The combined organic layers were dried over Na$_2$SO$_4$, filtered, and the solvent removed in vacuo. The resultant red oil was dissolved in DCM (50 mL) and filtered through a silica pad. The silica pad was washed with DCM (500 mL), and the solvent was removed in vacuo to afford crude (1r,4r)-4-((tert-butoxycarbonyl)amino)cyclohexyl 4-methylbenzenesulfonate (4.5 g), which was used without further purification.

(1r,4r)-4-((tert-Butoxycarbonyl)(methyl)amino)cyclohexyl 4-methylbenzenesulfonate

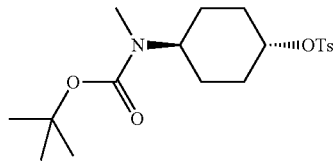 [SMILES: Cc1ccc(S(=O)(=O)O[C@H]2CC[C@H](N(C)C(=O)OC(C)(C)C)CC2)cc1]

To crude (1r,4r)-4-((tert-butoxycarbonyl)amino)cyclohexyl 4-methylbenzenesulfonate (4.5 g) and NaH (60 wt. %) (731 mg, 18.3 mmol) in DMF (10 mL) was added iodomethane (6.9 g, 48.6 mmol) dropwise at rt, the resulting mixture was stirred at 60° C. After 2 h, the reaction mixture was allowed to cool to rt, quenched with water (20 mL) and extracted with EtOAc (3×25 mL). The combined organic layers were dried over Na$_2$SO$_4$, filtered, and the solvent was removed in vacuo. The resulting residue was purified using C18-flash chromatography (eluting with 30% to 60% MeCN in water (0.05% FA)) to afford crude (1r,4r)-4-((tert-butoxycarbonyl)(methyl)amino)cyclohexyl 4-methylbenzenesulfonate (2.4 g), which was used without further purification.

tert-Butyl ((1s,4s)-4-(5-(imidazo[1,2-b]pyridazin-3-ylcarbamoyl)-6-methoxy-2H-indazol-2-yl)cyclohexyl)(methyl)carbamate

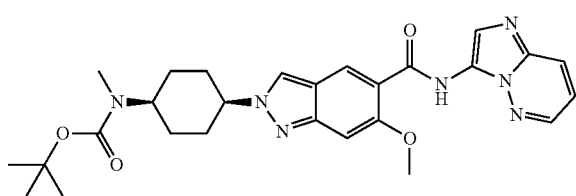 [SMILES: COc1cc2nn([C@H]3CC[C@@H](N(C)C(=O)OC(C)(C)C)CC3)cc2cc1C(=O)Nc1cnc2cccnn12]

To crude (1r,4r)-4-((tert-butoxycarbonyl)(methyl)amino)cyclohexyl 4-methylbenzenesulfonate (2.4 g) and KOH (182 mg, 3.2 mmol) in DMF (10 mL) was added N-(imidazo[1,2-b]pyridazin-3-yl)-6-methoxy-1H-indazole-5-carboxamide (Int II-1) (500 mg, 1.6 mmol) and the resulting solution was stirred at 100° C. After 12 h, the reaction mixture was allowed to cool to rt and directly purified using C18-flash chromatography (eluting with 20% to 100% MeCN in water (0.05% FA)) to afford crude tert-butyl ((1s,4s)-4-(5-(imidazo[1,2-b]pyridazin-3-ylcarbamoyl)-6-methoxy-2H-indazol-2-yl)cyclohexyl)(methyl)carbamate (0.6 g). m/z (ESI+), [M+H]$^+$=520.

N-(Imidazo[1,2-b]pyridazin-3-yl)-6-methoxy-2-((1s,4s)-4-(methylamino)cyclohexyl)-2H-indazole-5-carboxamide

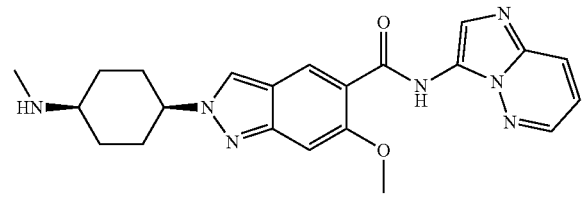 [SMILES: CN[C@H]1CC[C@@H](n2cc3cc(C(=O)Nc4cnc5cccnn45)c(OC)cc3n2)CC1]

To crude tert-butyl ((1s,4s)-4-(5-(imidazo[1,2-b]pyridazin-3-ylcarbamoyl)-6-methoxy-2H-indazol-2-yl)cyclohexyl)(methyl)carbamate (0.6 g) in 1,4-dioxane (6 mL) was added aq. HCl solution (12N, 1 mL, 12.0 mmol) and the resulting mixture was stirred at rt. After 2 h, the solvent was removed in vacuo to afford crude HCl salt of N-(imidazo[1,2-b]pyridazin-3-yl)-6-methoxy-2-((1s,4s)-4-(methylamino)cyclohexyl)-2H-indazole-5-carboxamide (0.5 g), which was used without further purification. m/z (ESI+), [M+H]$^+$=420.

N-(Imidazo[1,2-b]pyridazin-3-yl)-6-methoxy-2-((1s,4s)-4-(N-methylacetamido)cyclohexyl)-2H-indazole-5-carboxamide (Example 22)

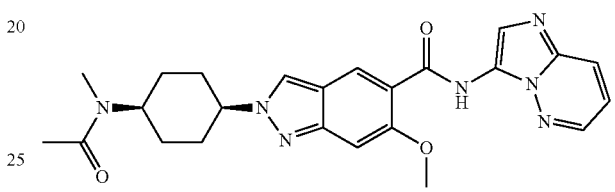

To crude HCl salt of N-(imidazo[1,2-b]pyridazin-3-yl)-6-methoxy-2-((1s,4s)-4-(methylamino)cyclohexyl)-2H-indazole-5-carboxamide (0.5 g) was added acetic anhydride (0.2 mL, 1.7 mmol) and TEA (0.6 mL, 4.4 mmol) in DCM (1 mL) at rt, and the resulting mixture was stirred at rt. After 5 min, additional acetic anhydride (0.2 mL, 1.7 mmol) was added and stirring was continued for 1 h. Then, the reaction mixture was quenched with water (5 mL) and the solvent was removed in vacuo. The resulting residue was purified using prep. HPLC (YMC-Actus Triart C18, 30×250, 5 μm; mobile Phase A: water (0.05% NH$_4$OH); mobile Phase B: MeCN; flow rate: 60 mL/min; gradient: 27% B to 47% B in 7 min) to afford N-(imidazo[1,2-b]pyridazin-3-yl)-6-methoxy-2-((1s,4s)-4-(N-methylacetamido) cyclohexyl)-2H-indazole-5-carboxamide (21.5 mg, 4%) as a yellow solid. $^1$H NMR (400 MHz, DMSO-d$_6$) (1:2 mixture of rotamers) δ 11.06 (s, 1H), 8.74 (s, 1H), 8.64 (dd, 1H), 8.60 (s, 1H), 8.15 (dd, 1H), 8.05 (s, 1H), 7.30 (s, 1H), 7.22 (dd, 1H), 4.40-4.49 (m, 1H), 4.13 (s, 3H), 3.75-3.86 (m, 1H), 2.68 (s, 2H), 2.55 (s, 1H), 1.99-2.15 (m, 3H), 2.07 (s, 1H), 1.96 (s, 2H), 1.63-1.88 (m, 3H), 1.52-1.63 (m, 1H), 1.38-1.47 (m, 1H). m/z (ESI+), [M+H]$^+$=462.

N-(Imidazo[1,2-b]pyridazin-3-yl)-6-methoxy-2-((1r,4r)-4-(N-methylacetamido)cyclohexyl)-2H-indazole-5-carboxamide (Example 23)

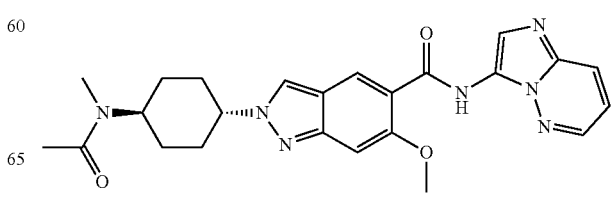

The crude HCl salt of N-(imidazo[1,2-b]pyridazin-3-yl)-6-methoxy-2-((1r,4r)-4-(methylamino) cyclohexyl)-2H-indazole-5-carboxamide (Int V-3) (390 mg) was added to TEA (477 μL, 3.4 mmol) in DCM (5 mL) at rt. After stirring of the resulting mixture for 5 min, acetic anhydride (1214, 1.3 mmol) was added. Stirring was continued for 1 h before the reaction was quenched with water (5 mL) and concentrated to give the crude product as a yellow oil. The crude product was purified by prep. HPLC (YMC-Actus Triart C18, 30×250, 5 μm; mobile phase A: Water (0.05% NH₄OH), mobile phase B: MeCN; flow rate: 60 mL/min; gradient: 27% B to 47% B in 7 min) to give N-(imidazo[1,2-b]pyridazin-3-yl)-6-methoxy-2-((1r,4r)-4-(N-methylacetamido)cyclohexyl)-2H-indazole-5-carboxamide (62 mg, 16%) as a yellow solid. 1H NMR (400 MHz, MeOD-d₄) (2:3 mixture of rotamers) δ 8.69-8.73 (m, 1H), 8.55-8.61 (m, 1H), 8.45-8.49 (m, 1H), 8.13 (m, 1H), 7.99-8.06 (m, 1H), 7.21-7.26 (m, 1H), 7.20 (s, 1H), 4.45-4.62/3.87-3.97 (m, 2H) (rotamers), 4.22/4.21 (s, 3H) (rotamers), 2.99/2.88 (s, 3H) (rotamers), 2.30-2.40 (m, 2H), 2.06-2.25 (m, 5H), 1.81-2.01 (m, 4H).

6-Methoxy-2-((1s,4s)-4-(N-methylacetamido)cyclohexyl)-N-(pyrazolo[1,5-c]pyrimidin-3-yl)-2H-indazole-5-carboxamide (Example 24) & 6-Methoxy-2-((1r,4r)-4-(N-methylacetamido)cyclohexyl)-N-(pyrazolo[1,5-c]pyrimidin-3-yl)-2H-indazole-5-carboxamide (Example 25)

tert-Butyl 4-(6-methoxy-5-(pyrazolo[1,5-c]pyrimidin-3-ylcarbamoyl)-2H-indazol-2-yl)cyclohexyl(methyl)carbamate

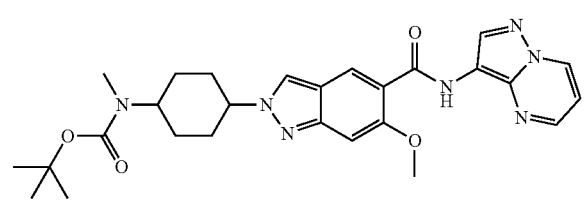 [SMILES: COc1cc2nn(C3CCC(N(C)C(=O)OC(C)(C)C)CC3)cc2cc1C(=O)Nc1cnn2cccnc12]

Cs₂CO₃ (3.2 g, 9.7 mmol) was added to a solution of 4-((tert-butoxycarbonyl)(methyl)amino)cyclohexyl 4-methylbenzenesulfonate (cis/trans ratio 1:5) (Int III-10) (2.5 g, 6.5 mmol) and 6-methoxy-N-(pyrazolo[1,5-a]pyrimidin-3-yl)-1H-indazole-5-carboxamide (Int II-2) (1.0 g, 3.2 mmol) in DMF (40 mL) under N₂ atmosphere. The resulting mixture was stirred at 90° C. for 4 h, allowed to cool to rt and purified directly first by flash C18-flash chromatography (eluting with 0 to 70% MeCN in water), followed by prep. HPLC (XBridge Prep OBD C18 column, 30×150 mm 5 μm; mobile phase A: Water (10 mM NH₄HCO₃+0.1% NH₄OH), mobile phase B: MeCN; flow rate: 60 mL/min; gradient: 40% B to 60% B in 7 min) to afford tert-butyl 4-(6-methoxy-5-(pyrazolo[1,5-c]pyrimidin-3-ylcarbamoyl)-2H-indazol-2-yl)cyclohexyl(methyl)carbamate (270 mg, 16%, cis/trans ratio 5:1) as a yellow solid. m/z (ES+), [M+H]⁺=520.

6-Methoxy-2-(4-(methylamino)cyclohexyl)-N-(pyrazolo[1,5-a]pyrimidin-3-yl)-2H-indazole-5-carboxamide

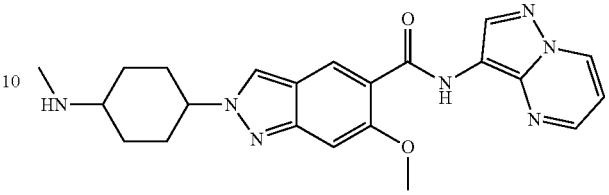

TFA (2 mL, 3.0 mmol) was added to tert-butyl (4-(6-methoxy-5-(pyrazolo[1,5-c]pyrimidin-3-ylcarbamoyl)-2H-indazol-2-yl)cyclohexyl(methyl)carbamate (150 mg, 0.3 mmol; cis/trans ratio 5:1) in DCM (4 mL). The resulting mixture was stirred at rt for 1 h. The solvent was removed under reduced pressure, the residue was dissolved in EtOAc and basified with aq. saturated NaHCO₃. The organic layer was washed with brine (3×50 mL), dried over Na₂SO₄, filtered and the solvent was evaporated under reduced pressure to afford the TFA salt of 6-methoxy-2-(4-(methylamino)cyclohexyl)-N-(pyrazolo[1,5-c]pyrimidin-3-yl)-2H-indazole-5-carboxamide (120 mg, 99%; cis/trans ratio 5:1). m/z (ES+), [M+H]⁺=420.

6-Methoxy-2-((1s,4s)-4-(N-methylacetamido)cyclohexyl)-N-(pyrazolo[1,5-c]pyrimidin-3-yl)-2H-indazole-5-carboxamide (Example 24) & 6-Methoxy-2-((1r,4r)-4-(N-methylacetamido)cyclohexyl)-N-(pyrazolo[1,5-c]pyrimidin-3-yl)-2H-indazole-5-carboxamide (Example 25)

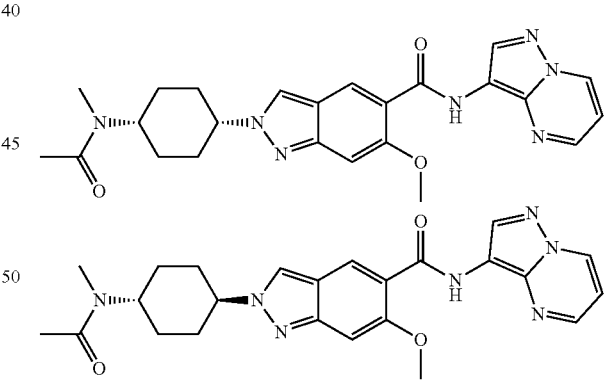

Acetic anhydride (58 mg, 0.6 mmol) was added to a solution of TEA (120 μL, 1.1 mmol) and the TFA salt of 6-methoxy-2-(4-(methylamino)cyclohexyl)-N-(pyrazolo[1,5-c]pyrimidin-3-yl)-2H-indazole-5-carboxamide (120 mg, 0.3 mmol) (cis/trans ratio 5:1) in DCM (3 mL). The resulting mixture was stirred at rt for 1 h. The solvent was removed under reduced pressure and the residue was purified first by C18-flash chromatography (eluting with 0 to 70% MeCN in water), then by prep. HPLC (XBridge Prep OBD C18 column, 30×150 mm 5 μm; mobile phase A: water (10 mmol/L NH₄HCO₃+0.1% NH₄OH), mobile phase B:

MeCN; flow rate: 60 mL/min; gradient: 16% B to 36% B in 7 min) to afford 6-methoxy-2-(4-(N-methylacetamido)cyclohexyl)-N-(pyrazolo[1,5-a]pyrimidin-3-yl)-2H-indazole-5-carboxamide (cis/trans ratio 5:1) as an orange solid. The two isomers were separated by chiral prep. HPLC (CHIRAL ART Cellulose-SB column, 2×25 cm, 5 μm; elution gradient 50% MTBE (0.5% 2N NH$_3$-MeOH) in EtOH; flow rate: 20 mL/min; over 13 min) to afford as first eluting isomer 6-methoxy-2-((1s,4s)-4-(N-methylacetamido)cyclohexyl)-N-(pyrazolo[1,5-c]pyrimidin-3-yl)-2H-indazole-5-carboxamide (90 mg, 68%, 100% ee) and as second eluting isomer 6-methoxy-2-((1r,4r)-4-(N-methylacetamido)cyclohexyl)-N-(pyrazolo[1,5-c]pyrimidin-3-yl)-2H-indazole-5-carboxamide (20 mg, 15%, 100% ee), both as yellow solid. (1s,4s)—Isomer: $^1$H NMR (300 MHz, DMSO-d$_6$) (1:1 mixture of rotamers) δ 10.37 (s, 1H), 9.05-9.12 (m, 1H), 8.75 (s, 1H), 8.70 (s, 1H), 8.53-8.57 (m, 1H), 8.49 (s, 1H), 7.27 (s, 1H), 7.00-7.11 (m, 1H), 4.70 (s, 1H), 4.39-4.54/3.74-3.88 (m, 1H) (rotamers), 4.08 (s, 3H), 2.54-2.72 (m, 5H), 1.92-2.20 (m, 5H), 1.52-1.90 (m, 3H), 1.38-1.50 (m, 1H). m/z (ES+), [M+H]$^+$=462. (1r,4r)—Isomer: $^1$H NMR (300 MHz, DMSO-d$_6$) (1:1 mixture of rotamers) δ 10.36 (s, 1H), 9.01-9.11 (m, 1H), 8.74 (s, 1H), 8.52-8.63 (m, 2H), 8.46-8.49 (m, 1H), 7.19-7.24 (m, 1H), 6.99-7.09 (m, 1H), 4.36-4.59/3.70-3.90 (m, 3H) (rotamers), 4.07 (s, 3H), 2.90 (s, 2H), 2.70 (s, 1H), 2.31-1.93 (m, 7H), 1.59-1.92 (m, 4H). m/z (ES+), [M+H]$^+$=462.

2-((1r,4r)-4-(Cyclopropanecarboxamido)cyclohexyl)-6-methoxy-N-(pyrazolo[1,5-c]pyrimidin-3-yl)-2H-indazole-5-carboxamide (Example 26) & 2-((1s,4s)-4-(Cyclopropanecarboxamido)cyclohexyl)-6-methoxy-N-(pyrazolo[1,5-c]pyrimidin-3-yl)-2H-indazole-5-carboxamide (Example 27)

tert-Butyl (4-(6-methoxy-5-(pyrazolo[1,5-c]pyrimidin-3-ylcarbamoyl)-2H-indazol-2-yl)cyclohexyl)carbamate

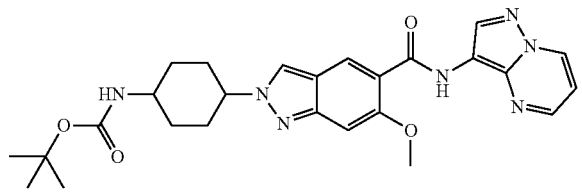 [SMILES: COc1cc2nn(C3CCC(NC(=O)OC(C)(C)C)CC3)cc2cc1C(=O)Nc1cnn2cccnc12]

To a suspension of 6-methoxy-N-(pyrazolo[1,5-c]pyrimidin-3-yl)-1H-indazole-5-carboxamide (Int II-2) (500 mg, 1.6 mmol) and 4-((tert-butoxycarbonyl)amino)cyclohexyl 4-methylbenzenesulfonate (cis/trans ratio 1:5) (Int III-9) (1.5 g, 4.1 mmol) in DMF (15 mL) under N$_2$ atmosphere was added Cs$_2$CO$_3$ (1.6 g, 4.9 mmol) at rt over a period of 2 min. The reaction mixture was stirred at 90° C. for 3 h. The mixture was cooled to rt and was purified directly by C18-flash chromatography (eluting with 0-80% MeCN in water (1% NH$_4$OH)) to afford tert-butyl (4-(6-methoxy-5-(pyrazolo[1,5-a]pyrimidin-3-ylcarbamoyl)-2H-indazol-2-yl)cyclohexyl)carbamate (cis/trans ratio 7:1) (280 mg, 34%) as a yellow solid. MS ESI, m/z=506 [M+H]$^+$.

2-(4-Aminocyclohexyl)-6-methoxy-N-(pyrazolo[1,5-c]pyrimidin-3-yl)-2H-indazole-5-carboxamide

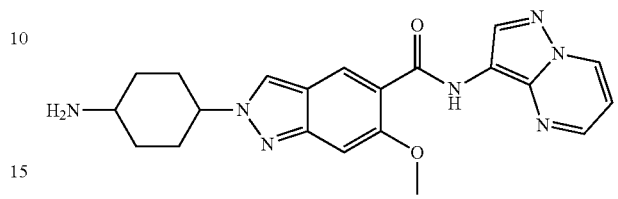

To a solution of tert-butyl (4-(6-methoxy-5-(pyrazolo[1,5-c]pyrimidin-3-ylcarbamoyl)-2H-indazol-2-yl)cyclohexyl)carbamate (cis/trans ratio 7:1)) (280 mg, 0.6 mmol) in DCM (20 mL) at rt was added 4N HCl in dioxane (1.4 mL, 5.6 mmol) dropwise over a period of 2 min under N$_2$ atmosphere. The reaction mixture was stirred for 2 h before it was concentrated under reduced pressure to afford the crude HCl salt of 2-(4-aminocyclohexyl)-6-methoxy-N-(pyrazolo[1,5-c]pyrimidin-3-yl)-2H-indazole-5-carboxamide (cis/trans ratio 7:1)) (270 mg, ~90 wt. %), which was used without further purification. MS ESI, m/z=406 [M+H]$^+$.

2-((1r,4r)-4-(Cyclopropanecarboxamido)cyclohexyl)-6-methoxy-N-(pyrazolo[1,5-c]pyrimidin-3-yl)-2H-indazole-5-carboxamide (Example 26) & 2-((1s,4s)-4-(Cyclopropanecarboxamido)cyclohexyl)-6-methoxy-N-(pyrazolo[1,5-c]pyrimidin-3-yl)-2H-indazole-5-carboxamide (Example 27)

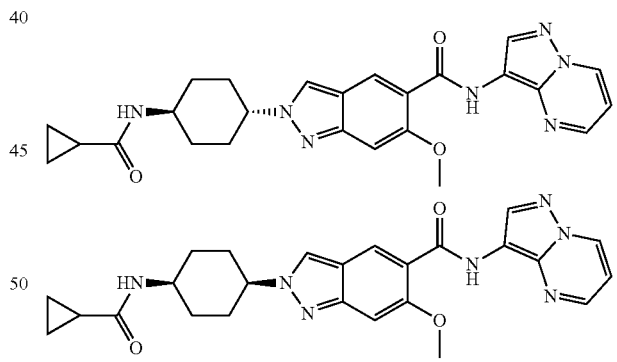

To a solution of the crude HCl salt of 2-(4-aminocyclohexyl)-6-methoxy-N-(pyrazolo[1,5-c]pyrimidin-3-yl)-2H-indazole-5-carboxamide (cis/trans ratio 7:1) (90 wt. %) (270 mg) and TEA (250 μL, 1.8 mmol) in DCM (4 mL) was slowly added 4-bromobutanoyl chloride (227 mg, 1.2 mmol) at rt over a period of 2 min under N$_2$ atmosphere and the resulting mixture was stirred for 2 h. The mixture was purified directly by C18-flash chromatography (eluting with 0-90% MeCN in water (0.5% FA)) and further by prep. HPLC (Waters Xbridge® Shield RP18 OBD, 5 μm 30×150 mm; elution gradient with 26-34% MeCN in water (0.05% NH$_4$OH) in 8 min; 60 mL/min) to afford 2-((1r,4r)-4-

(cyclopropanecarboxamido)cyclohexyl)-6-methoxy-N-(pyrazolo[1,5-a]pyrimidin-3-yl)-2H-indazole-5-carboxamide (8 mg, 3%), after this material was purified again by prep. HPLC (Waters Xbridge® BEH OBD C18, 5 μm 30×150 mm; elution gradient with 35-50% MeCN in water (10 mM NH$_4$HCO$_3$ and 0.1% NH$_4$OH) in 7 min; 60 mL/min), and 2-((1s,4s)-4-(cyclopropanecarboxamido)cyclohexyl)-6-methoxy-N-(pyrazolo[1,5-c]pyrimidin-3-yl)-2H-indazole-5-carboxamide (52 mg, 20%), both as yellow solids. (1r,4r)—Isomer: $^1$H NMR (300 MHz, DMSO-d$_6$) δ 10.34 (s, 1H), 9.07 (dd, 1H), 8.73 (s, 1H), 8.51-8.59 (m, 2H), 8.47 (s, 1H), 8.04 (d, 1H), 7.22 (s, 1H), 7.05 (dd, 1H), 4.42-4.56 (m, 1H), 4.06 (s, 3H), 3.60-3.74 (m, 1H), 2.10-2.23 (m, 2H), 1.89-2.06 (m, 4H), 1.33-1.61 (m, 3H), 0.58-0.74 (m, 4H). MS ESI, m/z=474 [M+H]$^+$. (1s,4s)—Isomer: $^1$H NMR (300 MHz, DMSO-d$_6$) δ 10.35 (s, 1H), 9.07 (dd, 1H), 8.73 (s, 1H), 8.59 (s, 1H), 8.54 (dd, 1H), 8.50 (s, 1H), 8.07 (d, 1H), 7.22 (s, 1H), 7.05 (dd, 1H), 4.46-4.60 (m, 1H), 4.07 (s, 3H), 3.87-4.00 (m, 1H), 2.25-2.39 (m, 2H), 1.89-2.10 (m, 2H), 1.58-1.87 (m, 5H), 0.56-0.76 (m, 4H). MS ESI, m/z=474 [M+H]$^+$.

rel-2-(6R,7R)-2-Acetyl-6-methyl-2-azaspiro[3.5]nonan-7-yl)-6-cyclopropoxy-N-(pyrazolo[1,5-c]pyrimidin-3-yl)-2H-indazole-5-carboxamide—Isomer 1 (Example 28) & Isomer 2 (Example 29)

rel-2-((6S,7R)-2-Acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 1 (Example 30) & Isomer 2 (Example 31)

rac-tert-Butyl (6R,7R)-7-(6-cyclopropoxy-5-(pyrazolo[1,5-c]pyrimidin-3-ylcarbamoyl)-2H-indazol-2-yl)-6-methyl-2-azaspiro[3.5]nonane-2-carboxylate

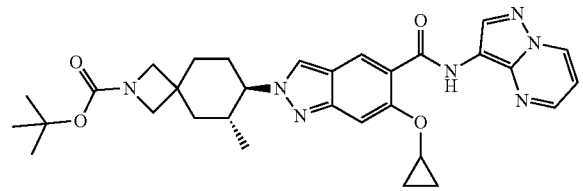

And Enantiomer

To a solution of 6-cyclopropoxy-N-(pyrazolo[1,5-c]pyrimidin-3-yl)-1H-indazole-5-carboxamide (Int II-3) (500 mg, 1.5 mmol) and rac-tert-butyl (6R,7S)-6-methyl-7-((methylsulfonyl)oxy)-2-azaspiro[3.5]nonane-2-carboxylate (Int III-5) (748 mg, 2.2 mmol) in DMF (10 mL) at rt was added Cs$_2$CO$_3$ (1.5 g, 4.5 mmol). The reaction mixture was stirred at 100° C. for 12 h. The mixture was cooled to rt and was purified directly by C18-flash chromatography (eluting with 80-100% MeCN in water (0.1% NH$_4$OH)) to afford crude rac-tert-butyl (6R,7R)-7-(6-cyclopropoxy-5-(pyrazolo[1,5-c]pyrimidin-3-ylcarbamoyl)-2H-indazol-2-yl)-6-methyl-2-azaspiro[3.5]nonane-2-carboxylate (400 mg). MS ESI, m/z=572 [M+H]$^+$.

rac-6-Cyclopropoxy-2-(6R,7R)-6-methyl-2-azaspiro[3.5]nonan-7-yl)-N-(pyrazolo[1,5-a]pyrimidin-3-yl)-2H-indazole-5-carboxamide

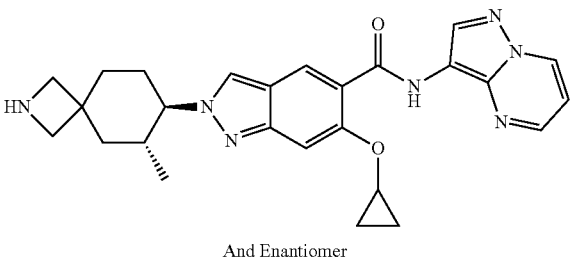 [SMILES: C[C@@H]1CC2(CC[C@H]1n1cc3cc(C(=O)Nc4cnn5cccnc45)c(OC4CC4)cc3n1)CNC2]

And Enantiomer

To a solution of crude rac-tert-butyl (6R,7R)-7-(6-cyclopropoxy-5-(pyrazolo[1,5-c]pyrimidin-3-ylcarbamoyl)-2H-indazol-2-yl)-6-methyl-2-azaspiro[3.5]nonane-2-carboxylate (400 mg) in DCM (8 mL) was added TFA (2.0 mL, 26.0 mmol) dropwise, and the resulting solution was stirred at rt for 4 h. The mixture was concentrated under reduced pressure to afford the crude TFA salt of rac-6-cyclopropoxy-2-(6R,7R)-6-methyl-2-azaspiro[3.5]nonan-7-yl)-N-(pyrazolo[1,5-a]pyrimidin-3-yl)-2H-indazole-5-carboxamide (350 mg) as a yellow oil, which was used without further purification. MS ESI, m/z=472 [M+H]$^+$.

rel-2-(6R,7R)-2-Acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 1 (Example 28) & Isomer 2 (Example 29)

ISOMER 1

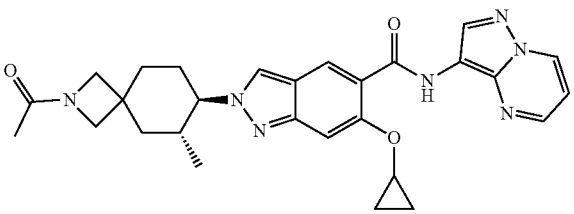

Or Enantiomer

ISOMER 2

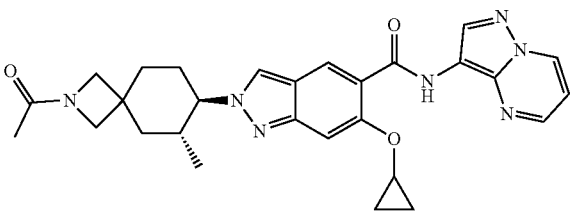

Or Enantiomer

To a solution of the crude TFA salt of rac-6-cyclopropoxy-2-((6R,7R)-6-methyl-2-azaspiro[3.5]nonan-7-yl)-N-(pyrazolo[1,5-c]pyrimidin-3-yl)-2H-indazole-5-carboxamide (350 mg) and TEA (250 µL, 1.8 mmol) in DCM (5 mL) was added acetyl chloride (110 mg, 1.4 mmol) at 0° C. under N₂ atmosphere. The resulting mixture was stirred at rt for 3 h. The reaction mixture was concentrated under reduced pressure. The residue was purified by prep. HPLC (Waters SunFire® C18 OBD, 5 µm 30×150 mm; elution gradient with 35-45% MeCN in water (0.1% FA) in 7 min; 60 mL/min) and then by prep. chiral HPLC (Chiralpak® IA 5 µm 20 mm×250 mm; isocratic with 25% MTBE (2 mM NH₃-MeOH) in EtOH in 27 min; 15 mL/min) to afford rel-2-((6R,7R)-2-acetyl-6-methyl-2-azaspiro[3.5]nonan-7-yl)-6-cyclopropoxy-N-(pyrazolo[1,5-c]pyrimidin-3-yl)-2H-indazole-5-carboxamide—Isomer 1 (15 mg, 5%, 100% ee) and rel-2-((6R,7R)-2-acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 2 (15 mg, 5%, 99.7% ee), both as yellow solids. The ¹H NMR and MS obtained for both products were identical. ¹H NMR (400 MHz, DMSO-d₆) (1:1 mixture of rotamers) δ 10.30 (s, 1H), 9.07 (d, 1H), 8.75 (s, 1H), 8.56 (s, 1H), 8.55 (d, 1H), 8.53 (s, 1H), 7.54/7.52 (s, 1H) (rotamers), 7.05 (dd, 1H), 4.16-4.24 (m, 1H), 4.05-4.16 (m, 1H), 3.97/3.80 (s, 2H) (rotamers), 3.68/3.53 (s, 2H) (rotamers), 2.06-2.17 (m, 1H), 1.88-2.06 (m, 4H), 1.80/1.77 (s, 3H) (rotamers), 1.60-1.72 (m, 1H), 1.42 (t, 1H), 1.03-1.11 (m, 2H), 0.93-1.03 (m, 2H), 0.59 (br. d, 3H). MS ESI, m/z=514 [M+H]⁺.

rac-tert-Butyl (6S,7R)-7-(6-cyclopropoxy-5-(pyrazolo[1,5-c]pyrimidin-3-ylcarbamoyl)-2H-indazol-2-yl)-6-methyl-2-azaspiro[3.5]nonane-2-carboxylate

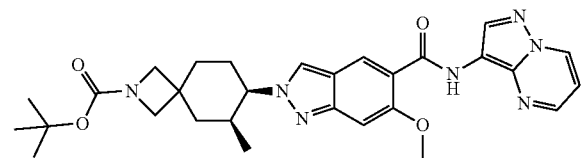

And Enantiomer

To a solution of 6-cyclopropoxy-N-(pyrazolo[1,5-c]pyrimidin-3-yl)-1H-indazole-5-carboxamide (Int II-3) (600 mg, 1.8 mmol) and rac-tert-butyl (6S,7S)-6-methyl-7-((methylsulfonyl)oxy)-2-azaspiro[3.5]nonane-2-carboxylate (Int III-6) (1.1 g, 3.2 mmol) in DMF (6 mL) at rt was added Cs₂CO₃ (1.8 g, 5.4 mmol) under N₂ atmosphere. The reaction mixture was stirred at 95° C. for 12 h. The mixture was cooled to rt and was purified directly by C18-flash chromatography (eluting with 0-100% MeOH in water (0.05% FA)) to afford crude rac-tert-butyl (6S,7R)-7-(6-cyclopropoxy-5-(pyrazolo[1,5-c]pyrimidin-3-ylcarbamoyl)-2H-indazol-2-yl)-6-methyl-2-azaspiro[3.5]nonane-2-carboxylate (900 mg) as a yellow solid, which contained ca. 30% N1-isomer. MS ESI, m/z=572 [M+H]⁺.

rac-6-Cyclopropoxy-2-(6S,7R)-6-methyl-2-azaspiro[3.5]nonan-7-yl)-N-(pyrazolo[1,5-a]pyrimidin-3-yl)-2H-indazole-5-carboxamide

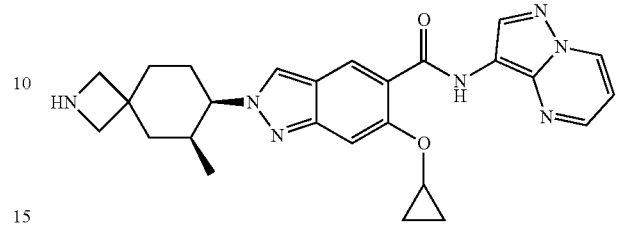

And Enantiomer

To a solution of crude rac-tert-butyl (6S,7R)-7-(6-cyclopropoxy-5-(pyrazolo[1,5-c]pyrimidin-3-ylcarbamoyl)-2H-indazol-2-yl)-6-methyl-2-azaspiro[3.5]nonane-2-carboxylate (900 mg) (containing 30% N1-isomer) in DCM (5 mL) was added TFA (243 mL, 31.5 mmol) dropwise under N₂ atmosphere, and the resulting solution was stirred at rt for 12 h. The mixture was concentrated under reduced pressure to afford the crude TFA salt of rac-6-cyclopropoxy-2-(6S,7R)-6-methyl-2-azaspiro[3.5]nonan-7-yl)-N-(pyrazolo[1,5-c]pyrimidin-3-yl)-2H-indazole-5-carboxamide (710 mg) as a yellow solid, containing some N1-isomer. MS ESI, m/z=472 [M+H]⁺.

rel-2-(6S,7R)-2-Acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 1 (Example 30) & Isomer 2 (Example 31)

ISOMER 1

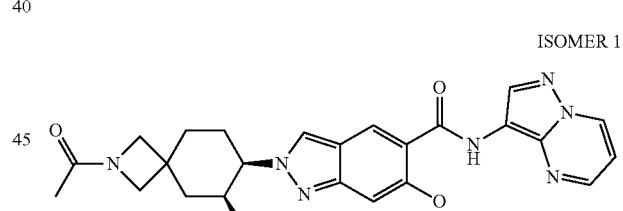

Or Enantiomer

ISOMER 2

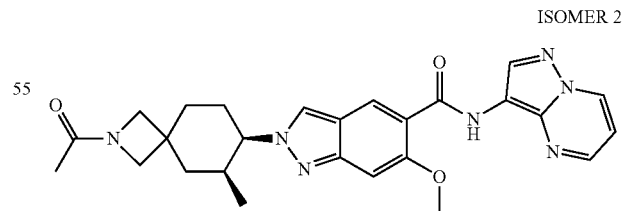

Or Enantiomer

To a solution of the crude TFA salt of rac-6-cyclopropoxy-2-(6S,7R)-6-methyl-2-azaspiro[3.5]nonan-7-yl)-N-(pyrazolo[1,5-a]pyrimidin-3-yl)-2H-indazole-5-carboxamide (700 mg) and TEA (833 μL, 6.0 mmol) in DCM (5 mL) was added acetyl chloride (188 mg, 2.4 mmol) at rt under N₂ atmosphere. The resulting mixture was stirred at rt for 3 h. The mixture was concentrated under reduced pressure. The residue was purified by C18-flash chromatography (eluting with 0-100% MeCN in water (0.05% TFA)) to afford rac-2-(6S,7R)-2-acetyl-6-methyl-2-azaspiro[3.5]nonan-7-yl)-6-cyclopropoxy-N-(pyrazolo[1,5-a]pyrimidin-3-yl)-2H-indazole-5-carboxamide (100 mg), which was further purified by prep. HPLC (Waters XBridge BEH OBD C18, 5 μm 30×150 mm; elution gradient with 30-50% MeCN in water (10 mM NH₄HCO₃+0.1% NH₄OH) in 7 min; 60 mL/min) and then separated by prep. chiral HPLC (YMC CHIRAL ART Cellulose-SB 5 μm 20 mm×250 mm; isocratic with 50% hexane/DCM (75/25, 10 mM NH₃-MeOH) in EtOH; 20 mL/min) to afford rel-2-((6S,7R)-2-acetyl-6-methyl-2-azaspiro[3.5]nonan-7-yl)-6-cyclopropoxy-N-(pyrazolo[1,5-a]pyrimidin-3-yl)-2H-indazole-5-carboxamide—Isomer 1 (30 mg, 4%, 99.5% ee) and rel-2-((6S,7R)-2-acetyl-6-methyl-2-azaspiro[3.5]nonan-7-yl)-6-cyclopropoxy-N-(pyrazolo[1,5-c]pyrimidin-3-yl)-2H-indazole-5-carboxamide—Isomer 2 (30 mg, 4%, 100% ee) as yellow solids. The ¹H NMR and MS obtained for both products were identical. ¹H NMR (400 MHz, DMSO-d₆) δ 10.31 (s, 1H), 9.07 (dd, 1H), 8.75 (s, 1H), 8.50-8.59 (m, 3H), 7.53 (d, 1H), 7.05 (dd, 1H), 4.68 (br. s, 1H), 4.24 (br. s, 1H), 3.82-3.93 (m, 2H), 3.56-3.67 (m, 2H), 2.30-2.42 (m, 1H), 1.90-2.30 (m, 4H), 1.69-1.83 (m, 5H), 1.03-1.12 (m, 2H), 0.92-1.03 (m, 2H), 0.52-0.67 (m, 3H). MS ESI, m/z=514 [M+H]⁺.

6-Cyclopropoxy-2-((1s,4s)-4-(N-methylacetamido)cyclohexyl)-N-(pyrazolo[1,5-a]pyrimidin-3-yl)-2H-indazole-5-carboxamide (Example 32) & 6-Cyclopropoxy-2-((1r,4r)-4-(N-methylacetamido)cyclohexyl)-N-(pyrazolo[1,5-a]pyrimidin-3-yl)-2H-indazole-5-carboxamide (Example 33)

tert-Butyl (4-(6-cyclopropoxy-5-(pyrazolo[1,5-c]pyrimidin-3-ylcarbamoyl)-2H-indazol-2-yl)cyclohexyl)(methyl)carbamate

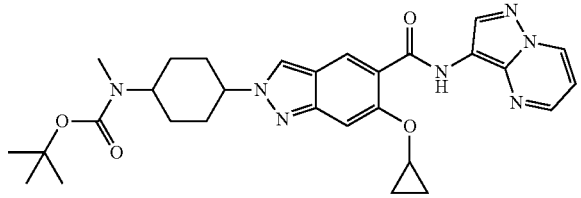 [SMILES: CN(C(=O)OC(C)(C)C)C1CCC(n2cc3cc(C(=O)Nc4cnn5cccnc45)c(OC4CC4)cc3n2)CC1]

To a solution of 4-((tert-butoxycarbonyl)(methyl)amino)cyclohexyl 4-methylbenzenesulfonate (cis/trans ratio 1:5) (Int III-10) (2.3 g, 6.0 mmol) and 6-cyclopropoxy-N-(pyrazolo[1,5-c]pyrimidin-3-yl)-1H-indazole-5-carboxamide (Int II-3) (1.0 g, 3.0 mmol) in DMF (30 mL) was added Cs₂CO₃ (2.9 g, 9.0 mmol). The reaction mixture was stirred at 90° C. for 4 h. The mixture was cooled to rt and purified directly by C18-flash chromatography (eluting with 0-80% MeCN in water (0.1% NH₄OH)) and further by prep. HPLC (Waters XBridge BEH OBD C18 5 μm 30×150 mm; elution gradient with 47-67% MeCN in water (10 mM NH₄HCO₃ and 0.1% NH₄OH) in 7 min; 60 mL/min) to afford tert-butyl (4-(6-cyclopropoxy-5-(pyrazolo[1,5-c]pyrimidin-3-ylcarbamoyl)-2H-indazol-2-yl)cyclohexyl)(methyl) carbamate (cis/trans ratio 5:1) (180 mg, 11%) as an orange solid. MS ESI, m/z=546 [M+H]⁺.

6-Cyclopropoxy-2-(4-(methylamino)cyclohexyl)-N-(pyrazolo[1,5-c]pyrimidin-3-yl)-2H-indazole-5-carboxamide

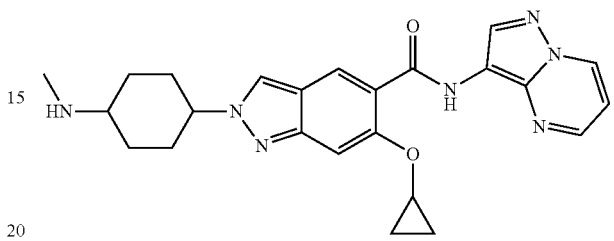

To a solution of tert-butyl (4-(6-cyclopropoxy-5-(pyrazolo[1,5-a]pyrimidin-3-ylcarbamoyl)-2H-indazol-2-yl)cyclohexyl)(methyl)carbamate (cis/trans ratio 5:1) (150 mg, 0.3 mmol) in DCM (6 mL) was added TFA (3.0 mL, 38.9 mmol) dropwise, and the resulting solution was stirred at rt for 1 h. The mixture was concentrated under reduced pressure to afford the crude TFA salt of 6-cyclopropoxy-2-(4-(methylamino)cyclohexyl)-N-(pyrazolo[1,5-c]pyrimidin-3-yl)-2H-indazole-5-carboxamide (cis/trans ratio 5:1) (130 mg, 94 wt. %). The crude product was used without further purification. MS ESI, m/z=446 [M+H]⁺.

6-Cyclopropoxy-2-((1s,4s)-4-(N-methylacetamido)cyclohexyl)-N-(pyrazolo[1,5-c]pyrimidin-3-yl)-2H-indazole-5-carboxamide (Example 32) & 6-Cyclopropoxy-2-((1r,4r)-4-(N-methylacetamido)cyclohexyl)-N-(pyrazolo[1,5-c]pyrimidin-3-yl)-2H-indazole-5-carboxamide (Example 33)

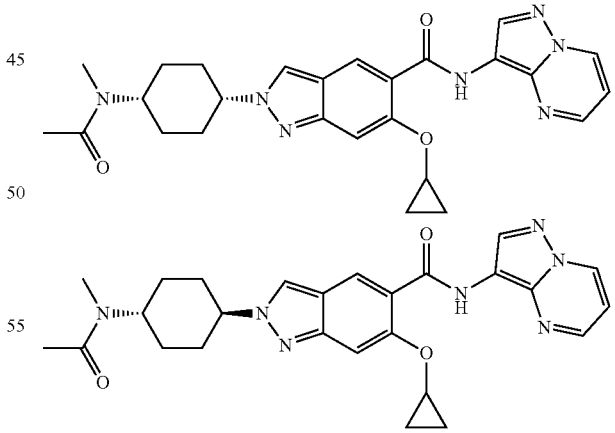

To a solution of the crude TFA salt of 6-cyclopropoxy-2-(4-(methylamino)cyclohexyl)-N-(pyrazolo[1,5-a]pyrimidin-3-yl)-2H-indazole-5-carboxamide (cis/trans ratio 5:1) (120 mg, 94 wt. %) and TEA (150 μL, 1.1 mmol) in DCM (5 mL) was added acetic anhydride (55 mg, 0.5 mmol) at rt. The resulting mixture was stirred for 1 h. The reaction mixture was concentrated under reduced pressure and the crude product was purified by C18-flash chromatography (eluting with 0-80% MeCN in water (0.1% FA)) to afford 6-cyclopropoxy-2-(4-(N-methylacetamido)cyclohexyl)-N-(pyrazolo[1,5-c]pyrimidin-3-yl)-2H-indazole-5-carboxamide as an orange solid. The solid was separated by prep. chiral HPLC (Chiralpak® ID-2, 5 μm 20×250 mm; isocratic with 70% hexane/DCM (3/1, 0.5% 2N NH₃-MeOH solution) in MeOH; flow rate: 20 mL/min) to afford 6-cyclopropoxy-2-((1s,4s)-4-(N-methylacetamido)cyclohexyl)-N-(pyrazolo[1,5-c]pyrimidin-3-yl)-2H-indazole-5-carboxamide (90 mg, 63%, 99.9% ee) and 6-cyclopropoxy-2-((1r,4r)-4-(N-methylacetamido)cyclohexyl)-N-(pyrazolo[1,5-c]pyrimidin-3-yl)-2H-indazole-5-carboxamide (20 mg, 14%, 99.0% ee). (1s,4s)—Isomer: ¹H NMR (300 MHz, DMSO-d₆) (mix of rotamers) δ 10.34 (s, 1H), 9.08 (dd, 1H), 8.76 (s, 1H), 8.73 (s, 1H), 8.50-8.65 (m, 2H), 7.55 (s, 1H), 7.06 (dd, 1H), 4.63-4.78 (m, 1H), 4.38-4.54/3.72-3.90 (m, 1H) (rotamers), 4.17-4.30 (m, 1H), 2.54-2.77 (m, 2H), 2.55/2.69 (s, 3H) (rotamers), 1.91-2.22 (m, 2H), 1.97/2.08 (s, 3H) (rotamers), 1.38-1.89 (m, 4H), 1.04-1.13 (m, 2H), 0.94-1.04 (m, 2H). MS ESI, m/z=488 [M+H]⁺. (1r,4r)—Isomer: ¹H NMR (300 MHz, DMSO-d₆) (mix of rotamers) δ 10.34 (s, 1H), 9.08 (dd, 1H), 8.76 (s, 1H), 8.49-8.67 (m, 3H), 7.44-7.57 (m, 1H), 7.06 (dd, 1H), 4.46-4.61 (m, 1H), 4.36-4.46/3.71-3.87 (m, 1H) (rotamers), 4.17-4.30 (m, 1H), 2.74/2.87 (s, 3H) (rotamers), 2.16-2.33 (m, 2H), 2.01/2.10 (s, 3H) (rotamers), 1.93-2.16 (m, 2H), 1.65-1.93 (m, 4H), 1.02-1.13 (m, 2H), 0.92-1.02 (m, 2H). MS ESI, m/z=488 [M+H]⁺.

N-(Imidazo[1,2-b]pyridazin-3-yl)-6-methoxy-2-((1S, 2S,4R*)-2-methyl-4-(N-methylacetamido) cyclohexyl)-2H-indazole-5-carboxamide—Isomer 1 (Example 34) & Isomer 2 (Example 35)

N-(Imidazo[1,2-b]pyridazin-3-yl)-6-methoxy-2-(1R, 2R,4R*)-2-methyl-4-(N-methylacetamido) cyclohexyl)-2H-indazole-5-carboxamide—Isomer 1 (Example 36) & Isomer 2 (Example 37)

N-(Imidazo[1,2-b]pyridazin-3-yl)-6-methoxy-2-((1S, 2S)-2-methyl-4-(methylamino)cyclohexyl)-2H-indazole-5-carboxamide

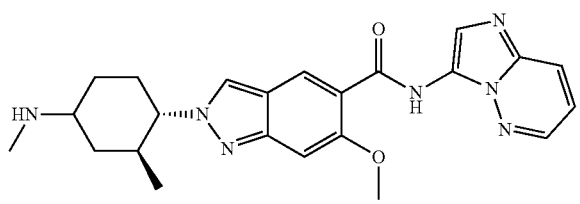 [SMILES: CNC1CC[C@H](n2cc3cc(C(=O)Nc4cnc5cccnn45)c(OC)cc3n2)[C@@H](C)C1]

To a solution of N-(imidazo[1,2-b]pyridazin-3-yl)-6-methoxy-2-((1S,2S)-2-methyl-4-oxocyclohexyl)-2H-indazole-5-carboxamide (Int v-1) (100 mg, 0.2 mmol) and 1M methylamine-MeOH solution (1.2 mL, 1.2 mmol) in DCM (5 mL) was added sodium triacetoxyborohydride (101 mg, 0.5 mmol). The resulting mixture was stirred at rt for 1 h. The reaction mixture was concentrated under reduced pressure. The residue was purified by C18-flash chromatography (eluting with 0-40% MeCN in water (0.1% FA)) to afford N-(imidazo[1,2-b]pyridazin-3-yl)-6-methoxy-2-((1S,2S)-2-methyl-4-(methylamino)cyclohexyl)-2H-indazole-5-carboxamide (90 mg, 87%) as a yellow solid. MS ESI, m/z=434 [M+H]⁺.

N-(Imidazo[1,2-b]pyridazin-3-yl)-6-methoxy-2-(1S, 2S,4R*)-2-methyl-4-(N-methylacetamido) cyclohexyl)-2H-indazole-5-carboxamide—Isomer 1 (Example 34) & Isomer 2 (Example 35)

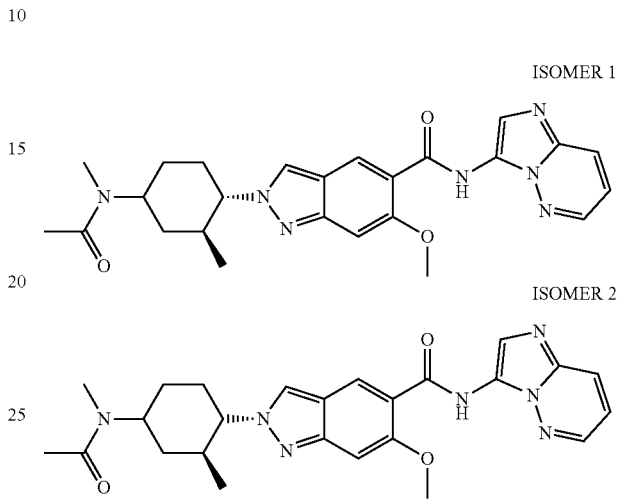

To a solution of N-(imidazo[1,2-b]pyridazin-3-yl)-6-methoxy-2-((1S,2S)-2-methyl-4-(methylamino)cyclohexyl)-2H-indazole-5-carboxamide (80 mg, 0.2 mmol) and TEA (1034, 0.7 mmol) in DCM (2 mL) was added acetic anhydride (38 mg, 0.4 mmol). The resulting mixture was stirred at rt for 1 h. The reaction mixture was concentrated under reduced pressure and purified by C18-flash chromatography (eluting with 0-60% MeCN in water) and further by prep. HPLC (Waters XSelect CSH C18 OBD, 5 μm 30×150 mm; elution gradient with 50-65% MeCN in water (0.1% FA) in 10 min; 60 mL/min) to afford N-(imidazo[1,2-b]pyridazin-3-yl)-6-methoxy-2-((1S,2S)-2-methyl-4-(N-methylacetamido)cyclohexyl)-2H-indazole-5-carboxamide (45 mg) as a yellow solid. The solid was separated by prep. chiral HPLC (Chiralpak® IF, 5 μm 20×250 mm; isocratic with 50% MTBE (0.5% 2N NH₃-MeOH solution) in MeOH in 28 min; flow rate: 15 mL/min) to afford N-(imidazo[1,2-b]pyridazin-3-yl)-6-methoxy-2-((1S,2S,4R*)-2-methyl-4-(N-methylacetamido)cyclohexyl)-2H-indazole-5-carboxamide—Isomer 1 (11 mg, 12%, 99.9% ee) and N-(imidazo[1,2-b]pyridazin-3-yl)-6-methoxy-2-((1S,2S,4R*)-2-methyl-4-(N-methylacetamido)cyclohexyl)-2H-indazole-5-carboxamide—Isomer 2 (20 mg, 22%, 99.9% ee), both as yellow solids. Isomer 1: ¹H NMR (300 MHz, DMSO-d₆) (1.2:1 mixture of rotamers) δ 11.05 (s, 1H), 8.64 (dd, 1H), 8.60 (d, 1H), 8.58 (s, 1H), 8.15 (dd, 1H), 8.05 (s, 1H), 7.27 (d, 1H), 7.22 (dd, 1H), 4.42-4.59/3.78-3.96 (m, 1H) (rotamers), 4.06-4.22 (m, 4H), 2.86/2.73 (s, 3H) (rotamers), 1.92-2.39 (m, 6H), 1.41-1.90 (m, 4H), 0.52-0.66 (m, 3H). MS ESI, m/z=476 [M+H]⁺. Isomer 2: ¹H NMR (300 MHz, DMSO-d₆) (3: 2 mixture of rotamers) δ 11.05 (s, 1H), 8.71 (s, 1H), 8.64 (dd, 1H), 8.59 (s, 1H), 8.15 (dd, 1H), 8.05 (s, 1H), 7.29 (s, 1H), 7.22 (dd, 1H), 4.51-4.76/3.90-4.08 (m, 1H) (rotamers), 4.31-4.48 (m, 1H), 4.13 (s, 3H), 2.59-2.99 (m, 4H), 2.24-2.40 (m, 1H), 1.74-2.24 (m, 6H), 1.26-1.74 (m, 2H), 0.92-1.20 (m, 3H). MS ESI, m/z=476 [M+H]⁺.

N-(Imidazo[1,2-b]pyridazin-3-yl)-6-methoxy-2-(1R, 2R)-2-methyl-4-(methylamino)cyclohexyl)-2H-indazole-5-carboxamide

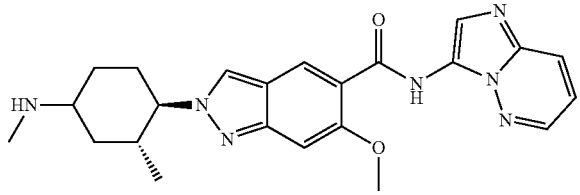 [SMILES: CNC1CC[C@@H](n2cc3cc(C(=O)Nc4cnc5cccnn45)c(OC)cc3n2)[C@H](C)C1]

To a solution of N-(imidazo[1,2-b]pyridazin-3-yl)-6-methoxy-2-((1R,2R)-2-methyl-4-oxocyclohexyl)-2H-indazole-5-carboxamide (Int V-2) (120 mg, 0.3 mmol) and 2M methylamine-MeOH solution (717 μL, 1.4 mmol) in DCM (2 mL) was added sodium triacetoxyborohydride (122 mg, 0.6 mmol). The resulting mixture was stirred at rt for 2 h. The reaction mixture was concentrated under reduced pressure. The residue was purified by C18-flash chromatography (eluting with 0-20% MeCN in water (0.1% FA)) to afford N-(imidazo[1,2-b]pyridazin-3-yl)-6-methoxy-2-((1R,2R)-2-methyl-4-(methylamino)cyclohexyl)-2H-indazole-5-carboxamide (100 mg, 80%) as a yellow solid. MS ESI, m/z=434 [M+H]$^+$.

N-(Imidazo[1,2-b]pyridazin-3-yl)-6-methoxy-2-(1R, 2R,4R*)-2-methyl-4-(N-methylacetamido) cyclohexyl)-2H-indazole-5-carboxamide—Isomer 1 (Example 36) & Isomer 2 (Example 37)

ISOMER 1

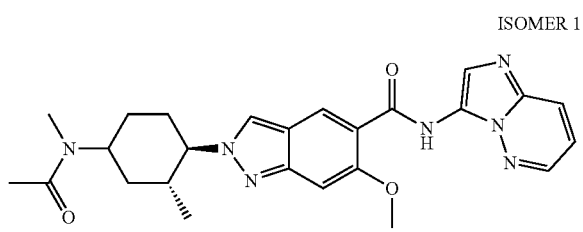

ISOMER 2

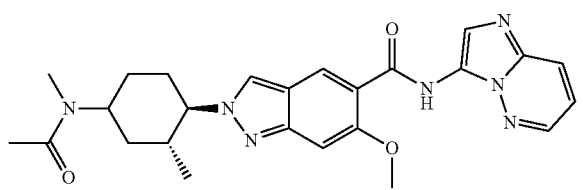

To a solution of N-(imidazo[1,2-b]pyridazin-3-yl)-6-methoxy-24 (1R,2R)-2-methyl-4-(methylamino)cyclohexyl)-2H-indazole-5-carboxamide (90 mg, 0.2 mmol) and TEA (1164, 0.8 mmol) in DCM (2 mL) was added acetic anhydride (42 mg, 0.4 mmol). The resulting mixture was stirred at rt for 2 h. The reaction mixture was concentrated under reduced pressure and purified by C18-flash chromatography (eluting with 0-50% MeCN in water) and further purified by prep. HPLC (Waters Xbridge® BEH C18 OBD, 5 μm 19×250 mm; elution gradient with 50-60% MeCN in water (10 mM NH$_4$HCO$_3$ and 0.1% NH$_4$OH) in 10 min; 25 mL/min) to afford N-(imidazo[1,2-b]pyridazin-3-yl)-6-methoxy-2-(1R,2R)-2-methyl-4-(N-methylacetamido)cyclohexyl)-2H-indazole-5-carboxamide (62 mg) as a yellow solid. The solid was separated by prep. chiral HPLC (Chiralpak® IF, 5 μm 20×250 mm; isocratic with 50% MTBE (0.5% 2N NH$_3$-MeOH solution) in MeOH in 18 min; flow rate: 15 mL/min) to afford N-(imidazo[1,2-b]pyridazin-3-yl)-6-methoxy-2-(1R,2R,4R*)-2-methyl-4-(N-methylacetamido) cyclohexyl)-2H-indazole-5-carboxamide—Isomer 1 (25 mg, 25%, 100% ee) and N-(imidazo[1,2-b]pyridazin-3-yl)-6-methoxy-2-(1R,2R,4R*)-2-methyl-4-(N-methylacetamido)cyclohexyl)-2H-indazole-5-carboxamide—Isomer 2 (20 mg, 20%, 99.8% ee), both as yellow solids. Isomer 1: $^1$H NMR (300 MHz, DMSO-d$_6$) (1.6:1 mixture of rotamers) δ 11.05 (s, 1H), 8.71 (s, 1H), 8.63 (d, 1H), 8.59 (s, 1H), 8.15 (d, 1H), 8.05 (s, 1H), 7.29 (s, 1H), 7.22 (dd, 1H), 4.51-4.74/3.89-4.08 (m, 1H) (rotamers), 4.31-4.48 (m, 1H), 4.13 (s, 3H), 2.60-2.94 (m, 4H), 1.76-2.42 (m, 7H), 1.25-1.73 (m, 2H), 0.91-1.20 (m, 3H). MS ESI, m/z=476 [M+H]$^+$. Isomer 2: $^1$H NMR (300 MHz, DMSO-d$_6$) (1.2:1 mix of rotamers) δ 11.05 (s, 1H), 8.53-8.73 (m, 3H), 8.15 (dd, 1H), 8.05 (s, 1H), 7.16-7.35 (m, 2H), 4.44-4.57/3.81-3.95 (m, 1H) (rotamers), 4.03-4.27 (m, 4H), 2.86/2.72 (s, 3H) (rotamers), 1.93-2.40 (m, 6H), 1.42-1.93 (m, 4H), 0.41-0.73 (m, 3H). MS ESI, m/z=476 [M+H]$^+$.

rel-2-(1S,2S,4S)-4-Hydroxy-2-methylcyclohexyl)-6-methoxy-N-(pyrazolo[1,5-c]pyrimidin-3-yl)-2H-indazole-5-carboxamide—Isomer 1 (Example 38) & Isomer 2 (Example 39)

rel-2-(1S,2S,4R)-4-Hydroxy-2-methylcyclohexyl)-6-methoxy-N-(pyrazolo[1,5-c]pyrimidin-3-yl)-2H-indazole-5-carboxamide—Isomer 1 (Example 40) & Isomer 2 (Example 41)

rac-6-Methoxy-2-(7S,8S)-7-methyl-1,4-dioxaspiro[4.5]decan-8-yl)-N-(pyrazolo[1,5-a]pyrimidin-3-yl)-2-indazole-5-carboxamide

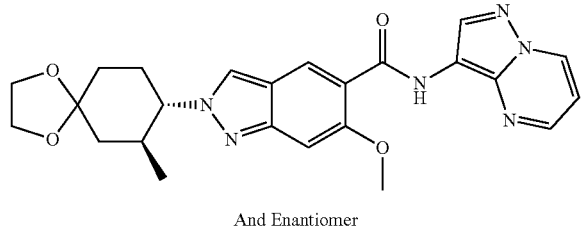 [SMILES: COc1cc2nn([C@H]3CCC4(C[C@@H]3C)OCCO4)cc2cc1C(=O)Nc1cnn2cccnc12]

And Enantiomer

To a solution of 6-methoxy-N-(pyrazolo[1,5-c]pyrimidin-3-yl)-1H-indazole-5-carboxamide (Int II-2) (1.1 g, 3.6 mmol) and rac-(7R,8S)-7-methyl-1,4-dioxaspiro[4.5]decan-8-yl methanesulfonate (Int III-13) (1.8 g, 7.1 mmol) in DMF (10 mL) was added Cs$_2$CO$_3$ (3.5 g, 10.7 mmol) under N$_2$ atmosphere. The reaction mixture was stirred at 90° C. for 12 h. The mixture was cooled to rt, poured into water (50 mL) and extracted with EtOAc (25 mL×3). The combined organic layers were dried over Na$_2$SO$_4$, filtered and concentrated under reduced pressure. The residue was purified by prep. HPLC (Waters Xbridge® Shield RP18 OBD, 5 μm 30×150 mm; elution gradient with 30-40% MeCN in water (0.1% FA) in 9 min; 60 mL/min) to afford rac-6-methoxy-2-((7S,8S)-7-methyl-1,4-dioxaspiro[4.5]decan-8-yl)-N-(pyrazolo[1,5-a]pyrimidin-3-yl)-2-indazole-5-carboxamide (700 mg, 42%). m/z (ESI+), [M+H]$^+$=463.

rac-6-Methoxy-2-(1S,2S)-2-methyl-4-oxocyclohexyl)-N-(pyrazolo[1,5-c]pyrimidin-3-yl)-2H-indazole-5-carboxamide

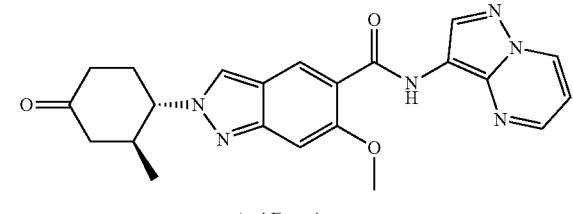

And Enantiomer

To a solution of rac-6-methoxy-2-((7S,8S)-7-methyl-1,4-dioxaspiro[4.5]decan-8-yl)-N-(pyrazolo[1,5-a]pyrimidin-3-yl)-2H-indazole-5-carboxamide (300 mg, 0.7 mmol) in 1,4-dioxane (2 mL) at rt under N₂ atmosphere was added aq. 3N HCl (2.7 mL, 8.0 mmol). The resulting mixture was stirred at rt for 2 h. The reaction mixture was basified with aq. concentrated NH₄OH solution and purified directly by C18-flash chromatography (eluting with 20-50% MeCN in water (1% FA)) to afford rac-6-methoxy-2-((1S,2S)-2-methyl-4-oxocyclohexyl)-N-(pyrazolo[1,5-c]pyrimidin-3-yl)-2H-indazole-5-carboxamide (200 mg, 74%) as a yellow solid. m/z (ESI+), [M+H]⁺=419.

rel-2-(1S,2S,4S)-4-Hydroxy-2-methylcyclohexyl)-6-methoxy-N-(pyrazolo[1,5-c]pyrimidin-3-yl)-2H-indazole-5-carboxamide—Isomer 1 (Example 38) & Isomer 2 (Example 39)

ISOMER 1

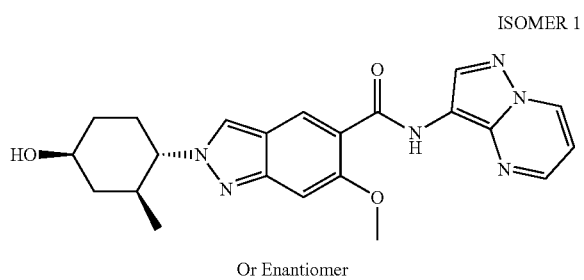

Or Enantiomer

ISOMER 2

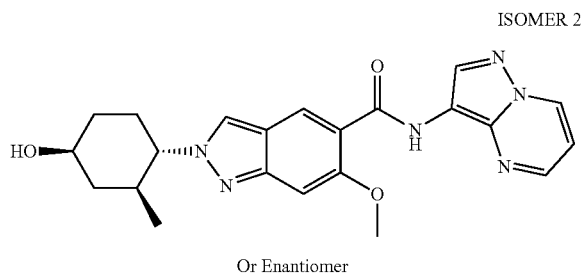

Or Enantiomer rel-2-(1S,2S,4R)-4-Hydroxy-2-methylcyclohexyl)-6-methoxy-N-(pyrazolo[1,5-c]pyrimidin-3-yl)-2H-indazole-5-carboxamide—Isomer 1 (Example 40) & Isomer 2 (Example 41)

ISOMER 1

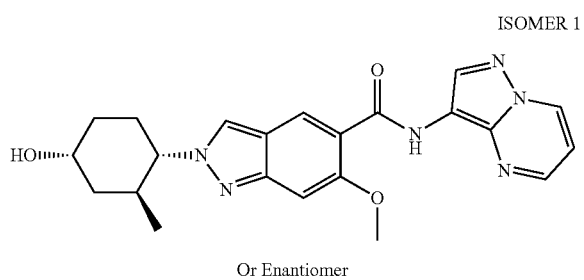

Or Enantiomer

ISOMER 2

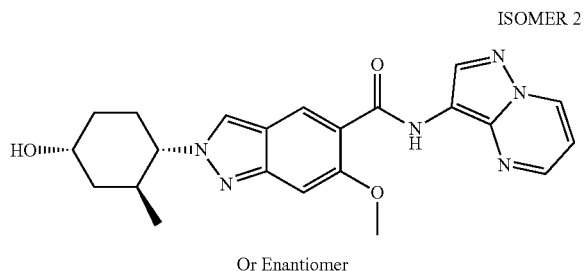

Or Enantiomer

To a solution of rac-6-methoxy-2-((1S,2S)-2-methyl-4-oxocyclohexyl)-N-(pyrazolo[1,5-c]pyrimidin-3-yl)-2H-indazole-5-carboxamide (200 mg, 0.5 mmol) in MeOH (5 mL) under N₂ atmosphere was added NaBH₄ (36 mg, 1.0 mmol). The resulting mixture was stirred at rt for 1 h. The reaction mixture was quenched with water (10 mL) and purified directly by C18-flash chromatography (eluting with 0-50% MeCN in water (0.5% FA)) to afford rac-2-((1S,2S)-4-hydroxy-2-methylcyclohexyl)-6-methoxy-N-(pyrazolo[1,5-a]pyrimidin-3-yl)-2H-indazole-5-carboxamide. This mixture was separated by prep. chiral HPLC (Chiralpak® ID-2, 5 μm 20×250 mm; isocratic with MTBE (0.1% 2N NH₃-MeOH)/MeOH, 60/40; flow rate: 16 mL/min) to afford as first eluting isomer rel-2-((1S,2S,4R)-4-hydroxy-2-methylcyclohexyl)-6-methoxy-N-(pyrazolo[1,5-c]pyrimidin-3-yl)-2H-indazole-5-carboxamide—Isomer (7 mg, 4%, 100% ee) and rel-2-((1S,2S,4S)-4-hydroxy-2-methylcyclohexyl)-6-methoxy-N-(pyrazolo[1,5-a]pyrimidin-3-yl)-2H-indazole-5-carboxamide—Isomer 1 (56 mg, 28%, 99.9% ee) as second eluting isomer. The following two compounds eluted as third and fourth isomer but with lower purity and were purified in a second chiral prep. HPLC (Chiralpak® IE, 5 μm 20×250 mm; isocratic with MTBE (2 mM NH₃-MeOH solution)/MeOH, 50/50; flow rate: 20 mL/min) to afford rel-2-((1S,2S,4S)-4-hydroxy-2-methylcyclohexyl)-6-methoxy-N-(pyrazolo[1,5-a]pyrimidin-3-yl)-2H-indazole-5-carboxamide—Isomer 2 (36 mg, 18%, 99.9% ee) and rel-2-((1S,2S,4R)-4-hydroxy-2-methylcyclohexyl)-6-methoxy-N-(pyrazolo[1,5-c]pyrimidin-3-yl)-2H-indazole-5-carboxamide—Isomer 2 (6 mg, 3%, 99.6% ee) as yellow solids.

rel-(1S,2S,4R)— Isomer 1: ¹H NMR (400 MHz, DMSO-d₆) δ 10.35 (s, 1H), 9.07 (dd, 1H), 8.74 (s, 1H), 8.54 (dd, 1H), 8.51 (s, 1H), 8.47 (s, 1H), 7.23 (s, 1H), 7.05 (dd, 1H), 4.55 (d, 1H), 4.01-4.12 (m, 4H), 3.96 (br. s, 1H), 2.52-2.59 (m, 1H), 2.31-2.47 (m, 1H), 1.78-1.89 (m, 2H), 1.67-1.77 (m, 1H), 1.55-1.65 (m, 1H), 1.28-1.40 (m, 1H), 0.54 (d, 3H). m/z (ESI+), [M+H]⁺=421.

rel-(1S,2S,4S)— Isomer 1: ¹H NMR (400 MHz, DMSO-d₆) δ 10.34 (s, 1H), 9.07 (dd, 1H), 8.73 (s, 1H), 8.54 (dd, 1H), 8.52 (s, 1H), 8.46 (s, 1H), 7.22 (s, 1H), 7.05 (dd, 1H), 4.71 (d, 1H), 4.01-4.11 (m, 4H), 3.55-3.67 (m, 1H), 2.11-2.24 (m, 1H), 1.88-2.10 (m, 4H), 1.29-1.45 (m, 1H), 1.16 (q, 1H), 0.57 (d, 3H). m/z (ESI+), [M+H]⁺=421.

rel-(1S,2S,4S)— Isomer 2: ¹H NMR (400 MHz, DMSO-d₆) δ 10.34 (s, 1H), 9.07 (dd, 1H), 8.73 (s, 1H), 8.54 (dd, 1H), 8.52 (s, 1H), 8.46 (s, 1H), 7.22 (s, 1H), 7.05 (dd, 1H), 4.71 (d, 1H), 4.00-4.14 (m, 4H), 3.56-3.67 (m, 1H), 2.11-2.26 (m, 1H), 1.89-2.11 (m, 4H), 1.30-1.45 (m, 1H), 1.16 (q, 1H), 0.57 (d, 3H). m/z (ESI+), [M+H]⁺=421.

rel-(1S,2S,4R)—Isomer 2: ¹H NMR (400 MHz, DMSO-d₆) δ 10.35 (s, 1H), 9.07 (dd, 1H), 8.74 (s, 1H), 8.54 (dd, 1H), 8.51 (s, 1H), 8.47 (s, 1H), 7.23 (s, 1H), 7.05 (dd, 1H), 4.55 (d, 1H), 4.03-4.12 (m, 4H), 3.92-3.99 (m, 1H), 2.52-2.59 (m, 1H), 2.34-2.47 (m, 1H), 1.78-1.89 (m, 2H), 1.68-1.77 (m, 1H), 1.55-1.67 (m, 1H), 1.25-1.40 (m, 1H), 0.54 (d, 3H). m/z (ESI+), [M+H]⁺=421.

rel-6-Cyclopropoxy-2-(1S,2S,4R)-4-hydroxy-2-
methylcyclohexyl)-N-(pyrazolo[1,5-a]pyrimidin-3-
yl)-2H-indazole-5-carboxamide—Isomer 1 (Example 42) & Isomer 2 (Example 43)

rel-6-cyclopropoxy-2-(1S,2S,4S)-4-hydroxy-2-methylcyclohexyl)-N-(pyrazolo[1,5-c]pyrimidin-3-yl)-2H-indazole-5-carboxamide—Isomer 1 (Example 44) & Isomer 2 (Example 45)

rac-6-Cyclopropoxy-2-(7S,8S)-7-methyl-1,4-dioxaspiro[4.5]decan-8-yl)-N-(pyrazolo[1,5-a]pyrimidin-3-yl)-2H-indazole-5-carboxamide

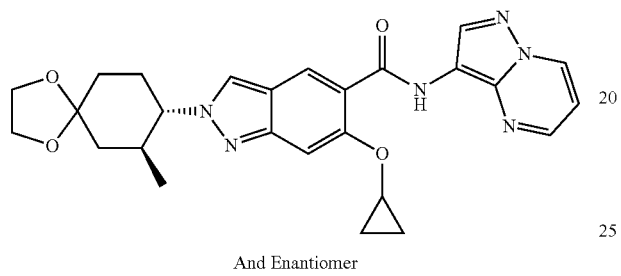

And Enantiomer

To a solution of 6-cyclopropoxy-N-(pyrazolo[1,5-c]pyrimidin-3-yl)-1H-indazole-5-carboxamide (Int II-3) (1.4 g, 4.2 mmol) and rac-(7R,8S)-7-methyl-1,4-dioxaspiro[4.5]decan-8-yl methanesulfonate (Int III-13) (1.1 g, 8.4 mmol) in DMF (30 mL) was added Cs$_2$CO$_3$ (2.9 g, 9.0 mmol). The reaction mixture was stirred at 95° C. for 3 h and after cooling to rt diluted with EtOAc (500 mL) and washed with brine (100 mL×3). The organic layer was dried over Na$_2$SO$_4$, filtered and concentrated under reduced pressure. The residue was purified by prep. SFC (DAICEL DCpak® P4VP, 5 µm 30 mm×250 mm; isocratic with 30% DCM/MeOH (50/50, 0.1% 2M NH$_3$-MEOH) in CO$_2$ (35° C., 70 bar); 60 mL/min) to afford rac-6-cyclopropoxy-2-((7S,8S)-7-methyl-1,4-dioxaspiro[4.5]decan-8-yl)-N-(pyrazolo[1,5-a]pyrimidin-3-yl)-2H-indazole-5-carboxamide (440 mg, 22%) as an orange solid. MS ESI, m/z=489 [M+H]$^+$.

rac-6-Cyclopropoxy-2-(1S,2S)-2-methyl-4-oxocyclohexyl)-N-(pyrazolo[1,5-c]pyrimidin-3-yl)-2H-indazole-5-carboxamide

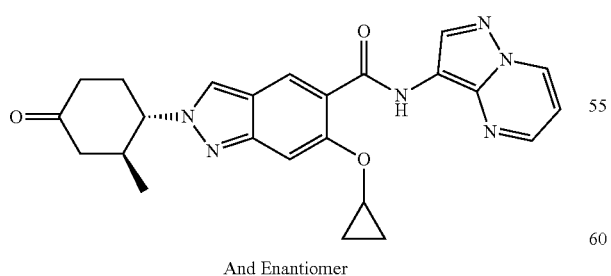

And Enantiomer

To a solution of rac-6-cyclopropoxy-2-(7S,8S)-7-methyl-1,4-dioxaspiro[4.5]decan-8-yl)-N-(pyrazolo[1,5-a]pyrimidin-3-yl)-2H-indazole-5-carboxamide (400 mg, 0.8 mmol) in THF (5 mL) and water (5 mL) was added concentrated aq. HCl (2.0 mL, 24.0 mmol). The resulting mixture was stirred at rt for 3 h. The reaction mixture was purified directly by C18-flash chromatography (eluting with 0-60% MeCN in water (0.1% FA)) and further by prep. SFC (YMC Chiral ART Amylose-C Neo 5 µm 30 mm×250 mm; isocratic with 60% MeOH/MeCN (50/50, 0.1% 2M NH$_3$-MeOH) in CO$_2$ (35° C., 78 bar); 60 mL/min) to afford rac-6-cyclopropoxy-2-(1S,2S)-2-methyl-4-oxocyclohexyl)-N-(pyrazolo[1,5-c]pyrimidin-3-yl)-2H-indazole-5-carboxamide (196 mg, 54%) as an orange solid. MS ESI, m/z=445 [M+H]$^+$.

rel-6-Cyclopropoxy-2-(1S,2S,4R)-4-hydroxy-2-methylcyclohexyl)-N-(pyrazolo[1,5-c]pyrimidin-3-yl)-2H-indazole-5-carboxamide—Isomer 1 (Example 42) & Isomer 2 (Example 43)

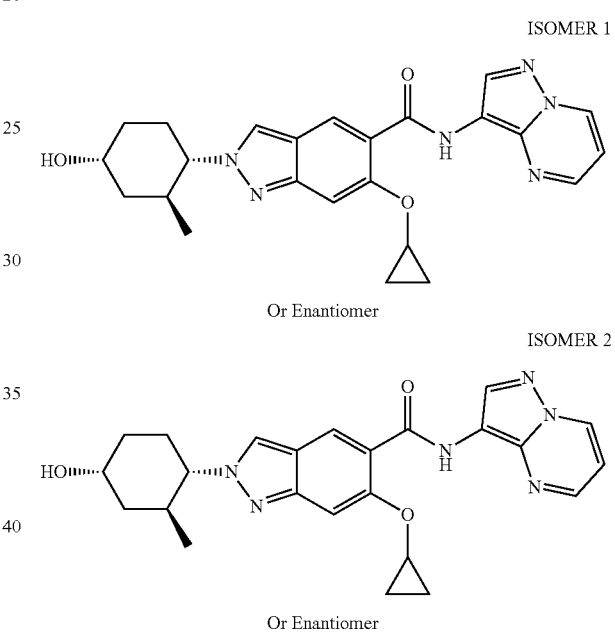

rel-6-cyclopropoxy-2-(1S,2S,4S)-4-hydroxy-2-methylcyclohexyl)-N-(pyrazolo[1,5-c]pyrimidin-3-yl)-2H-indazole-5-carboxamide—Isomer 1 (Example 44) & Isomer 2 (Example 45)

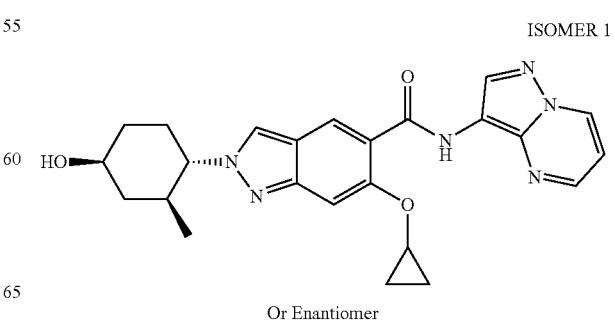

-continued

ISOMER 2

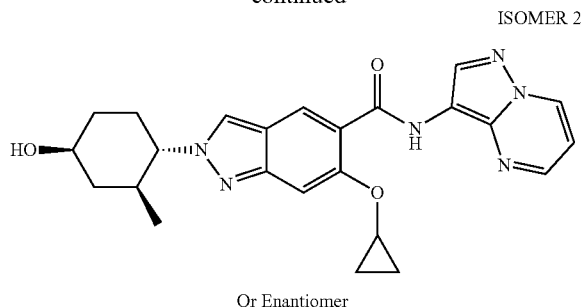

Or Enantiomer

To a solution of rac-6-cyclopropoxy-2-((1S,2S)-2-methyl-4-oxocyclohexyl)-N-(pyrazolo[1,5-c]pyrimidin-3-yl)-2H-indazole-5-carboxamide (180 mg, 0.4 mmol) in MeOH (5 mL) under $N_2$ atmosphere was added $NaBH_4$ (31 mg, 0.8 mmol). The resulting mixture was stirred at rt for 2 h. The reaction mixture was quenched with water (1 mL) and then concentrated under reduced pressure. The residue was purified by C18-flash chromatography (eluting with 0-50% MeCN in water) to afford rac-6-cyclopropoxy-2-((1S,2S)-4-hydroxy-2-methylcyclohexyl)-N-(pyrazolo[1,5-c]pyrimidin-3-yl)-2H-indazole-5-carboxamide as an orange solid. The solid was separated by prep. chiral HPLC (Chiralpak® IA 5 μm 20 mm×250 mm; isocratic with 80% MTBE (0.1% 2N $NH_3$-MeOH) in MeOH; 17 mL/min) to afford as first eluting isomer rel-6-cyclopropoxy-2-((1S,2S,4R)-4-hydroxy-2-methylcyclohexyl)-N-(pyrazolo[1,5-c]pyrimidin-3-yl)-2H-indazole-5-carboxamide—Isomer 1 (8 mg, 4%, 98.9% ee), as second eluting isomer rel-6-cyclopropoxy-2-((1S,2S,4R)-4-hydroxy-2-methylcyclohexyl)-N-(pyrazolo[1,5-c]pyrimidin-3-yl)-2H-indazole-5-carboxamide—Isomer 2 (7 mg, 4%, 98.4% ee), as third eluting isomer rel-6-cyclopropoxy-2-((1S,2S,4S)-4-hydroxy-2-methylcyclohexyl)-N-(pyrazolo[1,5-a]pyrimidin-3-yl)-2H-indazole-5-carboxamide—Isomer 1 (40 mg, 22%, 99.6% ee) and rel-6-cyclopropoxy-2-((1S,2S,4S)-4-hydroxy-2-methylcyclohexyl)-N-(pyrazolo[1,5-a]pyrimidin-3-yl)-2H-indazole-5-carboxamide—Isomer 2 (30 mg, 17%, 99.5% ee) as fourth eluting isomer, all as yellow solids. rel-(1S,2S,4R)—Isomer 1: $^1$H NMR (300 MHz, DMSO-$d_6$) δ 10.31 (s, 1H), 9.07 (dd, 1H), 8.75 (s, 1H), 8.48-8.61 (m, 3H), 7.53 (s, 1H), 7.05 (dd, 1H), 4.55 (d, 1H), 4.16-4.27 (m, 1H), 4.10 (td, 1H), 3.96 (br. s, 1H), 2.24-2.47 (m, 2H), 1.77-1.90 (m, 2H), 1.50-1.77 (m, 2H), 1.28-1.42 (m, 1H), 0.93-1.15 (m, 4H), 0.55 (d, 3H). MS ESI, m/z=447 [M+H]$^+$.

rel-(1S,2S,4R)—Isomer 2: $^1$H NMR (300 MHz, DMSO-$d_6$) δ 10.31 (s, 1H), 9.07 (d, 1H), 8.75 (s, 1H), 8.48-8.64 (m, 3H), 7.53 (s, 1H), 7.05 (dd, 1H), 4.55 (d, 1H), 4.22 (br. s, 1H), 4.01-4.15 (m, 1H), 3.96 (br. s, 1H), 2.22-2.46 (m, 2H), 1.77-1.92 (m, 2H), 1.50-1.77 (m, 2H), 1.27-1.45 (m, 1H), 0.92-1.15 (m, 4H), 0.55 (d, 3H). MS ESI, m/z=447 [M+H]$^+$.

rel-(1S,2S,4S)—Isomer 1: $^1$H NMR (300 MHz, DMSO-$d_6$) δ 10.30 (s, 1H), 9.06 (dd, 1H), 8.75 (s, 1H), 8.48-8.65 (m, 3H), 7.51 (s, 1H), 7.04 (dd, 1H), 4.71 (d, 1H), 4.15-4.25 (m, 1H), 4.02-4.15 (m, 1H), 3.54-3.69 (m, 1H)), 1.87-2.30 (m, 5H), 1.29-1.50 (m, 1H), 1.11-1.29 (m, 1H), 0.92-1.11 (m, 4H), 0.58 (d, 3H). MS ESI, m/z=447 [M+H]$^+$.

rel-(1S,2S,4S)—Isomer 2: $^1$H NMR (300 MHz, DMSO-$d_6$) δ 10.30 (s, 1H), 9.02-9.11 (m, 1H), 8.75 (s, 1H), 8.48-8.65 (m, 3H), 7.51 (s, 1H), 7.10-7.00 (m, 1H), 4.71 (d, 1H), 4.15-4.25 (m, 1H), 4.02-4.15 (m, 1H), 3.54-3.69 (m, 1H), 1.87-2.30 (m, 5H), 1.27-1.50 (m, 1H), 1.11-1.27 (m, 1H), 0.92-1.11 (m, 4H), 0.58 (d, 3H). MS ESI, m/z=447 [M+H]$^+$.

6-Cyclopropoxy-2-(2-hydroxyspiro[3.5]nonan-7-yl)-N-(pyrazolo[1,5-a]pyrimidin-3-yl)-2H-indazole-5-carboxamide—Isomer 1 (Example 46) & Isomer 2 (Example 47)

8,11-Dioxadispiro[3.2.4$^7$.2$^4$]tridecan-2-ol

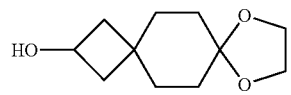

To a solution of 8,11-dioxadispiro[3.2.4$^7$.2$^4$]tridecan-2-one (3.0 g, 15.3 mmol) in MeOH (50 mL) at 0° C. under $N_2$ atmosphere was added $NaBH_4$ (867 mg, 22.9 mmol). The resulting mixture was stirred at rt for 2 h. The reaction solution was purified by silica gel chromatography (eluting with 0-50% EtOAc in PE) to afford 8,11-dioxadispiro[3.2.4$^7$.2$^4$]tridecan-2-ol (3.0 g, 99%) as a colorless solid. $^1$H NMR (400 MHz, DMSO-$d_6$) δ 4.80-4.90 (m, 1H), 3.98-4.11 (m, 1H), 3.83 (s, 4H), 2.02-2.15 (m, 2H), 1.40-1.55 (m, 10H).

8,11-Dioxadispiro[3.2.4$^7$.2$^4$]tridecan-2-yl 4-nitrobenzoate

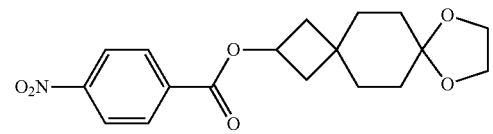

4-Nitrobenzoyl chloride (3.7 g, 19.7 mmol) was added to a solution of TEA (5.3 mL, 37.8 mmol) and 8,11-dioxadispiro[3.2.4$^7$.2$^4$]tridecan-2-ol (3.0 g, 15.1 mmol) in DCM (50 mL) at 0° C. The resulting solution was stirred at rt for 2 h. The reaction mixture was concentrated under reduced pressure and purified by silica gel chromatography (eluting with 20-50% EtOAc in PE) to afford crude 8,11-dioxadispiro[3.2.4$^7$.2$^4$]tridecan-2-yl 4-nitrobenzoate (6.0 g, 75 wt. %). MS ESI, m/z=348 [M+H]$^+$.

7-Oxospiro[3.5]nonan-2-yl 4-nitrobenzoate

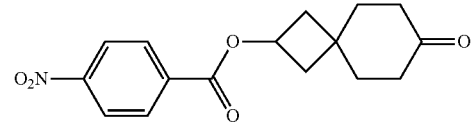

To a solution of crude 8,11-dioxadispiro[3.2.4⁷.2⁴]tridecan-2-yl 4-nitrobenzoate (75 wt. %) (6.0 g) in THF (40 mL) was added 2N HCl (40.0 mL, 80.0 mmol), and the reaction mixture was stirred at rt 2 h. The reaction mixture was diluted with EtOAc (200 mL), washed with water (100 mL), dried over Na$_2$SO$_4$, filtered and then concentrated under reduced pressure to afford 7-oxospiro[3.5]nonan-2-yl 4-nitrobenzoate (3.5 g, 50%). $^1$H NMR (300 MHz, DMSO-d$_6$) δ 8.36 (d, 2H), 8.22 (d, 2H), 5.15-5.36 (m, 1H), 2.52-2.61 (m, 2H), 2.17-2.43 (m, 4H), 2.04-2.17 (m, 2H), 1.82-2.00 (m, 4H).

7-Hydroxyspiro[3.5]nonan-2-yl 4-nitrobenzoate

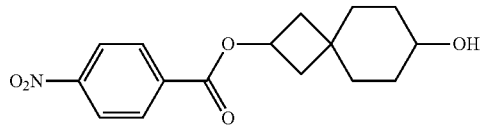 [SMILES: O=C(OC1CC2(CCC(O)CC2)C1)c1ccc([N+](=O)[O-])cc1]

To a solution of 7-oxospiro[3.5]nonan-2-yl 4-nitrobenzoate (3.4 g, 11.2 mmol) in MeOH (60 mL) at rt under N$_2$ atmosphere was added NaBH$_4$ (848 mg, 22.4 mmol). The resulting solution was stirred for 2 h. The reaction mixture was diluted with EtOAc (250 mL) and washed with water (75 mL). The organic layer was dried over Na$_2$SO$_4$, filtered and concentrated under reduced pressure to afford 7-hydroxyspiro[3.5]nonan-2-yl 4-nitrobenzoate (2.0 g, 58%) as colorless solid. $^1$H NMR (300 MHz, DMSO-d$_6$) δ 8.34 (d, 1H), 8.18 (d, 1H), 5.18 (p, 1H), 4.42 (d, 1H), 3.34-3.50 (m, 2H), 2.19-2.46 (m, 2H), 1.89 (td, 2H), 1.50-1.78 (m, 4H), 1.06-1.50 (m, 4H).

7-(Tosyloxy)spiro[3.5]nonan-2-yl 4-nitrobenzoate

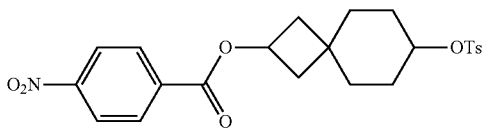 [SMILES: Cc1ccc(S(=O)(=O)OC2CCC3(CC2)CC(OC(=O)c2ccc([N+](=O)[O-])cc2)C3)cc1]

TsCl (2.8 g, 14.7 mmol) was slowly added to a solution of 7-hydroxyspiro[3.5]nonan-2-yl 4-nitrobenzoate (1.8 g, 5.9 mmol), DMAP (72 mg, 0.6 mmol) and TEA (2.5 mL, 17.7 mmol) in DCM (50 mL). The resulting mixture was stirred at rt for 2 h, then diluted with DCM (100 mL) and washed with 0.1N HCl (75 mL). The organic layer was dried over Na$_2$SO$_4$, filtered, and concentrated under reduced pressure. The residue was purified by silica gel chromatography (eluting with 0-30% EtOAc in PE) to afford 7-(tosyloxy)spiro[3.5]nonan-2-yl 4-nitrobenzoate (1.20 g, 44%) as a colorless solid. $^1$H NMR (400 MHz, DMSO-d$_6$) δ 8.34 (d, 2H), 8.14 (d, 2H), 7.80 (d, 2H), 7.47 (d, 2H), 5.16 (p, 1H), 4.41-4.59 (m, 1H), 2.43 (s, 3H), 2.24-2.42 (m, 2H), 1.83-1.95 (m, 2H), 1.60-1.71 (m, 4H), 1.38-1.60 (m, 4H).

6-Cyclopropoxy-2-(2-hydroxyspiro[3.5]nonan-7-yl)-N-(pyrazolo[1,5-a]pyrimidin-3-yl)-2H-indazole-5-carboxamide—Isomer 1 (Example 46), Isomer 2 (Example 47)

ISOMER 1

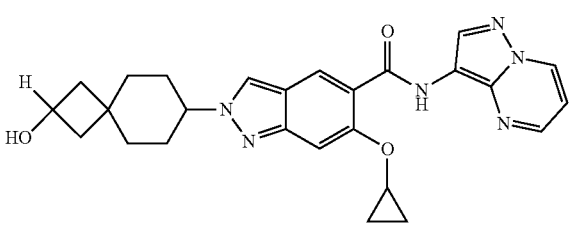

ISOMER 2

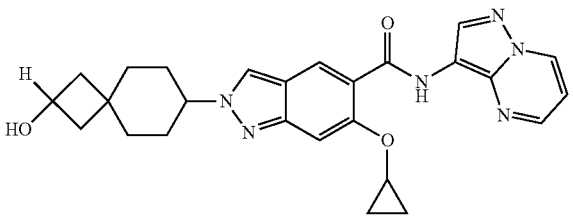

To a solution of 7-(tosyloxy)spiro[3.5]nonan-2-yl 4-nitrobenzoate (1.2 g, 2.6 mmol) and 6-cyclopropoxy-N-(pyrazolo[1,5-c]pyrimidin-3-yl)-1H-indazole-5-carboxamide (Int II-3) (350 mg, 1.1 mmol) in DMF (20 mL) at rt was added Cs$_2$CO$_3$ (1.0 g, 3.1 mmol). The reaction mixture was stirred at 90° C. for 12 h. Hereafter, the reaction mixture was cooled to rt, followed by the addition of Cs$_2$CO$_3$ (314 mg, 1.0 mmol) and MeOH (20 mL). The resulting mixture was stirred for another 3 h. The reaction mixture was purified directly by C18-flash chromatography (eluting with 0-100% MeCN in water (0.1% FA)) to afford 6-cyclopropoxy-2-(2-hydroxyspiro[3.5]nonan-7-yl)-N-(pyrazolo[1,5-c]pyrimidin-3-yl)-2H-indazole-5-carboxamide as a yellow solid, which contained some N1-regiomer. 6-Cyclopropoxy-2-(2-hydroxyspiro[3.5]nonan-7-yl)-N-(pyrazolo[1,5-a]pyrimidin-3-yl)-2H-indazole-5-carboxamide (70 mg) was further purified by prep. HPLC (Waters XBridge BEH OBD C18 5 μm 30×150 mm; elution gradient with 30-40% MeCN in water (10 mM NH$_4$HCO$_3$ and 0.1% NH$_4$OH) in 7 min; 60 mL/min) and then separated by chiral prep. HPLC (Chiralpak® IF, 20×250 mm, 5 μm; isocratic with MTBE/MeOH (0.1% 2N NH$_3$-MeOH), 80/20; flow rate: 14 mL/min) to afford 6-cyclopropoxy-2-(2-hydroxyspiro[3.5]nonan-7-yl)-N-(pyrazolo[1,5-a]pyrimidin-3-yl)-2H-indazole-5-carboxamide—Isomer 1 (12 mg, 9%, 100% ee) and 6-cyclopropoxy-2-(2-hydroxyspiro[3.5]nonan-7-yl)-N-(pyrazolo[1,5-a]pyrimidin-3-yl)-2H-indazole-5-carboxamide—Isomer 2 (9 mg, 7%, 99% ee) as yellow solids. The $^1$H NMR and MS obtained for both products were identical. $^1$H NMR (300 MHz, DMSO-d$_6$) δ 10.32 (s, 1H), 9.08 (dd, 1H), 8.76 (s, 1H), 8.50-8.60 (m, 3H), 7.53 (s, 1H), 7.06 (dd, 1H), 4.92 (d, 1H), 4.33-4.52 (m, 1H), 4.18-4.27 (m, 1H), 4.06-4.18 (m, 1H), 2.24-2.39 (m, 1H), 1.82-2.15 (m, 5H), 1.42-1.82 (m, 6H), 1.02-1.10 (m, 2H), 0.93-1.02 (m, 2H). MS ESI, m/z=473 [M+H]⁺.

2-(4-Hydroxy-4-methylcyclohexyl)-N-(imidazo[1,2-b]pyridazin-3-O-6-methoxy-2H-indazole-5-carboxamide—Isomer 1 (Example 48) & Isomer 2 (Example 49)

5-Bromo-6-methoxy-2-(1,4-dioxaspiro[4.5]decan-8-yl)-2H-indazole

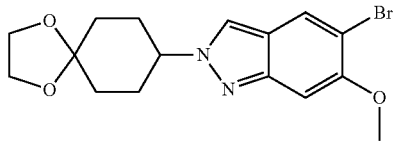 [SMILES: COc1cc2nn(C3CCC4(CC3)OCCO4)cc2cc1Br]

To a solution of 5-bromo-4-methoxy-2-nitrobenzaldehyde (Intl-1) (3.3 g, 12.7 mmol) in i-PrOH (30 mL) at rt under N₂ atmosphere was added 1,4-dioxaspiro[4.5]decan-8-amine (2.0 g, 12.7 mmol). The resulting mixture was stirred at 80° C. for 1 h, then cooled to rt and followed by the addition of tri-n-butylphosphine (12.9 g, 63.6 mmol). The reaction mixture was stirred at 80° C. for 13 h. The mixture was cooled to rt and concentrated under reduced pressure. The residue was purified by silica gel chromatography (eluting with 10-100% EtOAc in PE) to afford crude 5-bromo-6-methoxy-2-(1,4-dioxaspiro[4.5]decan-8-yl)-2H-indazole as a yellow solid (8.2 g, 41 wt. %), which was used in the next step without further purification. MS ESI, m/z=367/369 [M+H]⁺.

4-(5-Bromo-6-methoxy-2H-indazol-2-yl)cyclohexan-1-one

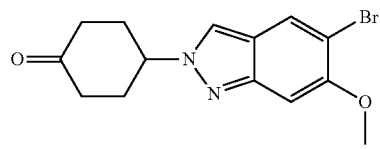 [SMILES: COc1cc2nn(C3CCC(=O)CC3)cc2cc1Br]

To a solution of crude 5-bromo-6-methoxy-2-(1,4-dioxaspiro[4.5]decan-8-yl)-2H-indazole (41 wt. %) (8.2 g) in THF (50 mL) at rt was added 4N HCl in water (22.9 mL, 91.6 mmol), and the resulting solution was stirred at rt for 12 h under N₂ atmosphere. The mixture was neutralized with 2N NaOH and extracted with EtOAc (150 mL×3). The combined organic layers were concentrated under reduced pressure. The residue was crystallized from PE/EtOAc (3/1, 100 mL) to afford 4-(5-bromo-6-methoxy-2H-indazol-2-yl)cyclohexan-1-one (3.0 g, 100%) as a pale-yellow solid. MS ESI, m/z=323/325 [M+H]⁺.

4-(5-Bromo-6-methoxy-2H-indazol-2-yl)-1-methyl-cyclohexan-1-ol

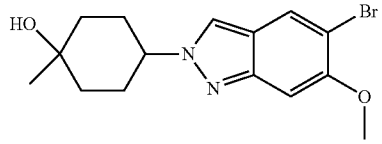 [SMILES: COc1cc2nn(C3CCC(C)(O)CC3)cc2cc1Br]

To a solution of 4-(5-bromo-6-methoxy-2H-indazol-2-yl)cyclohexan-1-one (700 mg, 2.2 mmol) in THF (120 mL) at −20° C. was slowly added 3N methylmagnesium bromide in THF (4.3 mL, 13.0 mmol) under N₂ atmosphere. The resulting mixture was stirred at −20° C. for 2 h. The reaction was quenched with aq. saturated NH₄Cl (5 mL) and then concentrated under reduced pressure. The residue was purified by C18-flash chromatography (eluting with 0-100% MeCN in water (0.05% FA)) to afford 4-(5-bromo-6-methoxy-2H-indazol-2-yl)-1-methylcyclohexan-1-ol (730 mg, 99%) as a brown solid. MS ESI, m/z=339/341 [M+H]⁺.

Methyl 2-(4-hydroxy-4-methylcyclohexyl)-6-methoxy-2H-indazole-5-carboxylate

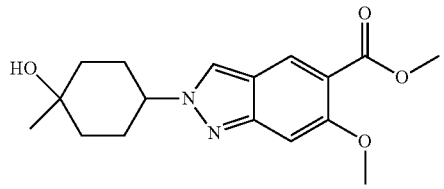 [SMILES: COC(=O)c1cc2cn(C3CCC(C)(O)CC3)nc2cc1OC]

A mixture of 4-(5-bromo-6-methoxy-2H-indazol-2-yl)-1-methylcyclohexan-1-ol (730 mg, 2.2 mmol), Pd(dppf)Cl₂ (157 mg, 0.2 mmol) and DIPEA (2.3 ml, 12.9 mmol) in MeOH (25 mL) was stirred under CO atmosphere at 15 atm and 110° C. for 24 h. The reaction mixture was cooled to rt and concentrated under reduced pressure. The residue was purified by C18-flash chromatography (eluting with 0-100% MeCN in water (0.05% NH₄OH)) to afford methyl 2-(4-hydroxy-4-methylcyclohexyl)-6-methoxy-2H-indazole-5-carboxylate (635 mg, 93%) as a brown oil. MS ESI, m/z=319 [M+H]⁺.

2-(4-Hydroxy-4-methylcyclohexyl)-6-methoxy-2H-indazole-5-carboxylic acid

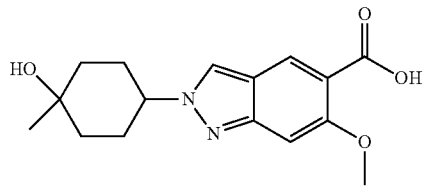 [SMILES: COc1cc2nn(C3CCC(C)(O)CC3)cc2cc1C(=O)O]

To a suspension of methyl 2-(4-hydroxy-4-methylcyclohexyl)-6-methoxy-2H-indazole-5-carboxylate (635 mg, 2.0 mmol) in MeOH (20 mL) under $N_2$ atmosphere was added a solution of LiOH (155 mg, 6.5 mmol) in water (20 mL). The resulting mixture was stirred at rt for 17 h. The reaction mixture was neutralized with 1N HCl and then purified directly by C18-flash chromatography (eluting with 0-100% MeCN in water (0.05% FA)) to afford 2-(4-hydroxy-4-methylcyclohexyl)-6-methoxy-2H-indazole-5-carboxylic acid (600 mg, 99%) as a brown gum. MS ESI, m/z=305 $[M+H]^+$.

2-(4-Hydroxy-4-methylcyclohexyl)-N-(imidazo[1,2-b]pyridazin-3-yl)-6-methoxy-2H-indazole-5-carboxamide—Isomer 1 (Example 48) & Isomer 2 (Example 49)

ISOMER 1

ISOMER 2

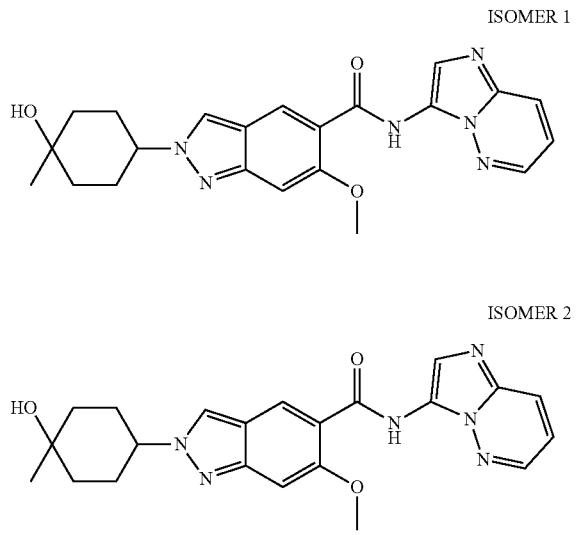

To a solution of 2-(4-hydroxy-4-methylcyclohexyl)-6-methoxy-2H-indazole-5-carboxylic acid (100 mg, 0.3 mmol) and HATU (150 mg, 0.4 mmol) in DMF (20 mL) at rt under $N_2$ atmosphere was added DIPEA (230 μL, 1.3 mmol), followed by the addition of imidazo[1,2-b]pyridazin-3-amine (53 mg, 0.4 mmol). The reaction mixture was stirred at rt for 19 h. The crude was purified directly by C18-flash chromatography (eluting with 0-100% MeCN in water (0.05% $NH_4OH$)), followed by chiral prep. HPLC (Chiralpak® ID, 5 μm 20 mm×250 mm; isocratic with 20% MTBE (0.1% 2N $NH_3$-MeOH) in DCM/MeOH (1:1) in 12 min; 20.0 mL/min) to afford 2-(4-hydroxy-4-methylcyclohexyl)-N-(imidazo[1,2-b]pyridazin-3-yl)-6-methoxy-2H-indazole-5-carboxamide—Isomer 1 (11 mg, 8%, 100% ee) and 2-(4-hydroxy-4-methylcyclohexyl)-N-(imidazo[1,2-b]pyridazin-3-yl)-6-methoxy-2H-indazole-5-carboxamide—Isomer 2 (7 mg, 5%, 99.9% ee), both as yellow solids. Isomer 1: $^1$H NMR (400 MHz, DMSO-$d_6$) δ 11.05 (s, 1H), 8.61-8.67 (m, 1H), 8.58 (s, 2H), 8.14 (dd, 1H), 8.05 (s, 1H), 7.25 (s, 1H), 7.21 (dd, 1H), 4.34-4.48 (m, 1H), 4.27 (s, 1H), 4.12 (s, 3H), 2.18-2.35 (m, 2H), 1.82-1.94 (m, 2H), 1.62-1.76 (m, 2H), 1.44-1.6 (m, 2H), 1.17 (s, 3H). MS ESI, m/z=421 $[M+H]^+$. Isomer 2: $^1$H NMR (400 MHz, DMSO-$d_6$) δ 11.04 (s, 1H), 8.60-8.68 (m, 2H), 8.57 (s, 1H), 8.14 (d, 1H), 8.05 (s, 1H), 7.27 (s, 1H), 7.21 (ddd, 1H), 4.44-4.56 (m, 2H), 4.11 (s, 3H), 1.98-2.12 (m, 4H), 1.53-1.73 (m, 4H), 1.23 (s, 3H). MS ESI, m/z=421 $[M+H]^+$.

rel-2-(1S,3R)-3-Hydroxy-3-methylcyclohexyl)-6-methoxy-N-(pyrazolo[1,5-a]pyrimidin-3-yl)-2H-indazole-5-carboxamide—Isomer 1 (Example 50) & Isomer 2 (Example 51)

rac-2-(1S,3S)-3-Hydroxy-3-methylcyclohexyl)-6-methoxy-N-(pyrazolo[1,5-c]pyrimidin-3-yl)-2H-indazole-5-carboxamide—Isomer 1 (Example 52) & Isomer 2 (Example 53)

3-(5-Bromo-6-methoxy-2H-indazol-2-yl)cyclohexan-1-one

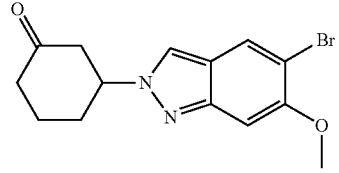 [SMILES: COc1cc2nn(C3CCCC(=O)C3)cc2cc1Br]

To a solution of 5-bromo-6-methoxy-1H-indazole (5.0 g, 22.0 mmol) and cyclohex-2-en-1-one (16.9 g, 176.2 mmol) in 1,4-dioxane (1 L) at rt was added $K_2CO_3$ (9.13 g, 66.06 mmol). The reaction mixture was stirred at 80° C. for 12 h. The mixture was allowed to cool to rt, quenched with water (1 L) and extracted with EtOAc (500 mL×3). The combined organic layers were dried over $Na_2SO_4$, filtered and concentrated under reduced pressure as a yellow oil. The oil was purified by silica gel chromatography (eluting with 0-60% EtOAc in PE) to afford 3-(5-bromo-6-methoxy-2H-indazol-2-yl)cyclohexan-1-one (1.6 g, 22%) as a colorless solid. m/z (ESI+), $[M+H]^+$=323/324.

3-(5-Bromo-6-methoxy-2H-indazol-2-yl)-1-methylcyclohexan-1-ol

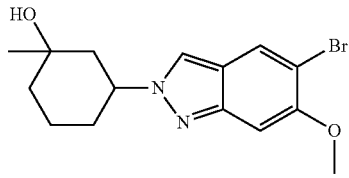

To a solution of 3-(5-bromo-6-methoxy-2H-indazol-2-yl)cyclohexan-1-one (2.0 g, 6.2 mmol) in THF (30 mL) at −40° C. was added 1M methylmagnesium bromide in THF (24.8 mL, 24.8 mmol) dropwise over a period of 10 min under $N_2$ atmosphere. The resulting mixture was stirred at −40° C. for 12 h. The reaction was quenched with water (10 mL) and extracted with EtOAc (20 mL×3). The combined organic layers were dried over $Na_2SO_4$, filtered and concentrated under reduced pressure. The residue was purified by C18-flash chromatography (eluting with 0-60% MeCN in water (0.5% FA)) to afford 3-(5-bromo-6-methoxy-2H-indazol-2-yl)-1-methylcyclohexan-1-ol (2.0 g, 95%) as a yellow solid. m/z (ESI+), [M+H]$^+$=339/341.

rac-Methyl 2-(1S,3R)-3-hydroxy-3-methylcyclohexyl)-6-methoxy-2H-indazole-5-carboxylate & rac-Methyl 2-(1S,3S)-3-hydroxy-3-methylcyclohexyl)-6-methoxy-2H-indazole-5-carboxylate

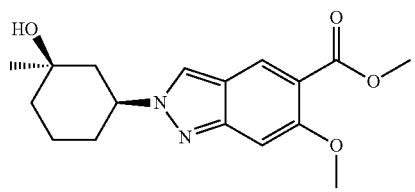

And Enantiomer

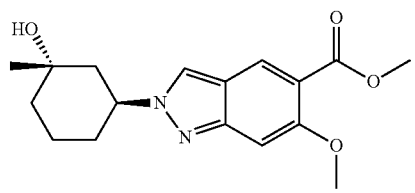

And Enantiomer

A suspension of 3-(5-bromo-6-methoxy-2H-indazol-2-yl)-1-methylcyclohexan-1-ol (2.0 g, 5.9 mmol), DIPEA (5.1 mL, 29.5 mmol) and Pd(dppf)Cl$_2$ (648 mg, 0.9 mmol) in MeOH (30 mL) was stirred under CO atmosphere at 15 atm and 110° C. for 12 h. The reaction mixture was allowed to cool to rt and concentrated under reduced pressure. The residue was purified by silica gel chromatography (eluting with 30-60% EtOAc in PE) and further by prep. HPLC (Waters XSelect CSH C18 OBD, 5 μm 30×150 mm; elution gradient with 20-45% MeCN in water (0.1% FA) in 10 min; 60 mL/min) to afford rac-methyl 2-((1S,3R)-3-hydroxy-3-methylcyclohexyl)-6-methoxy-2H-indazole-5-carboxylate (550 mg, 29%) and rac-methyl 2-((1S,3S)-3-hydroxy-3-methylcyclohexyl)-6-methoxy-2H-indazole-5-carboxylate (800 mg, 43%), both as yellow solids. m/z (ESI+), [M+H]$^+$=319.

rac-2-(1S,3R)-3-Hydroxy-3-methylcyclohexyl)-6-methoxy-2H-indazole-5-carboxylic acid

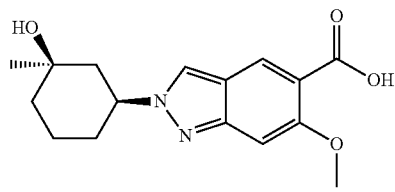

And Enantiomer

To a solution of rac-methyl 2-((1S,3R)-3-hydroxy-3-methylcyclohexyl)-6-methoxy-2H-indazole-5-carboxylate (500 mg, 1.6 mmol) in MeOH (2 mL) at rt was added a solution of LiOH (113 mg, 4.7 mmol) in water (2 mL). The resulting solution was stirred at rt for 12 h. The reaction mixture was acidified to pH 4-5 with 0.1N HCl and then purified by C18-flash chromatography (eluting with 40-60% MeCN in water (0.05% FA)) to afford rac-2-((1S,3R)-3-hydroxy-3-methylcyclohexyl)-6-methoxy-2H-indazole-5-carboxylic acid (400 mg, 84%) as a colorless solid. m/z (ESI+), [M+H]$^+$=305.

rel-2-((1S,3R)-3-Hydroxy-3-methylcyclohexyl)-6-methoxy-N-(pyrazolo[1,5-a]pyrimidin-3-yl)-2H-indazole-5-carboxamide—Isomer 1 (Example 50) & Isomer 2 (Example 51)

ISOMER 1

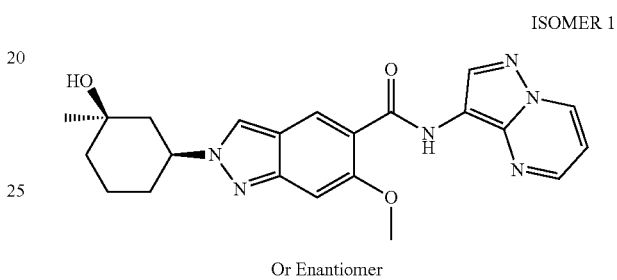

Or Enantiomer

ISOMER 2

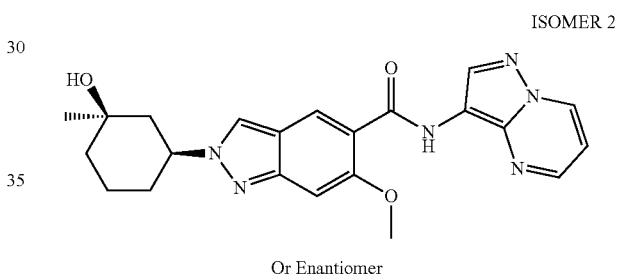

Or Enantiomer

To a solution of rac-2-((1S,3R)-3-hydroxy-3-methylcyclohexyl)-6-methoxy-2H-indazole-5-carboxylic acid (200 mg, 0.7 mmol), HATU (300 mg, 0.8 mmol) and DIPEA (5744, 3.3 mmol) in DMF (3 mL) was added pyrazolo[1,5-a]pyrimidin-3-amine (Int I-5) (141 mg, 1.1 mmol). The resulting solution was stirred at rt for 6 h. The reaction mixture was quenched with water (5 mL) and then purified directly by C18-flash chromatography (eluting with 10 to 60% MeCN in water (0.05% FA)) followed by prep. chiral HPLC (Chiralpak IA, 2×25 cm, 5 μm; mobile phase A: Hex/DCM (2:1, 0.5% 2N NH$_3$-MeOH), mobile phase B: MeOH; flow rate: 20 mL/min; gradient: 50% B for 12 min) to afford rel-2-((1S,3R)-3-hydroxy-3-methylcyclohexyl)-6-methoxy-N-(pyrazolo[1,5-a]pyrimidin-3-yl)-2H-indazole-5-carboxamide Isomer 1 (44 mg, 16%, 100% ee) and rel-2-((1S,3R)-3-hydroxy-3-methylcyclohexyl)-6-methoxy-N-(pyrazolo[1,5-a]pyrimidin-3-yl)-2H-indazole-5-carboxamide Isomer 2 (42 mg, 15%, 98.4% ee). The $^1$H NMR and MS obtained for both products were identical. $^1$H NMR (400 MHz, DMSO-d$_6$) δ 10.34 (s, 1H), 9.07 (dd, 1H), 8.73 (s, 1H), 8.52-8.58 (m, 2H), 8.47 (s, 1H), 7.21 (s, 1H), 7.05 (dd, 1H), 4.68 (s, 1H), 4.51-4.61 (m, 1H), 4.06 (s, 3H), 1.93-2.12 (m, 3H), 1.72-1.87 (m, 2H), 1.58-1.67 (m, 1H), 1.38-1.55 (m, 2H), 1.24 (s, 3H). m/z (ESI+), [M+H]$^+$=421.

rac-2-(1S,3S)-3-Hydroxy-3-methylcyclohexyl)-6-methoxy-2H-indazole-5-carboxylic acid

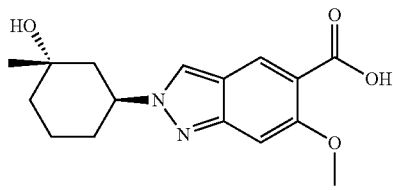

And Enantiomer

To a solution of rac-methyl 2-((1S,3S)-3-hydroxy-3-methylcyclohexyl)-6-methoxy-2H-indazole-5-carboxylate (800 mg, 2.5 mmol) in MeOH (6 mL) at rt under N₂ atmosphere was added a solution of LiOH (181 mg, 7.5 mmol) in water (6 mL). The resulting solution was stirred at rt for 12 h. The reaction mixture was acidified to pH 4-5 with 0.1N HCl and then purified by C18-flash chromatography (eluting with 30-60% MeCN in water (0.05% FA)) to afford rac-2-((1S,3S)-3-hydroxy-3-methylcyclohexyl)-6-methoxy-2H-indazole-5-carboxylic acid (600 mg, 78%) as a colorless solid. MS ESI, m/z=305 [M+H]⁺.

rac-2-(1S,3S)-3-Hydroxy-3-methylcyclohexyl)-6-methoxy-N-(pyrazolo[1,5-c]pyrimidin-3-yl)-2H-indazole-5-carboxamide—Isomer 1 (Example 52) & Isomer 2 (Example 53)

ISOMER 1

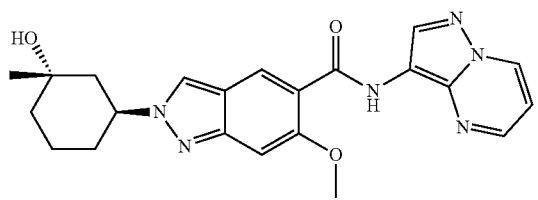

Or Enantiomer

ISOMER 2

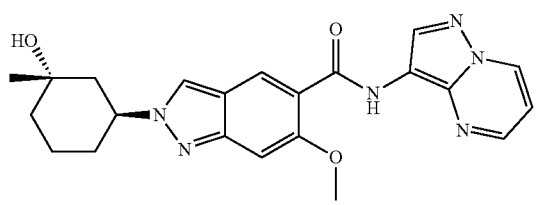

Or Enantiomer

A solution of rac-2-((1S,3S)-3-hydroxy-3-methylcyclohexyl)-6-methoxy-2H-indazole-5-carboxylic acid (200 mg, 0.7 mmol), HATU (300 mg, 0.8 mmol) and DIPEA (5744, 3.3 mmol) in THF (15 mL) under N₂ atmosphere was stirred for 1 h, followed by the addition of pyrazolo[1,5-a]pyrimidin-3-amine (IntI-5) (132 mg, 1.0 mmol). The resulting solution was stirred at rt for 4 h. The reaction was quenched with water (5 mL) and the formed precipitate was collected by filtration to afford rac-2-((1S,3S)-3-hydroxy-3-methylcyclohexyl)-6-methoxy-N-(pyrazolo[1,5-c]pyrimidin-3-yl)-2H-indazole-5-carboxamide as a yellow solid. The solid was separated by prep. chiral HPLC (Chiralpak® ID-2, 5 μm 20 mm×250 mm; isocratic with 50% MTBE (0.5% 2N NH₃-MeOH solution) in MeOH in 25 min; 17 mL/min) to afford rel-2-((1S,3S)-3-hydroxy-3-methylcyclohexyl)-6-methoxy-N-(pyrazolo[1,5-a]pyrimidin-3-yl)-2H-indazole-5-carboxamide—Isomer 1 (40 mg, 19%, 99.8% ee) and rel-2-((1S,3S)-3-hydroxy-3-methylcyclohexyl)-6-methoxy-N-(pyrazolo[1,5-a]pyrimidin-3-yl)-2H-indazole-5-carboxamide—Isomer 2 (48 mg, 23%, 99.8% ee), both as yellow solids. Isomer 1: ¹H NMR (300 MHz, DMSO-d₆) δ 10.35 (s, 1H), 9.07 (dd, 1H), 8.73 (s, 1H), 8.51-8.59 (m, 2H), 8.46 (d, 1H), 7.20 (s, 1H), 7.05 (dd, 1H), 4.64-4.83 (m, 1H), 4.41 (s, 1H), 4.05 (s, 3H), 1.87-2.13 (m, 3H), 1.71-1.87 (m, 2H), 1.55-1.71 (m, 2H), 1.27-1.43 (m, 1H), 1.20 (s, 3H). MS ESI, m/z=421 [M+H]⁺. Isomer 2: ¹H NMR (400 MHz, DMSO-d₆) δ 10.34 (s, 1H), 9.07 (dd, 1H), 8.73 (s, 1H), 8.52-8.57 (m, 2H), 8.46 (d, 1H), 7.20 (s, 1H), 7.05 (dd, 1H), 4.68-4.79 (m, 1H), 4.41 (s, 1H), 4.06 (s, 3H), 2.04-2.12 (m, 1H), 1.98-2.04 (m, 1H), 1.92 (t, 1H), 1.70-1.87 (m, 2H), 1.55-1.69 (m, 2H), 1.29-1.40 (m, 1H), 1.20 (s, 3H). MS ESI, m/z=421 [M+H]⁺.

rel-6-Cyclopropoxy-2-(1S,3R)-3-hydroxy-3-methylcyclohexyl)-N-(pyrazolo[1,5-c]pyrimidin-3-yl)-2H-indazole-5-carboxamide—Isomer 1 (Example 54) & Isomer 2 (Example 55)

3-(6-Cyclopropoxy-5-iodo-2H-indazol-2-yl)cyclohexan-1-one

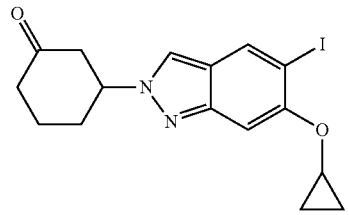 [SMILES: O=C1CCCC(n2cc3cc(I)c(OC4CC4)cc3n2)C1]

To a solution of 6-cyclopropoxy-5-iodo-1H-indazole (Int I-3) (3.0 g, 10.0 mmol) and cyclohex-2-en-1-one (7.7 g, 80.0 mmol) in 1,4-dioxane (500 mL) at rt was added K₂CO₃ (4.1 g, 30.0 mmol). The reaction mixture was stirred at 80° C. for 12 h. The mixture was cooled to rt, quenched with water (100 mL) and extracted with EtOAc (300 mL×3). The combined organic layers were dried over Na₂SO₄, filtered and concentrated under reduced pressure. The residue was purified by silica gel chromatography (eluting with 0-50% EtOAc in PE) to afford 3-(5-iodo-6-methoxy-2H-indazol-2-yl)cyclohexan-1-one (980 mg, 25%) as a colorless solid. MS ESI, m/z=397 [M+H]⁺.

3-(6-Cyclopropoxy-5-iodo-2H-indazol-2-yl)-1-methylcyclohexan-1-ol

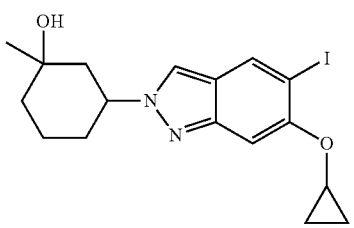 [SMILES: CC1(O)CCCC(n2cc3cc(I)c(OC4CC4)cc3n2)C1]

To a solution of 3-(6-cyclopropoxy-5-iodo-2H-indazol-2-yl)cyclohexan-1-one (800 mg, 2.0 mmol) in THF (10 mL) at rt was added 1M methylmagnesium bromide in THF (8.1 mL, 8.1 mmol) dropwise under N₂ atmosphere. The resulting mixture was stirred at −40° C. for 5 h. The reaction was quenched with water (20 mL) and extracted with EtOAc (50 mL×3). The combined organic layers were dried over Na₂SO₄, filtered and concentrated under reduced pressure. The residue was purified by C18-flash chromatography (eluting with 30-60% MeCN in water (0.05% FA)) to afford crude 3-(6-cyclopropoxy-5-iodo-2H-indazol-2-yl)-1-methylcyclohexan-1-ol (720 mg) as a colorless solid, which was used directly without further purification. MS ESI, m/z=413 [M+H]⁺.

rac-Methyl 6-cyclopropoxy-2-(1S,3R)-3-hydroxy-3-methylcyclohexyl)-2H-indazole-5-carboxylate

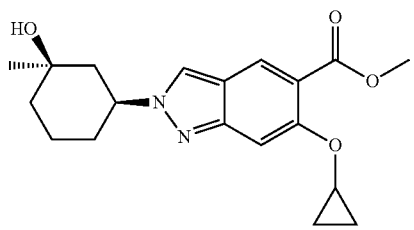

And Enantiomer

A suspension of crude 3-(6-cyclopropoxy-5-iodo-2H-indazol-2-yl)-1-methylcyclohexan-1-ol (720 mg), DIPEA (1.5 mL, 8.7 mmol) and Pd(dppf)Cl₂ (128 mg, 0.2 mmol) in MeOH (100 mL) was stirred under CO atmosphere at 15 atm and 110° C. for 12 h. The mixture was cooled to rt and filtered. The filtrate was purified directly by C18-flash chromatography (eluting with 0-60% MeCN in PE) and further purified by prep. HPLC (Waters Xbridge® Shield RP18 OBD, 5 μm 30×150 mm; elution gradient with 30-40% MeCN in water (0.1% FA) in 7 min; 60 mL/min) to afford rac-methyl 6-cyclopropoxy-2-((1S,3R)-3-hydroxy-3-methylcyclohexyl)-2H-indazole-5-carboxylate (240 mg, 40%). MS ESI, m/z=345 [M+H]⁺.

rac-6-Cyclopropoxy-2-(1S,3R)-3-hydroxy-3-methylcyclohexyl)-2H-indazole-5-carboxylic acid

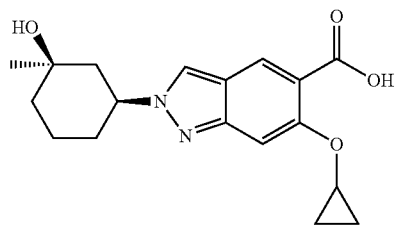

And Enantiomer

To a solution of rac-methyl 6-cyclopropoxy-2-((1S,3R)-3-hydroxy-3-methylcyclohexyl)-2H-indazole-5-carboxylate (180 mg, 0.5 mmol) in MeOH (2 mL) was added a solution of LiOH (38 mg, 1.6 mmol) in water (2 mL). The resulting mixture was stirred at rt for 12 h. The mixture was acidified to pH 4-5 with 0.1N HCl. The mixture was purified directly by C18-flash chromatography (eluting with 0-60% MeCN in water (0.5% FA)) to afford rac-6-cyclopropoxy-2-((1S,3R)-3-hydroxy-3-methylcyclohexyl)-2H-indazole-5-carboxylic acid (160 mg, 93%) as a colorless solid. MS ESI, m/z=331 [M+H]⁺.

rel-6-Cyclopropoxy-2-(1S,3R)-3-hydroxy-3-methylcyclohexyl)-N-(pyrazolo[1,5-c]pyrimidin-3-yl)-2H-indazole-5-carboxamide—Isomer 1 (Example 54) & Isomer 2 (Example 55)

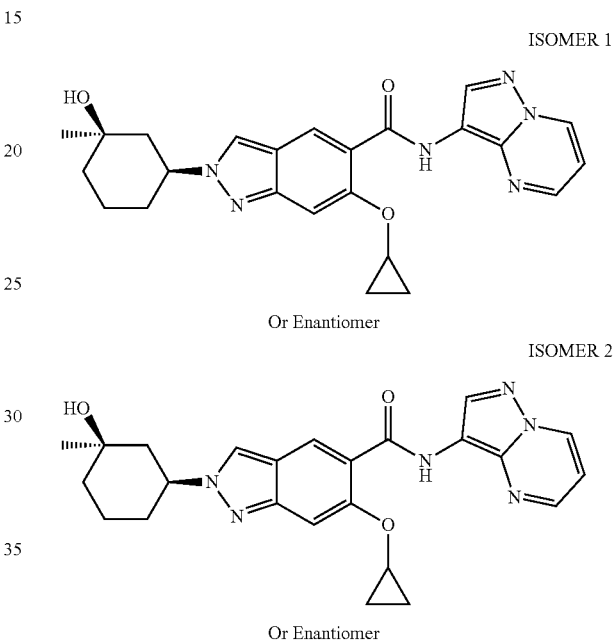

To a solution of rac-6-cyclopropoxy-2-(1S,3R)-3-hydroxy-3-methylcyclohexyl)-2H-indazole-5-carboxylic acid (100 mg, 0.3 mmol), HATU (115 mg, 0.3 mmol) and DIPEA (534, 0.3 mmol) in THF (10 mL) under N₂ atmosphere was added pyrazolo[1,5-a]pyrimidin-3-amine (Int I-5) (41 mg, 0.3 mmol). The resulting solution was stirred at rt for 2 h. The reaction was quenched with water (1 mL). The mixture was purified directly by prep. chiral-HPLC (Chiralpak® IA, 5 μm 20 mm×250 mm; isocratic with 50% MTBE (0.5% 2N NH₃-MeOH) in MeOH; 50 mL/min) to afford rel-6-cyclopropoxy-2-(1S,3R)-3-hydroxy-3-methylcyclohexyl)-N-(pyrazolo[1,5-a]pyrimidin-3-yl)-2H-indazole-5-carboxamide—Isomer 1 (42 mg, 42%, 100% ee) and rel-6-cyclopropoxy-2-(1S,3R)-3-hydroxy-3-methylcyclohexyl)-N-(pyrazolo[1,5-a]pyrimidin-3-yl)-2H-indazole-5-carboxamide—Isomer 2 (46 mg, 46%, 100% ee), both as yellow solids. The ¹H NMR and MS obtained for both products were identical. ¹H NMR (400 MHz, DMSO-d₆) δ 10.31 (s, 1H), 9.07 (dd, 1H), 8.75 (s, 1H), 8.58 (s, 1H), 8.55 (dd, 1H), 5.53 (s, 1H), 7.51 (s, 1H), 7.05 (dd, 1H), 4.50-4.64 (m, 1H), 4.19-4.25 (m, 1H), 1.94-2.11 (m, 3H), 1.72-1.86 (m, 2H), 1.63 (br. d, 1H), 1.37-1.56 (m, 2H), 1.25 (s, 3H), 1.01-1.11 (m, 2H), 0.93-1.03 (m, 2H). MS ESI, m/z=447 [M+H]⁺.

6-Cyclopropoxy-2-((1s,4s)-4-hydroxycyclohexyl)-N-(pyrazolo[1,5-c]pyrimidin-3-yl)-2H-indazole-5-carboxamide (Example 56)

Methyl 6-cyclopropoxy-2-((1s,4s)-4-hydroxycyclohexyl)-2H-indazole-5-carboxylate

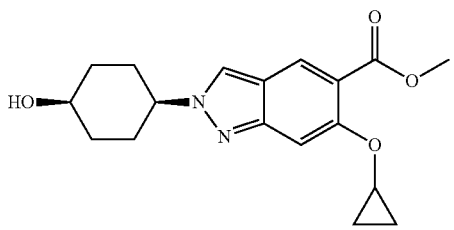 [SMILES: COC(=O)c1cc2cn([C@H]3CC[C@@H](O)CC3)nc2cc1OC1CC1]

A suspension of (1s,4s)-4-(6-cyclopropoxy-5-iodo-2H-indazol-2-yl)cyclohexan-1-ol (Int IV-1) (110 mg, 0.3 mmol), TEA (1154, 0.8 mmol) and Pd(dppf)Cl$_2$—CH$_2$Cl$_2$ (226 mg, 0.3 mmol) in MeOH (20 mL) was stirred under CO atmosphere at 15 atm and 100° C. for 14 h. The mixture was cooled to rt, concentrated and purified by C18-flash chromatography (eluting with 0-100% MeOH in water (0.1% FA)) to afford methyl 6-cyclopropoxy-2-((1s,4s)-4-hydroxycyclohexyl)-2H-indazole-5-carboxylate (67 mg, 73%) as a yellow solid. MS ESI, m/z=331 [M+H]$^+$.

6-Cyclopropoxy-2-((1s,4s)-4-hydroxycyclohexyl)-2H-indazole-5-carboxylic acid

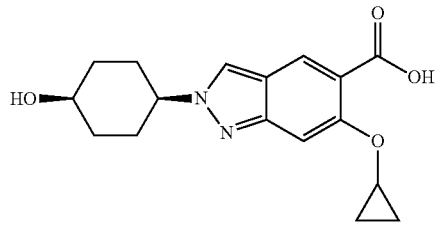 [SMILES: O=C(O)c1cc2cn([C@H]3CC[C@@H](O)CC3)nc2cc1OC1CC1]

To a solution of NaOH (35 mg, 0.9 mmol) in MeOH (1 mL) and water (0.5 mL) was added methyl 6-cyclopropoxy-2-((1s,4s)-4-hydroxycyclohexyl)-2H-indazole-5-carboxylate (57 mg, 0.2 mmol). The resulting solution was stirred at rt for 4 h. The reaction mixture was acidified to pH ~6 with 0.1N HCl and then concentrated under reduced pressure. The residue was purified by C18-flash chromatography (eluting with 0-100% MeCN in water (0.1% FA)) to afford crude 6-cyclopropoxy-2-((1s,4s)-4-hydroxycyclohexyl)-2H-indazole-5-carboxylic acid (64 mg, 86 wt. %) as a colorless solid. MS ESI, m/z=317 [M+H]$^+$.

6-Cyclopropoxy-2-((1s,4s)-4-hydroxycyclohexyl)-N-(pyrazolo[1,5-c]pyrimidin-3-yl)-2H-indazole-5-carboxamide (Example 56)

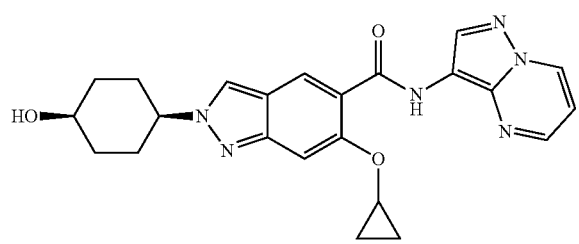 [SMILES: O=C(Nc1cnn2cccnc12)c1cc2cn([C@H]3CC[C@@H](O)CC3)nc2cc1OC1CC1]

To a solution of crude 6-cyclopropoxy-2-((1s,4s)-4-hydroxycyclohexyl)-2H-indazole-5-carboxylic acid (86 wt. %) (54 mg), DIPEA (1194, 0.7 mmol), HOBt (5 mg, 0.03 mmol) and HATU (97 mg, 0.3 mmol) in DMF (5 mL) was added pyrazolo[1,5-a]pyrimidin-3-amine (Int I-5) (46 mg, 0.34 mmol). The resulting mixture was stirred at rt for 4 h. The reaction mixture was diluted with EtOAc (50 mL) and washed with water (25 mL). The organic layer was concentrated under reduced pressure. The residue was purified by C18-flash chromatography (eluting with 0-100% MeCN in water (0.1% FA)) and further by prep. HPLC (Waters XBridge BEH C18 OBD 5 μm 30×150 mm; elution gradient with 27-34% MeCN in water (10 mM NH$_4$HCO$_3$+0.1% NH$_4$OH) in 7 min; 60 mL/min) to afford 6-cyclopropoxy-2-((1s,4s)-4-hydroxycyclohexyl)-N-(pyrazolo[1,5-c]pyrimidin-3-yl)-2H-indazole-5-carboxamide (20 mg, 27%) as a yellow solid. $^1$H NMR (400 MHz, DMSO-d$_6$) δ 10.32 (s, 1H), 9.07 (dd, 1H), 8.75 (s, 1H), 8.58 (s, 1H), 8.49-8.58 (m, 2H), 7.51 (s, 1H), 7.05 (dd, 1H), 4.52 (d, 1H), 4.42-4.51 (m, 1H), 4.18-4.27 (m, 1H), 3.85-3.94 (m, 1H), 2.24-2.39 (m, 2H), 1.82-1.92 (m, 2H), 1.72-1.82 (m, 2H), 1.58-1.72 (m, 2H), 1.03-1.13 (m, 2H), 0.94-1.03 (m, 2H). MS ESI, m/z=433 [M+H]$^+$.

6-Cyclopropoxy-2-((1r,4r)-4-hydroxycyclohexyl)-N-(pyrazolo[1,5-a]pyrimidin-3-yl)-2H-indazole-5-carboxamide (Example 57)

Methyl 6-cyclopropoxy-2-((1r,4r)-4-hydroxycyclohexyl)-2H-indazole-5-carboxylate

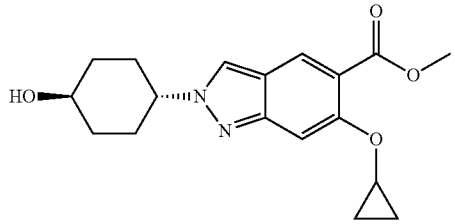 [SMILES: COC(=O)c1cc2cn([C@H]3CC[C@H](O)CC3)nc2cc1OC1CC1]

A suspension of (1r,4r)-4-(6-cyclopropoxy-5-iodo-2H-indazol-2-yl)cyclohexan-1-ol (Int IV-2) (110 mg, 0.3 mmol), TEA (115 μL, 0.8 mmol) and Pd(dppf)Cl$_2$—CH$_2$Cl$_2$ (45 mg, 0.1 mmol) in MeOH (10 mL) was stirred under CO atmosphere at 15 atm and 100° C. for 13 h. The reaction mixture was cooled to rt and purified directly by C18-flash chromatography (eluting with 0-100% MeOH in water (0.1% FA)) to afford methyl 6-cyclopropoxy-2-((1r,4r)-4-hydroxycyclohexyl)-2H-indazole-5-carboxylate (80 mg, 88%) as a yellow solid. MS ESI, m/z=331 [M+H]$^+$.

6-Cyclopropoxy-2-((1r,4r)-4-hydroxycyclohexyl)-2H-indazole-5-carboxylic Acid

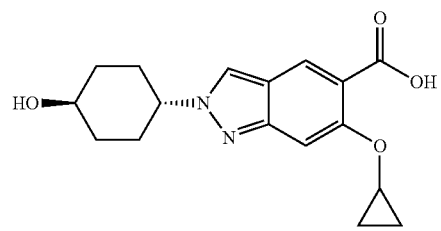 [SMILES: O=C(O)c1cc2cn([C@H]3CC[C@H](O)CC3)nc2cc1OC1CC1]

To a solution of methyl 6-cyclopropoxy-2-((1r,4r)-4-hydroxycyclohexyl)-2H-indazole-5-carboxylate (70 mg, 0.2 mmol) in MeOH (1 mL) was added a solution of NaOH (34 mg, 0.9 mmol) in water (1 mL). The resulting solution was stirred at rt for 14 h. The reaction mixture was adjusted to pH 5-6 with 2N HCl and then concentrated under reduced pressure. The residue was purified by C18-flash chromatography (eluting with 0-100% MeCN in water (0.1% FA)) to afford 6-cyclopropoxy-2-((1r,4r)-4-hydroxycyclohexyl)-2H-indazole-5-carboxylic acid (45 mg, 67%) as a yellow solid. MS ESI, m/z=317 [M+H]+.

6-Cyclopropoxy-2-((1r,4r)-4-hydroxycyclohexyl)-N-(pyrazolo[1,5-c]pyrimidin-3-yl)-2H-indazole-5-carboxamide (Example 57)

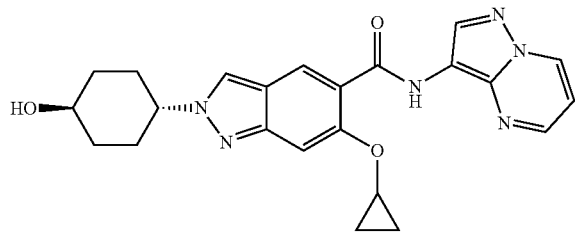 [SMILES: O=C(Nc1cnn2cccnc12)c1cc2cn([C@H]3CC[C@H](O)CC3)nc2cc1OC1CC1]

To a solution of 6-cyclopropoxy-2-((1r,4r)-4-hydroxycyclohexyl)-2H-indazole-5-carboxylic acid (40 mg, 0.1 mmol), the TFA salt of pyrazolo[1,5-a]pyrimidin-3-amine (62 mg, 0.3 mmol), HOBt (4 mg, 0.03 mmol) and HATU (72 mg, 0.2 mmol) in DMF (5 mL) was added DIPEA (664, 0.4 mmol). The resulting mixture was stirred at rt for 3 h. The reaction mixture was diluted with EtOAc (50 mL) and washed with water (50 mL). The organic layer was concentrated under reduced pressure. The residue was purified by C18-flash chromatography (eluting with 0-100% MeCN in water (0.1% FA)) and further by prep. HPLC (Waters XBridge BEH C18 OBD 5 μm 30×150 mm; elution gradient with 24-32% MeCN in water (10 mM NH4HCO3+0.1% NH4OH) in 7 min; 60 mL/min) to afford 6-cyclopropoxy-2-((1r,4r)-4-hydroxycyclohexyl)-N-(pyrazolo[1,5-c]pyrimidin-3-yl)-2H-indazole-5-carboxamide (12 mg, 22%) as a yellow solid. 1H NMR (300 MHz, DMSO-d6) δ 10.30 (s, 1H), 9.07 (dd, 1H), 8.74 (s, 1H), 8.55 (s, 1H), 8.54 (dd, 1H), 8.53 (s, 1H), 7.50 (s, 1H), 7.04 (dd, 1H), 4.72 (d, 1H), 4.41-4.55 (m, 1H), 4.15-4.25 (m, 1H), 3.48-3.63 (m, 1H), 2.04-2.16 (m, 2H), 1.89-2.04 (m, 4H), 1.30-1.51 (m, 2H), 0.93-1.10 (m, 4H). MS ESI, m/z=433 [M+H]+.

2-((1R,4r)-4-((R)-2-Hydroxy-N-methylpropanamido)cyclohexyl)-6-methoxy-N-(pyrazolo[1,5-c]pyrimidin-3-yl)-2H-indazole-5-carboxamide (Example 58)

(R)-1-(((1r,4R)-4-(6-Methoxy-5-(pyrazolo[1,5-c]pyrimidin-3-ylcarbamoyl)-2H-indazol-2-yl)cyclohexyl)(methyl)amino)-1-oxopropan-2-yl acetate

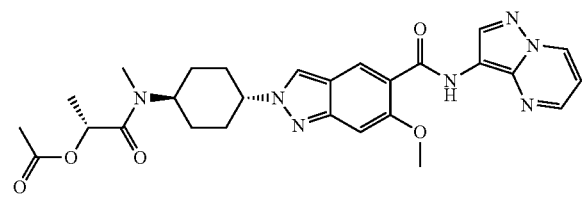 [SMILES: COc1cc2nn([C@H]3CC[C@H](N(C)C(=O)[C@@H](C)OC(C)=O)CC3)cc2cc1C(=O)Nc1cnn2cccnc12]

To a solution of the HCl salt of 6-methoxy-2-((1r,4r)-4-(methylamino)cyclohexyl)-N-(pyrazolo[1,5-a]pyrimidin-3-yl)-2H-indazole-5-carboxamide (Int V-4) (300 mg, 0.7 mmol), and TEA (200 mg, 2.0 mmol) in DCM (10 mL) at rt under N2 atmosphere was added (R)-1-chloro-1-oxopropan-2-yl acetate (149 mg, 1.0 mmol). The resulting mixture was stirred at rt for 1 h. The reaction mixture was quenched with MeOH (2 mL) and concentrated under reduced pressure. The residue was purified by C18-flash chromatography (eluting with 0-80% MeCN in water (0.1% FA)) to afford (R)-1-(((1r,4R)-4-(6-methoxy-5-(pyrazolo[1,5-c]pyrimidin-3-ylcarbamoyl)-2H-indazol-2-yl)cyclohexyl)(methyl)amino)-1-oxopropan-2-yl acetate (320 mg, 91%) as a yellow solid. MS ESI, m/z=534 [M+H]+.

2-((1R,4r)-4-((R)-2-Hydroxy-N-methylpropanamido)cyclohexyl)-6-methoxy-N-(pyrazolo[1,5-c]pyrimidin-3-yl)-2H-indazole-5-carboxamide (Example 58)

To a solution of (R)-1-(((1r,4R)-4-(6-methoxy-5-(pyrazolo[1,5-c]pyrimidin-3-ylcarbamoyl)-2H-indazol-2-yl)cyclohexyl)(methyl)amino)-1-oxopropan-2-ylacetate (300 mg, 0.6 mmol) in MeOH (10 mL)/water (5 mL) at rt under N2 atmosphere was added NaOH (68 mg, 1.7 mmol). The resulting solution was stirred at rt for 12 h. The reaction mixture was concentrated under reduced pressure. The residue was purified directly by prep. HPLC (Waters Xbridge® BEH OBD C18, 5 μm 30×150 mm; elution gradient with 12-42% MeCN in water (10 mM NH4HCO3+0.1% NH4OH) in 8 min; 60 mL/min) to afford 2-((1R,4r)-4-((R)-2-hydroxy-N-methylpropanamido)cyclohexyl)-6-methoxy-N-(pyrazolo[1,5-c]pyrimidin-3-yl)-2H-indazole-5-carboxamide (265 mg, 96%, 100% ee) as a yellow solid. 1H NMR (400 MHz, DMSO-d6) (5:6 mixture of rotamers) δ 10.35 (s, 1H), 9.08 (dd, 1H), 8.73 (s, 1H), 8.53-8.59 (m, 2H), 8.48/8.47 (s, 1H) (rotamers), 7.22/7.20 (s, 1H) (rotamers), 7.05 (dd, 1H), 4.93/4.74 (d, 1H) (rotamers), 4.34-4.58/3.93-4.02 (m, 3H) (rotamers), 4.06 (s, 3H), 2.91/2.77 (s, 3H) (rotamers), 1.62-2.27 (m, 8H), 1.22/1.18 (d, 3H) (rotamers). MS ESI, m/z=492 [M+H]+.

2-((1S,4r)-4-((S)-2-Hydroxy-N-methylpropanamido)cyclohexyl)-6-methoxy-N-(pyrazolo[1,5-c]pyrimidin-3-yl)-2H-indazole-5-carboxamide (Example 59)

(S)-1-(((1r,4S)-4-(6-Methoxy-5-(pyrazolo[1,5-a]pyrimidin-3-ylcarbamoyl)-2H-indazol-2-yl)cyclohexyl)(methyl)amino)-1-oxopropan-2-yl acetate

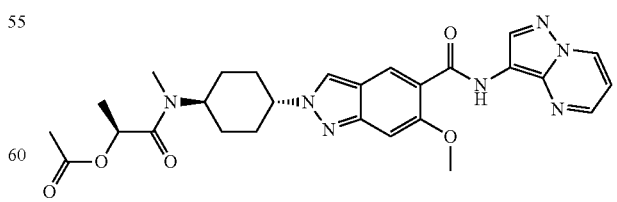

To a solution of the HCl salt of 6-methoxy-2-((1r,4r)-4-(methylamino)cyclohexyl)-N-(pyrazolo[1,5-c]pyrimidin-3-yl)-2H-indazole-5-carboxamide (Int V-4) (130 mg, 0.3 mmol), and TEA (87 mg, 0.9 mmol) in DCM (8 mL) at rt under N2 atmosphere was added (S)-1-chloro-1-oxopropan- 2-yl acetate (64 mg, 0.4 mmol). The resulting mixture was stirred at rt for 1 h. The reaction mixture was quenched with MeOH (2 mL) and then purified directly by C18-flash chromatography (eluting with 0-80% MeCN in water (0.1% FA)) to afford (S)-1-(((1r,4S)-4-(6-methoxy-5-(pyrazolo[1,5-c]pyrimidin-3-ylcarbamoyl)-2H-indazol-2-yl)cyclohexyl)(methyl)amino)-1-oxopropan-2-yl acetate (152 mg, 100%) as a yellow solid. MS ESI, m/z=534 [M+H]+.

2-((1S,4r)-4-((S)-2-Hydroxy-N-methylpropanamido)cyclohexyl)-6-methoxy-N-(pyrazolo[1,5-a]pyrimidin-3-yl)-2H-indazole-5-carboxamide (Example 59)

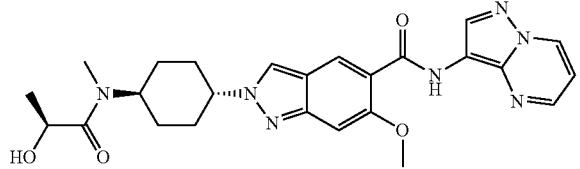 [SMILES: COc1cc2nn([C@H]3CC[C@H](N(C)C(=O)[C@H](C)O)CC3)cc2cc1C(=O)Nc1cnn2cccnc12]

To a solution of (S)-1-(((1r,4S)-4-(6-methoxy-5-(pyrazolo[1,5-c]pyrimidin-3-ylcarbamoyl)-2H-indazol-2-yl)cyclohexyl)(methyl)amino)-1-oxopropan-2-yl acetate (145 mg, 0.3 mmol) in MeOH (5 mL)/water (2.5 mL) at rt under $N_2$ atmosphere was added NaOH (22 mg, 0.5 mmol). The resulting solution was stirred at rt for 12 h. The reaction mixture was diluted with water (10 mL) and the formed precipitate was collected by filtration. The solid was washed with acetonitrile (2 mL) and water (5 mL) sequentially, and then dried in vacuo to afford 2-((1S,4r)-4-((S)-2-hydroxy-N-methylpropanamido)cyclohexyl)-6-methoxy-N-(pyrazolo[1,5-c]pyrimidin-3-yl)-2H-indazole-5-carboxamide (118 mg, 88%, 100% ee) as a yellow solid. $^1$H NMR (400 MHz, DMSO-$d_6$) (1:1 mixture of rotamers) δ 10.35 (s, 1H), 9.08 (dd, 1H), 8.73 (s, 1H), 8.52-8.59 (m, 2H), 8.48/8.47 (s, 1H) (rotamers), 7.22/7.20 (s, 1H) (rotamers), 7.05 (dd, 1H), 4.93/4.75 (d, 1H) (rotamers), 4.45-4.57/3.93-4.03 (m, 2H) (rotamers), 4.34-4.45 (m, 1H), 4.06 (s, 3H), 2.91/2.77 (s, 3H) (rotamers), 1.62-2.28 (m, 8H), 1.22/1.18 (d, 3H) (rotamers). MS ESI, m/z=492 [M+H]+.

6-Methoxy-2-(1R,2R,4R*)-2-methyl-4-(N-methylacetamido)cyclohexyl)-N-(pyrazolo[1,5-c]pyrimidin-3-yl)-2H-indazole-5-carboxamide—Isomer 1 (Example 60) & Isomer 2 (Example 61)

6-Methoxy-2-(1S,2S,4R*)-2-methyl-4-(N-methylacetamido)cyclohexyl)-N-(pyrazolo[1,5-c]pyrimidin-3-yl)-2H-indazole-5-carboxamide—Isomer 1 (Example 62) & Isomer 2 (Example 63)

Methyl 6-methoxy-2-(7R,8R)-7-methyl-1,4-dioxaspiro[4.5]decan-8-yl)-2H-indazole-5-carboxylate

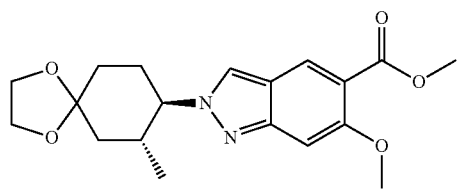 [SMILES: COC(=O)c1cc2cn([C@@H]3CCC4(C[C@H]3C)OCCO4)nc2cc1OC]

A mixture of 5-bromo-6-methoxy-2-((7R,8R)-7-methyl-1,4-dioxaspiro[4.5]decan-8-yl)-2H-indazole (Int IV-4) (380 mg, 1.0 mmol), Pd(dppf)Cl$_2$—CH$_2$Cl$_2$ (163 mg, 0.2 mmol) and TEA (695 μL, 5.0 mmol) in MeOH (10 mL) was stirred under CO atmosphere at 15 atm and 110° C. for 20 h. The reaction mixture was cooled to rt and concentrated under reduced pressure. The residue was purified by C18-flash chromatography (eluting with 0-100% MeCN in water (0.1% NH$_4$OH)) to afford methyl 6-methoxy-2-((7R,8R)-7-methyl-1,4-dioxaspiro[4.5]decan-8-yl)-2H-indazole-5-carboxylate (350 mg, 97%) as a colorless solid. MS ESI, m/z=361 [M+H]+.

Methyl 6-methoxy-2-(1R,2R)-2-methyl-4-oxocyclohexyl)-2H-indazole-5-carboxylate

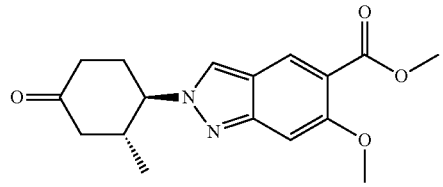 [SMILES: COC(=O)c1cc2cn([C@@H]3CCC(=O)C[C@H]3C)nc2cc1OC]

To a solution of methyl 6-methoxy-2-((7R,8R)-7-methyl-1,4-dioxaspiro[4.5]decan-8-yl)-2H-indazole-5-carboxylate (340 mg, 0.9 mmol) in THF (5 mL)/water (5 mL) was added aq. HCl (12N) (2.0 mL, 24.0 mmol). The resulting mixture was stirred at rt for 2 h. The mixture was neutralized with aq. saturated NaHCO$_3$, diluted with EtOAc (200 mL) and washed with water (100 mL×2). The organic layer was dried over Na$_2$SO$_4$, filtered and concentrated under reduced pressure. The residue was purified directly by C18-flash chromatography (eluting with 0-100% MeCN in water (0.1% FA)) to afford methyl 6-methoxy-2-((1R,2R)-2-methyl-4-oxocyclohexyl)-2H-indazole-5-carboxylate (290 mg, 97%) as a colorless solid. MS ESI, m/z=317 [M+H]+.

6-Methoxy-2-(1R,2R)-2-methyl-4-oxocyclohexyl)-2H-indazole-5-carboxylic acid

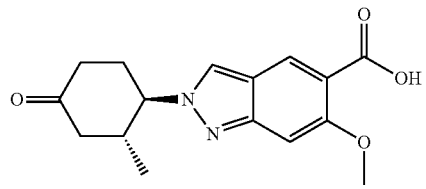 [SMILES: COc1cc2nn([C@@H]3CCC(=O)C[C@H]3C)cc2cc1C(=O)O]

To a suspension of methyl 6-methoxy-2-((1R,2R)-2-methyl-4-oxocyclohexyl)-2H-indazole-5-carboxylate (285 mg, 0.9 mmol) in MeOH (5 mL)/water (2.5 mL) was added NaOH (144 mg, 3.6 mmol). The resulting mixture was stirred at rt for 2 h. The mixture was acidified to pH 5 with 2N HCl and then purified by C18-flash chromatography (eluting with 0-100% MeCN in water (0.1% FA)) to afford 6-methoxy-2-((1R,2R)-2-methyl-4-oxocyclohexyl)-2H-indazole-5-carboxylic acid (270 mg, 99%) as a colourless gum. MS ESI, m/z=303 [M+H]+.

6-Methoxy-2-(1R,2R)-2-methyl-4-oxocyclohexyl)-N-(pyrazolo[1,5-c]pyrimidin-3-yl)-2H-indazole-5-carboxamide

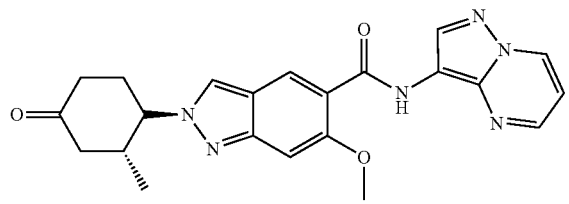

To a solution of 6-methoxy-2-((1R,2R)-2-methyl-4-oxocyclohexyl)-2H-indazole-5-carboxylic acid (265 mg, 0.9 mmol) and HATU (367 mg, 1.0 mmol) in DMF (5 mL) under N₂ atmosphere was added DIPEA (612 μL, 3.5 mmol). The resulting solution was stirred at rt for 15 min, followed by the addition of pyrazolo[1,5-a]pyrimidin-3-amine (Int I-5) (176 mg, 1.3 mmol). The reaction mixture was stirred at rt for 2 h and then purified directly by C18-flash chromatography (eluting with 0-100% MeCN in water (0.1% NH₄OH)) to afford 6-methoxy-2-((1R,2R)-2-methyl-4-oxocyclohexyl)-N-(pyrazolo[1,5-c]pyrimidin-3-yl)-2H-indazole-5-carboxamide (230 mg, 63%) as a yellow solid. MS ESI, m/z=419 [M+H]⁺.

6-Methoxy-2-(1R,2R)-2-methyl-4-(methylamino)cyclohexyl)-N-(pyrazolo[1,5-c]pyrimidin-3-O-2H-indazole-5-carboxamide

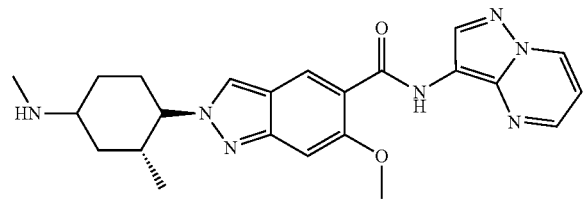

To a solution of 6-methoxy-2-((1R,2R)-2-methyl-4-oxocyclohexyl)-N-(pyrazolo[1,5-c]pyrimidin-3-yl)-2H-indazole-5-carboxamide (105 mg, 0.3 mmol) and methanamine (31 wt. % in MeOH) (126 mg, 1.3 mmol) in DCE (5 mL) was added sodium triacetoxyborohydride (106 mg, 0.5 mmol). The resulting mixture was stirred at rt for 3 h. The mixture was concentrated under reduced pressure and then purified by C18-flash chromatography (eluting with 0-100% MeCN in water (0.1% NH₄OH)) to afford 6-methoxy-2-((1R,2R)-2-methyl-4-(methylamino)cyclohexyl)-N-(pyrazolo[1,5-c]pyrimidin-3-yl)-2H-indazole-5-carboxamide (100 mg, 92%) as a yellow solid. MS ESI, m/z=434 [M+H]⁺.

6-Methoxy-2-(1R,2R,4R*)-2-methyl-4-(N-methylacetamido)cyclohexyl)-N-(pyrazolo[1,5-c]pyrimidin-3-yl)-2H-indazole-5-carboxamide—Isomer 1 (Example 60) & Isomer 2 (Example 61)

ISOMER 1

ISOMER 2

To a solution of 6-methoxy-2-((1R,2R)-2-methyl-4-(methylamino)cyclohexyl)-N-(pyrazolo[1,5-a]pyrimidin-3-yl)-2H-indazole-5-carboxamide (95 mg, 0.2 mmol) and TEA (122 μL, 0.9 mmol) in DCM (2 mL) was added acetic anhydride (45 mg, 0.4 mmol). The resulting mixture was stirred at rt for 2 h. The mixture was concentrated under reduced pressure and purified by C18-flash chromatography (eluting with 0-100% MeCN in water (0.1% NH₄OH)) to afford 6-methoxy-2-((1R,2R)-2-methyl-4-(N-methylacetamido)cyclohexyl)-N-(pyrazolo[1,5-c]pyrimidin-3-yl)-2H-indazole-5-carboxamide. This material was separated by chiral prep. HPLC (Chiralpak® IH, 5 μm 20 mm×250 mm; isocratic with 50% MTBE (0.1% 2N NH₃-MeOH) in MeOH in 7.5 min; 20.0 mL/min) to afford 6-methoxy-2-((1R,2R,4R*)-2-methyl-4-(N-methylacetamido)cyclohexyl)-N-(pyrazolo[1,5-c]pyrimidin-3-yl)-2H-indazole-5-carboxamide Isomer 1 (20 mg, 19%, 99.9% ee) and 6-methoxy-2-((1R,2R,4R*)-2-methyl-4-(N-methylacetamido)cyclohexyl)-N-(pyrazolo[1,5-c]pyrimidin-3-yl)-2H-indazole-5-carboxamide Isomer 2 (68 mg, 65%, 100% ee), both as yellow solids. Isomer 1: ¹H NMR (400 MHz, DMSO-d₆) (2:3 mixture of rotamers) δ 10.36 (s, 1H), 9.08 (dd, 1H), 8.73 (s, 1H), 8.56/8.53 (s, 1H)(rotamers), 8.54 (dd, 1H), 8.47/8.46 (s, 1H)(rotamers), 7.24/7.21 (s, 1H)(rotamers), 7.05 (dd, 1H), 4.45-4.59/3.8-3.93 (m, 1H) (rotamers), 4.08-4.18 (m, 1H), 4.06 (s, 3H), 2.86/2.73 (s, 3H) (rotamers), 1.97-2.38 (m, 6H), 1.43-1.89 (m, 4H), 0.53-0.65 (m, 3H). MS ESI, m/z=476 [M+H]⁺. Isomer 2: ¹H NMR (400 MHz, DMSO-d₆) (1:1 mixture of rotamers) δ 10.36 (s, 1H), 9.08 (dd, 1H), 8.74 (s, 1H), 8.66 (s, 1H), 8.54 (dd, 1H), 8.48 (s, 1H), 7.25 (s, 1H), 7.05 (dd, 1H), 4.63/4.02 (br. s, 1H) (rotamers), 4.38 (s, 1H), 4.06 (s, 3H), 2.65-2.93 (m, 3H), 1.26-2.39 (m, 10H), 0.94-1.21 (m, 3H). MS ESI, m/z=476 [M+H]⁺.

117

Methyl 6-methoxy-2-(7S,8S)-7-methyl-1,4-dioxas-piro[4.5]decan-8-yl)-2H-indazole-5-carboxylate

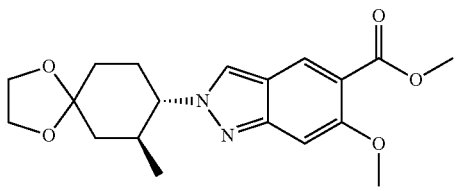 [SMILES: COC(=O)c1cc2cn([C@H]3CCC4(C[C@@H]3C)OCCO4)nc2cc1OC]

A mixture of 5-bromo-6-methoxy-2-((7S,8S)-7-methyl-1,4-dioxaspiro[4.5]decan-8-yl)-2H-indazole (Int IV-5) (1.0 g, 2.6 mmol), Pd(dppf)Cl$_2$ (384 mg, 0.5 mmol) and DIPEA (2.3 mL, 13.1 mmol) in MeOH (60 mL) was stirred under CO atmosphere at 15 atm and 110° C. for 15 h. The reaction mixture was cooled to rt and concentrated under reduced pressure. The residue was purified by C18-flash chromatography (eluting with 0-100% MeCN in water (0.05% NH$_4$OH)) to afford methyl 6-methoxy-2-((7S,8S)-7-methyl-1,4-dioxaspiro[4.5]decan-8-yl)-2H-indazole-5-carboxylate (860 mg, 91%) as a yellow solid. MS ESI, m/z=361 [M+H]$^+$.

6-Methoxy-2-(7S,8S)-7-methyl-1,4-dioxaspiro[4.5]decan-8-yl)-2H-indazole-5-carboxylic acid

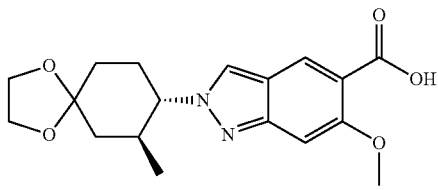 [SMILES: COc1cc2nn([C@H]3CCC4(C[C@@H]3C)OCCO4)cc2cc1C(=O)O]

To a suspension of methyl 6-methoxy-2-((7S,8S)-7-methyl-1,4-dioxaspiro[4.5]decan-8-yl)-2H-indazole-5-carboxylate (850 mg, 2.4 mmol) in MeOH (6 mL) under N$_2$ atmosphere was added a solution of LiOH (169 mg, 7.1 mmol) in water (6 mL). The resulting mixture was stirred at rt for 2 h. The reaction mixture was acidified to pH 6 with 0.1N HCl and then purified directly by C18-flash chromatography (eluting with 0-100% MeCN in water (0.05% FA)) to afford crude 6-methoxy-2-((7S,8S)-7-methyl-1,4-dioxaspiro[4.5]decan-8-yl)-2H-indazole-5-carboxylic acid (720 mg) containing 32% of 6-methoxy-2-((1S,2S)-2-methyl-4-oxocyclohexyl)-2H-indazole-5-carboxylic acid as a yellow solid. MS ESI, m/z=347 [M+H]$^+$.

6-Methoxy-2-(7S,8S)-7-methyl-1,4-dioxaspiro[4.5]decan-8-yl)-N-(pyrazolo[1,5-a]pyrimidin-3-yl)-2H-indazole-5-carboxamide

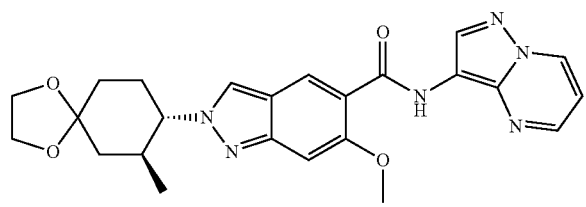 [SMILES: COc1cc2nn([C@H]3CCC4(C[C@@H]3C)OCCO4)cc2cc1C(=O)Nc1cnn2cccnc12]

118

To a solution of crude 6-methoxy-2-((7S,8S)-7-methyl-1,4-dioxaspiro[4.5]decan-8-yl)-2H-indazole-5-carboxylic acid (710 mg) and DIPEA (1.4 mL, 8.2 mmol) in DMF (10 mL) at rt under N$_2$ atmosphere was added HATU (935 mg, 2.5 mmol), followed by the addition of pyrazolo[1,5-a]pyrimidin-3-amine (412 mg, 3.1 mmol). The reaction was stirred at rt for 2 h. The crude was purified directly by C18-flash chromatography (eluting with 0-100% MeCN in water (0.05% NH$_4$OH)) to afford 6-methoxy-2-((7S,8S)-7-methyl-1,4-dioxaspiro[4.5]decan-8-yl)-N-(pyrazolo[1,5-a]pyrimidin-3-yl)-2H-indazole-5-carboxamide (640 mg, 68%) as a yellow solid. MS ESI, m/z=463 [M+H]$^+$.

6-Methoxy-2-(1S,2S)-2-methyl-4-oxocyclohexyl)-N-(pyrazolo[1,5-c]pyrimidin-3-yl)-2H-indazole-5-carboxamide

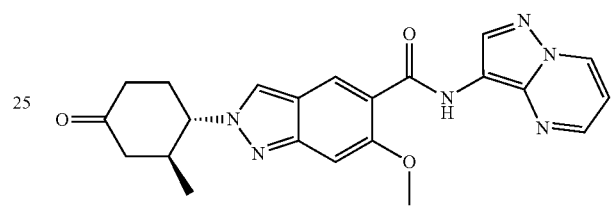

To a suspension of 6-methoxy-2-((7S,8S)-7-methyl-1,4-dioxaspiro[4.5]decan-8-yl)-N-(pyrazolo[1,5-a]pyrimidin-3-yl)-2H-indazole-5-carboxamide (630 mg, 1.4 mmol) in THF (8 mL) was added 2.4N HCl (10.0 mL, 24.0 mmol). The resulting mixture was stirred at rt for 12 h. The reaction mixture was neutralized with aq. saturated NaHCO$_3$ and then purified directly by C18-flash chromatography (eluting with 0-100% MeCN in water (0.1% FA)) to afford 6-methoxy-2-((1S,2S)-2-methyl-4-oxocyclohexyl)-N-(pyrazolo[1,5-c]pyrimidin-3-yl)-2H-indazole-5-carboxamide (570 mg, 100%) as a colourless solid. MS ESI, m/z=419 [M+H]$^+$.

6-Methoxy-2-(1S,2S)-2-methyl-4-(methylamino)cyclohexyl)-N-(pyrazolo[1,5-c]pyrimidin-3-yl)-2H-indazole-5-carboxamide

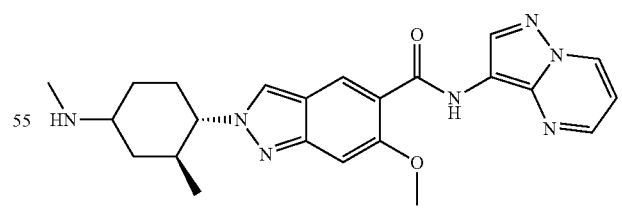

To a solution of 6-methoxy-2-((1S,2S)-2-methyl-4-oxocyclohexyl)-N-(pyrazolo[1,5-c]pyrimidin-3-yl)-2H-indazole-5-carboxamide (200 mg, 0.5 mmol) and methanamine (30 wt. % in MeOH) (495 mg, 4.8 mmol) in DCE (6 mL) was added sodium triacetoxyborohydride (203 mg, 1.0 mmol). The resulting mixture was stirred at rt for 3 h. The mixture was concentrated under reduced pressure and then purified by C18-flash chromatography (eluting with 0-100% MeCN in water (0.05% NH₄OH)) to afford 6-methoxy-2-((1S,2S)-2-methyl-4-(methylamino)cyclohexyl)-N-(pyrazolo[1,5-c]pyrimidin-3-yl)-2H-indazole-5-carboxamide (170 mg, 82%) as a yellow solid. MS ESI, m/z=434 [M+H]⁺.

6-Methoxy-2-(1S,2S,4R*)-2-methyl-4-(N-methylacetamido)cyclohexyl)-N-(pyrazolo[1,5-c]pyrimidin-3-yl)-2H-indazole-5-carboxamide—Isomer 1 (Example 62) & Isomer 2 (Example 63)

ISOMER 1

ISOMER 2

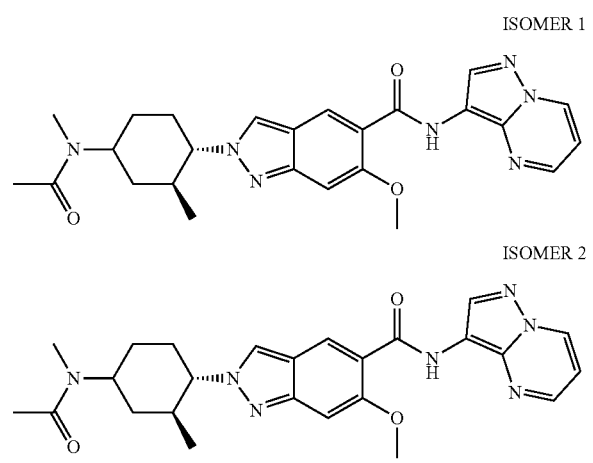

To a solution of 6-methoxy-2-((1S,2S)-2-methyl-4-(methylamino)cyclohexyl)-N-(pyrazolo[1,5-a]pyrimidin-3-yl)-2H-indazole-5-carboxamide (160 mg, 0.4 mmol) and TEA (2574, 1.9 mmol) in DCM (5 mL) was added acetic anhydride (94 mg, 0.9 mmol). The resulting mixture was stirred at rt for 1 h. The mixture was concentrated under reduced pressure and purified by C18-flash chromatography (eluting with 0-100% MeCN in water (0.1% FA)) to afford 6-methoxy-2-((1S,2S)-2-methyl-4-(N-methylacetamido)cyclohexyl)-N-(pyrazolo[1,5-c]pyrimidin-3-yl)-2H-indazole-5-carboxamide as a yellow solid. The solid was separated by chiral prep. HPLC (Chiralpak® IH, 5 µm 20 mm×250 mm; isocratic with 80% MTBE (0.1% 2N NH₃-MeOH) in MeOH in 14 min; 20.0 mL/min) to afford 6-methoxy-2-((1S,2S,4R*)-2-methyl-4-(N-methylacetamido)cyclohexyl)-N-(pyrazolo[1,5-a]pyrimidin-3-yl)-2H-indazole-5-carboxamide—Isomer 1 (17 mg, 10%, 99.4% ee) and 6-methoxy-2-((1S,2S,4R*)-2-methyl-4-(N-methylacetamido) cyclohexyl)-N-(pyrazolo[1,5-c]pyrimidin-3-yl)-2H-indazole-5-carboxamide—Isomer 2 (59 mg, 34%, 99.9% ee), both as yellow solids. Isomer 1: ¹H NMR (400 MHz, DMSO-d₆) (3:4 mixture of rotamers) δ 10.36 (s, 1H), 9.08 (dd, 1H), 8.74 (s, 1H), 8.56/8.53 (s, 1H) (rotamers), 8.54 (dd, 1H), 8.47/8.46 (s, 1H) (rotamers), 7.24/7.21 (s, 1H) (rotamers), 7.05 (dd, 1H), 4.45-4.56/3.82-3.93 (m, 1H) (rotamers), 4.08-4.18 (m, 1H), 4.06 (s, 3H), 2.86/2.73 (s, 3H) (rotamers), 1.94-2.39 (m, 6H), 1.44-1.87 (m, 4H), 0.54-0.65 (m, 3H). MS ESI, m/z=476 [M+H]⁺. Isomer 2: ¹H NMR (400 MHz, DMSO-d₆) (2:3 mixture of rotamers) δ 10.36 (s, 1H), 9.08 (dd, 1H), 8.74 (s, 1H), 8.66 (s, 1H), 8.54 (dd, 1H), 8.48 (s, 1H), 7.25 (s, 1H), 7.05 (dd, 1H), 4.63/4.02 (br. s, 1H) (rotamers), 4.38 (s, 1H), 4.06 (s, 3H), 2.61-2.93 (m, 3H), 1.25-2.43 (m, 10H), 0.95-1.17 (m, 3H). MS ESI, m/z=476 [M+H]⁺.

rel-2-(6S,7R)-2-Acetyl-6-methyl-2-azaspiro[3.5] nonan-7-yl)-N-(imidazo[1,2-b]pyridazin-3-yl)-6-methoxy-2H-indazole-5-carboxamide Isomer 1 (Example 64) & Isomer 2 (Example 65)

tert-Butyl 7-hydroxy-6-methyl-2-azaspiro[3.5] nonane-2-carboxylate

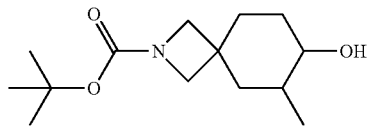 [SMILES: CC1CC2(CCC1O)CN(C(=O)OC(C)(C)C)C2]

NaBH₄ (388 mg, 10.3 mmol) was added in portions over a period of 5 min to a solution of tert-butyl 6-methyl-7-oxo-2-azaspiro[3.5]nonane-2-carboxylate (Int III-4) (1.3 g, 5.1 mmol) in MeOH (20 mL) at 0° C. under N₂ atmosphere. The resulting mixture was stirred at rt for 1 h. The reaction was quenched with water (5 mL) and directly concentrated. The residue was purified by silica gel chromatography (eluting with 30 to 40% EtOAc in PE) to afford tert-butyl 7-hydroxy-6-methyl-2-azaspiro[3.5]nonane-2-carboxylate (1.2 g, 92%) (cis/trans 1:2) as a yellow oil.

tert-Butyl 6-methyl-7-(methylsulfonyloxy)-2-azaspiro[3.5]nonane-2-carboxylate

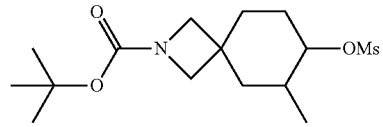 [SMILES: CC1CC2(CCC1OS(C)(=O)=O)CN(C(=O)OC(C)(C)C)C2]

MsCl (1.6 g, 14.1 mmol) was added dropwise over a period of 5 min to a solution of TEA (2.6 mL, 18.8 mmol) and tert-butyl 7-hydroxy-6-methyl-2-azaspiro[3.5]nonane-2-carboxylate (1.2 g, 4.7 mmol) (cis/trans 1:2) in DCM (25 mL) at 0° C. under N₂ atmosphere. The resulting mixture was stirred at rt for 12 h. The reaction mixture was quenched with water (50 mL) and extracted with DCM (100 mL×3). The combined organic layers were dried over Na₂SO₄, filtered and the solvent was evaporated to afford crude tert-butyl 6-methyl-7-(methylsulfonyloxy)-2-azaspiro[3.5] nonane-2-carboxylate (1.5 g) (predominantly trans isomer) as a yellow oil. The product was used in the next step without further purification.

rac-tert-Butyl (6S,7R)-7-(5-bromo-6-methoxy-2H-indazol-2-yl)-6-methyl-2-azaspiro[3.5]nonane-2-carboxylate

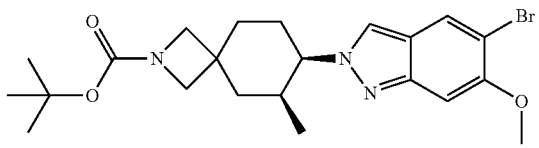 [SMILES: COc1cc2nn([C@@H]3CCC4(C[C@@H]3C)CN(C(=O)OC(C)(C)C)C4)cc2cc1Br]

KOH (1.2 g, 22.0 mmol) was slowly added to a solution of crude tert-butyl 6-methyl-7-(methylsulfonyloxy)-2- azaspiro[3.5]nonane-2-carboxylate (1.5 g) (predominantly trans isomer) and 5-bromo-6-methoxy-1H-indazole (1.0 g, 4.4 mmol) in DMF (20 mL) at rt. The reaction mixture was stirred at 100° C. overnight. The mixture was cooled to rt, quenched with water (5 mL) and the aq. layer was extracted with EtOAc (100 mL×3). The combined organic layers were washed with brine (100 mL×2), dried over Na$_2$SO$_4$, filtered and the solvent was evaporated. The crude was purified by silica gel chromatography (eluting with 20 to 30% EtOAc in PE), to afford crude rac-(6S,7R)-tert-butyl 7-(5-bromo-6-methoxy-2H-indazol-2-yl)-6-methyl-2-azaspiro[3.5]nonane-2-carboxylate (400 mg) as a yellow solid. m/z (ESI+) [M−tBu]$^+$=408/410.

rac-5-Bromo-6-methoxy-2-(6S,7R)-6-methyl-2-azaspiro[3.5]nonan-7-yl)-2H-indazole

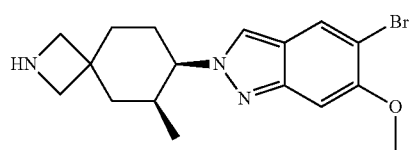

And Enantiomer

TFA (4 mL) was added dropwise to a solution of crude rac-(6S,7R)-tert-butyl 7-(5-bromo-6-methoxy-2H-indazol-2-yl)-6-methyl-2-azaspiro[3.5]nonane-2-carboxylate (400 mg) in DCM (20 mL) at 0° C. under N$_2$ atmosphere. The resulting mixture was stirred at rt for 2 h. The solvent was removed under reduced pressure to give the crude TFA salt of rac-5-bromo-6-methoxy-2-((6S,7R)-6-methyl-2-azaspiro[3.5]nonan-7-yl)-2H-indazole (500 mg), which was used without further purification. MS ESI, m/z=364/366 [M+H]$^+$.

rac-1-((6S,7R)-7-(5-Bromo-6-methoxy-2H-indazol-2-yl)-6-methyl-2-azaspiro[3.5]nonan-2-yl)ethanone

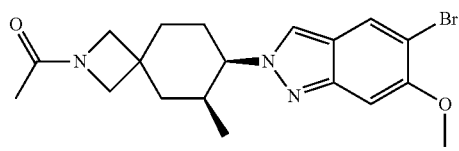

And Enantiomer

Acetyl chloride (223 μL, 3.1 mmol) was added dropwise to a solution of the crude TFA salt of rac-5-bromo-6-methoxy-2-((6S,7R)-6-methyl-2-azaspiro[3.5]nonan-7-yl)-2H-indazole (500 mg) and TEA (1.5 mL, 10.5 mmol) in DCM (10 mL) at 0° C. under N$_2$ atmosphere. The resulting mixture was stirred at rt for 2 h. The reaction was quenched with water (5 mL) and the aq. layer was extracted with DCM (50 mL×3). The combined organic layers were washed with brine (50 mL×2), dried over Na$_2$SO$_4$, filtered and concentrated. The residue was purified by C18-flash chromatography (eluting with 50-100% MeCN in water (0.05% HCOOH)) to afford rac-1-((6S,7R)-7-(5-bromo-6-methoxy-2H-indazol-2-yl)-6-methyl-2-azaspiro[3.5]nonan-2-yl)ethanone (190 mg, 45%) as a yellow solid. m/z (ESI+) [M+H]$^+$=406, 408.

rel-2-(6S,7R)-2-Acetyl-6-methyl-2-azaspiro[3.5]nonan-7-yl)-N-(imidazo[1,2-b]pyridazin-3-yl)-6-methoxy-2H-indazole-5-carboxamide Isomer 1 (Example 64) & Isomer 2 (Example 65)

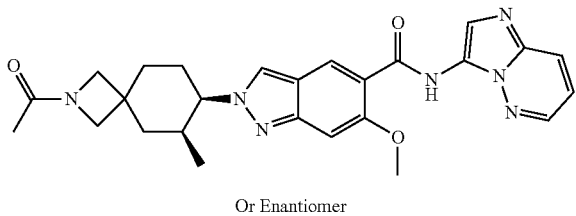

Or Enantiomer

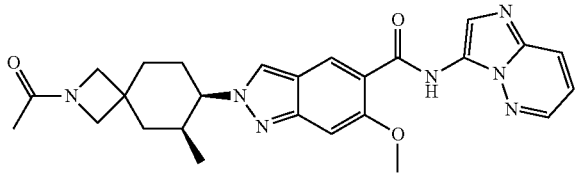

Or Enantiomer

Pd(OAc)$_2$ (9 mg, 0.04 mmol) was added to a solution of dppp (41 mg, 0.1 mmol), TEA (123 μL, 0.9 mmol), imidazo[1,2-b]pyridazin-3-amine (174 mg, 1.3 mmol) and rac-1-((6S,7R)-7-(5-bromo-6-methoxy-2H-indazol-2-yl)-6-methyl-2-azaspiro[3.5]nonan-2-yl)ethan-1-one (180 mg, 0.4 mmol) in MeCN (10 mL). The resulting mixture was stirred at 90° C. overnight under CO atmosphere at 15 atm. The crude product was cooled to rt and was directly purified by C18-flash chromatography (eluting with 50% to 55% MeCN in water (0.1% HCOOH)). The obtained material was then purified by prep. HPLC (XBridge Prep OBD C18 column, 30×150 mm 5 μm; mobile phase A: water (10 mM NH$_4$HCO$_3$+0.1% NH$_4$OH), mobile phase B: MeCN; flow rate: 60 mL/min; gradient: 20% B to 47% B in 7 min) to afford rac-2-((6S,7R)-2-acetyl-6-methyl-2-azaspiro[3.5]nonan-7-yl)-N-(imidazo[1,2-b]pyridazin-3-yl)-6-methoxy-2H-indazole-5-carboxamide as a yellow solid. The solid was separated by chiral prep. SFC (CelluCoat column, 250×30 mm, 5 μm, with mobile phase 30% MeOH in CO$_2$ at 120 bar and 40 C, and a flow rate of 100 mL/min) to give rel-2-((6S,7R)-2-acetyl-6-methyl-2-azaspiro[3.5]nonan-7-yl)-N-(imidazo[1,2-b]pyridazin-3-yl)-6-methoxy-2H-indazole-5-carboxamide—Isomer 1 (37 mg, 21%, 100% ee) and rel-2-((6S,7R)-2-acetyl-6-methyl-2-azaspiro[3.5]nonan-7-yl)-N-(imidazo[1,2-b]pyridazin-3-yl)-6-methoxy-2H-indazole-5-carboxamide—Isomer 2 (34 mg, 19%, 100% ee). Both isomers were collected as gums. The $^1$H NMR and MS obtained for both products were identical. $^1$H NMR (500 MHz, DMSO-d$_6$) (3:4 mixture of rotamers) δ 11.05 (s, 1H), 8.64 (dd, 1H), 8.55-8.61 (m, 2H), 8.15 (dd, 1H), 8.05 (s, 1H), 7.30/7.29 (s, 1H) (rotamers), 7.22 (dd, 1H), 4.65-4.74 (m, 1H), 4.13 (s, 3H), 3.83-3.93 (m, 2H), 3.55-3.65 (m, 2H), 1.93-2.41 (m, 5H), 1.77 (br. s, 3H), 1.67-1.76 (m, 2H), 0.57/0.56 (d, 3H) (rotamers). m/z (ESI+) [M+H]$^+$=488.

rel-2-(6R,7R)-2-Acetyl-6-methyl-2-azaspiro[3.5]nonan-7-yl)-N-(imidazo[1,2-b]pyridazin-3-yl)-6-methoxy-2H-indazole-5-carboxamide Isomer 1 (Example 66) & Isomer 2 (Example 67)

rac-tert-Butyl (6R,7R)-7-(5-bromo-6-methoxy-2H-indazol-2-yl)-6-methyl-2-azaspiro[3.5]nonane-2-carboxylate

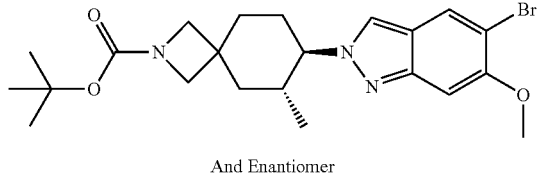 [SMILES: COc1cc2nn([C@@H]3CCC4(C[C@H]3C)CN(C(=O)OC(C)(C)C)C4)cc2cc1Br]

And Enantiomer

KOH (1.4 g, 25.0 mmol) was added to a solution of rac-tert-butyl (6R,7S)-6-methyl-7-((methylsulfonyl)oxy)-2-azaspiro[3.5]nonane-2-carboxylate (Int III-5) (3.0 g, 9.0 mmol) and 5-bromo-6-methoxy-1H-indazole (1.9 g, 8.2 mmol) in THF (50 mL) at 0° C. under $N_2$ atmosphere. The resulting mixture was stirred at 80° C. for 12 h. The reaction mixture was cooled to rt, diluted with water (100 mL) and exacted with EtOAc (2×75 mL). The combined organic layers were dried over $Na_2SO_4$, filtered and concentrated to afford a yellow oil. The oil was purified by C18-flash chromatography (eluting with 50 to 90% MeCN in water (0.05% FA)) to afford rac-tert-butyl (6R,7R)-7-(5-bromo-6-methoxy-2H-indazol-2-yl)-6-methyl-2-azaspiro[3.5]nonane-2-carboxylate (0.5 g, 13%) as a yellow solid. m/z (ESI+) [M+H]+=464/466.

rac-tert-Butyl (6R,7R)-7-(5-(imidazo[1,2-b]pyridazin-3-ylcarbamoyl)-6-methoxy-2H-indazol-2-yl)-6-methyl-2-azaspiro[3.5]nonane-2-carboxylate

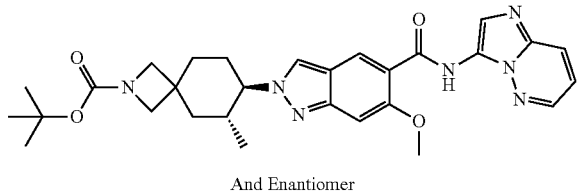 [SMILES: COc1cc2nn([C@@H]3CCC4(C[C@H]3C)CN(C(=O)OC(C)(C)C)C4)cc2cc1C(=O)Nc1cnc2cccnn12]

And Enantiomer

A solution of Imidazo[1,2-b]pyridazin-3-amine (255 mg, 1.9 mmol), dppp (82 mg, 0.2 mmol), Pd(OAc)$_2$ (44 mg, 0.2 mmol), TEA (588 mg, 5.8 mmol) and rac-tert-butyl (6R,7R)-7-(5-bromo-6-methoxy-2H-indazol-2-yl)-6-methyl-2-azaspiro[3.5]nonane-2-carboxylate (450 mg, 1.0 mmol) in MeCN (8 mL) under CO atmosphere at 15 atm and 90° C. was stirred for 12 h and then allowed to cool to rt. The solvent was removed under reduced pressure and the residue was purified by C18-flash chromatography (eluting with 40 to 90% MeCN in water (0.05% FA)) to afford crude rac-tert-butyl (6R,7R)-7-(5-(imidazo[1,2-b]pyridazin-3-ylcarbamoyl)-6-methoxy-2H-indazol-2-yl)-6-methyl-2-azaspiro[3.5]nonane-2-carboxylate (450 mg) as a yellow oil. m/z (ESI+) [M+H]+=546.

rac-N-(Imidazo[1,2-b]pyridazin-3-yl)-6-methoxy-2-(6R,7R)-6-methyl-2-azaspiro[3.5]nonan-7-yl)-2H-indazole-5-carboxamide

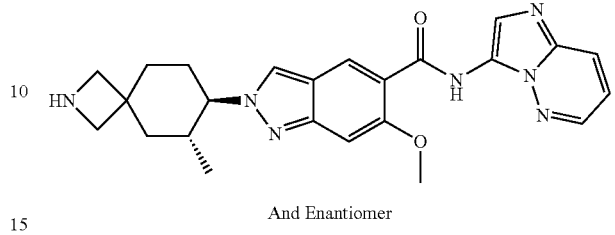

And Enantiomer

To crude rac-tert-butyl (6R,7R)-7-(5-(imidazo[1,2-b]pyridazin-3-ylcarbamoyl)-6-methoxy-2H-indazol-2-yl)-6-methyl-2-azaspiro[3.5]nonane-2-carboxylate (450 mg) was added TFA (2 mL, 26.0 mmol) in DCM (4 mL). The resulting mixture was stirred at rt for 2 h. The solvent was removed under reduced pressure to afford the crude TFA salt of rac-N-(imidazo[1,2-b]pyridazin-3-yl)-6-methoxy-2-((6R,7R)-6-methyl-2-azaspiro[3.5]nonan-7-yl)-2H-indazole-5-carboxamide (350 mg) as a yellow oil. The product was used without further purification. m/z (ESI+) [M+H]+=446.

rel-2-(6R,7R)-2-Acetyl-6-methyl-2-azaspiro[3.5]nonan-7-yl)-N-(imidazo[1,2-b]pyridazin-3-yl)-6-methoxy-2H-indazole-5-carboxamide Isomer 1 (Example 66) & Isomer 2 (Example 67)

ISOMER 1

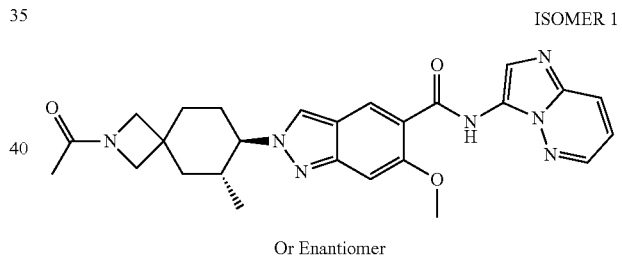

Or Enantiomer

ISOMER 2

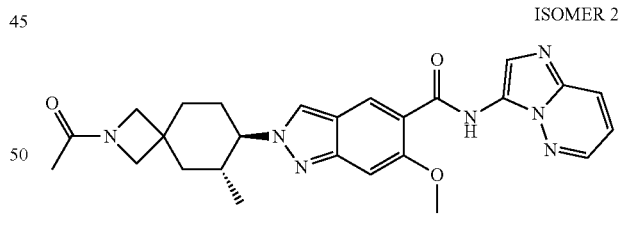

Or Enantiomer

The crude TFA salt of rac-N-(imidazo[1,2-b]pyridazin-3-yl)-6-methoxy-2-((6R,7R)-6-methyl-2-azaspiro[3.5]nonan-7-yl)-2H-indazole-5-carboxamide (350 mg) was added to TEA (195 mg, 1.9 mmol) in DCM (8 mL) at rt. The mixture was stirred at rt for 5 min and then acetic anhydride (99 mg, 1.0 mmol) was added. The reaction mixture was stirred at rt for 1 h. The mixture was quenched with water (5 mL) and purified by C18-flash chromatography (eluting with 20 to 100% MeCN in water (0.05% FA)) to afford rac-2-((6R,7R)-2-acetyl-6-methyl-2-azaspiro[3.5]nonan-7-yl)-N-(imidazo[1,2-b]pyridazin-3-yl)-6-methoxy-2H-indazole-5-carboxamide as a yellow solid. The isomers were separated by chiral prep. HPLC (CHIRALPAK IF, 2×25 cm, 5 µm; mobile phase A: MTBE (2 mM NH₃-MeOH), mobile phase B: MeOH; flow rate: 17 mL/min; isocratic 50% B in 18 min) to afford rel-2-((6R,7R)-2-acetyl-6-methyl-2-azaspiro[3.5]nonan-7-yl)-N-(imidazo[1,2-b]pyridazin-3-yl)-6-methoxy-2H-indazole-5-carboxamide—Isomer 1 (95 mg, 30%, 100% ee) and Isomer 2, which after a second purification by prep. HPLC (XBridge Prep OBD C18 column, 30×150 mm, 5 µm; mobile phase A: water (10 mM NH₄HCO₃+0.1% NH₄OH), mobile phase B: MeCN; flow rate: 60 mL/min; gradient: 20% B to 40% B in 7 min) yielded rel-2-((6R,7R)-2-acetyl-6-methyl-2-azaspiro[3.5]nonan-7-yl)-N-(imidazo[1,2-b]pyridazin-3-yl)-6-methoxy-2H-indazole-5-carboxamide—Isomer 2 (66 mg, 21%, 99% ee). Both isomers were collected as yellow solids. Isomer 1: $^1$H NMR (400 MHz, DMSO-d₆) (1:1 mixture of rotamers) δ 11.04 (s, 1H), 8.64 (dd, 1H), 8.59 (s, 1H), 8.580/8.577 (s, 1H) (rotamers), 8.15 (dd, 1H), 8.05 (s, 1H), 7.29 (d, 1H), 7.22 (dd, 1H), 4.12 (s, 3H), 4.06-4.17 (m, 1H), 3.93-4.01/3.65-3.73 (m, 2H) (rotamers), 3.80/3.53 (s, 2H) (rotamers), 2.06-2.19 (m, 1H), 1.90-2.05 (m, 4H), 1.80/1.77 (s, 3H) (rotamers), 1.60-1.73 (m, 1H), 1.38-1.49 (m, 1H), 0.60/0.58 (d, 3H) (rotamers). m/z (ESI+) [M+H]⁺=488. Isomer 2: $^1$H NMR (400 MHz, DMSO-d₆) (1:1 mixture of rotamers) δ 11.04 (s, 1H), 8.63 (d, 1H), 8.55-8.61 (m, 2H), 8.15 (d, 1H), 8.05 (s, 1H), 7.28 (d, 1H), 7.22 (dd, 1H), 4.12 (s, 3H), 4.05-4.17 (m, 1H), 3.92-4.00/3.65-3.72 (m, 2H) (rotamers), 3.79/3.52 (s, 2H) (rotamers), 2.05-2.20 (m, 1H), 1.89-2.05 (m, 4H), 1.79/1.76 (s, 3H) (rotamers), 1.61-1.72 (m, 1H), 1.42 (t, 1H), 0.59/0.57 (s, 3H) (rotamers). m/z (ESI+) [M+H]⁺=488.

N-(Imidazo[1,2-b]pyridazin-3-yl)-6-methoxy-2-((5s,8s)-2-methyl-3-oxo-2-azaspiro[4.5]decan-8-yl)-2H-indazole-5-carboxamide (Example 68)

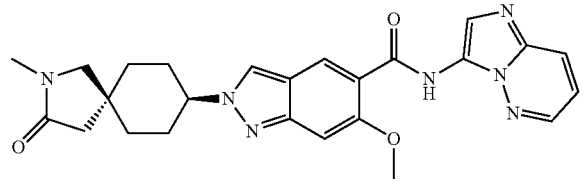 [SMILES: COc1cc2nn([C@H]3CC[C@@]4(CC3)CC(=O)N(C)C4)cc2cc1C(=O)Nc1cnc2cccnn12]

Methyldiphenylsilanecarboxylic acid (95 mg, 0.4 mmol) and KF (23 mg, 0.4 mmol) were added to chamber A of a dried and N₂-flushed COware gas reactor. (5s,8s)-8-(5-bromo-6-methoxy-2H-indazol-2-yl)-2-methyl-2-azaspiro[4.5]decan-3-one (Int IV-6) (35 mg, 0.3 mmol), dppp (14 mg, 0.03 mmol), Pd(OAc)₂ (7 mg, 0.03 mmol), imidazo[1,2-b]pyridazin-3-amine (80 mg, 0.6 mmol) and DIPEA (1384, 0.8 mmol) in degassed anhydrous MeCN (1 mL) were added to chamber B. Then, DMSO (350 µL) was added to chamber A and chamber B was stirred at 85° C. overnight. The reaction mixture was allowed to cool to rt. The reaction in chamber B was quenched with aq. saturated NaHCO₃, concentrated under reduced pressure, dissolved in DCM (30 mL) and loaded on a 5 g Isolute®SCX2 exchange cartridge. The cartridge was washed with DCM/MeOH (1:1; 100 mL), then eluted with DCM/4N NH₃-MeOH solution (1:1; 100 mL) and then with 2N NH₃-MeOH solution (100 mL) to give a dark-yellow solid. The solid was purified by silica gel chromatography (eluting with 0-2.5% 2N NH₃-MeOH solution in DCM) to give a yellow solid. The solid was suspended and stirred in MeCN (2 mL) at rt for 48 h. Then the suspension was filtered and washed with ice cold MeCN (500 µL×2) to give N-(imidazo[1,2-b]pyridazin-3-yl)-6-methoxy-2-((5s,8s)-2-methyl-3-oxo-2-azaspiro[4.5]decan-8-yl)-2H-indazole-5-carboxamide (36 mg, 58%) as a pale-yellow solid. $^1$H NMR (500 MHz, CDCl₃) δ 11.25 (s, 1H), 8.83 (d, 1H), 8.35-8.44 (m, 2H), 8.10 (d, 1H), 7.99 (d, 1H), 7.19 (s, 1H), 7.02 (dd, 1H), 4.36-4.46 (m, 1H), 4.19 (s, 3H), 3.38 (s, 2H), 2.89 (s, 3H), 2.33 (s, 2H), 2.20-2.28 (m, 2H), 2.06-2.17 (m, 2H), 1.97 (d, 2H), 1.68 (td, 2H). MS ESI, m/z=474 [M+H]⁺.

N-(Imidazo[1,2-b]pyridazin-3-yl)-6-methoxy-2-((5r,8r)-2-methyl-3-oxo-2-azaspiro[4.5]decan-8-yl)-2H-indazole-5-carboxamide (Example 69)

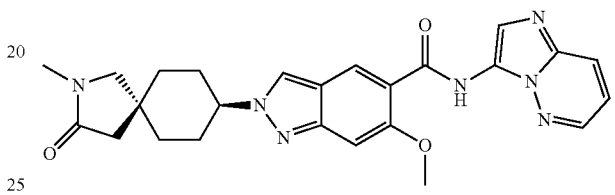

Methyldiphenylsilanecarboxylic acid (88 mg, 0.4 mmol) and KF (21 mg, 0.4 mmol) were added to chamber A of a dried and N₂-flushed COware gas reactor. (5r,8r)-8-(5-Bromo-6-methoxy-2H-indazol-2-yl)-2-methyl-2-azaspiro[4.5]decan-3-one (Int IV-7) (49 mg, 0.1 mmol), imidazo[1,2-b]pyridazin-3-amine (27 mg, 0.2 mmol), dppp (13 mg, 0.03 mmol), Pd(OAc)₂ (7 mg, 0.03 mmol) and DIPEA (1274, 0.7 mmol) in degassed anhydrous MeCN (1 mL) were added to chamber B. Then, DMSO (200 µL) was added to chamber A and chamber B was stirred at 85° C. overnight. The reaction mixture was allowed to cool to rt. The reaction in chamber B was quenched with aq. saturated NaHCO₃, concentrated under reduced pressure, dissolved in DCM (30 mL) and loaded on a 5 g Isolute®SCX2 exchange cartridge. The loaded SCX2 cartridge was washed with DCM/MeOH (1:1; 100 mL), then eluted with DCM/4N NH₃-MeOH solution (1:1; 100 mL) and then with 2N NH₃-MeOH solution (100 mL) to give a dark-yellow solid. The solid was purified by silica gel chromatography (eluting with 0-2.5% 2N NH₃-MeOH solution in DCM) to give a yellow solid, which was suspended and stirred in MeCN (3 mL) at rt for 48 h. The suspension was filtered and washed with ice cold MeCN (500 µL×2) to give a solid. The solid was dissolved in 15 mL boiling MeCN, and slowly concentrated to 5 mL under reduced pressure at 45° C. to give a suspension, which was kept at rt overnight. The suspension was filtered and the residue was washed with ice cold MeCN (500 µL×2) to give N-(imidazo[1,2-b]pyridazin-3-yl)-6-methoxy-2-((5r,8r)-2-methyl-3-oxo-2-azaspiro[4.5]decan-8-yl)-2H-indazole-5-carboxamide (46 mg, 90%) as a pale-yellow solid. $^1$H NMR (500 MHz, CDCl₃) δ 11.28 (s, 1H), 8.8-8.84 (m, 1H), 8.47 (dd, 1H), 8.40 (s, 1H), 8.16 (d, 1H), 8.10 (d, 1H), 7.18 (s, 1H), 7.12 (dd, 1H), 4.40 (tt, 1H), 4.19 (s, 3H), 3.20 (s, 2H), 2.87 (t, 3H), 2.44 (s, 2H), 2.22-2.30 (m, 2H), 2.04-2.15 (m, 2H), 1.91-1.98 (m, 2H), 1.65 (td, 2H). MS ESI, m/z=474 [M+H]⁺.

rel-2-(5R,7R,8R)-2,7-Dimethyl-3-oxo-2-azaspiro[4.5]decan-8-yl)-N-(imidazo[1,2-b]pyridazin-3-yl)-6-methoxy-2H-indazole-5-carboxamide or rel-2-((5R,7S,8S)-2,7-Dimethyl-3-oxo-2-azaspiro[4.5]decan-8-yl)-N-(imidazo[1,2-b]pyridazin-3-yl)-6-methoxy-2H-indazole-5-carboxamide—Isomer 1 (Example 70), Isomer 2 (Example 71), Isomer 3 (Example 72) & Isomer 4 (Example 73)

tert-Butyl 7-methyl-8-oxo-2-azaspiro[4.5]decane-2-carboxylate

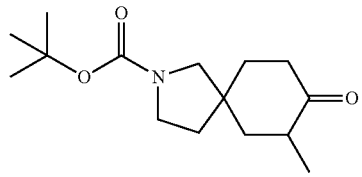 [SMILES: CC1CC2(CCC1=O)CCN(C(=O)OC(C)(C)C)C2]

To a solution of tert-butyl 8-oxo-2-azaspiro[4.5]decane-2-carboxylate (15.0 g, 59.2 mmol) in THF (150 mL) was added 1M LiHMDS in THF (118.5 mL, 118.5 mmol) dropwise over a period of 20 min at −78° C. under N$_2$ atmosphere. The resulting mixture was stirred at −78° C. for 2 h. Subsequently, iodomethane (7.4 mL, 118.5 mmol) was added slowly. The reaction mixture was allowed to warm to rt and stirred for 15 h. Then, the reaction was quenched with aq. saturated NH$_4$Cl solution (300 mL) and extracted with EtOAc (250 mL×3). The combined organic layers were washed with brine (30 mL), dried over Na$_2$SO$_4$, filtered and concentrated under reduced pressure. The residue was purified by silica gel chromatography (eluting with 5-20% EtOAc in PE) to afford tert-butyl 7-methyl-8-oxo-2-azaspiro[4.5]decane-2-carboxylate (6.6 g, 42%) as a yellow semi-solid. MS ESI, m/z=212 [M−tBu]$^+$.

Mixture of rac-tert-butyl (5R,7R,8S)-7,8-dihydroxy-2-azaspiro[4.5]decane-2-carboxylate and rac-tert-butyl (5R,7S,8R)-7,8-dihydroxy-2-azaspiro[4.5]decane-2-carboxylate

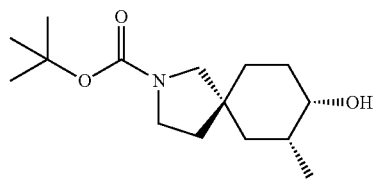
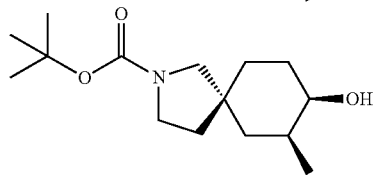

And Enantiomers

To a solution of tert-butyl 7-methyl-8-oxo-2-azaspiro[4.5]decane-2-carboxylate (5.0 g, 18.7 mmol) in THF (70 mL) at 0° C. under N$_2$ atmosphere was added 2M lithium tri-sec-butylborohydride in THF (18.7 mL, 37.4 mmol) over a period of 1 min. The resulting mixture was stirred at 0° C. for 3 h. The reaction mixture was quenched with acteone (20 mL) and then concentrated under reduced pressure. The residue was purified by silica gel chromatography (eluting with 25-50% EtOAc in PE) to afford a mixture of rac-tert-butyl (5R,7R,8S)-7,8-dihydroxy-2-azaspiro[4.5]decane-2-carboxylate and rac-tert-butyl (5R,7S,8R)-7,8-dihydroxy-2-azaspiro[4.5]decane-2-carboxylate (4.8 g, 95%) as a pale-yellow oil. MS ESI, m/z=214 [M−tBu]$^+$.

Mixture of rac-tert-butyl (5R,7R,8R)-8-(1,3-dioxoisoindolin-2-yl)-7-methyl-2-azaspiro[4.5]decane-2-carboxylate and rac-tert-butyl (5R,7S,8S)-8-(1,3-dioxoisoindolin-2-yl)-7-methyl-2-azaspiro[4.5]decane-2-carboxylate

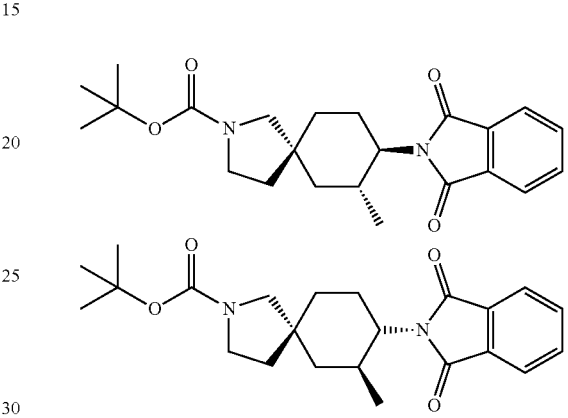

And Enantiomers

To a solution of a mixture of rac-tert-butyl (5R,7R,8S)-7,8-dihydroxy-2-azaspiro[4.5]decane-2-carboxylate and rac-tert-butyl (5R,7S,8R)-7,8-dihydroxy-2-azaspiro[4.5]decane-2-carboxylate (3.4 g, 12.6 mmol), triphenylphosphine (6.6 g, 25.2 mmol) and isoindoline-1,3-dione (2.8 g, 18.9 mmol) in THF (60 mL) at 0° C. under N$_2$ atmosphere was added DIAD (4.9 mL, 25.2 mmol). The resulting mixture was stirred at 45° C. for 15 h. The mixture was cooled to rt, poured into brine (200 mL) and extracted with EtOAc (250 mL). The organic layer was dried over Na$_2$SO$_4$, filtered and concentrated under reduced pressure. The residue was purified by silica gel chromatography (eluting with DCM) and further purified by C18-flash chromatography (eluting with 0-100% MeCN in water (0.05% NH$_4$OH)) to afford a mixture of rac-tert-butyl (5R,7R,8R)-8-(1,3-dioxoisoindolin-2-yl)-7-methyl-2-azaspiro[4.5]decane-2-carboxylate and rac-tert-butyl (5R,7S,8S)-8-(1,3-dioxoisoindolin-2-yl)-7-methyl-2-azaspiro[4.5]decane-2-carboxylate (1.9 g, 37%) as a pale-yellow solid. MS ESI, m/z=384 [M−tBu+CH$_3$CN]$^+$.

Mixture of rac-tert-butyl (5R,7R,8R)-8-amino-7-methyl-2-azaspiro[4.5]decane-2-carboxylate and rac-tert-butyl (5R,7S,8S)-8-amino-7-methyl-2-azaspiro[4.5]decane-2-carboxylate

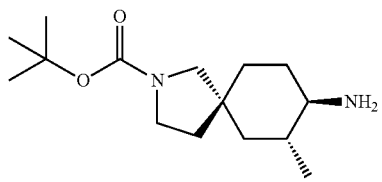

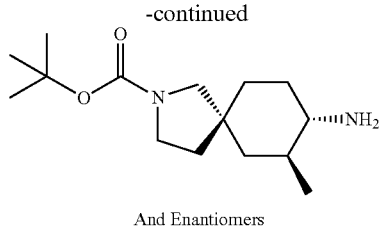

And Enantiomers

To a solution of a mixture of rac-tert-butyl (5R,7R,8R)-8-(1,3-dioxoisoindolin-2-yl)-7-methyl-2-azaspiro[4.5]decane-2-carboxylate and rac-tert-butyl (5R,7S,8S)-8-(1,3-dioxoisoindolin-2-yl)-7-methyl-2-azaspiro[4.5]decane-2-carboxylate (1.9 g, 4.6 mmol) in EtOH (30 mL) was added hydrazine hydrate (80% in water) (2.9 g, 46.4 mmol). The resulting mixture was stirred at 50° C. for 3 h. The reaction mixture was cooled to rt and concentrated under reduced pressure. The residue was purified by silica gel chromatography (eluting with DCM) and further purified by C18-flash chromatography (eluting with 0-100% MeCN in water (0.1% FA)) to give the formate salt of the titled compound. The formate was dissolved in water (50 mL), basified with aq. saturated NaHCO$_3$ solution to pH 9 and then extracted with EtOAc (100 mL×2) and chloroform (100 mL). The combined organic layers were dried over Na$_2$SO$_4$, filtered and concentrated under reduced pressure to afford a mixture of rac-tert-butyl (5R,7R,8R)-8-amino-7-methyl-2-azaspiro[4.5]decane-2-carboxylate and rac-tert-butyl (5R,7S,8S)-8-amino-7-methyl-2-azaspiro[4.5]decane-2-carboxylate (380 mg, 31%) as a pale-yellow oil. MS ESI, m/z=269 [M+H]$^+$.

Mixture of rac-tert-butyl (5R,7R,8R)-8-(5-bromo-6-methoxy-2H-indazol-2-yl)-7-methyl-2-azaspiro[4.5]decane-2-carboxylate and rac-tert-butyl (5R,7S,8S)-8-(5-bromo-6-methoxy-2H-indazol-2-yl)-7-methyl-2-azaspiro[4.5]decane-2-carboxylate

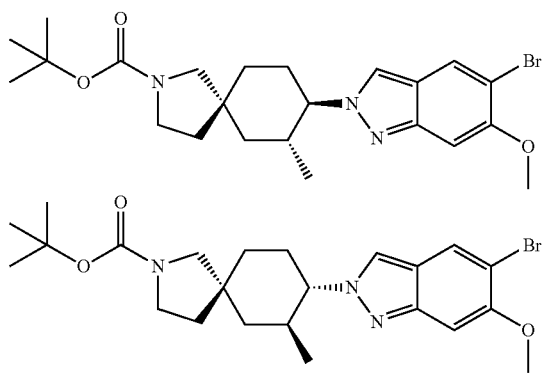

And Enantiomers

To a solution of a mixture of rac-tert-butyl (5R,7R,8R)-8-amino-7-methyl-2-azaspiro[4.5]decane-2-carboxylate and rac-tert-butyl (5R,7S,8S)-8-amino-7-methyl-2-azaspiro[4.5]decane-2-carboxylate (360 mg, 1.3 mmol) in i-PrOH (15 mL) was added 5-bromo-4-methoxy-2-nitrobenzaldehyde (Int I-1) (384 mg, 1.5 mmol). The resulting mixture was stirred at 50° C. for 2 h, then cooled to 30° C., followed by the addition of tri-n-butylphosphine (814 mg, 4.0 mmol). The reaction mixture was stirred at 80° C. overnight under N$_2$ atmosphere. The mixture was cooled to rt and concentrated under reduced pressure. The residue was purified by C18-flash chromatography (eluting with 0-100% MeCN in water (0.05% FA)) to afford a mixture of rac-tert-butyl (5R,7R,8R)-8-(5-bromo-6-methoxy-2H-indazol-2-yl)-7-methyl-2-azaspiro[4.5]decane-2-carboxylate and rac-tert-butyl (5R,7S,8S)-8-(5-bromo-6-methoxy-2H-indazol-2-yl)-7-methyl-2-azaspiro[4.5]decane-2-carboxylate (440 mg, 69%) as a pale-yellow solid. MS ESI, m/z=478/480 [M+H]$^+$.

Mixture of rac-(5R,7R,8R)-8-(5-bromo-6-methoxy-2H-indazol-2-yl)-7-methyl-2-azaspiro[4.5]decane and rac-(5R,7S,8S)-8-(5-bromo-6-methoxy-2H-indazol-2-yl)-7-methyl-2-azaspiro[4.5]decane

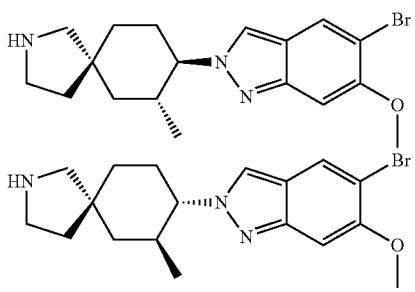

And Enantiomers

To a solution of a mixture of rac-tert-butyl (5R,7R,8R)-8-(5-bromo-6-methoxy-2H-indazol-2-yl)-7-methyl-2-azaspiro[4.5]decane-2-carboxylate and rac-tert-butyl (5R,7S,8S)-8-(5-bromo-6-methoxy-2H-indazol-2-yl)-7-methyl-2-azaspiro[4.5]decane-2-carboxylate (410 mg, 0.9 mmol) in dioxane (4 mL) was added 4N HCl in dioxane (2.0 mL, 8.0 mmol) and the resulting solution was stirred at rt for 20 h. The reaction mixture was concentrated under reduced pressure to afford the crude mixture of the HCl salts of rac-(5R,7R,8R)-8-(5-bromo-6-methoxy-2H-indazol-2-yl)-7-methyl-2-azaspiro[4.5]decane and rac-(5R,7S,8S)-8-(5-bromo-6-methoxy-2H-indazol-2-yl)-7-methyl-2-azaspiro[4.5]decane (354 mg), that was used directly without further purification. MS ESI, m/z=378/380 [M+H]$^+$.

Mixture of rac-(5R,7R,8R)-8-(5-bromo-6-methoxy-2H-indazol-2-yl)-2,7-dimethyl-2-azaspiro[4.5]decane and rac-(5R,7S,8S)-8-(5-bromo-6-methoxy-2H-indazol-2-yl)-2,7-dimethyl-2-azaspiro[4.5]decane

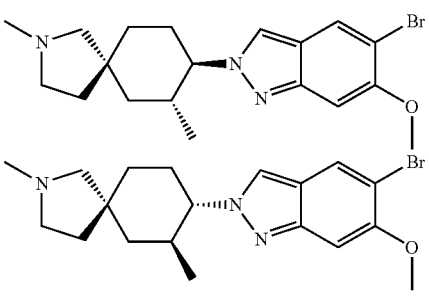

And Enantiomers

To the crude mixture of the HCl salts of rac-(5R,7R,8R)-8-(5-bromo-6-methoxy-2H-indazol-2-yl)-7-methyl-2-azaspiro[4.5]decane and rac-(5R,7S,8S)-8-(5-bromo-6-methoxy-2H-indazol-2-yl)-7-methyl-2-azaspiro[4.5]decane (354 mg, 0.9 mmol), acetic acid (51 mg, 0.9 mmol) and aq. formaldehyde solution (40 wt. %) (674 mg, 8.3 mmol) in MeOH (10 mL) at rt under N₂ atmosphere was added sodium triacetoxyborohydride (362 mg, 1.7 mmol). The reaction mixture was stirred at rt for 3 h. The mixture was purified directly by C18-flash chromatography (eluting with 0-100% MeOH in water (2% NH₄OH)) to afford a mixture of rac-(5R,7R,8R)-8-(5-bromo-6-methoxy-2H-indazol-2-yl)-2,7-dimethyl-2-azaspiro[4.5]decane and rac-(5R,7S,8S)-8-(5-bromo-6-methoxy-2H-indazol-2-yl)-2,7-dimethyl-2-azaspiro[4.5]decane (335 mg, 100%) as a pale-yellow solid. MS ESI, m/z=392/394 [M+H]⁺.

Mixture of rac-(5R,7R,8R)-8-(5-bromo-6-methoxy-2H-indazol-2-yl)-2,7-di methyl-2-azaspiro[4.5]decan-3-one and rac-(5R,7S,8S)-8-(5-bromo-6-methoxy-2H-indazol-2-yl)-2,7-dimethyl-2-azaspiro[4.5]decan-3-one

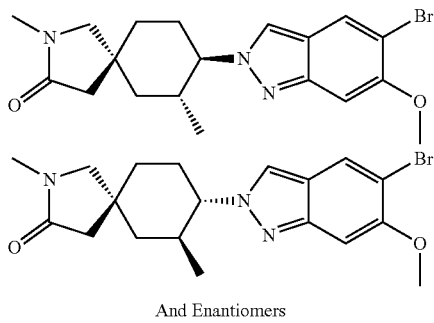

And Enantiomers

To a solution of a mixture of rac-(5R,7R,8R)-8-(5-bromo-6-methoxy-2H-indazol-2-yl)-2,7-dimethyl-2-azaspiro[4.5]decane and rac-(5R,7S,8S)-8-(5-bromo-6-methoxy-2H-indazol-2-yl)-2,7-dimethyl-2-azaspiro[4.5]decane (310 mg, 0.8 mmol) in THF (25 mL) was added iodine solution (1.5 g, 5.9 mmol). The resulting solution was stirred at rt for 2 h, followed by the addition of sodium bicarbonate (664 mg, 7.9 mmol) in water (10 mL). Then, the reaction mixture was stirred at rt for another 2 h. The reaction was quenched with aq. saturated Na₂SO₃ solution until the color turned light-yellow and then extracted with DCM (200 mL). The organic layer was washed with brine (100 mL), dried over Na₂SO₄, filtered and concentrated under reduced pressure. The residue was purified by prep. HPLC (Waters XSelect CSH Fluoro-Phenyl OBD, 5 μm 30×150 mm; elution gradient with 32-42% MeCN in water (0.1% FA) in 12 min; 60 mL/min) to afford a mixture of rac-(5R,7R,8R)-8-(5-bromo-6-methoxy-2H-indazol-2-yl)-2,7-dimethyl-2-azaspiro[4.5]decan-3-one and rac-(5R,7S,8S)-8-(5-bromo-6-methoxy-2H-indazol-2-yl)-2,7-dimethyl-2-azaspiro[4.5]decan-3-one) containing 40% of 8-(5-bromo-6-methoxy-2H-indazol-2-yl)-2,7-dimethyl-2-azaspiro[4.5]decan-1-one (120 mg) as a pale-yellow solid, which was used without further separation.

rel-2-(5R,7R,8R)-2,7-Dimethyl-3-oxo-2-azaspiro[4.5]decan-8-yl)-N-(imidazo[1,2-b]pyridazin-3-yl)-6-methoxy-2H-indazole-5-carboxamide or rel-2-(5R,7S,8S)-2,7-Dimethyl-3-oxo-2-azaspiro[4.5]decan-8-yl)-N-(imidazo[1,2-b]pyridazin-3-yl)-6-methoxy-2H-indazole-5-carboxamide—Isomer 1 (Example 70), Isomer 2 (Example 71), Isomer 3 (Example 72) & Isomer 4 (Example 73)

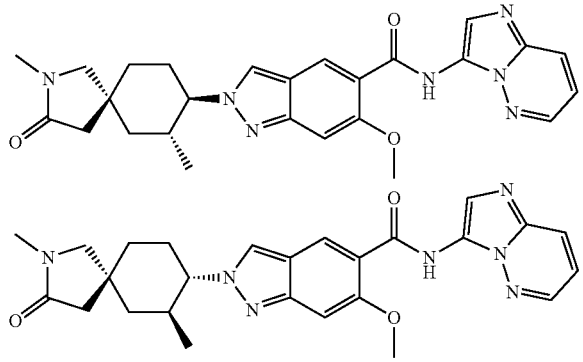

And Enantiomers

A suspension of a mixture of rac-(5R,7R,8R)-8-(5-bromo-6-methoxy-2H-indazol-2-yl)-2,7-dimethyl-2-azaspiro[4.5]decan-3-one and rac-(5R,7S,8S)-8-(5-bromo-6-methoxy-2H-indazol-2-yl)-2,7-dimethyl-2-azaspiro[4.5]decan-3-one) containing 40% of 8-(5-bromo-6-methoxy-2H-indazol-2-yl)-2,7-dimethyl-2-azaspiro[4.5]decan-1-one (115 mg), imidazo[1,2-b]pyridazin-3-amine (80 mg, 0.6 mmol), Pd(OAc)₂ (14 mg, 0.06 mmol), dppp (41 mg, 0.1 mmol) and DIPEA (183 mg, 1.4 mmol) in MeCN (15 mL) was stirred under CO atmosphere at 15 atm and 100° C. for 15 h. The mixture was cooled to rt and concentrated under reduced pressure. The residue was purified by C18-flash chromatography (eluting with 0-100% acetonitrile in water (0.05% FA)) to afford a mixture of rel-2-((5R,7R,8R)-2,7-dimethyl-3-oxo-2-azaspiro[4.5]decan-8-yl)-N-(imidazo[1,2-b]pyridazin-3-yl)-6-methoxy-2H-indazole-5-carboxamide and rel-2-((5R,7S,8S)-2,7-dimethyl-3-oxo-2-azaspiro[4.5]decan-8-yl)-N-(imidazo[1,2-b]pyridazin-3-yl)-6-methoxy-2H-indazole-5-carboxamide—Isomers 1-4 containing 40% of 2-(2,7-dimethyl-1-oxo-2-azaspiro[4.5]decan-8-yl)-N-(imidazo[1,2-b]pyridazin-3-yl)-6-methoxy-2H-indazole-5-carboxamide. The desired products were separated from the byproduct and were separated by three consecutive chiral prep. HPLC runs (first run: Chiralpak® IA, 5 μm 20 mm×250 mm; isocratic with 50% MTBE (0.1% 2N NH₃-MeOH) in EtOH; 20.0 mL/min; second and third run: Chiralpak® ID, 5 μm 20 mm×250 mm; isocratic with 50% MTBE (0.1% 2N NH₃-MeOH) in MeOH in 16 min; 20.0 mL/min) to afford the following four isomers as pale-yellow solids: Isomer 1 (7 mg, 5%), Isomer 2 (7 mg, 5%), Isomer 3 (5 mg, 3%) and Isomer 4 (5 mg, 3%). Isomer 1 and 2 are enantiomers to each other, the LCMS/¹H NMR obtained for both isomers are identical; Isomer 3 and Isomer 4 are enantiomers to each other and the LCMS/¹H NMR obtained for both isomers are identical. Isomer 1/Isomer 2: ¹H NMR (400 MHz, DMSO-d₆) δ 11.05 (s, 1H), 8.64 (dd, 1H), 8.62 (d, 1H), 8.58 (s, 1H), 8.15 (dd, 1H), 8.05 (s, 1H), 7.31 (s, 1H), 7.22 (dd, 1H), 4.06-4.17 (m, 4H), 3.14 (s, 2H), 2.73 (s, 3H), 2.34 (s, 2H), 2.04-2.27 (m, 2H), 1.87-1.98 (m, 1H), 1.72-1.83 (m, 2H), 1.54-1.66 (m, 1H), 1.34 (t, 1H), 0.57 (d, 3H). MS ESI, m/z=488 [M+H]$^+$. Isomer 3/Isomer 4: $^1$H NMR (400 MHz, DMSO-d$_6$) δ 11.05 (s, 1H), 8.64 (dd, 1H), 8.62 (d, 1H), 8.58 (s, 1H), 8.15 (dd, 1H), 8.05 (s, 1H), 7.28 (s, 1H), 7.22 (dd, 1H), 4.07-4.17 (m, 4H), 3.38 (s, 2H), 2.76 (s, 3H), 2.06-2.28 (m, 4H), 1.86-1.96 (m, 1H), 1.76-1.86 (m, 2H), 1.51-1.63 (m, 1H), 1.33 (t, 1H), 0.57 (d, 3H). MS ESI, m/z=488 [M+H]$^+$.

N-(Imidazo[1,2-b]pyridazin-3-yl)-6-methoxy-2-(1-methyl-2-oxo-3-oxa-1-azaspiro[4.5]decan-8-yl)-2H-indazole-5-carboxamide—Isomer 1 (Example 74) & Isomer 2 (Example 75)

(4-(5-Bromo-6-methoxy-2H-indazol-2-yl)cyclohexyl)methanol

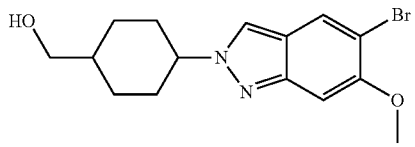 [SMILES: COc1cc2nn(C3CCC(CO)CC3)cc2cc1Br]

To a solution of (4-aminocyclohexyl)methanol (2.0 g, 15.5 mmol) in i-PrOH (20 mL) at rt was added 5-bromo-4-methoxy-2-nitrobenzaldehyde (Int I-1) (4.0 g, 15.5 mmol) under N$_2$ atmosphere. The resulting mixture was stirred at 80° C. for 1 h, then cooled to rt, followed by the addition of tri-n-butylphosphine (15.7 g, 77.4 mmol). The reaction mixture was stirred at 80° C. for 15 h. The mixture was cooled to rt and concentrated under reduced pressure. The residue was purified by silica gel chromatography (eluting with 20-50% EtOAc in PE) to yield a yellow oil. The oil was subsequently crystalized from EtOAc (2 mL)/PE (12 ml) to afford (4-(5-bromo-6-methoxy-2H-indazol-2-yl)cyclohexyl)methanol (900 mg, 17%) as a colorless solid. The filtrate from the crystallization was concentrated under reduced pressure to give (4-(5-bromo-6-methoxy-2H-indazol-2-yl)cyclohexyl)methanol (5.0 g, 47 wt. %) as a solid, which was used in the next step without further purification. MS ESI, m/z=339/341 [M+H]$^+$.

(4-(5-Bromo-6-methoxy-2H-indazol-2-yl)cyclohexyl)methyl carbamate

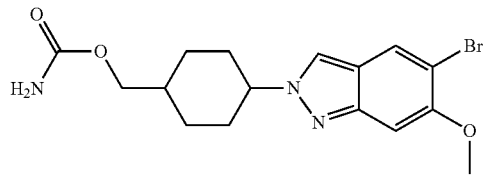 [SMILES: COc1cc2nn(C3CCC(COC(N)=O)CC3)cc2cc1Br]

To a solution of crude (4-(5-bromo-6-methoxy-2H-indazol-2-yl)cyclohexyl)methanol (47 wt. %) (4.9 g) in DCM (20 mL) at 0° C. was added 2,2,2-trichloroacetyl isocyanate (1.5 g, 8.2 mmol). The resulting solution was warmed to rt and stirred for 2 h. Subsequently, MeOH and K$_2$CO$_3$ (94 mg, 0.7 mmol) were added. The resulting mixture was stirred at rt for 15 h. The reaction was quenched with water (20 mL) and extracted with DCM (20 mL×3). The combined organic layers were dried over Na$_2$SO$_4$, filtered and concentrated under reduced pressure. The residue was crystallized from EtOAc/pentane (3/1) (20 mL) to afford (4-(5-bromo-6-methoxy-2H-indazol-2-yl)cyclohexyl)methyl carbamate (2.5 g, 96%) as a colorless solid. MS ESI, m/z=382/384 [M+H]$^+$.

8-(5-Bromo-6-methoxy-2H-indazol-2-yl)-3-oxa-1-azaspiro[4.5]decan-2-one

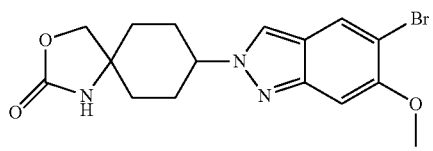 [SMILES: COc1cc2nn(C3CCC4(CC3)COC(=O)N4)cc2cc1Br]

To a solution of magnesium oxide (728 mg, 18.1 mmol), [acetyloxy(phenyl)-λ$^3$-iodanyl]acetate (3.5 g, 11.0 mmol) and (4-(5-bromo-6-methoxy-2H-indazol-2-yl)cyclohexyl)methyl carbamate (1.5 g, 3.9 mmol) in DCM (150 mL) at rt was added rhodium(II) acetate (347 mg, 0.8 mmol) over a period of 3 min under N$_2$ atmosphere. The resulting solution was stirred at 40° C. for 15 h. The mixture was cooled to rt, poured into water (100 mL) and extracted with DCM (200 mL×2). The combined organic layers were dried over Na$_2$SO$_4$, filtered and concentrated under reduced pressure. The residue was purified by C18-flash chromatography (eluting with 0-100% MeCN in water (0.1% FA)) and further by prep. HPLC (Waters XSelect CSH C18 OBD, 5 μm 30×150 mm; elution gradient with 34-35% MeCN in water (0.05% TFA) in 8 min; 60 mL/min) to afford 8-(5-bromo-6-methoxy-2H-indazol-2-yl)-3-oxa-1-azaspiro[4.5]decan-2-one (340 mg, 23%) as a pale-yellow solid. MS ESI, m/z=380/382 [M+H]$^+$.

8-(5-Bromo-6-methoxy-2H-indazol-2-yl)-1-methyl-3-oxa-1-azaspiro[4.5]decan-2-one

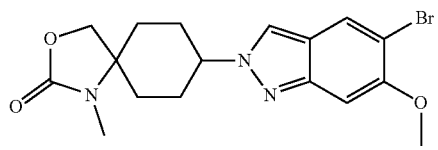 [SMILES: COc1cc2nn(C3CCC4(CC3)COC(=O)N4C)cc2cc1Br]

Iodomethane (134 mg, 1.0 mmol) was added dropwise to a suspension of NaH (60 wt. %) (19 mg, 0.5 mmol) and 8-(5-bromo-6-methoxy-2H-indazol-2-yl)-3-oxa-1-azaspiro[4.5]decan-2-one (120 mg, 0.3 mmol) in DMF (6 mL) at rt under N$_2$ atmosphere. The resulting mixture was stirred at rt for 15 h. The reaction was quenched with aq. saturated NH$_4$Cl solution (5 mL) and purified directly by C18-flash chromatography (eluting with 0-100% MeCN in water (0.1% FA)) to afford 8-(5-bromo-6-methoxy-2H-indazol-2-yl)-1-methyl-3-oxa-1-azaspiro[4.5]decan-2-one (70 mg, 56%) as a red solid. MS ESI, m/z=380/382 [M+H]$^+$.

N-(Imidazo[1,2-b]pyridazin-3-yl)-6-methoxy-2-(1-methyl-2-oxo-3-oxa-1-azaspiro[4.5]decan-8-yl)-2H-indazole-5-carboxamide—Isomer 1 (Example 74) & Isomer 2 (Example 75)

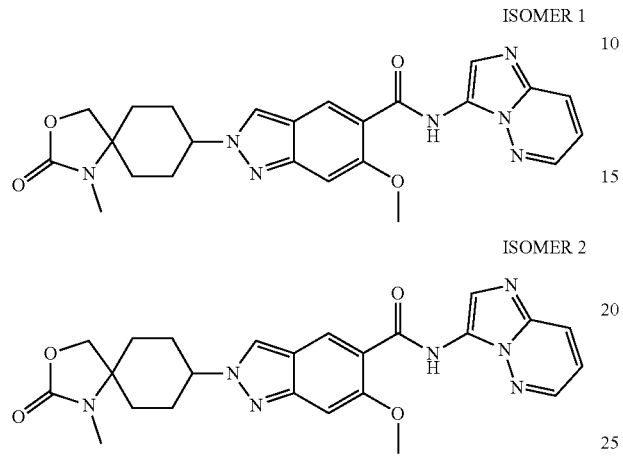

ISOMER 1

ISOMER 2

A suspension of 8-(5-bromo-6-methoxy-2H-indazol-2-yl)-1-methyl-3-oxa-1-azaspiro[4.5]decan-2-one (124 mg, 0.3 mmol), imidazo[1,2-b]pyridazin-3-amine (121 mg, 0.9 mmol), Pd(OAc)₂ (14 mg, 0.06 mmol), dppp (41 mg, 0.1 mmol) and TEA (438 μL, 3.2 mmol) in MeCN (10 mL) was stirred under CO atmosphere at 15 atm and 100° C. for 15 h. The mixture was allowed to cool to rt and concentrated under reduced pressure. The residue was purified by C18-flash chromatography (eluting with 0-90% MeCN in water (0.1% FA)) and further by prep. HPLC (Waters Xbridge® BEH OBD C18, 5 μm 30×150 mm; elution gradient with 30-60% MeOH in water (10 mM NH₄HCO₃+0.1% NH₄OH) in 8 min; 60 mL/min) to afford N-(imidazo[1,2-b]pyridazin-3-yl)-6-methoxy-2-(1-methyl-2-oxo-3-oxa-1-azaspiro[4.5]decan-8-yl)-2H-indazole-5-carboxamide as a yellow solid. The solid was separated by chiral prep. HPLC (Chiralpak® IF, 5 μm 20 mm×250 mm; isocratic with 50% MTBE (0.5% 2M NH₃-MeOH) in EtOH for 26 min; 13.0 mL/min) to afford rel-N-(imidazo[1,2-b]pyridazin-3-yl)-6-methoxy-24 (5r,8r)-1-methyl-2-oxo-3-oxa-1-azaspiro[4.5]decan-8-yl)-2H-indazole-5-carboxamide—Isomer 1 (7 mg, 4%, 100% ee) and rel-N-(imidazo[1,2-b]pyridazin-3-yl)-6-methoxy-2-(5r,8r)-1-methyl-2-oxo-3-oxa-1-azaspiro[4.5]decan-8-yl)-2H-indazole-5-carboxamide—Isomer 2 (1 mg, 1%, 98.9% ee), both as yellow solids. Isomer 1: ¹H NMR (400 MHz, DMSO-d₆) δ 11.05 (s, 1H), 8.74 (s, 1H), 8.63 (dd, 1H), 8.59 (s, 1H), 8.15 (dd, 1H), 8.05 (s, 1H), 7.30 (s, 1H), 7.22 (dd, 1H), 4.65-4.73 (m, 1H), 4.23 (s, 2H), 4.13 (s, 3H), 2.60 (s, 3H), 2.51-2.58 (m, 2H), 1.93-2.15 (m, 4H), 1.53 (d, 2H). MS ESI, m/z=476 [M+H]⁺. Isomer 2: ¹H NMR (400 MHz, DMSO-d₆) δ 11.04 (s, 1H), 8.62-8.66 (m, 1H), 8.61 (s, 1H), 8.59 (s, 1H), 8.15 (dd, 1H), 8.05 (s, 1H), 7.25-7.29 (m, 1H), 7.22 (dd, 1H), 4.48-4.61 (m, 1H), 4.27 (s, 2H), 4.12 (s, 3H), 2.72 (s, 3H), 2.18 (s, 2H), 1.95-2.09 (m, 4H), 1.66-1.76 (m, 2H). MS ESI, m/z=476 [M+H]⁺.

rel-2-(1R,3R,4S)-4-Hydroxy-3-methylcyclohexyl)-N-(imidazo[1,2-b]pyridazin-3-yl)-6-methoxy-2H-indazole-5-carboxamide—Isomer 1 (Example 76), Isomer 2 (Example 77)

rel-2-(1S,3R,4S)-4-Hydroxy-3-methylcyclohexyl)-N-(imidazo[1,2-b]pyridazin-3-yl)-6-methoxy-2H-indazole-5-carboxamide—Isomer 1 (Example 78) & Isomer 2 (Example 79) rac-(3R,4S)-4-Hydroxy-3-methylcyclohexan-1-one

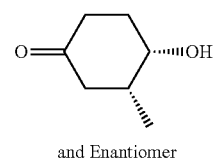

and Enantiomer

Aq. HCl (12N) (10.0 mL, 120.0 mmol) was added to THF (10 mL) and water (10 mL), followed by the addition of rac-(7R,8S)-7-methyl-1,4-dioxaspiro[4.5]decan-8-ol (Int III-11) (3.1 g, 18.0 mmol). The resulting mixture was stirred at rt for 12 h. The pH of the reaction mixture was adjusted to pH 5-6 with 30 wt. % aq. NH₄OH solution, then mixture was concentrated under reduced pressure. The residue was purified by silica gel chromatography (eluting with 0-50% EtOAc in PE) to afford rac-(3R,4S)-4-hydroxy-3-methylcyclohexan-1-one (2.1 g, 91%) as a yellow oil. MS ESI, m/z=170 [M+CH₃CN+H]⁺.

Mixture of rac-(1S,2R,4R)-4-(benzylamino)-2-methylcyclohexan-1-ol and rac-(1S,2R,4S)-4-(benzylamino)-2-methylcyclohexan-1-ol

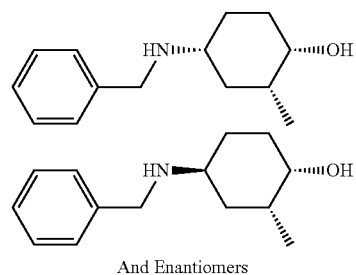

And Enantiomers

To a solution of rac-(3R,4S)-4-hydroxy-3-methylcyclohexan-1-one (2.0 g, 15.6 mmol) in DCE (40 mL) at rt under N₂ atmosphere was added phenylmethanamine (2.0 g, 18.7 mmol). The resulting solution was stirred for 1 h, followed by the addition of sodium triacetoxyborohydride (9.9 g, 46.8 mmol). The mixture was stirred at rt for another 3 h. The reaction was quenched with water (15 mL) and concentrated under reduced pressure. The residue was purified by C18-flash chromatography (eluting with 0-80% MeCN in water (0.1% NH₄OH)) to afford a mixture of rac-(1S,2R,4R)-4-(benzylamino)-2-methylcyclohexan-1-ol and rac-(1S,2R,4S)-4-(benzylamino)-2-methylcyclohexan-1-ol (2.10 g, 61%) as a brown solid.

Mixture of rac-(1S,2R,4R)-4-amino-2-methylcyclohexan-1-ol and rac-(1S,2R,4S)-4-amino-2-methylcyclohexan-1-ol

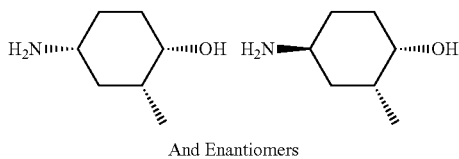

And Enantiomers

To a solution of a mixture of rac-(1S,2R,4R)-4-(benzylamino)-2-methylcyclohexan-1-ol and rac-(1S,2R,4S)-4-(benzylamino)-2-methylcyclohexan-1-ol (2.0 g, 9.1 mmol) in MeOH (30 mL) under $N_2$ atmosphere was added Pd(OH)$_2$ on carbon (20 wt. %) (640 mg, 0.9 mmol). The resulting suspension was stirred at rt under hydrogen at 2 atm for 12 h. The reaction mixture was filtered through silica gel, and the silica gel cake was washed with MeOH (30 mL). The combined MeOH solution was concentrated under reduced pressure to afford a crude mixture of rac-(1S,2R,4R)-4-amino-2-methylcyclohexan-1-ol and rac-(1S,2R,4S)-4-amino-2-methylcyclohexan-1-ol (1.20 g, 90 wt. %) as a yellow oil, which was used for the next step without further purification.

Mixture of rac-(1S,2R,4R)-4-(5-bromo-6-methoxy-2H-indazol-2-yl)-2-methylcyclohexan-1-ol and rac-(1S,2R,4S)-4-(5-bromo-6-methoxy-2H-indazol-2-yl)-2-methylcyclohexan-1-ol

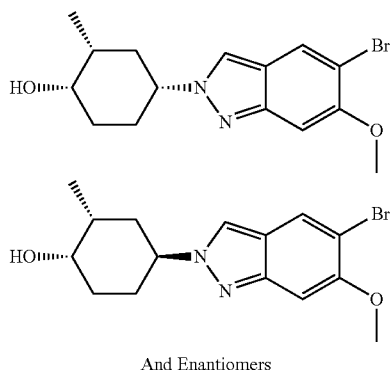

And Enantiomers

To a solution of 5-bromo-4-methoxy-2-nitrobenzaldehyde (Int I-1) (2.2 g, 8.4 mmol) in i-PrOH (20 mL) at rt under $N_2$ atmosphere was added a crude mixture of rac-(1S,2R,4R)-4-amino-2-methylcyclohexan-1-ol and rac-(1S,2R,4S)-4-amino-2-methylcyclohexan-1-ol (90 wt. %) (1.0 g). The resulting mixture was stirred at 80° C. for 2 h, then cooled to rt, followed by the addition of tri-n-butylphosphine (5.6 g, 27.9 mmol). The reaction mixture was stirred at 80° C. for 12 h. The mixture was allowed to cool to rt and concentrated under reduced pressure. The residue was purified by C18-flash chromatography (eluting with 0-50% MeOH in water (0.05% FA)) to give a crude mixture of rac-(1S,2R,4R)-4-(5-bromo-6-methoxy-2H-indazol-2-yl)-2-methylcyclohexan-1-ol and rac-(1S,2R,4S)-4-(5-bromo-6-methoxy-2H-indazol-2-yl)-2-methylcyclohexan-1-ol (5.0 g, 45 wt. %) as a yellow oil, which was used in the next step without further purification. MS ESI, m/z=339/341 [M+H]$^+$.

Mixture of rac-2-((1R,3R,4S)-4-hydroxy-3-methylcyclohexyl)-N-(imidazo[1,2-b]pyridazin-3-yl)-6-methoxy-2H-indazole-5-carboxamide and rac-2-((1S,3R,4S)-4-hydroxy-3-methylcyclohexyl)-N-(imidazo[1,2-b]pyridazin-3-yl)-6-methoxy-2H-indazole-5-carboxamide

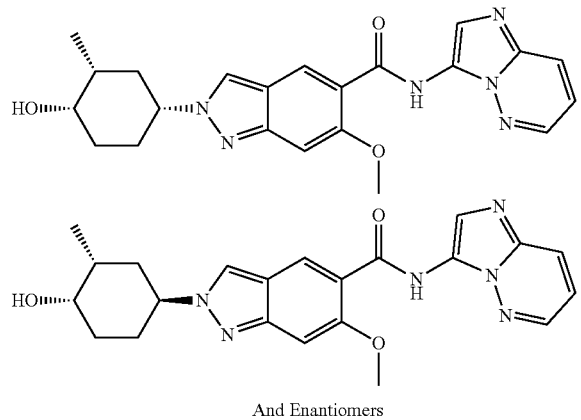

And Enantiomers

A suspension of a crude mixture of rac-(1S,2R,4R)-4-(5-bromo-6-methoxy-2H-indazol-2-yl)-2-methylcyclohexan-1-ol and rac-(1S,2R,4S)-4-(5-bromo-6-methoxy-2H-indazol-2-yl)-2-methylcyclohexan-1-ol (45 wt. %) (5.0 g), imidazo[1,2-b]pyridazin-3-amine (978 mg, 7.3 mmol), Pd(OAc)$_2$ (291 mg, 1.3 mmol), dppp (1.1 g, 2.7 mmol) and TEA (2.8 mL, 19.9 mmol) in MeCN (80 mL) was stirred under CO atmosphere at 10 atm and 100° C. for 12 h. The mixture was allowed to cool to rt and concentrated under reduced pressure. The residue was purified by silica gel chromatography (eluting with 0-100% EtOAc in PE) and further by prep. SFC (DAICEL DCpak® P4VP, 5 µm 20 mm×250 mm; isocratic with 35% MeOH (2 mM NH$_3$-MeOH) in CO$_2$ (35° C., 100 bar)) to afford a mixture of rac-2-((1R,3R,4S)-4-hydroxy-3-methylcyclohexyl)-N-(imidazo[1,2-b]pyridazin-3-yl)-6-methoxy-2H-indazole-5-carboxamide and rac-2-((1S,3R,4S)-4-hydroxy-3-methylcyclohexyl)-N-(imidazo[1,2-b]pyridazin-3-yl)-6-methoxy-2H-indazole-5-carboxamide (600 mg, 22%) as a yellow solid. MS ESI, m/z=421 [M+H]$^+$.

rac-2-(1R,3R,4S)-4-Hydroxy-3-methylcyclohexyl)-N-(imidazo[1,2-b]pyridazin-3-yl)-6-methoxy-2H-indazole-5-carboxamide & rac-2-(1S,3R,4S)-4-Hydroxy-3-methylcyclohexyl)-N-(imidazo[1,2-b]pyridazin-3-yl)-6-methoxy-2H-indazole-5-carboxamide

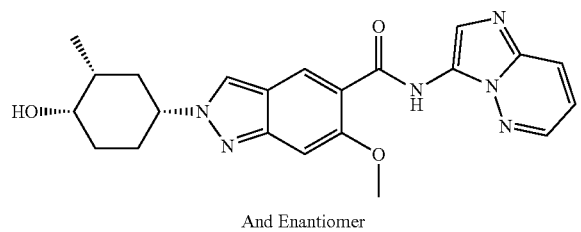

And Enantiomer

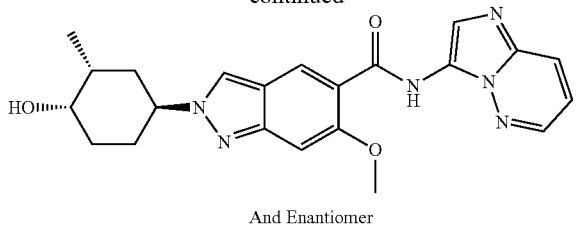

And Enantiomer

A mixture of rac-2-((1R,3R,4S)-4-hydroxy-3-methylcyclohexyl)-N-(imidazo[1,2-b]pyridazin-3-yl)-6-methoxy-2H-indazole-5-carboxamide and rac-2-((1S,3R,4S)-4-hydroxy-3-methylcyclohexyl)-N-(imidazo[1,2-b]pyridazin-3-yl)-6-methoxy-2H-indazole-5-carboxamide (600 mg, 1.4 mmol) was separated by chiral prep. SFC (Chiralpak® IH, 5 µm 30×250 mm; isocratic with 32% MeOH (2 mM NH₃-MeOH) in CO₂ (35° C., 100 bar); 70 mL/min) to afford rac-2-((1R,3R,4S)-4-hydroxy-3-methylcyclohexyl)-N-(imidazo[1,2-b]pyridazin-3-yl)-6-methoxy-2H-indazole-5-carboxamide (200 mg, 33%) and rac-2-((1S,3R,4S)-4-hydroxy-3-methylcyclohexyl)-N-(imidazo[1,2-b]pyridazin-3-yl)-6-methoxy-2H-indazole-5-carboxamide (220 mg, 37%), both as yellow solids.

rel-2-(1R,3R,4S)-4-Hydroxy-3-methylcyclohexyl)-N-(imidazo[1,2-b]pyridazin-3-yl)-6-methoxy-2H-indazole-5-carboxamide—Isomer 1 (Example 76) & Isomer 2 (Example 77)

ISOMER 1

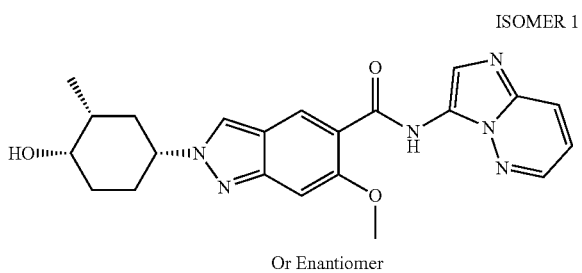

Or Enantiomer

ISOMER 2

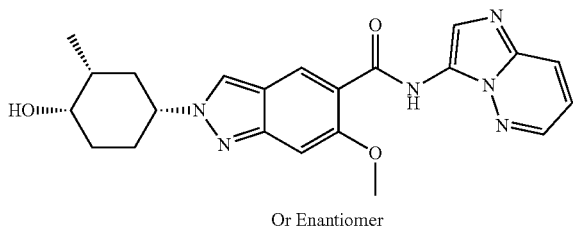

Or Enantiomer rac-2-((1R,3R,4S)-4-hydroxy-3-methylcyclohexyl)-N-(imidazo[1,2-b]pyridazin-3-yl)-6-methoxy-2H-indazole-5-carboxamide (200 mg, 0.5 mmol) was further separated and purified by chiral prep. HPLC (Chiralpak® IA, 5 µm 20 mm×250 mm; isocratic with 50% hexane/DCM (75/25, 0.5% 2M NH₃-MeOH) in EtOH in 23 min; 18.0 mL/min) and achiral prep. HPLC (for Isomer 1: Waters XSelect CSH C18 OBD, 5 µm 30×150 mm; elution gradient with 22-26% MeCN in water (0.1% FA) in 7 min; 60 mL/min) to afford rel-2-((1R,3R,4S)-4-hydroxy-3-methylcyclohexyl)-N-(imidazo[1,2-b]pyridazin-3-yl)-6-methoxy-2H-indazole-5-carboxamide—Isomer 1 (40 mg, 20%, 100% ee) and rel-2-((1R,3R,4S)-4-hydroxy-3-methylcyclohexyl)-N-(imidazo[1,2-b]pyridazin-3-yl)-6-methoxy-2H-indazole-5-carboxamide—Isomer 2 (40 mg, 20%, 100% ee), both as yellow solids. The ¹H NMR and MS obtained for both products were identical. ¹H NMR (400 MHz, DMSO-d₆) δ 11.05 (s, 1H), 8.64 (dd, 1H), 8.58 (br. s, 2H), 8.15 (dd, 1H), 8.05 (s, 1H), 7.25 (s, 1H), 7.22 (dd, 1H), 4.36-4.62 (m, 2H), 4.12 (s, 3H), 3.66 (s, 1H), 2.11-2.27 (m, 1H), 2.00 (q, 1H), 1.80-1.93 (m, 2H), 1.56-1.80 (m, 3H), 0.96 (d, 3H). MS ESI, m/z=421 [M+H]⁺.

rel-2-(1S,3R,4S)-4-Hydroxy-3-methylcyclohexyl)-N-(imidazo[1,2-b]pyridazin-3-yl)-6-methoxy-2H-indazole-5-carboxamide—Isomer 1 (Example 78) & Isomer 2 (Example 79)

ISOMER 1

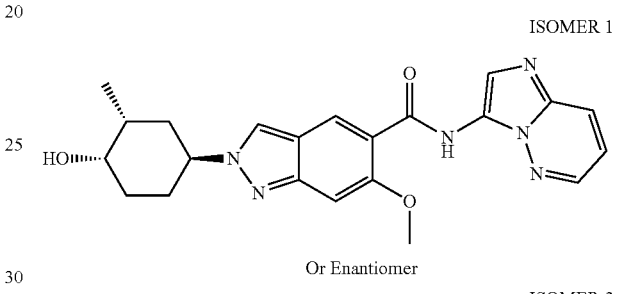

Or Enantiomer

ISOMER 2

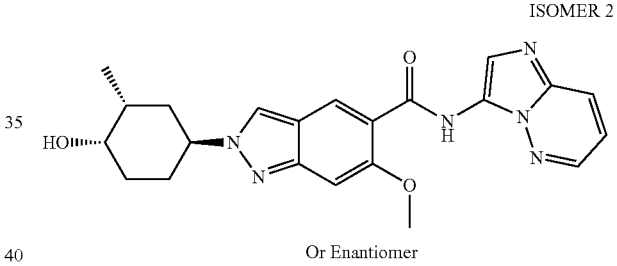

Or Enantiomer rac-2-((1S,3R,4S)-4-hydroxy-3-methylcyclohexyl)-N-(imidazo[1,2-b]pyridazin-3-yl)-6-methoxy-2H-indazole-5-carboxamide (200 mg, 0.5 mmol) was further separated by chiral prep. HPLC (Chiralpak® ID-2, 5 µm 20 mm×250 mm; isocratic with 50% MTBE (0.1% 2N NH₃-MeOH) in MeOH in 19 min; 20.0 mL/min) to afford rel-2-((1S,3R,4S)-4-hydroxy-3-methylcyclohexyl)-N-(imidazo[1,2-b]pyridazin-3-yl)-6-methoxy-2H-indazole-5-carboxamide—Isomer 1 (80 mg, 40%, 98.2% ee) and rel-2-((1S,3R,4S)-4-hydroxy-3-methylcyclohexyl)-N-(imidazo[1,2-b]pyridazin-3-yl)-6-methoxy-2H-indazole-5-carboxamide—Isomer 2 (80 mg, 40%, 97.9% ee), both as yellow solids. Isomer 1: ¹H NMR (400 MHz, DMSO-d₆) δ 11.04 (s, 1H), 8.63 (dd, 1H), 8.61 (s, 1H), 8.57 (s, 1H), 8.15 (dd, 1H), 8.05 (s, 1H), 7.25 (s, 1H), 7.21 (dd, 1H), 4.68 (tt, 1H), 4.60 (br. s, 1H), 4.11 (s, 3H), 3.71 (dt, 1H), 1.92-2.20 (m, 5H), 1.57-1.76 (m, 2H), 1.00 (d, 3H). MS ESI, m/z=421 [M+H]⁺. Isomer 2: ¹H NMR (400 MHz, DMSO-d₆) δ 11.05 (s, 1H), 8.63 (dd, 1H), 8.61 (br. s, 1H), 8.57 (s, 1H), 8.15 (dd, 1H), 8.05 (s, 1H), 7.26 (s, 1H), 7.22 (dd, 1H), 4.63-4.73 (m, 1H), 4.60 (d, 1H), 4.12 (s, 3H), 3.67-3.76 (m, 1H), 1.92-2.21 (m, 5H), 1.58-1.75 (m, 2H), 1.00 (d, 3H). MS ESI, m/z=421 [M+H]⁺.

rel-2-(1S,3S,4S)-4-Hydroxy-3-methylcyclohexyl)-N-(imidazo[1,2-b]pyridazin-3-yl)-6-methoxy-2H-indazole-5-carboxamide—Isomer 1 (Example 80) & Isomer 2 (Example 81)

rel-2-(1R,3S,4S)-4-Hydroxy-3-methylcyclohexyl)-N-(imidazo[1,2-b]pyridazin-3-yl)-6-methoxy-2H-indazole-5-carboxamide Isomer 1 (Example 82) & Isomer 2 (Example 83) rac-(3S,4S)-4-Hydroxy-3-methylcyclohexan-1-one

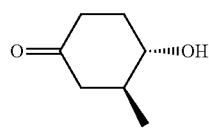

and Enantiomer

Aq. HCl (12N) (8.0 mL, 96.0 mmol) was added to THF (8 mL) and water (8 mL) followed by the addition of rac-(7S,8S)-7-methyl-1,4-dioxaspiro[4.5]decan-8-ol (Int III-12) (2.0 g, 11.6 mmol). The resulting mixture was stirred at rt for 12 h. The pH of the mixture was adjusted to pH 5-6 with 30 wt. % aq. NH$_4$OH solution, the mixture was then concentrated under reduced pressure. The residue was purified by silica gel chromatography (eluting with 0-50% EtOAc in PE) to afford rac-(3S,4S)-4-hydroxy-3-methylcyclohexan-1-one (1.3 g, 89%) as a yellow oil. MS ESI, m/z=211 [M+2CH$_3$CN+H]$^+$.

rac-(1S,2S,4S)-4-(Benzylamino)-2-methylcyclohexan-1-ol & rac-(1S,2S,4R)-4-(Benzylamino)-2-methylcyclohexan-1-ol

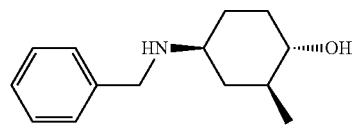

and Enantiomer

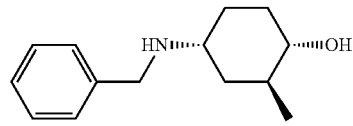

and Enantiomer

To a solution of rac-(3S,4S)-4-hydroxy-3-methylcyclohexan-1-one (1.3 g, 10.1 mmol) in DCE (50 mL) at rt under N$_2$ atmosphere was added phenylmethanamine (1.3 g, 12.2 mmol). The resulting solution was stirred for 1 h, followed by the addition of sodium triacetoxyborohydride (6.6 g, 30.4 mmol). The reaction mixture was stirred at rt for another 3 h. The reaction was quenched with water (10 mL) and concentrated under reduced pressure. The residue was purified by C18-flash chromatography (eluting with 30-60% MeCN in water (0.1% NH$_4$OH)) to afford rac-(1S,2S,4S)-4-(benzylamino)-2-methylcyclohexan-1-ol (200 mg, 9%) and rac-(1S,2S,4R)-4-(benzylamino)-2-methylcyclohexan-1-ol (700 mg, 32%), both as yellow solids. MS ESI, m/z=220 [M+H]$^+$.

rac-(1S,2S,4S)-4-Amino-2-methylcyclohexan-1-ol

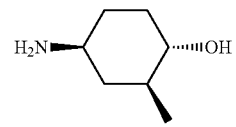

and Enantiomer

To a solution of rac-(1S,2S,4S)-4-(benzylamino)-2-methylcyclohexan-1-ol (180 mg, 0.8 mmol) in MeOH (20 mL) under N$_2$ atmosphere was added Pd(OH)$_2$ on carbon (20 wt. %) (175 mg, 0.2 mmol). The resulting suspension was stirred at rt under hydrogen at 1~2 atm for 12 h. The reaction mixture was filtered through silica gel, and the silica gel cake was washed with MeOH (100 mL). The combined MeOH solution was concentrated under reduced pressure to afford rac-(1S,2S,4S)-4-amino-2-methylcyclohexan-1-ol (100 mg, 94%) as a yellow oil, which was used for the next step without further purification. MS ESI, m/z=130 [M+H]$^+$.

rac-(1S,2S,4S)-4-(5-Bromo-6-methoxy-2H-indazol-2-yl)-2-methylcyclohexan-1-ol

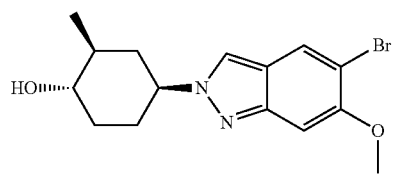

and Enantiomer

To a solution of 5-bromo-4-methoxy-2-nitrobenzaldehyde (Int I-1) (242 mg, 0.9 mmol) in i-PrOH (20 mL) at rt under N$_2$ atmosphere was added rac-(1S,2S,4S)-4-amino-2-methylcyclohexan-1-ol (100 mg, 0.8 mmol). The resulting mixture was stirred at 80° C. for 1 h, then cooled to rt, followed by the addition of tri-n-butylphosphine (626 mg, 3.1 mmol). The reaction mixture was stirred at 80° C. for 12 h. The mixture was cooled to rt and concentrated under reduced pressure. The residue was purified by C18-flash chromatography (eluting with 0-80% acetonitrile in water (0.05% FA)) to afford rac-(1S,2S,4S)-4-(5-bromo-6-methoxy-2H-indazol-2-yl)-2-methylcyclohexan-1-ol (200 mg, 76%) as a yellow oil, which was used in the next step without further purification. MS ESI, m/z=339/341 [M+H]$^+$.

rel-2-(1S,3S,4S)-4-Hydroxy-3-methylcyclohexyl)-N-(imidazo[1,2-b]pyridazin-3-yl)-6-methoxy-2H-indazole-5-carboxamide—Isomer 1 (Example 80) & Isomer 2 (Example 81)

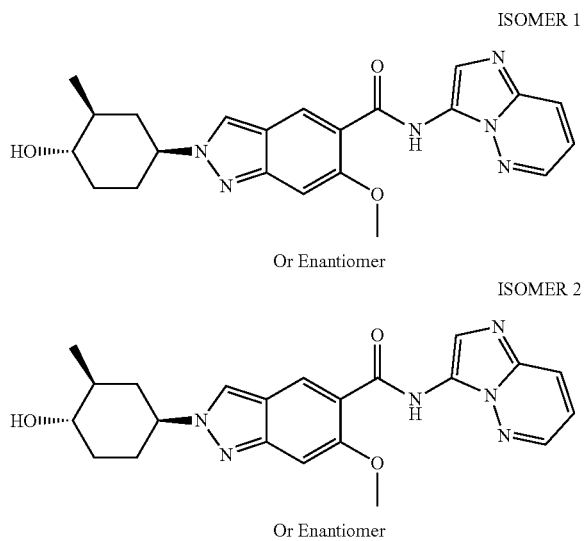

ISOMER 1

Or Enantiomer

ISOMER 2

Or Enantiomer

A suspension of rac-(1S,2S,4R)-4-(5-bromo-6-methoxy-2H-indazol-2-yl)-2-methylcyclohexan-1-ol (200 mg, 0.3 mmol), imidazo[1,2-b]pyridazine-3-amine (40 mg, 0.3 mmol), Pd(OAc)$_2$ (14 mg, 0.06 mmol), dppp (41 mg, 0.1 mmol) and TEA (164 μL, 1.2 mmol) in MeCN (50 mL) was stirred under CO atmosphere at 10 atm and 100° C. for 12 h. The mixture was allowed to cool to rt and concentrated under reduced pressure. The residue was purified by C18-flash chromatography (eluting with 0-80% acetonitrile in water (0.05% FA)) to afford rac-2-((1S,3S,4S)-4-hydroxy-3-methylcyclohexyl)-N-(imidazo[1,2-b]pyridazin-3-yl)-6-methoxy-2H-indazole-5-carboxamide. This material was further separated by chiral prep. HPLC (Chiralpak® IA, 5 μm 20 mm×250 mm; isocratic with 10% MTBE (0.1% 2N NH$_3$-MeOH) in DCM/MeOH (1:1) in 11 min; 20.0 mL/min) to afford rel-2-((1S,3S,4S)-4-hydroxy-3-methylcyclohexyl)-N-(imidazo[1,2-b]pyridazin-3-yl)-6-methoxy-2H-indazole-5-carboxamide—Isomer 1 (16 mg, 13%, 100% ee) and rel-2-((1S,3S,4S)-4-hydroxy-3-methylcyclohexyl)-N-(imidazo[1,2-b]pyridazin-3-yl)-6-methoxy-2H-indazole-5-carboxamide—Isomer 2 (16 mg, 13%, 100% ee); both as yellow solids. The $^1$H NMR and MS obtained for both products were identical. $^1$H NMR (400 MHz, DMSO-d$_6$) δ 11.04 (s, 1H), 8.63 (dd, 1H), 8.54-8.59 (m, 2H), 8.15 (dd, 1H), 8.05 (s, 1H), 7.24 (s, 1H), 7.22 (dd, 1H), 4.66 (d, 1H), 4.46-4.59 (m, 1H), 4.12 (s, 3H), 3.02-3.14 (m, 1H), 2.02-2.16 (m, 2H), 1.96 (td, 2H), 1.70 (q, 1H), 1.37-1.58 (m, 2H), 1.01 (d, 3H). MS ESI, m/z=421 [M+H]$^+$.

rac-(1S,2S,4R)-4-Amino-2-methylcyclohexan-1-ol

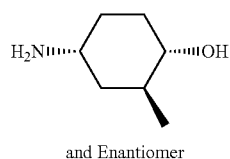

and Enantiomer

To a solution of rac-(1S,2S,4R)-4-(benzylamino)-2-methylcyclohexan-1-ol (600 mg, 2.7 mmol) in MeOH (20 mL) under N$_2$ atmosphere was added Pd(OH)$_2$ on carbon (20 wt. %) (582 mg, 0.6 mmol). The resulting suspension was stirred at rt under hydrogen at 1~2 atm for 12 h. The reaction mixture was filtered through silica gel, and the silica gel cake was washed with MeOH (100 mL). The combined MeOH solution was concentrated under reduced pressure to afford crude rac-(1S,2S,4R)-4-amino-2-methylcyclohexan-1-ol (400 mg) as a yellow oil, which was used without further purification. MS ESI, m/z=130 [M+H]$^+$.

rac-(1S,2S,4R)-4-(5-Bromo-6-methoxy-2H-indazol-2-yl)-2-methylcyclohexan-1-ol

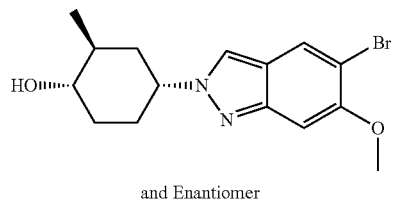 [SMILES: COc1cc2nn([C@@H]3CC[C@H](O)[C@@H](C)C3)cc2cc1Br]

and Enantiomer

To a solution of 5-bromo-4-methoxy-2-nitrobenzaldehyde (Int I-1) (740 mg, 2.9 mmol) in i-PrOH (30 mL) at rt under N$_2$ atmosphere was added rac-(1S,2S,4R)-4-amino-2-methylcyclohexan-1-ol (380 mg, 2.6 mmol). The resulting mixture was stirred at 80° C. for 1 h, then cooled to rt, followed by the addition of tri-n-butylphosphine (1.6 g, 7.8 mmol). The reaction mixture was stirred at 80° C. for 12 h. The mixture was cooled to rt and concentrated under reduced pressure. The residue was purified by C18-flash chromatography (eluting with 0-80% acetonitrile in water (0.05% FA)) to afford rac-(1S,2S,4R)-4-(5-bromo-6-methoxy-2H-indazol-2-yl)-2-methylcyclohexan-1-ol (600 mg, 68%) as a brown oil, which was used in the next step without further purification. MS ESI, m/z=339/341 [M+H]$^+$.

rel-2-(1R,3S,4S)-4-Hydroxy-3-methylcyclohexyl)-N-(imidazo[1,2-b]pyridazin-3-yl)-6-methoxy-2H-indazole-5-carboxamide Isomer 1 (Example 82) & Isomer 2 (Example 83)

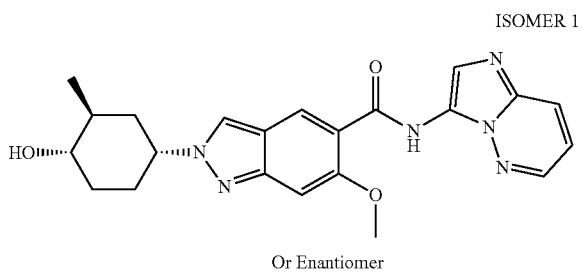

ISOMER 1

Or Enantiomer

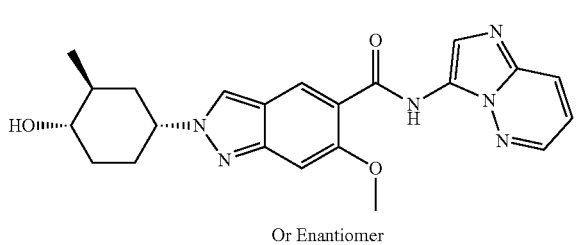

ISOMER 2

Or Enantiomer

A suspension of rac-(1S,2S,4R)-4-(5-bromo-6-methoxy-2H-indazol-2-yl)-2-methylcyclohexan-1-ol (580 mg, 1.7 mmol), imidazo[1,2-b]pyridazin-3-amine (257 mg, 1.9 mmol), Pd(OAc)₂ (67 mg, 0.3 mmol), dppp (288 mg, 0.7 mmol) and TEA (994 µL, 7.1 mmol) in MeCN (55 mL) was stirred under CO atmosphere at 10 atm and 100° C. for 12 h. The mixture was cooled to rt and concentrated under reduced pressure. The residue was purified by C18-flash chromatography (eluting with 0-80% acetonitrile in water (0.05% FA)) and further by prep. HPLC (Waters Xbridge® BEH OBD C18, 5 µm 19×250 mm; elution gradient with 22-32% MeCN in water (10 mM NH₄HCO₃+0.1% NH₄OH) in 11 min; 25 mL/min) to afford rac-2-((1R,3S,4S)-4-hydroxy-3-methylcyclohexyl)-N-(imidazo[1,2-b]pyridazin-3-yl)-6-methoxy-2H-indazole-5-carboxamide. This material was further purified by chiral prep. HPLC (Chiralpak® IE, 5 µm 20 mm×250 mm; isocratic with 50% MTBE (0.1% 2N NH₃-MeOH) in DCM/MeOH (1:1) in 27 min; 20.0 mL/min) and achiral prep. HPLC (for Isomer 1: Waters Xbridge® BEH OBD C18, 5 µm 30×150 mm; elution gradient with 18-48% MeCN in water (10 mM NH₄HCO₃+0.1% NH₄OH) in 7 min; 60 mL/min) to afford rel-2-((1R,3S,4S)-4-hydroxy-3-methylcyclohexyl)-N-(imidazo[1,2-b]pyridazin-3-yl)-6-methoxy-2H-indazole-5-carboxamide—Isomer 1 (13 mg, 1%, 98.5% ee) and rel-2-((1R,3S,4S)-4-hydroxy-3-methylcyclohexyl)-N-(imidazo[1,2-b]pyridazin-3-yl)-6-methoxy-2H-indazole-5-carboxamide—Isomer 2 (19 mg, 3%, 99.6% ee), both as yellow solids. Isomer 1: ¹H NMR (400 MHz, DMSO-d₆) δ 11.05 (s, 1H), 8.65 (s, 1H), 8.64 (dd, 1H), 8.59 (s, 1H), 8.15 (dd, 1H), 8.05 (s, 1H), 7.28 (s, 1H), 7.22 (dd, 1H), 4.61-4.70 (m, 1H), 4.55 (d, 1H), 4.13 (s, 3H), 2.44-2.49 (m, 1H), 2.35-2.48 (m, 1H), 1.84-1.94 (m, 1H), 1.72-1.82 (m, 2H), 1.63-1.70 (m, 1H), 1.47-1.56 (m, 1H), 1.01 (d, 3H). MS ESI, m/z=421 [M+H]⁺. Isomer 2: ¹H NMR (400 MHz, DMSO-d₆) δ 11.05 (s, 1H), 8.65 (s, 1H), 8.64 (dd, 1H), 8.59 (s, 1H), 8.15 (dd, 1H), 8.05 (s, 1H), 7.28 (s, 1H), 7.22 (dd, 1H), 4.59-4.70 (m, 1H), 4.55 (d, 1H), 4.13 (s, 3H), 3.30-3.37 (m, 1H), 2.45-2.50 (m, 1H), 2.35-2.48 (m, 1H), 1.83-1.95 (m, 1H), 1.71-1.83 (m, 2H), 1.61-1.71 (m, 1H), 1.47-1.56 (m, 1H), 1.01 (d, 3H). MS ESI, m/z=421 [M+H]⁺.

6-Cyclopropoxy-2-((1r,4r)-4-hydroxycyclohexyl)-N-(imidazo[1,2-b]pyridazin-3-yl)-2H-indazole-5-carboxamide (Example 84)

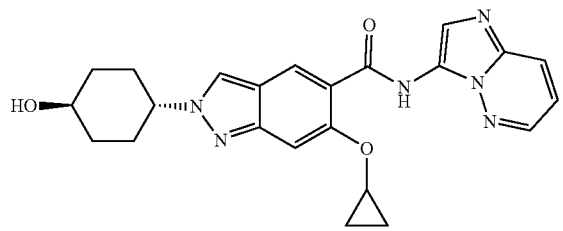 [SMILES: O=C(Nc1cnc2cccnn12)c1cc2cn([C@H]3CC[C@H](O)CC3)nc2cc1OC1CC1]

(1r,4r)-4-(6-Cyclopropoxy-5-iodo-2H-indazol-2-yl)cyclohexan-1-ol (Int IV-2) (80 mg, 0.2 mmol) and Pd(OAc)₂ (5 mg, 0.02 mmol) were added to TEA (61 mg, 0.6 mmol), dppp (17 mg, 0.04 mmol), and imidazo[1,2-b]pyridazin-3-amine (54 mg, 0.4 mmol) in MeCN (10 mL) and the resulting mixture was stirred in a 15 atm CO atmosphere at 90° C. After 12 h the reaction mixture was allowed to cool to rt and directly subjected to C18-flash chromatography (eluting with 0% to 100% MeCN in water (0.1% FA)) followed by prep. HPLC (XBridge Prep OBD C18 Column, 30×150 mm 5 µm; mobile phase A: water (10 mM NH₄HCO₃+0.1% NH₄OH); mobile phase B: MeCN; gradient: 25% B to 30% B in 10 min; flow rate: 60 mL/min) to afford 6-cyclopropoxy-2-((1r,4r)-4-hydroxycyclohexyl)-N-(imidazo[1,2-b]pyridazin-3-yl)-2H-indazole-5-carboxamide (17 mg, 20%) as a yellow solid. ¹H NMR (300 MHz, DMSO-d₆) δ 10.91 (s, 1H), 8.63 (dd, 1H), 8.60 (s, 1H), 8.58 (s, 1H), 8.13 (dd, 1H), 8.06 (s, 1H), 7.52 (s, 1H), 7.19 (dd, 1H), 4.75 (d, 1H), 4.38-4.55 (m, 1H), 4.16-4.28 (m, 1H), 3.48-3.62 (m, 1H), 1.84-2.23 (m, 6H), 1.30-1.53 (m, 2H), 0.94-1.18 (m, 4H). m/z (ESI+), [M+H]⁺=433.

6-Cyclopropoxy-2-((1s,4s)-4-hydroxycyclohexyl)-N-(imidazo[1,2-b]pyridazin-3-yl)-2H-indazole-5-carboxamide (Example 85)

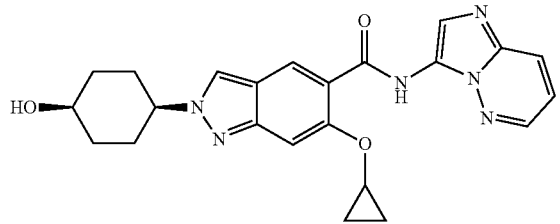

To crude (1s,4s)-4-(6-cyclopropoxy-5-iodo-2H-indazol-2-yl)cyclohexan-1-ol (Int IV-1) (70 mg, 0.2 mmol), dppp (7 mg, 0.02 mmol), TEA (98 µL, 0.7 mmol), and imidazo[1,2-b]pyridazin-3-amine (54 mg, 0.4 mmol) in MeCN (5 mL) was added Pd(OAc)₂ (5 mg, 0.02 mmol) and the resulting mixture was stirred under a 15 atm CO atmosphere at 90° C. After 12 h the reaction mixture was allowed to cool to rt and the solvent was removed in vacuo. The resulting residue was purified using C18-flash chromatography (eluting with 0% to 100% MeCN in water (0.1% FA)) to afford 6-cyclopropoxy-2-((1s,4s)-4-hydroxycyclohexyl)-N-(imidazo[1,2-b]pyridazin-3-yl)-2H-indazole-5-carboxamide (7 mg, 9%) as a pale-yellow solid. ¹H NMR (300 MHz, DMSO-d₆) δ 10.94 (s, 1H), 8.65 (dd, 1H), 8.63 (s, 1H), 8.62 (s, 1H), 8.15 (dd, 1H), 8.07 (s, 1H), 7.55 (s, 1H), 7.22 (dd, 1H), 4.43-4.59 (m, 2H), 4.20-4.29 (m, 1H), 3.86-3.93 (m, 1H), 2.22-2.39 (m, 2H), 1.72-1.95 (m, 4H), 1.57-1.72 (m, 2H), 1.07-1.15 (m, 2H), 0.97-1.07 (m, 2H). m/z (ESI+), [M+H]⁺=433.

6-Methoxy-2-(5r,8r)-2-methyl-3-oxo-2-azaspiro[4.5]decan-8-yl)-N-(pyrazolo[1,5-a]pyrimidin-3-yl)-2H-indazole-5-carboxamide (Example 86)

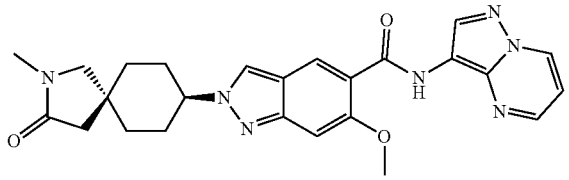 [SMILES: COc1cc2nn([C@H]3CC[C@]4(CC3)CC(=O)N(C)C4)cc2cc1C(=O)Nc1cnn2cccnc12]

Methyldiphenylsilanecarboxylic acid (84 mg, 0.4 mmol) and KF (20 mg, 0.4 mmol) were added to chamber A of a dried and N₂-flushed COware gas reactor. (5r,8r)-8-(5-Bromo-6-methoxy-2H-indazol-2-yl)-2-methyl-2-azaspiro[4.5]decan-3-one (Int IV-7) (47 mg, 0.1 mmol), pyrazolo[1, 5-a]pyrimidin-3-amine (Intl-5) (35 mg, 0.2 mmol), dppp (12 mg, 0.03 mmol), Pd(OAc)₂ (7 mg, 0.03 mmol) and DIPEA (122 μL, 0.7 mmol) in degassed anhydrous MeCN (1.5 mL) were added to chamber B. Then, DMSO (200 μL) was added to chamber A and chamber B was stirred at 85° C. overnight. The reaction mixture was allowed to cool to rt. The reaction in chamber B was quenched with aq. saturated NaHCO₃, concentrated under reduced pressure, dissolved in DCM (30 mL) and loaded on a 5 g Isolute®SCX2 exchange cartridge. The cartridge was washed with DCM/MeOH (1:1; 100 mL), then eluted with 4N NH₃-MeOH solution (100 mL) to give a dark-brown solid. The brown solid was purified by silica gel chromatography (eluting with 0-2.5% 2N NH₃-MeOH solution in DCM) and further by prep. HPLC (Waters XBridge BEH C18 OBD, 5 μm 19 mm×150 mm; eluted with 10-31% MeCN in water/MeCN (95/5; 0.2% 26 wt. % NH₄OH), within 20 min; flow rate: 19 mL/min) to give a yellow solid. This solid was was dissolved in DCM and loaded on a 5 g Isolute®SCX2 exchange cartridge and the loaded cartridge was washed with water (20 mL) and MeOH (50 mL) to remove byproducts and then eluted with 20 mL 2N NH₃ solution in MeOH/DCM (1:1; 100 mL) to afford 6-methoxy-2-((5r,8r)-2-methyl-3-oxo-2-azaspiro[4.5]decan-8-yl)-N-(pyrazolo[1,5-a]pyrimidin-3-yl)-2H-indazole-5-carboxamide (14 mg, 25%). ¹H NMR (500 MHz, CDCl₃) δ 10.46 (s, 1H), 8.99 (s, 1H), 8.79 (s, 1H), 8.60 (dd, 1H), 8.40 (dd, 1H), 8.06 (d, 1H), 7.16 (s, 1H), 6.79 (dd, 1H), 4.39 (tt, 1H), 4.16 (s, 3H), 3.20 (s, 2H), 2.87 (s, 3H), 2.44 (s, 2H), 2.22-2.32 (m, 2H), 2.04-2.15 (m, 2H), 1.89-1.98 (m, 2H), 1.61-1.69 (m, 2H). MS ESI, m/z=474 [M+H]⁺.

6-Methoxy-2-(5s,8s)-2-methyl-3-oxo-2-azaspiro[4.5] decan-8-yl)-N-(pyrazolo[1,5-a]pyrimidin-3-yl)-2H-indazole-5-carboxamide (Example 87)

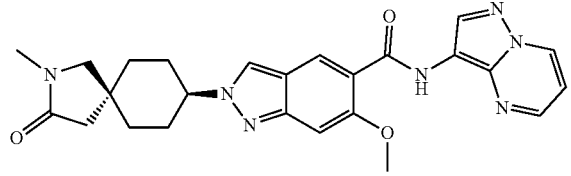 [SMILES: COc1cc2nn([C@H]3CC[C@@]4(CC3)CC(=O)N(C)C4)cc2cc1C(=O)Nc1cnn2cccnc12]

Methyldiphenylsilanecarboxylic acid (95 mg, 0.4 mmol) and KF (23 mg, 0.4 mmol) were added to chamber A of a dried and N₂-flushed COware gas reactor. (5s,8s)-8-(5-Bromo-6-methoxy-2H-indazol-2-yl)-2-methyl-2-azaspiro [4.5]decan-3-one (Int IV-6) (52 mg, 0.13 mmol), pyrazolo [1,5-a]pyrimidin-3-amine (Int I-5) (39 mg, 0.3 mmol), dppp (14 mg, 0.03 mmol), Pd(OAc)₂ (7 mg, 0.03 mmol) and DIPEA (138 μL, 0.8 mmol) in degassed anhydrous MeCN (1 mL) were added to chamber B. Then, DMSO (350 μL) was added to chamber A and chamber B was stirred at 85° C. overnight. The reaction mixture was allowed to cool to rt. The reaction in chamber B was quenched with aq. saturated NaHCO₃, concentrated under reduced pressure, dissolved in DCM (30 mL) and loaded on a 5 g Isolute®SCX2 exchange cartridge. The cartridge was washed with DCM/MeOH (1:1; 100 mL), then eluted with 4N NH₃-MeOH solution (100 mL) to give a dark-brown solid. The solid was purified by silica gel chromatography (eluting with 0-2.5% 2N NH₃-MeOH solution in DCM) and further by prep. HPLC (Wa-ters XBridge BEH C18 OBD, 5 μm 19 mm×150 mm; eluted with 5-35% MeCN in water/MeCN (95/5; 0.2% 26 wt. % aq. NH₄OH), pH 10, within 20 min; flow rate: 19 mL/min) to afford 6-methoxy-2-((5s,8s)-2-methyl-3-oxo-2-azaspiro [4.5]decan-8-yl)-N-(pyrazolo[1,5-a]pyrimidin-3-yl)-2H-indazole-5-carboxamide (3 mg, 5%). ¹H NMR (500 MHz, CDCl₃) δ 10.45 (s, 1H), 8.99 (s, 1H), 8.80 (d, 1H), 8.61 (dd, 1H), 8.41 (dd, 1H), 8.08 (d, 1H), 7.17 (s, 1H), 6.80 (dd, 1H), 4.41 (tt, 1H), 4.17 (s, 3H), 3.39 (s, 2H), 2.88 (d, 3H), 2.3-2.35 (m, 2H), 2.2-2.27 (m, 2H), 2.14 (qd, 2H), 1.94-1.99 (m, 2H), 1.67 (td, 2H). MS ESI, m/z=474 [M+H]⁺.

2-(1R,2R,4S)-4-Hydroxy-2-methylcyclohexyl)-N-(imidazo[1,2-b]pyridazin-3-yl)-6-methoxy-2H-indazole-5-carboxamide (Example 88) & 2-(1R,2R,4R)-4-Hydroxy-2-methylcyclohexyl)-N-(imidazo[1,2-b] pyridazin-3-yl)-6-methoxy-2H-indazole-5-carboxamide (Example 89)

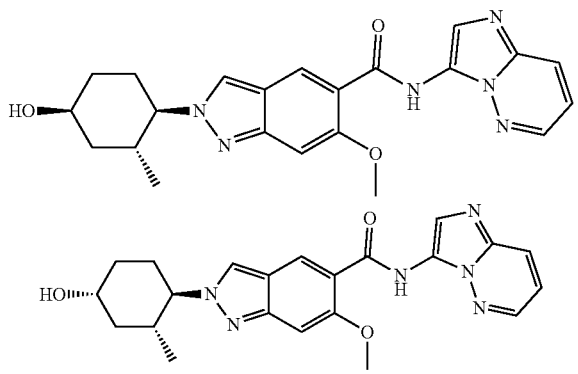

To a solution of N-(imidazo[1,2-b]pyridazin-3-yl)-6-methoxy-2-((1R,2R)-2-methyl-4-oxocyclohexyl)-2H-indazole-5-carboxamide (Int V-2) (180 mg, 0.4 mmol) in MeOH (10 mL) at rt under N₂ atmosphere was added NaBH₄ (33 mg, 0.9 mmol). The resulting mixture was stirred at rt for 2 h. The reaction solution was purified directly by C18-flash chromatography (eluting with 0-60% MeCN in water (0.1% FA)) to afford 2-((1R,2R)-4-hydroxy-2-methylcyclohexyl)-N-(imidazo[1,2-b]pyridazin-3-yl)-6-methoxy-2H-indazole-5-carboxamide as a brown solid. This material was separated by prep. chiral-HPLC (Chiralpak® ID 5 μm 20 mm×250 mm; isocratic with 50% MTBE (0.1% 2N NH₃-MeOH) in MeOH in 19 min; 40 mL/min) to afford the first eluting isomer 2-((1R,2R,4S)-4-hydroxy-2-methylcyclohexyl)-N-(imidazo[1,2-b]pyridazin-3-yl)-6-methoxy-2H-indazole-5-carboxamide (15 mg, 8%) and the second eluting isomer 2-((1R,2R,4R)-4-hydroxy-2-methylcyclohexyl)-N-(imidazo [1,2-b]pyridazin-3-yl)-6-methoxy-2H-indazole-5-carboxamide (105 mg, 50%), both as yellow solids. (1R,2R,4S)—Isomer: ¹H NMR (300 MHz, DMSO-d₆) δ 11.07 (s, 1H), 8.65 (d, 1H), 8.59 (s, 1H), 8.58 (s, 1H), 8.16 (d, 1H), 8.06 (s, 1H), 7.29 (s, 1H), 7.23 (dd, 1H), 4.58 (d, 1H), 4.13 (s, 3H), 4.03-4.15 (m, 1H), 3.93-4.01 (m, 1H), 2.25-2.46 (m, 2H), 1.55-1.90 (m, 4H), 1.29-1.42 (m, 1H), 0.54 (d, 3H). MS ESI, m/z=421 [M+H]⁺. (1R,2R,4R)—Isomer: ¹H NMR (300 MHz, DMSO-d₆) δ 11.05 (s, 1H), 8.64 (dd, 1H), 8.58 (s, 2H), 8.16 (dd, 1H), 8.06 (s, 1H), 7.27 (s, 1H), 7.22 (dd, 1H), 4.74 (d, 1H), 4.12 (s, 3H), 4.02-4.11 (m, 1H), 3.54-3.71 (m, 1H), 2.10-2.26 (m, 1H), 1.86-2.10 (m, 4H), 1.28-1.48 (m, 1H), 1.09-1.26 (m, 1H), 0.57 (d, 3H). MS ESI, m/z=421 [M+H]$^+$.

2-(1S,2S,4R)-4-Hydroxy-2-methylcyclohexyl)-N-(imidazo[1,2-b]pyridazin-3-yl)-6-methoxy-2H-indazole-5-carboxamide (Example 90) & 2-(1S,2S,4S)-4-Hydroxy-2-methylcyclohexyl)-N-(imidazo[1,2-b]pyridazin-3-yl)-6-methoxy-2H-indazole-5-carboxamide (Example 91)

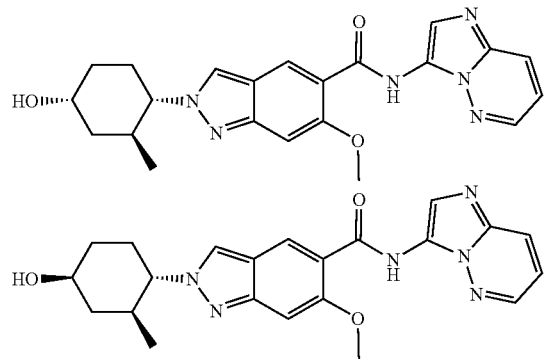

To a solution of N-(imidazo[1,2-b]pyridazin-3-yl)-6-methoxy-2-((1S,2S)-2-methyl-4-oxocyclohexyl)-2H-indazole-5-carboxamide (Int v-1) (180 mg, 0.4 mmol) in MeOH (10 mL) at rt under N$_2$ atmosphere was added NaBH$_4$ (33 mg, 0.9 mmol). The resulting mixture was stirred at rt for 2 h. The reaction solution was purified by C18-flash chromatography (eluting with 0-70% MeCN in water (0.1% FA)) to afford 2-((1S,2S)-4-hydroxy-2-methylcyclohexyl)-N-(imidazo[1,2-b]pyridazin-3-yl)-6-methoxy-2H-indazole-5-carboxamide as a brown solid. This material was separated by prep. chiral-HPLC (Chiralpak® IA 5 μm 20 mm×250 mm; isocratic with 50% MTBE (0.1% 2N NH$_3$-MeOH) in MeOH; 20 mL/min) to afford the first eluting isomer 2-((1S, 2S,4R)-4-hydroxy-2-methylcyclohexyl)-N-(imidazo[1,2-b]pyridazin-3-yl)-6-methoxy-2H-indazole-5-carboxamide (23 mg, 13%) and the second eluting isomer 2-((1S,2S,4S)-4-hydroxy-2-methylcyclohexyl)-N-(imidazo[1,2-b]pyridazin-3-yl)-6-methoxy-2H-indazole-5-carboxamide (120 mg, 67%), both as yellow solids. (1S,2S,4R)—Isomer: $^1$H NMR (400 MHz, DMSO-d$_6$) δ 11.06 (s, 1H), 8.64 (dd, 1H), 8.58 (s, 1H), 8.57 (s, 1H), 8.15 (dd, 1H), 8.05 (s, 1H), 7.28 (s, 1H), 7.22 (dd, 1H), 4.57 (d, 1H), 4.13 (s, 3H), 4.02-4.12 (m, 1H), 3.96 (s, 1H), 2.30-2.58 (m, 2H), 1.77-1.89 (m, 2H), 1.68-1.77 (m, 1H), 1.55-1.68 (m, 1H), 1.30-1.40 (m, 1H), 0.54 (d, 3H). MS ESI, m/z=421 [M+H]$^+$. (1S,2S,4S)—Isomer: $^1$H NMR (400 MHz, DMSO-d$_6$) δ 11.04 (s, 1H), 8.63 (dd, 1H), 8.57 (s, 2H), 8.15 (dd, 1H), 8.05 (s, 1H), 7.27 (s, 1H), 7.22 (dd, 1H), 4.73 (d, 1H), 4.12 (s, 3H), 4.03-4.11 (m, 1H), 3.54-3.68 (m, 1H), 2.20-2.30 (m, 1H), 1.85-2.10 (m, 4H), 1.29-1.46 (m, 1H), 1.08-1.25 (m, 1H), 0.57 (d, 3H). MS ESI, m/z=421 [M+H]$^+$.

2-(1R,2R,4S)-4-Hydroxy-2,4-dimethylcyclohexyl)-N-(imidazo[1,2-b]pyridazin-3-yl)-6-methoxy-2H-indazole-5-carboxamide (Example 92) & 2-(1R,2R,4R)-4-Hydroxy-2,4-dimethylcyclohexyl)-N-(imidazo[1,2-b]pyridazin-3-yl)-6-methoxy-2H-indazole-5-carboxamide (Example 93)

rac-(7R,8R)—N-Benzyl-7-methyl-1,4-dioxaspiro[4.5]decan-8-amine

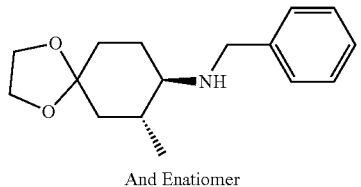 [SMILES: C[C@@H]1CC2(CC[C@H]1NCc1ccccc1)OCCO2]

And Enatiomer

To a solution of 7-methyl-1,4-dioxaspiro[4.5]decan-8-one (3.0 g, 17.6 mmol) and phenylmethanamine (2.8 g, 26.4 mmol) in toluene (50 mL) under N$_2$ atmosphere was added 4-methylbenzenesulfonic acid monohydrate (335 mg, 1.8 mmol). The resulting solution was stirred at 120° C. for 15 h. Subsequently, the reaction mixture was allowed to cool to rt and was concentrated under reduced pressure to give the crude imine intermediate. To a solution of the imine in MeOH (60 mL) at −60° C. was added NaBH$_4$ (0.6 g, 15.8 mmol) portionwise over a period of 5 min under N$_2$ atmosphere. The resulting mixture was stirred at −60° C. for 1 h, then slowly warmed up to rt and stirred for 3 h. Five batches of crude product solution where prepared in parallel as described above and combined before the purification. The reaction mixture was concentrated under reduced pressure, dissolved with EtOAc (500 mL) and washed with brine (300 mL×3). The organic layer was dried over Na$_2$SO$_4$, filtered and was concentrated under reduced pressure. The residue was purified by C18-flash chromatography (eluting with 0-100% MeCN in water (0.05% NH$_4$HCO$_3$)) to afford rac-(7R,8R)—N-benzyl-7-methyl-1,4-dioxaspiro[4.5]decan-8-amine (8.1 g, 35%) as an orange oil. MS ESI, m/z=262 [M+H]$^+$.

rac-(7R,8R)-7-Methyl-1,4-dioxaspiro[4.5]decan-8-amine

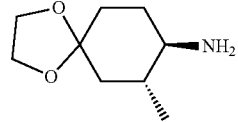

And Enatiomer

To a solution of rac-(7R,8R)—N-benzyl-7-methyl-1,4-dioxaspiro[4.5]decan-8-amine (8.1 g, 31.0 mmol) in MeOH (100 mL) under N$_2$ atmosphere was added Pd(OH)$_2$ on carbon (20 wt. %) (872 mg, 1.2 mmol).

The resulting suspension was stirred at rt under hydrogen at 2 atm for 15 h. The reaction mixture was filtered through celite, and the celite cake was washed with MeOH (150 mL). The combined MeOH solution was concentrated under reduced pressure to afford crude rac-(7R,8R)-7-methyl-1,4- dioxaspiro[4.5]decan-8-amine (5.0 g) as a brown oil, which was used without further purification.

5-Bromo-6-methoxy-2-(7R,8R)-7-methyl-1,4-dioxaspiro[4.5]decan-8-yl)-2H-indazole

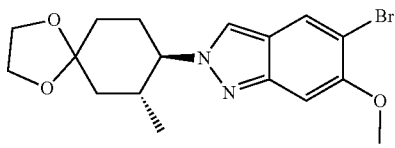 [SMILES: COc1cc2nn([C@@H]3CCC4(C[C@H]3C)OCCO4)cc2cc1Br]

To a solution of 5-bromo-4-methoxy-2-nitrobenzaldehyde (Int I-1) (10.6 g, 40.9 mmol) in i-PrOH (200 mL) at rt was added crude rac-(7R,8R)-7-methyl-1,4-dioxaspiro[4.5]decan-8-amine (7.0 g) under $N_2$ atmosphere. The resulting mixture was stirred at 80° C. for 2 h, then cooled to rt and followed by the addition of tri-n-butylphosphine (41.4 g, 204.4 mmol). The reaction mixture was stirred at 80° C. for 24 h. The mixture was allowed to cool to rt and concentrated under reduced pressure. The residue was purified by silica gel chromatography (eluting with 0-10% MeOH in DCM) and further by C18-flash chromatography (eluting with 0-100% MeCN in water (0.05% $NH_4OH$)) to afford rac-5-bromo-6-methoxy-2-((7R,8R)-7-methyl-1,4-dioxaspiro[4.5]decan-8-yl)-2H-indazole as a yellow solid. This material was purified by chiral prep. SFC (Chiralpak® IG, 5 μm 50×250 mm; isocratic with 50% MeOH (0.1% 2N $NH_3$-MeOH) in $CO_2$ (35° C., 100 bar)) to afford 5-bromo-6-methoxy-2-((7R,8R)-7-methyl-1,4-dioxaspiro[4.5]decan-8-yl)-2H-indazole (3.0 g, 19%, 100% ee) as a gray solid. $^1$H NMR (300 MHz, DMSO-$d_6$) δ 8.25 (d, 1H), 7.96 (s, 1H), 7.12 (s, 1H), 4.13 (td, 1H), 3.87-3.99 (m, 4H), 3.87 (s, 3H), 2.26-2.43 (m, 1H), 2.19 (td, 1H), 1.75-1.96 (m, 3H), 1.68 (td, 1H), 1.46 (t, 1H), 0.52 (d, 3H). MS ESI, m/z=381/383 [M+H]$^+$.

(3R,4R)-4-(5-Bromo-6-methoxy-2H-indazol-2-yl)-3-methylcyclohexan-1-one

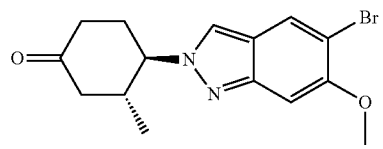 [SMILES: COc1cc2nn([C@@H]3CCC(=O)C[C@H]3C)cc2cc1Br]

To a solution of 5-bromo-6-methoxy-2-((7R,8R)-7-methyl-1,4-dioxaspiro[4.5]decan-8-yl)-2H-indazole (185 mg, 0.5 mmol) in THF (5 mL) at rt under $N_2$ atmosphere was added aq. 4N HCl (5 mL, 20.0 mmol). The reaction mixture was stirred at rt for 12 h. The reaction mixture was neutralized with aq. $NH_4OH$ solution to pH ~7 and then concentrated under reduced pressure. The residue was purified by silica gel chromatography (eluting with 0-50% EtOAc in PE) to afford (3R,4R)-4-(5-bromo-6-methoxy-2H-indazol-2-yl)-3-methylcyclohexan-1-one (160 mg, 98%) as a yellow oil. MS ESI, m/z=337/339 [M+H]$^+$.

(3R,4R)-4-(5-Bromo-6-methoxy-2H-indazol-2-yl)-1,3-dimethylcyclohexan-1-ol

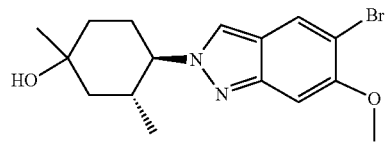 [SMILES: COc1cc2nn([C@@H]3CCC(C)(O)C[C@H]3C)cc2cc1Br]

To a solution of (3R,4R)-4-(5-bromo-6-methoxy-2H-indazol-2-yl)-3-methylcyclohexan-1-one (120 mg, 0.4 mmol) in THF (3 mL) at 0° C. under $N_2$ atmosphere was slowly added 3N methylmagnesium bromide in THF (1784, 0.5 mmol) over a period of 2 min. The resulting mixture was stirred at 0° C. for 5 h. The reaction was quenched with water (1 mL) and purified directly by C18-flash chromatography (eluting with 0-80% MeCN in water) to afford (3R,4R)-4-(5-bromo-6-methoxy-2H-indazol-2-yl)-1,3-dimethylcyclohexan-1-ol (80 mg, 64%) as a yellow oil. MS ESI, m/z=353/355 [M+H]$^+$.

2-(1R,2R,4S)-4-Hydroxy-2,4-dimethylcyclohexyl)-N-(imidazo[1,2-b]pyridazin-3-yl)-6-methoxy-2H-indazole-5-carboxamide (Example 92) & 2-(1R,2R,4R)-4-Hydroxy-2,4-dimethylcyclohexyl)-N-(imidazo[1,2-b]pyridazin-3-yl)-6-methoxy-2H-indazole-5-carboxamide (Example 93)

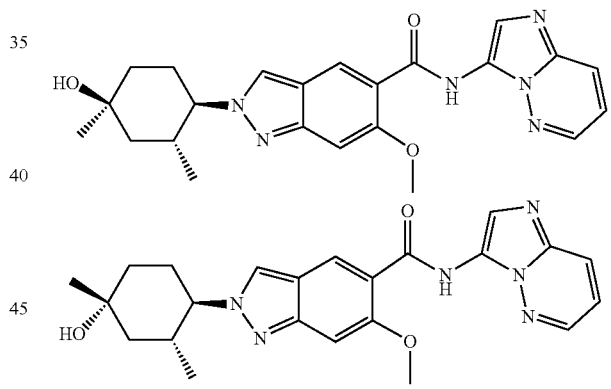

A suspension of (3R,4R)-4-(5-bromo-6-methoxy-2H-indazol-2-yl)-1,3-dimethylcyclohexan-1-ol (80 mg, 0.2 mmol), imidazo[1,2-b]pyridazin-3-amine (92 mg, 0.7 mmol), Pd(OAc)$_2$ (10 mg, 0.05 mmol), dppp (37 mg, 0.09 mmol) and TEA (1584, 1.1 mmol) in MeCN (5 mL) was stirred under CO atmosphere at 15 atm and 90° C. for 10 h. The mixture was allowed to cool to rt and concentrated under reduced pressure. The residue was purified by C18-flash chromatography (eluting with 0-100% MeCN in water) to afford 2-((1R,2R)-4-hydroxy-2,4-dimethylcyclohexyl)-N-(imidazo[1,2-b]pyridazin-3-yl)-6-methoxy-2H-indazole-5-carboxamide as a colourless liquid. This material was separated by prep. HPLC (Waters Xbridge® BEH C18 OBD, 5 μm 30 mm×150 mm; eluted with 23-43% MeCN in water (10 mM $NH_4HCO_3$+0.1% $NH_4OH$) in 7 min; flow rate: 60 mL/min) to afford 2-((1R,2R,4S)-4-hydroxy-2,4-dimethylcyclohexyl)-N-(imidazo[1,2-b]pyridazin-3-yl)-6-methoxy-2H-indazole-5-carboxamide (7 mg, 7%) and 2-((1R,2R,4R)-4-hydroxy-2,4-dimethylcyclohexyl)-N-(imidazo[1,2-b]pyridazin-3-yl)-6-methoxy-2H-indazole-5-carboxamide (20 mg, 20%), both as pale-yellow solids. (1R,2R,4S)-isomer: ¹H NMR (300 MHz, DMSO-d₆) δ 11.04 (s, 1H), 8.64 (dd, 1H), 8.62 (s, 1H), 8.57 (s, 1H), 8.15 (dd, 1H), 8.05 (s, 1H), 7.30 (s, 1H), 7.22 (dd, 1H), 4.53 (s, 1H), 4.12 (s, 3H), 4.02-4.10 (m, 1H), 2.12-2.25 (m, 1H), 1.99-2.12 (m, 1H), 1.85-1.97 (m, 1H), 1.53-1.77 (m, 3H), 1.32-1.43 (m, 1H), 1.30 (s, 3H), 0.55 (d, 3H). MS ESI, m/z=435 [M+H]⁺. (1R,2R,4R)-isomer: ¹H NMR (500 MHz, CDCl₃) δ 11.22 (s, 1H), 8.83 (s, 1H), 8.35-8.4 (m, 2H), 8.09 (s, 1H), 7.96 (dd, 1H), 7.21 (s, 1H), 6.99 (dd, 1H), 4.19 (s, 3H), 3.94 (td, 1H), 2.53-2.63 (m, 1H), 2.48 (qd, 1H), 2.00 (m, 1H), 1.81-1.94 (m, 2H), 1.63 (m, 1H), 1.35-1.38 (m, 1H), 1.34 (s, 3H), 0.70 (d, 3H). MS ESI, m/z=435 [M+H]⁺.

2-((1S,4r)-4-((S)-2-Hydroxy-N-methylpropanamido)cyclohexyl)-N-(imidazo[1,2-b]pyridazin-3-yl)-6-methoxy-2H-indazole-5-carboxamide (Example 94)

(S)-1-(((1r,4S)-4-(5-(Imidazo[1,2-b]pyridazin-3-ylcarbamoyl)-6-methoxy-2H-indazol-2-yl)cyclohexyl)(methyl)amino)-1-oxopropan-2-ylacetate

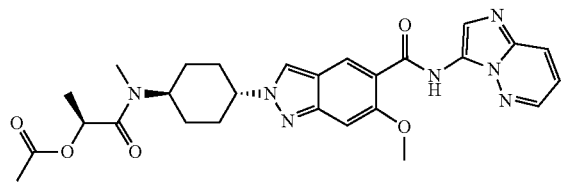

To a solution of the HCl salt of N-(imidazo[1,2-b]pyridazin-3-yl)-6-methoxy-2-((1r,4r)-4-(methylamino)cyclohexyl)-2H-indazole-5-carboxamide (IntV-3) (140 mg, 0.3 mmol) and TEA (171 µL, 1.2 mmol) in DCM (7 mL) was added (S)-1-chloro-1-oxopropan-2-yl acetate (69 mg, 0.5 mmol). The resulting mixture was stirred at rt for 2 h, then quenched with water (10 mL) and extracted with DCM (20 mL×3). The combined organic layers were dried over Na₂SO₄, filtered and concentrated under reduced pressure. The residue was purified directly by C18-flash chromatography (eluting with 0-80% MeCN in water (0.1% TFA)) to afford (S)-1-(((1r,4S)-4-(5-(imidazo[1,2-b]pyridazin-3-ylcarbamoyl)-6-methoxy-2H-indazol-2-yl)cyclohexyl)(methyl)amino)-1-oxopropan-2-yl acetate (52 mg, 32%) as a colorless solid. MS ESI, m/z=534 [M+H]⁺.

2-((1S,4r)-4-((S)-2-Hydroxy-N-methylpropanamido)cyclohexyl)-N-(imidazo[1,2-b]pyridazin-3-yl)-6-methoxy-2H-indazole-5-carboxamide (Example 94)

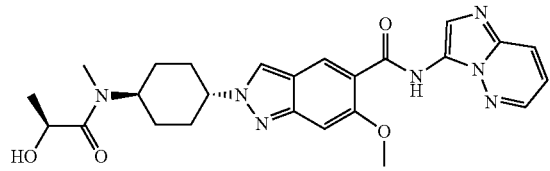

To a solution of (S)-1-(((1r,4S)-4-(5-(imidazo[1,2-b]pyridazin-3-ylcarbamoyl)-6-methoxy-2H-indazol-2-yl)cyclohexyl)(methyl)amino)-1-oxopropan-2-yl acetate (41 mg, 0.1 mmol) in THF (1.5 mL)/water (1.5 mL) was added LiOH (13 mg, 0.5 mmol). The resulting solution was stirred at rt for 2 h, then quenched with water (10 mL) and extracted with EtOAc (20 mL×3). The combined organic layers were dried over Na₂SO₄, filtered and concentrated under reduced pressure. The residue was purified by prep. HPLC (Waters XSelect CSH Fluoro-Phenyl OBD, 5 µm 19×250 mm; elution gradient with 30-45% MeCN in water (0.1% FA) in 10 min; 25 mL/min) to afford a mixture of 2-((1S,4r)-4-((S)-2-hydroxy-N-methylpropanamido)cyclohexyl)-N-(imidazo[1,2-b]pyridazin-3-yl)-6-methoxy-2H-indazole-5-carboxamide and 2-((1R,4r)-4-((R)-2-hydroxy-N-methylpropanamido)cyclohexyl)-N-(imidazo[1,2-b]pyridazin-3-yl)-6-methoxy-2H-indazole-5-carboxamide (85:15) (6 mg, 15%) as a yellow solid. The cause of racemization in this step is unknown. MS ESI, m/z=492 [M+H]⁺. Further separation and purification of the desired product is described under Example 95 below.

2-((1R,4r)-4-((R)-2-Hydroxy-N-methylpropanamido)cyclohexyl)-N-(imidazo[1,2-b]pyridazin-3-yl)-6-methoxy-2H-indazole-5-carboxamide (Example 95)

(R)-1-(((1r,4R)-4-(5-(Imidazo[1,2-b]pyridazin-3-ylcarbamoyl)-6-methoxy-2H-indazol-2-yl)cyclohexyl)(methyl)amino)-1-oxopropan-2-ylacetate

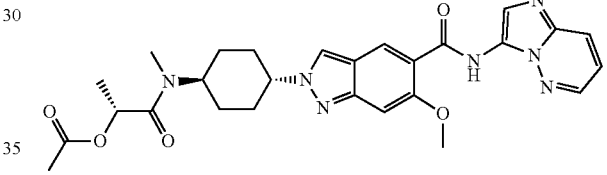

To a solution of the crude HCl salt of N-(imidazo[1,2-b]pyridazin-3-yl)-6-methoxy-2-((1r,4r)-4-(methylamino)cyclohexyl)-2H-indazole-5-carboxamide (Int V-3) (130 mg, 0.3 mmol) and TEA (159 µL, 1.1 mmol) in DCM (7 mL) was added (R)-1-chloro-1-oxopropan-2-yl acetate (64 mg, 0.4 mmol). The resulting mixture was stirred at rt for 2 h, then quenched with water (10 mL) and extracted with DCM (20 mL×3). The combined organic layers were dried over Na₂SO₄, filtered and concentrated under reduced pressure. The residue was purified directly by C18-flash chromatography (eluting with 0-80% MeCN in water (0.1% FA)) to afford (R)-1-(((1r,4R)-4-(5-(imidazo[1,2-b]pyridazin-3-ylcarbamoyl)-6-methoxy-2H-indazol-2-yl)cyclohexyl)(methyl)amino)-1-oxopropan-2-yl acetate (92 mg, 61%) as a yellow solid. MS ESI, m/z=534 [M+H]⁺.

2-((1R,4r)-4-((R)-2-Hydroxy-N-methylpropanamido)cyclohexyl)-N-(imidazo[1,2-b]pyridazin-3-yl)-6-methoxy-2H-indazole-5-carboxamide (Example 95)

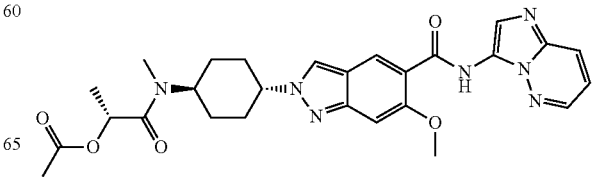

To a solution of (R)-1-(((1r,4R)-4-(5-(imidazo[1,2-b]pyridazin-3-ylcarbamoyl)-6-methoxy-2H-indazol-2-yl)cyclohexyl)(methyl)amino)-1-oxopropan-2-yl acetate (75 mg, 0.1 mmol) in THF (2.5 mL)/water (2.5 mL) was added LiOH (24 mg, 1.0 mmol). The resulting solution was stirred at rt for 2 h, then quenched with water (15 mL) and extracted with EtOAc (25 mL×3). The combined organic layers were dried over Na$_2$SO$_4$, filtered and concentrated under reduced pressure. The residue was purified by prep. HPLC (YMC-Actus Triart C18 ExRS 5 μm 30×150 mm; elution gradient with 11-44% MeCN in water (10 mM NH$_4$HCO$_3$+0.1% NH$_4$OH) in 7 min; 60 mL/min) to afford a mixture of 2-((1R,4r)-4-((R)-2-hydroxy-N-methylpropanamido)cyclohexyl)-N-(imidazo[1,2-b]pyridazin-3-yl)-6-methoxy-2H-indazole-5-carboxamide and 2-((1S,4r)-4-((S)-2-hydroxy-N-methylpropanamido)cyclohexyl)-N-(imidazo[1,2-b]pyridazin-3-yl)-6-methoxy-2H-indazole-5-carboxamide (85:15) (27 mg, 39%) as a yellow solid. The cause of racemization in this step is unknown. This mixture was combined with the product mixture obtained in Example 94 and separated by prep. chiral HPLC (Chiralpak® IA, 5 μm 20 mm×250 mm; isocratic with 50% MTBE (0.5% 2N NH3-MeOH) in MeOH in 20 min; 20.0 mL/min) to afford 2-((1S,4r)-4-((S)-2-hydroxy-N-methylpropanamido)cyclohexyl)-N-(imidazo[1,2-b]pyridazin-3-yl)-6-methoxy-2H-indazole-5-carboxamide (4 mg, 100% ee) and 2-((1R,4r)-4-((R)-2-hydroxy-N-methylpropanamido)cyclohexyl)-N-(imidazo[1,2-b]pyridazin-3-yl)-6-methoxy-2H-indazole-5-carboxamide (13 mg, 99.8% ee), both as yellow solids.

2-((1S,4r)-4-((S)-2-hydroxy-N-methylpropanamido)cyclohexyl)-N-(imidazo[1,2-b]pyridazin-3-yl)-6-methoxy-2H-indazole-5-carboxamide (Example 94): $^1$H NMR (400 MHz, DMSO-d$_6$) (4:5 mixture of rotamers) δ 11.05 (s, 1H), 8.56-8.67 (m, 3H), 8.15 (dd, 1H), 8.05 (s, 1H), 7.18-7.30 (m, 2H), 4.94/4.76 (d, 1H) (rotamers), 4.33-4.59/3.92-4.03 (m, 3H) (rotamers), 4.12 (s, 3H), 2.91/2.77 (s, 3H) (rotamers), 1.60-2.27 (m, 8H), 1.22/1.18 (d, 3H) (rotamers). MS ESI, m/z=492 [M+H]$^+$.

2-((1R,4r)-4-((R)-2-hydroxy-N-methylpropanamido)cyclohexyl)-N-(imidazo[1,2-b]pyridazin-3-yl)-6-methoxy-2H-indazole-5-carboxamide (Example 95): $^1$H NMR (400 MHz, DMSO-d$_6$) (4:5 mixture of rotamers) δ 11.05 (s, 1H), 8.52-8.68 (m, 3H), 8.15 (dd, 1H), 8.05 (s, 1H), 7.17-7.31 (m, 2H), 4.81 (br. s, 1H), 4.34-4.59/3.91-4.05 (m, 3H) (rotamers), 4.12 (s, 3H), 2.91/2.77 (s, 3H) (rotamers), 1.60-2.28 (m, 8H), 1.22/1.18 (d, 3H) (rotamers). MS ESI, m/z=492 [M+H]$^+$.

6-Methoxy-2-((1r,4r)-4-(N-methylcyclopropanecarboxamido)cyclohexyl)-N-(pyrazolo[1,5-c]pyrimidin-3-yl)-2H-indazole-5-carboxamide (Example 96)

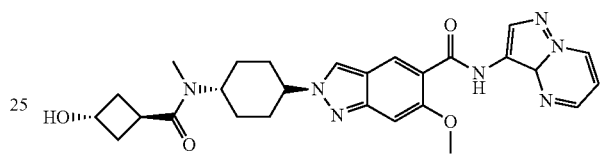

To a solution of the HCl salt of 6-methoxy-2-((1r,4r)-4-(methylamino)cyclohexyl)-N-(pyrazolo[1,5-c]pyrimidin-3-yl)-2H-indazole-5-carboxamide (Int V-4) (50 mg, 0.1 mmol) and TEA (504, 0.4 mmol) in DCM (2 mL) at rt under N$_2$ atmosphere was added cyclopropanecarbonyl chloride (25 mg, 0.2 mmol). The resulting mixture was stirred at rt for 1 h, then quenched with MeOH (0.5 mL) and concentrated under reduced pressure. The residue was purified directly by C18-flash chromatography (eluting with 0-100% MeCN in water (0.05% NH$_4$OH)) to afford 6-methoxy-2-((1r,4r)-4-(N-methylcyclopropanecarboxamido)cyclohexyl)-N-(pyrazolo[1,5-c]pyrimidin-3-yl)-2H-indazole-5-carboxamide (29 mg, 54%) as a yellow solid. $^1$H NMR (400 MHz, DMSO-d$_6$) (2:3 mixture of rotamers) δ 10.35 (s, 1H), 9.08 (dd, 1H), 8.73 (s, 1H), 8.52-8.59 (m, 2H), 8.48/8.47 (s, 1H) (rotamers), 7.23/7.20 (s, 1H) (rotamers), 7.05 (dd, 1H), 4.46-4.58 (m, 1H), 4.36-4.46/4.19-4.30 (m, 1H) (rotamers), 4.06 (s, 3H), 3.04/2.77 (s, 3H) (rotamers), 1.72-2.28 (m, 8H), 1.58-1.71 (m, 1H), 0.60-0.84 (m, 4H). MS ESI, m/z=488 [M+H]$^+$.

2-(1R,4r)-4-((1r,3R)-3-Hydroxy-N-methylcyclobutane-1-carboxamido)cyclohexyl)-6-methoxy-N-(pyrazolo[1,5-c]pyrimidin-3-yl)-2H-indazole-5-carboxamide (Example 97)

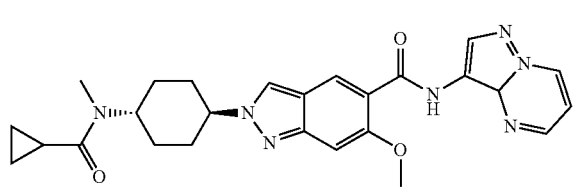

To a solution of (1r,3r)-3-hydroxycyclobutane-1-carboxylic acid (78 mg, 0.7 mmol) and DIPEA (2534, 1.5 mmol) in DMF (6 mL) at rt under N$_2$ atmosphere was added HATU (220 mg, 0.6 mmol). The resulting mixture was stirred at rt for 10 min, followed by the addition of the HCl salt of 6-methoxy-2-((1r,4r)-4-(methylamino)cyclohexyl)-N-(pyrazolo[1,5-c]pyrimidin-3-yl)-2H-indazole-5-carboxamide (Int V-4) (220 mg, 0.48 mmol). The reaction mixture was stirred at rt for 2 h, then purified directly by C18-flash chromatography (eluting with 0-80% MeCN in water (0.1% FA)) and further by prep. HPLC (YMC-Actus Triart C18 ExRS 5 μm 30×150 mm; elution gradient with 10-41% MeCN in water (10 mM NH$_4$HCO$_3$+0.1% NH$_4$OH) in 7 min; 60 mL/min) to afford 2-((1R,4r)-4-((1r,3R)-3-hydroxy-N-methylcyclobutane-1-carboxamido)cyclohexyl)-6-methoxy-N-(pyrazolo[1,5-a]pyrimidin-3-yl)-2H-indazole-5-carboxamide (182 mg, 73%, 100% ee) as a yellow solid. $^1$H NMR (400 MHz, DMSO-d$_6$) (4:5 mixture of rotamers) δ 10.35 (s, 1H), 9.08 (dd, 1H), 8.73 (s, 1H), 8.52-8.59 (m, 2H), 8.48/8.47 (s, 1H) (rotamers), 7.23/7.21 (s, 1H) (rotamers), 7.05 (dd, 1H), 5.08/5.06 (d, 1H) (rotamers), 4.44-4.54 (m, 1H), 4.36-4.44/3.54-3.64 (m, 1H) (rotamers), 4.08-4.18 (m, 1H), 4.06 (s, 3H), 3.23-3.30/3.10-3.21 (m, 1H) (rotamers), 2.75/2.74 (s, 3H) (rotamers), 2.29-2.42 (m, 2H), 2.15-2.25 (m, 2H), 1.96-2.14 (m, 4H), 1.6-1.94 (m, 4H). MS ESI, m/z=518 [M+H]$^+$.

2-(1R,4r)-4-((1s,3S)-3-Hydroxy-N-methylcyclobutane-1-carboxamido)cyclohexyl)-6-methoxy-N-(pyrazolo[1,5-c]pyrimidin-3-yl)-2H-indazole-5-carboxamide (Example 98)

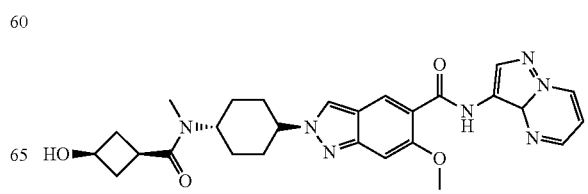

To a solution of (1s,3s)-3-hydroxycyclobutane-1-carboxylic acid (78 mg, 0.7 mmol) and DIPEA (253 µL, 1.5 mmol) in DMF (6 mL) at rt under N₂ atmosphere was added HATU (220 mg, 0.6 mmol). The resulting mixture was stirred at rt for 10 min, followed by the addition of the HCl salt of 6-methoxy-2-((1r,4r)-4-(methylamino)cyclohexyl)-N-(pyrazolo[1,5-c]pyrimidin-3-yl)-2H-indazole-5-carboxamide (Int V-4) (220 mg, 0.5 mmol). The reaction mixture was stirred at rt for 2 h, then purified directly by C18-flash chromatography (eluting with 0-80% MeCN in water (0.1% FA)) and further by prep. HPLC (YMC-Actus Triart C18 ExRS 5 µm 30×150 mm; elution gradient with 10-41% MeCN in water (10 mM NH₄HCO₃+0.1% NH₄OH) in 7 min; 60 mL/min) to afford 2-((1R,4r)-4-((1s,3S)-3-hydroxy-N-methylcyclobutane-1-carboxamido)cyclohexyl)-6-methoxy-N-(pyrazolo[1,5-c]pyrimidin-3-yl)-2H-indazole-5-carboxamide (178 mg, 71%, 100% ee) as a yellow solid. ¹H NMR (400 MHz, DMSO-d₆) (1:1 mixture of rotamers) δ 10.35 (s, 1H), 9.07 (dd, 1H), 8.73 (s, 1H), 8.51-8.60 (m, 2H), 8.48/8.47 (s, 1H) (rotamers), 7.22/7.20 (s, 1H) (rotamers), 7.05 (dd, 1H), 5.02-5.09 (m, 1H), 4.43-4.55 (m, 1H), 4.34-4.43/3.67-3.79 (m, 1H) (rotamers), 4.06 (s, 3H), 3.92-4.04 (m, 1H), 2.76-2.88 (m, 2H), 2.65-2.76/2.30-2.43 (m, 4H) (rotamers), 2.15-2.26 (m, 2H), 1.59-2.14 (m, 8H). MS ESI, m/z=518 [M+H]⁺.

2-((1r,4r)-4-(2-Hydroxy-N,2-dimethylpropanamido)cyclohexyl)-6-methoxy-N-(pyrazolo[1,5-c]pyrimidin-3-yl)-2H-indazole-5-carboxamide (Example 99)

1-(((1r,4r)-4-(6-Methoxy-5-(pyrazolo[1,5-a]pyrimidin-3-ylcarbamoyl)-2H-indazol-2-yl)cyclohexyl)(methyl)amino)-2-methyl-1-oxopropan-2-ylacetate

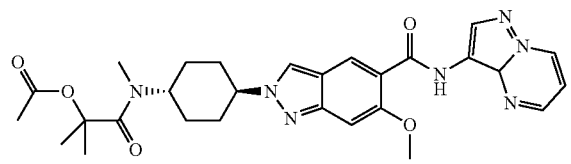

To a solution of the HCl salt of 6-methoxy-2-((1r,4r)-4-(methylamino)cyclohexyl)-N-(pyrazolo[1,5-c]pyrimidin-3-yl)-2H-indazole-5-carboxamide (Int V-4) (230 mg, 0.5 mmol) and TEA (153 mg, 1.5 mmol) in DCM (10 mL) at rt under N₂ atmosphere was added 1-chloro-2-methyl-1-oxopropan-2-yl acetate (125 mg, 0.8 mmol). The resulting mixture was stirred at rt for 1 h, then quenched with MeOH (2 mL) and concentrated under reduced pressure to obtain a solid. The solid was washed with water (25 mL) and then with PE/EtOAc (10: 1) (44 mL) to afford 1-(((1r,4r)-4-(6-methoxy-5-(pyrazolo[1,5-c]pyrimidin-3-ylcarbamoyl)-2H-indazol-2-yl)cyclohexyl)(methyl)amino)-2-methyl-1-oxopropan-2-yl acetate (265 mg, 96%) as a yellow solid, which was used without further purification. MS ESI, m/z=548 [M+H]⁺.

2-((1r,4r)-4-(2-Hydroxy-N,2-dimethylpropanamido)cyclohexyl)-6-methoxy-N-(pyrazolo[1,5-c]pyrimidin-3-yl)-2H-indazole-5-carboxamide (Example 99)

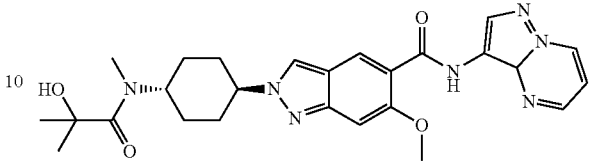

To a suspension of 1-(((1r,4r)-4-(6-methoxy-5-(pyrazolo[1,5-c]pyrimidin-3-ylcarbamoyl)-2H-indazol-2-yl)cyclohexyl)(methyl)amino)-2-methyl-1-oxopropan-2-ylacetate (250 mg, 0.5 mmol) in MeOH (10 mL)/water (5 mL) at rt under N₂ atmosphere was added NaOH (55 mg, 1.4 mmol), followed by the addition of DCM (1 mL) to dissolve insoluble solid. The resulting solution was stirred at rt for 2 h, then concentrated under reduced pressure, redissolved in MeOH/DMF (2 mL/3 mL) and purified by prep. HPLC (Waters Xbridge® BEH OBD C18, 5 µm 30×150 mm; elution gradient with 30-45% MeCN in water (10 mM NH₄HCO₃+0.1% NH₄OH) in 7 min; 60 mL/min) to afford 2-((1r,4r)-4-(2-hydroxy-N,2-dimethylpropanamido)cyclohexyl)-6-methoxy-N-(pyrazolo[1,5-c]pyrimidin-3-yl)-2H-indazole-5-carboxamide (215 mg, 93%) as a yellow solid. ¹H NMR (400 MHz, DMSO-d₆) (2:3 mixture of rotamers) δ 10.35 (s, 1H), 9.08 (dd, 1H), 8.73 (s, 1H), 8.58 (s, 1H), 8.54 (dd, 1H), 8.47 (s, 1H), 7.22 (s, 1H), 7.05 (dd, 1H), 5.43/5.32 (s, 1H) (rotamers), 4.69-4.93/4.28-4.43 (m, 1H) (rotamers), 4.43-4.58 (m, 1H), 4.06 (s, 3H), 3.16/2.71 (s, 3H) (rotamers), 2.14-2.27 (m, 2H), 1.96-2.11 (m, 2H), 1.59-1.95 (m, 4H), 1.35 (s, 6H). MS ESI, m/z=506 [M+H]⁺.

2-(2-Acetyl-2-azaspiro[3.5]nonan-7-yl)-N-(imidazo[1,2-b]pyridazin-3-yl)-6-((1r,3r)-3-methoxycyclobutoxy)-2H-indazole-5-carboxamide (Example 100)

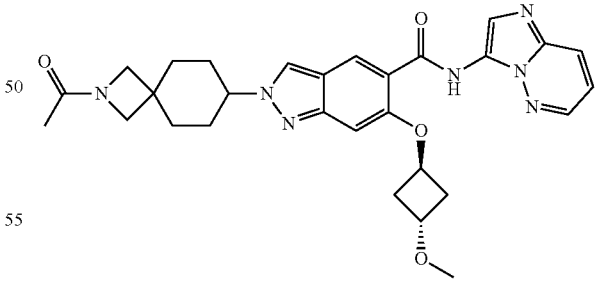

A mixture of 2-(2-acetyl-2-azaspiro[3.5]nonan-7-yl)-6-hydroxy-N-(imidazo[1,2-b]pyridazin-3-yl)-2H-indazole-5-carboxamide (Int V-5) (20 mg, 0.04 mmol), (1s,3s)-3-methoxycyclobutan-1-ol (45 mg, 0.4 mmol), triphenylphosphine (23 mg, 0.1 mmol) and DIAD (42 µL, 0.2 mmol) in 1,4-dioxane (3 mL) was stirred in a microwave at 140° C. After 2 h the reaction mixture was allowed to cool to rt and directly subjected to C18-flash chromatography (eluting with 0% to 50% MeCN in water (0.1% NH₄OH)) followed by prep. HPLC (XBridge Prep C18 OBD, 30×150 mm 5 μm; mobile Phase A: water (10 mM NH₄HCO₃+0.1% NH₄OH); mobile Phase B: MeCN; gradient: 22% B to 42% B in 7 min; flow rate: 60 mL/min) to afford 2-(2-acetyl-2-azaspiro[3.5]nonan-7-yl)-N-(imidazo[1,2-b]pyridazin-3-yl)-6-((1r,3r)-3-methoxycyclobutoxy)-2H-indazole-5-carboxamide (8 mg, 34%) as a yellow solid. $^1$H NMR (300 MHz, DMSO-d₆) (1:1 mixture of rotamers) δ 11.13 (s, 1H), 8.67 (s, 1H), 8.62 (dd, 1H), 8.61 (s, 1H), 8.16 (dd, 1H), 8.11 (s, 1H), 7.21 (dd, 1H), 6.97/6.99 (s, 1H) (rotamers), 5.14-5.27 (m, 1H), 4.42-4.56 (m, 1H), 4.20-4.35 (m, 1H), 3.91 (s, 1H), 3.80 (s, 1H), 3.63 (s, 1H), 3.53 (s, 1H), 3.23 (s, 3H), 2.71-2.83 (m, 2H), 2.57-2.68 (m, 2H), 1.86-2.10 (m, 6H), 1.76/1.78 (s, 3H) (rotamers), 1.59-1.74 (m, 2H). m/z (ESI+), [M+H]⁺=544.

2-(2-Acetyl-2-azaspiro[3.5]nonan-7-yl)-N-(imidazo[1,2-b]pyridazin-3-yl)-6-((1s,3s)-3-methoxycyclobutoxy)-2H-indazole-5-carboxamide (Example 101)

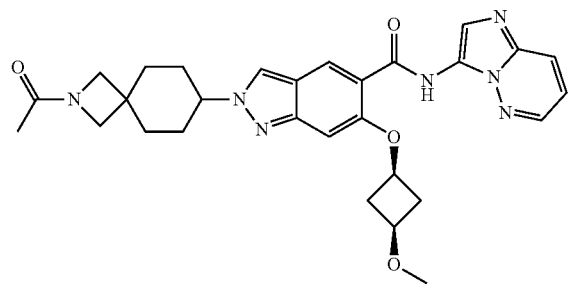 [SMILES: CO[C@H]1C[C@@H](Oc2cc3nn(C4CCC5(CC4)CN(C(C)=O)C5)cc3cc2C(=O)Nc2cnc3cccnn23)C1]

A mixture of 2-(2-acetyl-2-azaspiro[3.5]nonan-7-yl)-6-hydroxy-N-(imidazo[1,2-b]pyridazin-3-yl)-2H-indazole-5-carboxamide (Int V-5) (20 mg, 0.04 mmol), (1r,3r)-3-methoxycyclobutan-1-ol (18 mg, 0.2 mmol), triphenylphosphine (46 mg, 0.2 mmol) and DIAD (344, 0.2 mmol) in 1,4-dioxane (3 mL) was stirred in a microwave at 140° C. After 1 h the reaction mixture was allowed to cool to rt and directly subjected to C18-flash chromatography (eluting with 0% to 40% MeCN in water (0.1% NH₄OH)) followed by prep. HPLC (XBridge Shield RP18 OBD, 30×150 mm, 5 μm; mobile Phase A: water (0.05% NH₄OH); mobile Phase B: MeCN; gradient: 28% B to 36% B in 8 min; flow rate: 60 mL/min) and a prep. chiral HPLC (CHIRAL ART Cellulose-SB S-5 μm, 2×25 cm, 5 μm; mobile Phase A: MTBE (0.5% 2N NH₃-MeOH); mobile Phase B: EtOH; gradient: isocratic 30% B for 27 min; flow rate: 18 mL/min) to afford 2-(2-acetyl-2-azaspiro[3.5]nonan-7-yl)-N-(imidazo[1,2-b]pyridazin-3-yl)-6-((1s,3s)-3-methoxycyclobutoxy)-2H-indazole-5-carboxamide (10 mg, 42%, 100% ee) as a yellow solid. $^1$H NMR (300 MHz, DMSO-d₆) (1:1 mixture of rotamers) δ 11.18 (s, 1H), 8.66 (s, 1H), 8.61 (s, 1H), 8.57 (dd, 1H), 8.16 (dd, 1H), 8.10 (s, 1H), 7.22 (dd, 1H), 7.08/7.09 (s, 1H) (rotamers), 4.74-4.84 (m, 1H), 4.40-4.58 (m, 2H), 3.91 (s, 1H), 3.80 (s, 1H), 3.63 (s, 1H), 3.53 (s, 1H), 3.22 (s, 3H), 3.02-3.17 (m, 2H), 2.34-2.45 (m, 2H), 1.85-2.15 (m, 6H), 1.76/1.78 (s, 3H) (rotamers), 1.62-1.74 (m, 2H). m/z (ESI+), [M+H]⁺=544.

2-((1r,4r)-4-(1H-1,2,3-triazol-1-yl)cyclohexyl)-N-(imidazo[1,2-b]pyridazin-3-yl)-6-methoxy-2H-indazole-5-carboxamide (Example 102)

2-((1r,4r)-4-(2H-1,2,3-triazol-2-yl)cyclohexyl)-N-(imidazo[1,2-b]pyridazin-3-yl)-6-methoxy-2H-indazole-5-carboxamide (Example 103)

(1s,4s)-4-(5-(Imidazo[1,2-b]pyridazin-3-ylcarbamoyl)-6-methoxy-2H-indazol-2-yl)cyclohexyl methanesulfonate

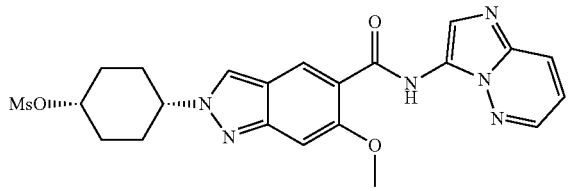 [SMILES: COc1cc2nn([C@H]3CC[C@@H](OS(C)(=O)=O)CC3)cc2cc1C(=O)Nc1cnc2cccnn12]

MsCl (288 μL, 3.7 mmol) was added dropwise to a solution of 2-((1s,4s)-4-hydroxycyclohexyl)-N-(imidazo[1,2-b]pyridazin-3-yl)-6-methoxy-2H-indazole-5-carboxamide (Example 7) (300 mg, 0.7 mmol) and TEA (6174, 4.4 mmol) in dichloromethane (50 mL) at 0° C. over a period of 2 min under N₂. The resulting solution was stirred at 30° C. for 5 h. The reaction mixture was quenched with water (20 mL) and extracted with DCM (25 mL×2). The combined organic layers were dried over Na₂SO₄, filtered, and concentrated under reduced pressure. The residue was purified by silica gel chromatography (eluting with 0-10% MeOH in DCM) to afford (1s,4s)-4-(5-(imidazo[1,2-b]pyridazin-3-ylcarbamoyl)-6-methoxy-2H-indazol-2-yl)cyclohexyl methanesulfonate (260 mg, 73%) as a yellow solid. $^1$H NMR (300 MHz, DMSO-d₆) δ 11.05 (s, 1H), 8.61-8.70 (m, 2H), 8.59 (s, 1H), 8.15 (dd, 1H), 8.05 (s, 1H), 7.30 (s, 1H), 7.22 (dd, 1H), 4.95-5.04 (m, 1H), 4.55-4.69 (m, 1H), 4.12 (s, 3H), 3.24 (s, 3H), 1.98-2.34 (m, 6H), 1.80-1.98 (m, 2H). MS ESI, m/z=485 [M+H]⁺.

2-((1r,4r)-4-(1H-1,2,3-triazol-1-yl)cyclohexyl)-N-(imidazo[1,2-b]pyridazin-3-yl)-6-methoxy-2H-indazole-5-carboxamide (Example 102)

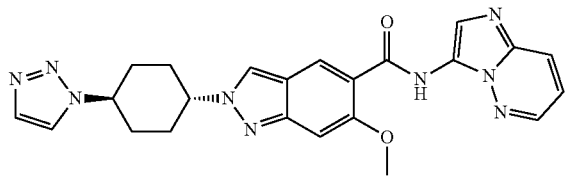 [SMILES: COc1cc2nn([C@H]3CC[C@H](n4ccnn4)CC3)cc2cc1C(=O)Nc1cnc2cccnn12]

2-((1r,4r)-4-(2H-1,2,3-triazol-2-yl)cyclohexyl)-N-(imidazo[1,2-b]pyridazin-3-yl)-6-methoxy-2H-indazole-5-carboxamide (Example 103)

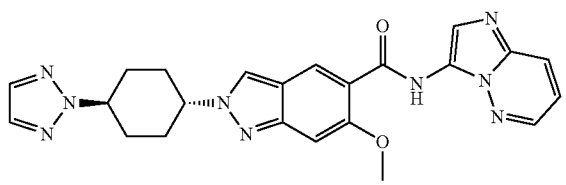 [SMILES: COc1cc2nn([C@H]3CC[C@H](n4nccn4)CC3)cc2cc1C(=O)Nc1cnc2cccnn12]

To a suspension of 1H-1,2,3-triazole (285 mg, 4.1 mmol) and $Cs_2CO_3$ (403 mg, 1.2 mmol) in DMF (10 mL) was added (1s,4s)-4-(5-(imidazo[1,2-b]pyridazin-3-ylcarbamoyl)-6-methoxy-2H-indazol-2-yl)cyclohexyl methanesulfonate (200 mg, 0.4 mmol). The resulting mixture was stirred at 90° C. for 2 h. The reaction mixture was purified directly by C18-flash chromatography (eluting with 0-100% MeCN in water (0.1% formic acid)) and further by preparative HPLC (Waters Xbridge® BEH OBD C18, 5 μm 30×150 mm; elution gradient with 27-47% MeCN in water (10 mM $NH_4HCO_3$+0.1% $NH_4OH$) in 7 min, followed by 47-95% for another 3 minutes; 60 mL/min) to afford 2-((1r,4r)-4-(1H-1,2,3-triazol-1-yl)cyclohexyl)-N-(imidazo[1,2-b]pyridazin-3-yl)-6-methoxy-2H-indazole-5-carboxamide (11 mg, 6%) and 2-((1r,4r)-4-(2H-1,2,3-triazol-2-yl)cyclohexyl)-N-(imidazo[1,2-b]pyridazin-3-yl)-6-methoxy-2H-indazole-5-carboxamide (26 mg, 14%), both as yellow solids. 2-((1r,4r)-4-(1H-1,2,3-triazol-1-yl)cyclohexyl)-N-(imidazo[1,2-b]pyridazin-3-yl)-6-methoxy-2H-indazole-5-carboxamide: $^1$H NMR (400 MHz, DMSO-$d_6$) δ 11.05 (s, 1H), 8.62-8.67 (m, 2H), 8.61 (s, 1H), 8.24 (d, 1H), 8.15 (dd, 1H), 8.05 (s, 1H), 7.76 (d, 1H), 7.29 (s, 1H), 7.22 (dd, 1H), 4.62-4.79 (m, 2H), 4.13 (s, 3H), 2.26-2.38 (m, 4H), 2.05-2.26 (m, 4H). MS ESI, m/z=458 [M+H]$^+$. 2-((1r,4r)-4-(2H-1,2,3-triazol-2-yl)cyclohexyl)-N-(imidazo[1,2-b]pyridazin-3-yl)-6-methoxy-2H-indazole-5-carboxamide: $^1$H NMR (400 MHz, DMSO-$d_6$) δ 11.05 (s, 1H), 8.64 (dd, 1H), 8.63 (s, 1H), 8.60 (s, 1H), 8.15 (dd, 1H), 8.05 (s, 1H), 7.81 (s, 2H), 7.28 (s, 1H), 7.22 (dd, 1H), 4.63-4.78 (m, 2H), 4.13 (s, 3H), 2.26-2.37 (m, 4H), 2.02-2.26 (m, 4H). MS ESI, m/z=458 [M+H]$^+$.

rel-2-(1S,2S,3R)-3-Hydroxy-2-methylcyclohexyl)-N-(imidazo[1,2-b]pyridazin-3-yl)-6-methoxy-2H-indazole-5-carboxamide—Isomer 1 (Example 104) & Isomer 2 (Example 105)

rac-(1R,2S,3S)-3-(5-Bromo-6-methoxy-2H-indazol-2-yl)-2-methylcyclohexan-1-ol

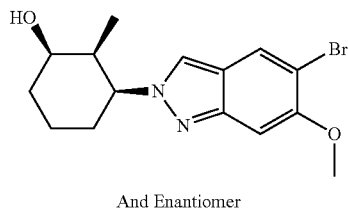 [SMILES: COc1cc2nn([C@H]3CCC[C@@H](O)[C@H]3C)cc2cc1Br]

And Enantiomer

5-Bromo-4-methoxy-2-nitrobenzaldehyde (75 mg, 0.29 mmol) was added to rac-(1R,2S,3S)-3-amino-2-methylcyclohexan-1-ol hydrochloride (45 mg, 0.27 mmol) (prepared according to the method of Cao, Hai Thuong et al. *Synthesis* 2011, 20, 3297-3300) and TEA (1214, 0.87 mmol) in i-PrOH (5 mL) at 25° C. under $N_2$. The resulting mixture was stirred at 80° C. for 2 h. The reaction was allowed to cool to rt, then tri-n-butylphosphine (213 μL, 0.87 mmol) was added to the reaction and the resulting solution was stirred at 80° C. for 12 h. The crude product was purified by C18-flash chromatography (eluting with 0-100% MeCN in water (with 0.1% FA)), followed by prep. HPLC (XBridge Prep OBD C18 Column, 5 μm 30×150 mm; elution gradient: 33-53% MeCN in water (10 mM $NH_4HCO_3$+0.1% $NH_4OH$); 60 mL/min) to afford rac-(1R,2S,3S)-3-(5-bromo-6-methoxy-2H-indazol-2-yl)-2-methylcyclohexan-1-ol (130 mg, 100%, 73% wt. purity), as a colourless oil. $^1$H NMR (400 MHz, CDCl$_3$) δ 7.86 (s, 1H), 7.80 (d, 1H), 7.04 (s, 1H), 4.56 (q, 1H), 3.94 (s, 3H), 3.87 (dt, 1H), 3.49 (d, 1H), 2.32 (s, 1H), 2.23-2.08 (m, 1H), 2.04-1.95 (m, 3H), 1.60-1.49 (m, 2H), 0.80 (d, 3H). MS ESI, m/z=339/341 [M+H]$^+$.

rel-2-(1S,2S,3R)-3-Hydroxy-2-methylcyclohexyl)-N-(imidazo[1,2-b]pyridazin-3-yl)-6-methoxy-2H-indazole-5-carboxamide—Isomer 1 (Example 104) & Isomer 2 (Example 105)

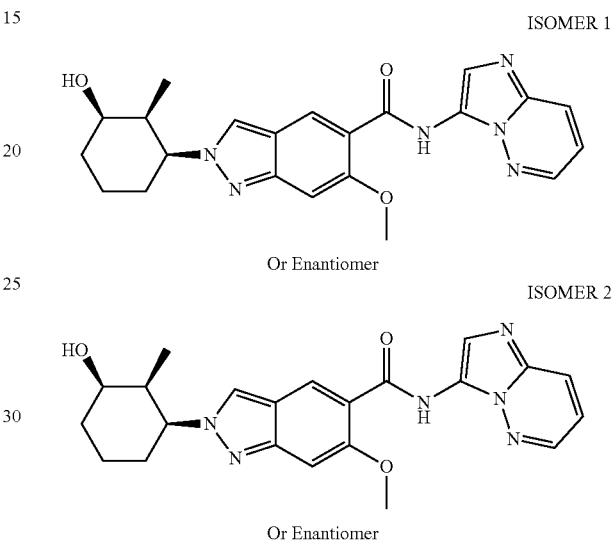

A solution of Pd(OAc)$_2$ (9.2 mg, 0.04 mmol), 1,3-bis(diphenylphosphino)propane (33.8 mg, 0.08 mmol), TEA (2864, 2.05 mmol), rac-(1R,2S,3S)-3-(5-bromo-6-methoxy-2H-indazol-2-yl)-2-methylcyclohexan-1-ol (120 mg, 0.21 mmol) and imidazo[1,2-b]pyridazin-3-amine (83 mg, 0.62 mmol) in MeCN (8 mL) was stirred under an atmosphere of CO at 15 atm and 100° C. for 15 h. The mixture was cooled to rt and concentrated under reduced pressure. The residue was purified by C18-flash chromatography (eluting with 0-100% acetonitrile in water (0.1% FA)) and then by prep. HPLC (Waters Xbridge® BEH OBD C18, 5 μm 30×150 mm; elution gradient: 16-46% MeCN in water (10 mM $NH_4HCO_3$+0.1% $NH_4OH$); 60 mL/min) to afford rac-2-((1S,2S,3R)-3-hydroxy-2-methylcyclohexyl)-N-(imidazo[1,2-b]pyridazin-3-yl)-6-methoxy-2H-indazole-5-carboxamide. This material was further purified by chiral prep. HPLC (Chiralpak® IA, 2×25 cm, 5 μm; isocratic elution with 50% MTBE (0.5% 2N $NH_3$-MeOH) in MeOH (1:1); 20 mL/min) to afford rel-2-((1S,2S,3R)-3-hydroxy-2-methylcyclohexyl)-N-(imidazo[1,2-b]pyridazin-3-yl)-6-methoxy-2H-indazole-5-carboxamide—Isomer 1 (10 mg, 11%, 98.7% ee) and rel-2-((1S,2S,3R)-3-hydroxy-2-methylcyclohexyl)-N-(imidazo[1,2-b]pyridazin-3-yl)-6-methoxy-2H-indazole-5-carboxamide—Isomer 2 (11 mg, 13%, 95.7% ee), both as yellow solids. The $^1$H NMR and MS obtained for both products were identical. $^1$H NMR (400 MHz, DMSO-$d_6$) δ 11.04 (s, 1H), 8.69-8.52 (m, 3H), 8.15 (d, 1H), 8.05 (s, 1H), 7.27 (s, 1H), 7.22 (dd, 1H), 4.99-4.73 (m, 1H), 4.63 (dd, 1H), 4.12 (s, 3H), 3.91-3.73 (m, 1H), 2.65-2.56 (m, 1H), 2.23-2.01 (m, 1H), 1.99-1.80 (m, 2H), 1.55 (d, 1H), 1.45 (q, 2H), 0.52 (d, 3H). MS ESI, m/z=421 [M+H]$^+$.

rel-2-(1S,2R,3S)-3-Hydroxy-2-methylcyclohexyl)-
N-(imidazo[1,2-b]pyridazin-3-yl)-6-methoxy-2H-
indazole-5-carboxamide—Isomer 1 (Example 106)
& Isomer 2 (Example 107)

rel-2-(1S,2R,3R)-3-Hydroxy-2-methylcyclohexyl)-
N-(imidazo[1,2-b]pyridazin-3-yl)-6-methoxy-2H-
indazole-5-carboxamide—Isomer 1 (Example 108)
& Isomer 2 (Example 109)

rac-(1S,2R,3S)-3-(5-Bromo-6-methoxy-2H-indazol-
2-yl)-2-methylcyclohexan-1-ol & rel-(1R,2R,3S)-3-
(5-bromo-6-methoxy-2H-indazol-2-yl)-2-methylcy-
clohexan-1-ol—Isomer 1 & Isomer 2

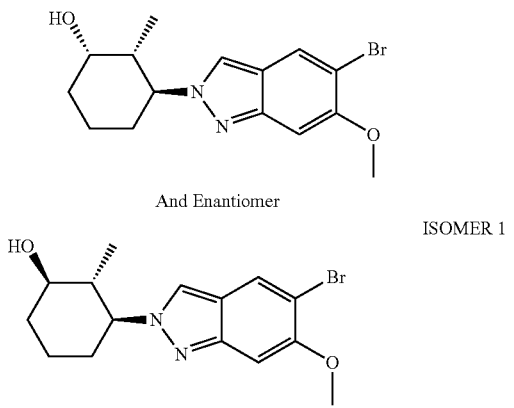

And Enantiomer

ISOMER 1

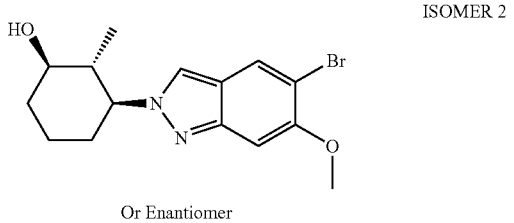

Or Enantiomer

ISOMER 2

Or Enantiomer

5-Bromo-4-methoxy-2-nitrobenzaldehyde (180 mg, 0.69 mmol) was added to a mixture of rac (1R,2R,3S)-3-amino-2-methylcyclohexan-1-ol hydrochloride and rac-(1S,2R,3S)-3-amino-2-methylcyclohexan-1-ol hydrochloride (89 mg, 0.69 mmol) (prepared according to the method of Cao, Hai Thuong et al. Synthesis 2011, 20, 3297-3300) and TEA (289 μL, 2.08 mmol) in i-PrOH (5 mL) at 25° C. under $N_2$. The resulting mixture was stirred at 80° C. for 2 h. The reaction was allowed to cool to rt, then tri-n-butylphosphine (512 μL, 0.87 mmol) was added, and the resulting solution was stirred at 80° C. for 12 h. The crude product was purified by C18-flash chromatography (eluting with 0 to 100% MeCN in water (with 0.1% FA) and then by prep. HPLC (XBridge Prep OBD C18 Column, 5 μm 30×150 mm; elution gradient: 43-73% MeOH in water (10 mM $NH_4HCO_3$+0.1% $NH_4OH$); 60 mL/min) to afford a mixture of rac-(1S,2R,3S)-3-(5-bromo-6-methoxy-2H-indazol-2-yl)-2-methylcyclohexan-1-ol and rac-(1R,2R,3S)-3-(5-bromo-6-methoxy-2H-indazol-2-yl)-2-methylcyclohexan-1-ol. This material was further purified by chiral prep. HPLC (Chiralpak® IC 2×25 cm, 5 μm; isocratic with MeOH 15% in hexane (0.5% 2N $NH_3$-MeOH); 20 mL/min) to afford rac-(1S,2R,3S)-3-(5-bromo-6-methoxy-2H-indazol-2-yl)-2-methylcyclohexan-1-ol (35 mg, 15%), rel-(1R,2R,3S)-3-(5-bromo-6-methoxy-2H-indazol-2-yl)-2-methylcyclohexan-1-ol—Isomer 1 (27 mg, 11%, 98% ee) and rel-(1R,2R,3S)-3-(5-bromo-6-methoxy-2H-indazol-2-yl)-2-methylcyclohexan-1-ol—Isomer 2 (20 mg, 9%, 99% ee), all as pale yellow solids. rac-(1S,2R,3S)-3-(5-bromo-6-methoxy-2H-indazol-2-yl)-2-methylcyclohexan-1-ol $^1$H NMR (300 MHz, $CDCl_3$) δ 7.82 (dt, 2H), 7.07 (d, 1H), 4.33 (td, 1H), 4.09 (s, 1H), 4.02-3.87 (m, 3H), 2.45-2.22 (m, 1H), 2.18-2.03 (m, 2H), 2.01-1.81 (m, 3H), 1.79-1.64 (m, 1H), 0.70 (dt, 3H). MS ESI, m/z=339/341 [M+H]$^+$. rel-(1R,2R,3S)-3-(5-bromo-6-methoxy-2H-indazol-2-yl)-2-methylcyclohexan-1-ol—Isomer 1 $^1$H NMR (300 MHz, $CDCl_3$) δ 7.87 (s, 1H), 7.79 (s, 1H), 7.07 (s, 1H), 4.10-3.80 (m, 4H), 3.47-3.31 (m, 1H), 2.15-2.05 (m, 3H), 1.96 (q, 1H), 1.70 (s, 1H), 1.59-1.45 (m, 2H), 0.82 (dd, 3H). MS ESI, m/z=339/341 [M+H]$^+$. rel-(1R,2R,3S)-3-(5-bromo-6-methoxy-2H-indazol-2-yl)-2-methylcyclohexan-1-ol-Isomer 2 $^1$H NMR (300 MHz, $CDCl_3$) δ 7.87 (s, 1H), 7.79 (s, 1H), 7.07 (s, 1H), 4.10-3.80 (m, 4H), 3.40 (s, 1H), 2.10 (tt, 3H), 1.96 (t, 1H), 1.80 (s, 1H), 1.50 (d, 2H), 0.81 (d, 3H). MS ESI, m/z=339/341 [M+H]$^+$.

rel-2-(1S,2R,3S)-3-Hydroxy-2-methylcyclohexyl)-
N-(imidazo[1,2-b]pyridazin-3-yl)-6-methoxy-2H-
indazole-5-carboxamide—Isomer 1 (Example 106)
& Isomer 2 (Example 107)

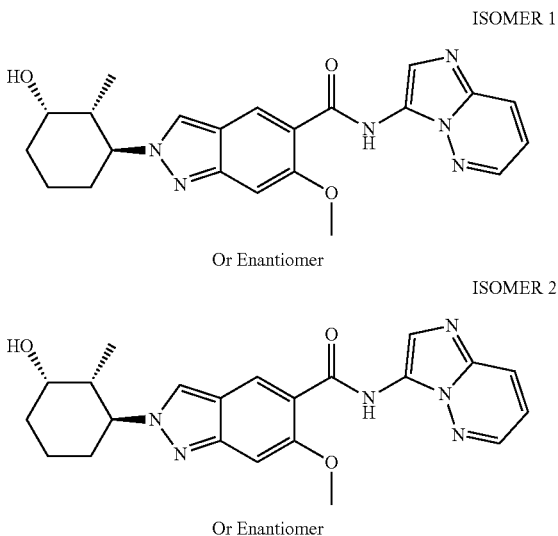

A solution of Pd(OAc)$_2$ (2.6 mg, 11 μmol), 1,3-bis(diphenylphosphino)propane (9.0 mg, 0.02 mmol), TEA (76 μL, 2.05 mmol), rac-(1S,2R,3S)-3-(5-bromo-6-methoxy-2H-indazol-2-yl)-2-methylcyclohexan-1-ol (32 mg, 0.05 mmol) and imidazo[1,2-b]pyridazin-3-amine (22 mg, 0.16 mmol) in MeCN (6 mL) was stirred under an atmosphere of CO at 15 atm and 100° C. for 15 h. The mixture was cooled to rt and concentrated under reduced pressure. The residue was purified by C18-flash chromatography (eluting with 0-100% acetonitrile in water (0.1% FA)) to afford rac-2-((1S,2R,3S)-3-hydroxy-2-methylcyclohexyl)-N-(imidazo[1,2-b]pyridazin-3-yl)-6-methoxy-2H-indazole-5-carboxamide. This material was further purified by chiral prep. HPLC (Chiralpak® IA 2×25 cm, 5 μm; isocratic elution with 50% MTBE (0.5% 2N NH$_3$-MeOH) in EtOH (1:1); 18 mL/min) to afford rel-2-(1S,2R,3S)-3-hydroxy-2-methylcyclohexyl)-N-(imidazo[1,2-b]pyridazin-3-yl)-6-methoxy-2H-indazole-5-carboxamide—Isomer 1 (3 mg, 14%, 99.7% ee) and rel-2-(1S,2R,3S)-3-hydroxy-2-methylcyclohexyl)-N-(imidazo[1,2-b]pyridazin-3-yl)-6-methoxy-2H-indazole-5-carboxamide—Isomer 2 (3.9 mg, 18%, 100% ee), both as yellow solids. Isomer 1: $^1$H NMR (400 MHz, DMSO-d$_6$) δ 11.05 (s, 1H), 8.64 (dd, 1H), 8.61 (d, 1H), 8.56 (s, 1H), 8.15 (dd, 1H), 8.05 (s, 1H), 7.27 (s, 1H), 7.22 (dd, 1H), 4.69 (d, 1H), 4.50-4.35 (m, 1H), 4.12 (s, 3H), 3.87 (s, 1H), 2.21-2.09 (m, 1H), 2.04-1.93 (m, 2H), 1.89-1.72 (m, 2H), 1.66-1.47 (m, 2H), 0.57 (d, 3H). MS ESI, m/z=421 [M+H]$^+$. Isomer 2: $^1$H NMR (400 MHz, DMSO-d$_6$) δ 11.05 (s, 1H), 8.64 (dd, 1H), 8.61 (s, 1H), 8.55 (s, 1H), 8.15 (dd, 1H), 8.05 (s, 1H), 7.27 (s, 1H), 7.22 (dd, 1H), 4.69 (d, 1H), 4.42 (td, 1H), 4.12 (s, 3H), 3.87 (s, 1H), 2.15 (t, 1H), 1.96 (dd, 2H), 1.82 (dd, 2H), 1.56 (q, 2H), 0.57 (d, 3H). MS ESI, m/z=421 [M+H]$^+$.

rel-2-(1S,2R,3R)-3-Hydroxy-2-methylcyclohexyl)-N-(imidazo[1,2-b]pyridazin-3-yl)-6-methoxy-2H-indazole-5-carboxamide—Isomer 1 (Example 108)

ISOMER 1

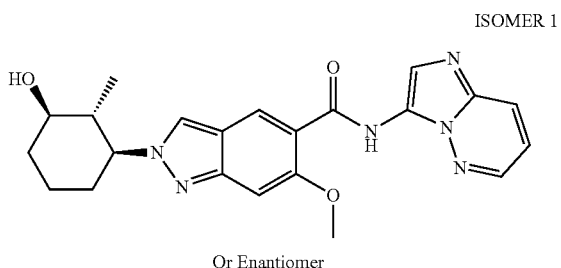 [SMILES: COc1cc2nn([C@H]3CCC[C@@H](O)[C@@H]3C)cc2cc1C(=O)Nc1cnc2cccnn12]

Or Enantiomer

A solution of Pd(OAc)$_2$ (1.9 mg, 8.55 μmol), 1,3-bis(diphenylphosphino)propane (7.1 mg, 0.02 mmol), TEA (60 μL, 0.43 mmol), rel-(1R,2R,3S)-3-(5-bromo-6-methoxy-2H-indazol-2-yl)-2-methylcyclohexan-1-ol—Isomer 1 (25 mg, 0.04 mmol) and imidazo[1,2-b]pyridazin-3-amine (17.2 mg, 0.13 mmol) in MeCN (8 mL) was stirred under an atmosphere of carbon monoxide at 15 atm and 100° C. for 15 h. The mixture was cooled to rt and concentrated under reduced pressure. The crude product was purified by C18-flash chromatography (eluting with 0 to 100% MeCN in water (0.1% NH$_4$OH) and further by prep. HPLC (YMC-Actus Triart C18 ExRS, 30 mm×150 mm, 5 μm; elution gradient: 12-45% MeCN in water (10 mM NH$_4$HCO$_3$+0.1% NH$_4$OH); 60 mL/min) to afford rel-2-((1S,2R,3R)-3-hydroxy-2-methylcyclohexyl)-N-(imidazo[1,2-b]pyridazin-3-yl)-6-methoxy-2H-indazole-5-carboxamide—Isomer 1 (2.9 mg, 16%) as a pale yellow solid. $^1$H NMR (400 MHz, DMSO-d$_6$) δ 11.05 (s, 1H), 8.64 (dd, 1H), 8.57 (s, 2H), 8.15 (dd, 1H), 8.05 (s, 1H), 7.28 (s, 1H), 7.22 (dd, 1H), 4.80 (d, 1H), 4.22-4.08 (m, 4H), 3.28-3.14 (m, 1H), 2.08-1.86 (m, 4H), 1.83-1.74 (m, 1H), 1.52-1.27 (m, 2H), 0.63 (d, 3H). MS ESI, m/z=421 [M+H]$^+$.

rel-2-(1S,2R,3R)-3-Hydroxy-2-methylcyclohexyl)-N-(imidazo[1,2-b]pyridazin-3-yl)-6-methoxy-2H-indazole-5-carboxamide—Isomer 2 (Example 109)

ISOMER 2

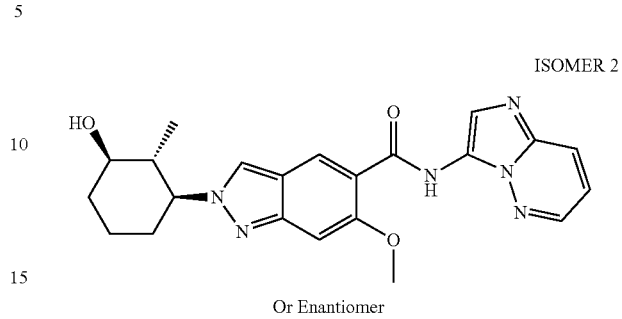

Or Enantiomer

A solution of Pd(OAc)$_2$ (1.3 mg, 5.81 μmol), 1,3-bis(diphenylphosphino)propane (4.8 mg, 0.01 mmol), TEA (41 μL, 0.29 mmol), rel-(1R,2R,3S)-3-(5-bromo-6-methoxy-2H-indazol-2-yl)-2-methylcyclohexan-1-ol—Isomer 2 (17 mg, 0.03 mmol) and imidazo[1,2-b]pyridazin-3-amine (11.7 mg, 0.09 mmol) in MeCN (6 mL) was stirred under an atmosphere of CO at 15 atm and 100° C. for 15 h. The mixture was cooled to rt and concentrated under reduced pressure. The crude product was purified by C18-flash chromatography (eluting with 0 to 100% MeCN in water (0.1% NH$_4$OH) and then by prep. HPLC (Waters Xbridge® OBD C18, 5 μm, 30×150 mm; elution gradient: 15-45% MeCN in water (10 mM NH$_4$HCO$_3$+0.1% NH$_4$OH); 60 mL/min) to afford rel-2-((1S,2R,3R)-3-hydroxy-2-methylcyclohexyl)-N-(imidazo[1,2-b]pyridazin-3-yl)-6-methoxy-2H-indazole-5-carboxamide—Isomer 2 (5.3 mg, 43%) as a yellow solid. $^1$H NMR (400 MHz, DMSO-d$_6$) δ 11.05 (s, 1H), 8.64 (dd, 1H), 8.58 (s, 2H), 8.15 (dd, 1H), 8.05 (s, 1H), 7.28 (s, 1H), 7.22 (dd, 1H), 4.79 (d, 1H), 4.20-4.08 (m, 4H), 3.25-3.07 (m, 1H), 2.06-1.86 (m, 4H), 1.80 (d, 1H), 1.56-1.29 (m, 2H), 0.63 (d, 3H). MS ESI, m/z=421 [M+H]$^+$.

2-((1S,4r)-4-((S)-3-Hydroxy-N-methylbutanamido)cyclohexyl)-6-methoxy-N-(pyrazolo[1,5-a]pyrimidin-3-yl)-2H-indazole-5-carboxamide (Example 110)

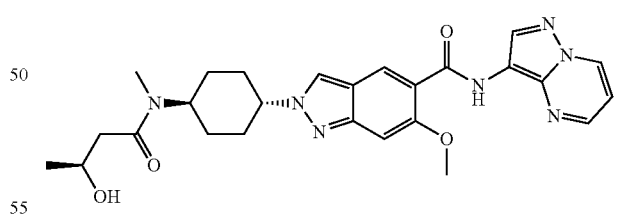

HATU (89 mg, 0.23 mmol) was added to DIPEA (103 μL, 0.59 mmol), (S)-3-hydroxybutanoic acid (20.4 mg, 0.20 mmol) and 6-methoxy-2-((1r,4r)-4-(methylamino)cyclohexyl)-N-(pyrazolo[1,5-c]pyrimidin-3-yl)-2H-indazole-5-carboxamide hydrochloride (Int V-4) (70 mg, 0.13 mmol) in DMF (6 mL). The resulting mixture was stirred at 25° C. for 15 h. The crude product was purified directly by C18-flash chromatography (eluting with 0-100% MeCN in water (0.1% NH$_4$·OH) and further purified by prep. HPLC (YMC-Actus Triart C18 ExRS 5 μm, 30×150 mm; elution gradient: 9-42% MeCN in water (10 mM NH$_4$HCO$_3$+0.1% NH$_4$OH);

60 mL/min) to afford 2-((1S,4r)-4-((S)-3-hydroxy-N-methylbutanamido)cyclohexyl)-6-methoxy-N-(pyrazolo[1,5-c]pyrimidin-3-yl)-2H-indazole-5-carboxamide (37 mg, 55.7%), as a yellow solid. $^1$H NMR (300 MHz, DMSO-d$_6$) (mixture of rotamers) δ 10.34 (s, 1H), 9.09-9.01 (m, 1H), 8.72 (s, 1H), 8.58-8.49 (m, 2H), 8.46 (d, 1H), 7.19 (d, 1H), 7.04 (s, 1H), 4.62 (d, 1H), 4.56-4.37 (m, 1.5H), 4.04 (s, 4H), 3.92-3.81 (m, 0.5H) 2.79 (d, 3H), 2.46-2.25 (m, 2H), 2.24-1.95 (m, 4H), 1.92-1.56 (m, 4H), 1.18-1.02 (m, 3H). MS ESI, m/z=506 [M+H]$^+$ 2-((1R,4r)-4-((R)-3-Hydroxy-N-methylbutanamido)cyclohexyl)-6-methoxy-N-(pyrazolo[1,5-a]pyrimidin-3-yl)-2H-indazole-5-carboxamide (Example 111)

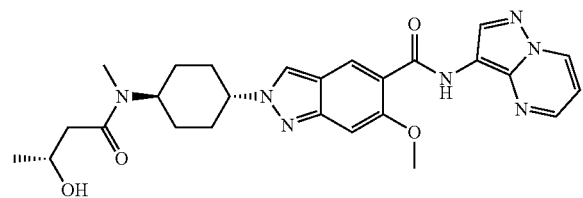 [SMILES: COc1cc2nn([C@H]3CC[C@H](N(C)C(=O)C[C@@H](C)O)CC3)cc2cc1C(=O)Nc1cnn2cccnc12]

HATU (96 mg, 0.25 mmol) was added to DIPEA (110 μL, 0.63 mmol), (R)-3-hydroxybutanoic acid (21.8 mg, 0.21 mmol) and 6-methoxy-2-((1r,4r)-4-(methylamino)cyclohexyl)-N-(pyrazolo[1,5-c]pyrimidin-3-yl)-2H-indazole-5-carboxamide hydrochloride (Int V-4) (70 mg, 0.14 mmol) in DMF (6 mL). The resulting mixture was stirred at 25° C. for 15 h. The crude product was purified directly by C18-flash chromatography (eluting with 0-100% MeCN in water (0.1% NH$_4$·OH) and further purified by prep. HPLC (YMC-Actus Triart C18 ExRS, 5 μm, 30×150 mm; elution gradient: 9-42% MeCN in water (10 mM NH$_4$HCO$_3$+0.1% NH$_4$OH); 60 mL/min) to afford 2-((1R,4r)-4-((R)-3-hydroxy-N-methylbutanamido)cyclohexyl)-6-methoxy-N-(pyrazolo[1,5-c]pyrimidin-3-yl)-2H-indazole-5-carboxamide (53 mg, 74.5%), as a yellow solid. $^1$H NMR (300 MHz, DMSO-d$_6$) (mixture of rotamers) δ 10.36 (s, 1H), 9.08 (dd, 1H), 8.73 (s, 1H), 8.58-8.52 (m, 2H), 8.48 (d, 1H), 7.21 (d, 1H), 7.06 (dd, 1H), 4.67-4.59 (m, 1H), 4.56-4.41 (m, 1.5H), 4.10-3.97 (m, 4H), 3.96-3.86 (m, 0.5H), 2.81 (d, 3H), 2.48-2.29 (m, 2H), 2.25-1.96 (m, 4H), 1.93-1.60 (m, 4H), 1.16-1.07 (m, 3H). MS ESI, m/z=506 [M+H]$^+$ rel-2-(1R,4r)-4-((1R,3R)-3-Hydroxy-N-methylcyclopentane-1-carboxamido)cyclohexyl)-6-methoxy-N-(pyrazolo[1,5-c]pyrimidin-3-yl)-2H-indazole-5-carboxamide—Isomer 1 (Example 112) & Isomer 2 (Example 113)

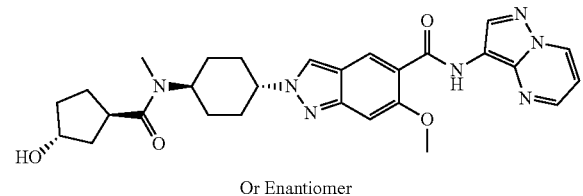

ISOMER 1

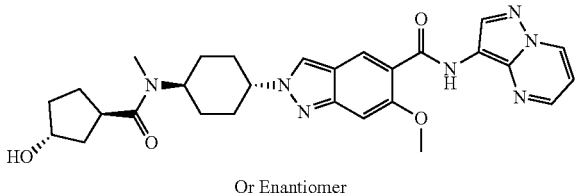

ISOMER 2

HATU (163 mg, 0.43 mmol) was added to DIEA (188 μL, 1.08 mmol), rac-(1R,3R)-3-hydroxycyclopentane-1-carboxylic acid (46.5 mg, 0.36 mmol) and 6-methoxy-2-((1r,4r)-4-(methylamino)cyclohexyl)-N-(pyrazolo[1,5-a]pyrimidin-3-yl)-2H-indazole-5-carboxamide hydrochloride (Int V-4) (150 mg, 0.33 mmol) in DMF (6 mL). The resulting mixture was stirred at rt for 3 h. The crude product was purified by flash C18-flash chromatography (eluting with 0 to 100% MeCN in water). The material was further purified by chiral prep. HPLC (Chiralpak® IF, 2×25 cm, 5 μm; isocratic elution with MTBE 40% (0.5% 2N NH$_3$-MeOH) in MeOH 60% in 22 min; 18 mL/min) to afford rel-2-((1R,4r)-4-((1R,3R)-3-Hydroxy-N-methylcyclopentane-1-carboxamido)cyclohexyl)-6-methoxy-N-(pyrazolo[1,5-c]pyrimidin-3-yl)-2H-indazole-5-carboxamide—Isomer 1 (45 mg, 26%) and rel-2-((1R,4r)-4-((1R,3R)-3-Hydroxy-N-methylcyclopentane-1-carboxamido)cyclohexyl)-6-methoxy-N-(pyrazolo[1,5-c]pyrimidin-3-yl)-2H-indazole-5-carboxamide—Isomer 2 (44 mg, 25%), both as yellow solids. Isomer 1: $^1$H NMR (400 MHz, DMSO-d$_6$) (mixture of rotamers) δ 10.35 (s, 1H), 9.08 (dd, 1H), 8.73 (s, 1H), 8.60-8.52 (m, 2H), 8.47 (d, 1H), 7.22 (d, 1H), 7.06 (dd, 1H), 4.48 (dd, 1.5H), 4.19 (dq, 1H), 4.06 (s, 3H), 3.92 (q, 0.5H), 3.30 (m, 0.5H), 3.22 (m, 0.5H), 2.82 (d, 3H), 2.16 (d, 3H), 2.08-1.87 (m, 3H), 1.87-1.6 (m, 7H), 1.51 (m, 1H). MS ESI, m/z=532 [M+H]$^+$. Isomer 2: $^1$H NMR (400 MHz, DMSO-d$_6$) (mixture of rotamers) δ 10.35 (s, 1H), 9.08 (dd, 1H), 8.73 (s, 1H), 8.60-8.52 (m, 2H), 8.52-8.43 (m, 1H), 7.22 (d, 1H), 7.06 (dd, 1H), 4.55 (m, 1.5H), 4.22-4.15 (m, 1H), 4.06 (s, 3H), 3.95 (d, 0.5H) 3.31 (d, 0.5H) 3.21 (d, 0.5H), 2.82 (d, 3H), 2.16 (d, 3H), 2.11-1.88 (m, 3H), 1.89-1.61 (m, 7H), 1.5 (m, 1H). MS ESI, m/z=532 [M+H]$^+$.

rel-2-((1R,4r)-4-((1R,3S)-3-hydroxy-N-methylcyclopentane-1-carboxamido)cyclohexyl)-6-methoxy-N-(pyrazolo[1,5-c]pyrimidin-3-yl)-2H-indazole-5-carboxamide—Isomer 1 (Example 114) & Isomer 2 (Example 115)

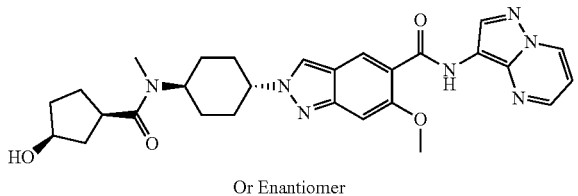

ISOMER 1

ISOMER 2

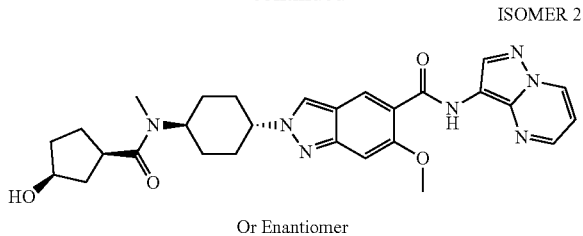

Or Enantiomer

HATU (163 mg, 0.43 mmol) was added to DIPEA (188 μL, 1.08 mmol), rac-(1R,3S)-3-hydroxycyclopentane-1-carboxylic acid (46.5 mg, 0.36 mmol) and 6-methoxy-2-((1r,4r)-4-(methylamino)cyclohexyl)-N-(pyrazolo[1,5-c]pyrimidin-3-yl)-2H-indazole-5-carboxamide hydrochloride (Int V-4) (150 mg, 0.33 mmol) in DMF (10 mL). The resulting mixture was stirred at rt for 15 h. The crude product was purified by C18-flash chromatography (eluting with 0 to 100% MeCN in water (0.1% NH$_4$OH)). The material was further purified by chiral prep. HPLC (Chiral Art Cellulose SB, 2×25 cm, 5 μm; isocratic elution with MTBE 70% (0.5% 2N NH$_3$-MeOH)/30% (DCM-MeOH, 1:1); 20 m L/m in) to afford rel-2-((1R,4r)-4-((1R,3S)-3-hydroxy-N-methylcyclopenta ne-1-carboxamido)cyclohexyl)-6-methoxy-N-(pyrazolo[1,5-a]pyrimidin-3-yl)-2H-indazole-5-carboxamide—Isomer 1 (22 mg, 12%) and rel-2-((1R,4r)-4-((1R,3S)-3-hydroxy-N-methylcyclopentane-1-carboxamido)cyclohexyl)-6-methoxy-N-(pyrazolo[1,5-c]pyrimidin-3-yl)-2H-indazole-5-carboxamide—Isomer 2 (18 mg, 10%), both as yellow solids. Isomer 1: $^1$H NMR (400 MHz, DMSO-d$_6$) (mixture of rotamers) δ 10.36 (s, 1H), 9.08 (dd, 1H), 8.74 (d, 1H), 8.59-8.54 (m, 2H), 8.49-8.45 (m, 1H), 7.22 (d, 1H), 7.06 (dd, 1H), 4.55 (m, 1.5H), 4.06 (s, 4H), 3.97 (m, 0.5H), 3.21-3.01 (m, 1H), 2.82 (d, 3H), 2.31-2.10 (m, 3H), 2.06-1.89 (m, 3H), 1.88 (m, 4H), 1.64 (m, 4H). MS ESI, m/z=532 [M+H]$^+$. Isomer 2: $^1$H NMR (400 MHz, DMSO-d$_6$) (mixture of rotamers) δ 10.36 (s, 1H), 9.08 (dd, 1H), 8.74 (d, 1H), 8.59-8.54 (m, 2H), 8.48 (dd, 1H), 7.21 (d, 1H), 7.06 (dd, 1H), 4.52 (m, 1.5H), 4.06 (s, 4H), 3.91 (m. 0.5H), 3.00 (t, 1H), 2.82 (d, 3H), 2.18 (q, 3H), 2.09-1.88 (m, 3H), 1.87 (m, 4H), 1.61 (m, 4H). MS ESI, m/z=532 [M+H]$^+$.

2-((1S,4r)-4-((S)-3-Hydroxy-N-methylpyrrolidine-1-carboxamido)cyclohexyl)-N-(imidazo[1,2-b]pyridazin-3-yl)-6-methoxy-2H-indazole-5-carboxamide (Example 116) & 2-((1R,4r)-4-((R)-3-Hydroxy-N-methylpyrrolidine-1-carboxamido)cyclohexyl)-N-(imidazo[1,2-b]pyridazin-3-yl)-6-methoxy-2H-indazole-5-carboxamide (Example 117)

4-Nitrophenyl ((1r,4r)-4-(5-(imidazo[1,2-b]pyridazin-3-ylcarbamoyl)-6-methoxy-2H-indazol-2-yl)cyclohexyl)(methyl)carbamate

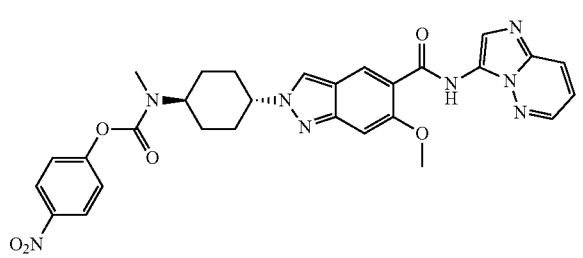 [SMILES: COc1cc2nn([C@H]3CC[C@H](N(C)C(=O)Oc4ccc([N+](=O)[O-])cc4)CC3)cc2cc1C(=O)Nc1cnc2cccnn12]

4-Nitrophenyl carbonochloridate (177 mg, 0.88 mmol) was added to N-(imidazo[1,2-b]pyridazin-3-yl)-6-methoxy-2-((1r,4r)-4-(methylamino)cyclohexyl)-2H-indazole-5-carboxamide hydrochloride (Int V-3) (200 mg, 0.44 mmol), TEA (245 μL, 1.75 mmol) in DCM (1 mL) at 0° C. under N$_2$. The resulting mixture was stirred at rt for 15 h. The solvent was removed under reduced pressure, then water (30 mL) and MeOH (5 mL) were added and the resulting mixture was stirred for 30 min. The resulting precipitate was collected by filtration, washed with water (25 mL) and dried under vacuum to afford 4-nitrophenyl ((1r,4r)-4-(5-(imidazo[1,2-b]pyridazin-3-ylcarbamoyl)-6-methoxy-2H-indazol-2-yl)cyclohexyl)(methyl)carbamate (260 mg, 100%) as a yellow solid. $^1$H NMR (300 MHz, DMSO-d$_6$) (mixture of rotamers) δ 11.05 (s, 1H), 8.67-8.60 (m, 2H), 8.59 (s, 1H), 8.30 (s, 1H), 8.28 (s, 1H), 8.17 (s, 1H), 8.05 (s, 1H), 7.51-7.43 (m, 2H), 7.29-7.18 (m, 2H), 4.61-4.45 (m, 1H), 4.25-3.99 (m, 1H), 4.12 (s, 3H), 3.01 and 2.91 (s, 3H), 2.32-2.20 (m, 2H), 2.16-2.03 (m, 2H), 2.01-1.82 (m, 4H). MS ESI, m/z=585 [M+H]$^+$.

2-((1S,4r)-4-((S)-3-Hydroxy-N-methylpyrrolidine-1-carboxamido)cyclohexyl)-N-(imidazo[1,2-b]pyridazin-3-yl)-6-methoxy-2H-indazole-5-carboxamide (Example 116)

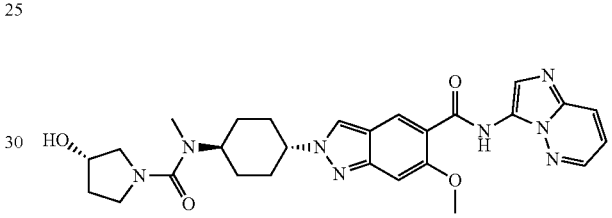

(S)-Pyrrolidin-3-ol (26.6 mg, 0.30 mmol) was added to 4-nitrophenyl ((1r,4r)-4-(5-(imidazo[1,2-b]pyridazin-3-ylcarbamoyl)-6-methoxy-2H-indazol-2-yl)cyclohexyl)(methyl)carbamate (110 mg, 0.15 mmol), TEA (106 μL, 0.76 mmol) in DMF (3 mL) at 25° C. under nitrogen. The resulting mixture was stirred at 70° C. for 15 h. The reaction mixture was allowed to cool to rt then purified by prep. HPLC (YMC-Actus Triart C18 ExRS, 5 μm, 30×150 mm; elution gradient with 10-43% MeCN in water (10 mM NH$_4$HCO$_3$+0.1% NH$_4$OH); 60 mL/min) to afford 2-((1S,4r)-4-((S)-3-hydroxy-N-methylpyrrolidine-1-carboxamido)cyclohexyl)-N-(imidazo[1,2-b]pyridazin-3-yl)-6-methoxy-2H-indazole-5-carboxamide (35 mg, 43%) as a yellow solid. $^1$H NMR (400 MHz, DMSO-d$_6$) δ 11.05 (s, 1H), 8.64 (dd, 1H), 8.59 (d, 2H), 8.15 (dd, 1H), 8.05 (s, 1H), 7.26 (s, 1H), 7.22 (dd, 1H), 4.86 (d, 1H), 4.57-4.41 (m, 1H), 4.26-4.18 (m, 1H), 4.12 (s, 3H), 3.77-3.62 (m, 1H), 3.51-3.39 (m, 2H), 3.29-3.19 (m, 1H), 3.10-3.00 (m, 1H), 2.67 (s, 3H), 2.27-2.15 (m, 2H), 2.10-1.94 (m, 2H), 1.89-1.77 (m, 4H), 1.77-1.66 (m, 2H). MS ESI, m/z=533 [M+H]$^+$.

2-((1R,4r)-4-((R)-3-Hydroxy-N-methylpyrrolidine-1-carboxamido)cyclohexyl)-N-(imidazo[1,2-b]pyridazin-3-yl)-6-methoxy-2H-indazole-5-carboxamide (Example 117)

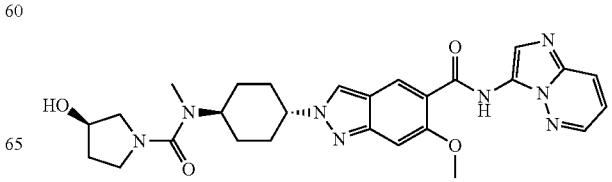

(R)-Pyrrolidin-3-ol (9.66 mg, 0.11 mmol) was added to 4-nitrophenyl ((1r,4r)-4-(5-(imidazo[1,2-b]pyridazin-3-yl-carbamoyl)-6-methoxy-2H-indazol-2-yl)cyclohexyl)(methyl)carbamate (40 mg, 0.06 mmol), TEA (39 µL, 0.28 mmol) in DMF (3 mL) at 25° C. under N₂. The resulting mixture was stirred at 70° C. for 15 h. The reaction mixture was allowed to cool to rt then purified by prep. HPLC (YMC-Actus Triart C18 ExRS, 5 µm, 30×150 mm; elution gradient with 10-43% MeCN in water (10 mM NH₄HCO₃+ 0.1% NH₄OH); 60 mL/min), to afford 2-((1R,4r)-4-((R)-3-hydroxy-N-methylpyrrolidine-1-carboxamido)cyclohexyl)-N-(imidazo[1,2-b]pyridazin-3-yl)-6-methoxy-2H-indazole-5-carboxamide (20 mg, 68%), as a yellow solid. ¹H NMR (400 MHz, DMSO-d₆) δ 11.05 (s, 1H), 8.64 (dd, 1H), 8.59 (d, 2H), 8.15 (dd, 1H), 8.05 (s, 1H), 7.26 (s, 1H), 7.22 (dd, 1H), 4.86 (d, 1H), 4.55-4.39 (m, 1H), 4.27-4.16 (m, 1H), 4.12 (s, 3H), 3.77-3.61 (m, 1H), 3.52-3.40 (m, 2H), 3.29-3.18 (m, 1H), 3.12-2.97 (m, 1H), 2.67 (s, 3H), 2.25-2.14 (m, 2H), 2.13-1.94 (m, 2H), 1.90-1.77 (m, 4H), 1.77-1.62 (m, 2H). MS ESI, m/z=533 [M+H]⁺.

6-Methoxy-2-(1-methyl-2-oxo-4-oxa-1-azaspiro[5.5]undecan-9-yl)-N-(pyrazolo[1,5-a]pyrimidin-3-yl)-2H-indazole-5-carboxamide—Isomer 1 (Example 118) & Isomer 2 (Example 119)

Methyl 1-amino-4-(benzylamino)cyclohexane-1-carboxylate

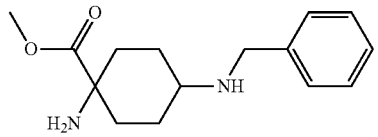 [SMILES: COC(=O)C1(N)CCC(NCc2ccccc2)CC1]

To a solution of methyl 1-amino-4-oxocyclohexane-1-carboxylate (1.5 g, 8.8 mmol) and phenylmethanamine (1.1 g, 10.5 mmol) in MeOH (28 mL) under N₂ at 0° C. was added sodium cyanoborohydride (826 mg, 13.1 mmol) over 3 min. The resulting mixture was stirred at 25° C. for 2 h. The reaction mixture was concentrated under reduced pressure. The residue was purified by C18 flash chromatography (eluting with 0-100% MeCN in water (2% NH₄OH)) to afford methyl 1-amino-4-(benzylamino)cyclohexane-1-carboxylate (1.4 g, 61%) as a colorless solid. ¹H NMR (400 MHz, DMSO-d₆) (1: 2 mixture of isomers) δ 7.35-7.24 (m, 4H), 7.24-7.15 (m, 1H), 3.70/3.67 (s, 2H) (isomers), 3.61/3.59 (s, 3H) (isomers), 2.45-2.30 (m, 1H), 2.09-1.98 (m, 1H), 1.84-1.73 (m, 1H), 1.67-1.41 (m, 5H), 1.28-0.99 (m, 1H). MS ESI, m/z=263 [M+H]⁺.

Methyl 1,4-diaminocyclohexane-1-carboxylate

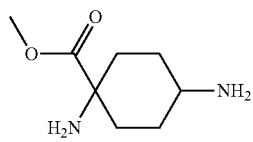

To a solution of methyl 1-amino-4-(benzylamino)cyclohexane-1-carboxylate (300 mg, 1.1 mmol) in MeOH (16 mL) under N₂ was added Pd(OH)₂ on carbon (20 wt. %) (60 mg, 0.4 mmol). The resulting suspension was stirred at 25° C. under hydrogen at 1 atm for 2 h. The reaction mixture was filtered through celite, and the celite cake was washed with MeOH (100 mL). The combined MeOH solution was concentrated under reduced pressure to afford methyl 1,4-diaminocyclohexane-1-carboxylate (120 mg, 61%) as a colourless oil, which was used directly without further purification. MS ESI, m/z=173 [M+H]⁺.

Methyl 1-amino-4-(5-bromo-6-methoxy-2H-indazol-2-yl)cyclohexane-1-carboxylate

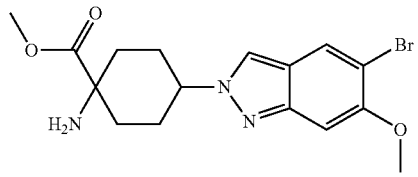

5-Bromo-4-methoxy-2-nitrobenzaldehyde (1.3 g, 4.9 mmol) was added to a solution of methyl 1,4-diaminocyclohexane-1-carboxylate (890 mg, 5.2 mmol) and TEA (2 mL, 14.8 mmol) in i-PrOH (32 mL) at 25° C. under N₂. The resulting mixture was stirred at 80° C. for 2 h, cooled to room temperature, followed by the addition of tri-n-butylphosphine (3.6 mL, 14.8 mmol). The mixture was stirred for 12 h at 80° C. The reaction mixture was concentrated under reduced pressure. The residue was purified by C18 flash chromatography (eluting with 0-100% MeCN in water (0.1% NH₄OH)) to afford methyl 1-amino-4-(5-bromo-6-methoxy-2H-indazol-2-yl)cyclohexane-1-carboxylate (650 mg, 35%) as a yellow solid. MS ESI, m/z=382/384 (1:1) [M+H]⁺.

(1-amino-4-(5-bromo-6-methoxy-2H-indazol-2-yl)cyclohexyl)methanol

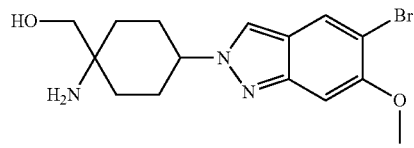 [SMILES: COc1cc2nn(C3CCC(N)(CO)CC3)cc2cc1Br]

To a solution of methyl 1-amino-4-(5-bromo-6-methoxy-2H-indazol-2-yl)cyclohexane-1-carboxylate (630 mg, 1.7 mmol) in THF (30 mL) was lithium aluminium hydride (94 mg, 2.5 mmol) at 0° C. under N₂. The resulting mixture was stirred at 25° C. for 2 h. The reaction mixture was poured into a suspension of Na₂SO₄.10H₂O in THF (50 mL), and then filtered through celite. The celite cake was washed with THF (500 mL). The combined filtrate was concentrated under reduced pressure to afford (1-amino-4-(5-bromo-6-methoxy-2H-indazol-2-yl)cyclohexyl)methanol (440 mg, 75%) as a pale yellow solid, which was used directly without further purification. MS ESI, m/z=354/356 (1:1) [M+H]⁺.

N-(4-(5-bromo-6-methoxy-2H-indazol-2-yl)-1-(hydroxymethyl)cyclohexyl)-2-chloroacetamide

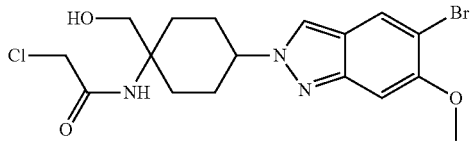 [SMILES: COc1cc2nn(C3CCC(CO)(NC(=O)CCl)CC3)cc2cc1Br]

2-Chloroacetyl chloride (140 mg, 1.3 mmol) was added dropwise over 2 min to a mixture of (1-amino-4-(5-bromo-6-methoxy-2H-indazol-2-yl)cyclohexyl)methanol (400 mg, 1.1 mmol) in DCM (4.5 mL) and aq.NaOH (2N) (4.5 mL, 2.3 mmol) at 0° C. under $N_2$. The resulting mixture was stirred at 25° C. for 2 h. The reaction mixture was poured into water (10 mL) and extracted with DCM (20 mL×3). The organic layer was dried over $Na_2SO_4$, filtered and concentrated under reduced pressure. The residue was purified by C18-flash chromatography (eluting with 0-100% MeCN in water (0.1% $NH_4OH$)) to afford N-(4-(5-bromo-6-methoxy-2H-indazol-2-yl)-1-(hydroxymethyl)cyclohexyl)-2-chloroacetamide (120 mg, 25%) as a pale-yellow solid. MS ESI, m/z=430/432 (1:1) $[M+H]^+$.

9-(5-Bromo-6-methoxy-2H-indazol-2-yl)-4-oxa-1-azaspiro[5.5]undecan-2-one

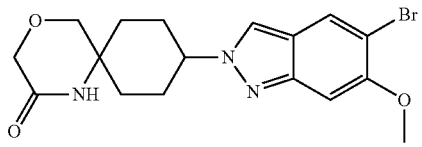 [SMILES: COc1cc2nn(C3CCC4(CC3)COCC(=O)N4)cc2cc1Br]

Potassium tert-butoxide (177 mg, 1.6 mmol) was added portionwise over 2 min to a solution of N-(4-(5-bromo-6-methoxy-2H-indazol-2-yl)-1-(hydroxymethyl)cyclohexyl)-2-chloroacetamide (170 mg, 0.4 mmol) in THF (10 mL) at 0° C. under $N_2$. The resulting mixture was stirred at 25° C. for 2 h. The reaction mixture was poured into aq. saturated $NH_4Cl$ solution (10 mL) and extracted with EtOAc (50 mL×3). The organic layer was dried over $Na_2SO_4$, filtered and concentrated under reduced pressure. The residue was purified by C18-flash chromatography (eluting with 0-100% MeCN in water (0.1% $NH_4OH$)) to afford 9-(5-bromo-6-methoxy-2H-indazol-2-yl)-4-oxa-1-azaspiro[5.5]undecan-2-one (105 mg, 68%) as a colorless solid. MS ESI, m/z=394/396 (1:1) $[M+H]^+$.

9-(5-Bromo-6-methoxy-2H-indazol-2-yl)-1-methyl-4-oxa-1-azaspiro[5.5]undecan-2-one

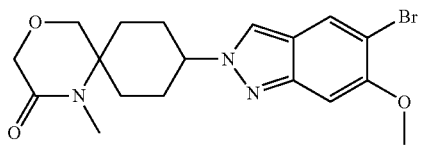 [SMILES: COc1cc2nn(C3CCC4(CC3)COCC(=O)N4C)cc2cc1Br]

Sodium hydride (60 wt. %) (14 mg, 0.4 mmol) was added portionwise over 2 min to a solution of 9-(5-bromo-6-methoxy-2H-indazol-2-yl)-4-oxa-1-azaspiro[5.5]undecan-2-one (95 mg, 0.2 mmol) in DMF (6 mL) at 0° C. under $N_2$. The resulting mixture was stirred at 0° C. for 15 min, followed by the addition of iodomethane (103 mg, 0.7 mmol). The mixture was stirred at 25° C. for 2 h. The reaction mixture was quenched with aq. saturated $NH_4Cl$ solution (10 mL) and extracted with EtOAc (50 mL×3). The organic layer was dried over $Na_2SO_4$, filtered and concentrated under reduced pressure. The residue was purified by C18-flash chromatography (eluting with 0-100% MeCN in water (0.1% FA)) to afford 9-(5-bromo-6-methoxy-2H-indazol-2-yl)-1-methyl-4-oxa-1-azaspiro[5.5]undecan-2-one (85 mg, 86%) as a colorless solid. MS ESI, m/z=408/410 (1:1) $[M+H]^+$.

Methyl 6-methoxy-2-(1-methyl-2-oxo-4-oxa-1-azaspiro[5.5]undecan-9-yl)-2H-indazole-5-carboxylate

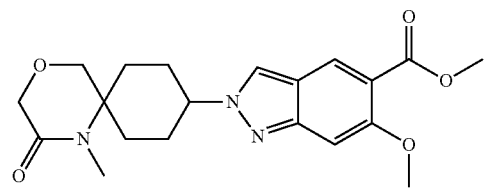 [SMILES: COC(=O)c1cc2cn(C3CCC4(CC3)COCC(=O)N4C)nc2cc1OC]

A mixture of 9-(5-bromo-6-methoxy-2H-indazol-2-yl)-1-methyl-4-oxa-1-azaspiro[5.5]undecan-2-one (85 mg, 0.2 mmol), Pd(dppf)$Cl_2$— $CH_2Cl_2$ (17 mg, 0.02 mmol) and TEA (2904, 2.1 mmol) in MeOH (10 mL) was heated at 100° C. for 15 h in a sealed vessel under CO atmosphere at 15 atm. The reaction mixture cooled to rt and concentrated under reduced pressure. The residue was purified by C18-flash chromatography (eluting with 0-100% MeCN in water (0.1% $NH_4OH$)) to afford methyl 6-methoxy-2-(1-methyl-2-oxo-4-oxa-1-azaspiro[5.5]undecan-9-yl)-2H-indazole-5-carboxylate (75 mg, 93%) as a red solid. MS ESI, m/z=388 $[M+H]^+$.

6-Methoxy-2-(1-methyl-2-oxo-4-oxa-1-azaspiro[5.5]undecan-9-yl)-2H-indazole-5-carboxylic Acid

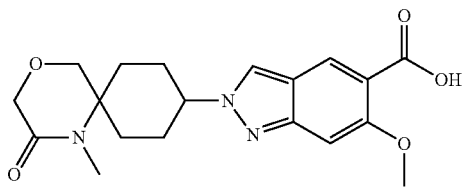 [SMILES: COc1cc2nn(C3CCC4(CC3)COCC(=O)N4C)cc2cc1C(=O)O]

Lithium hydroxide (20 mg, 0.8 mmol) was added to a solution of methyl 6-methoxy-2-(1-methyl-2-oxo-4-oxa-1-azaspiro[5.5]undecan-9-yl)-2H-indazole-5-carboxylate (65 mg, 0.2 mmol) in THF (3 mL)/water (3 mL). The resulting solution was stirred at 25° C. for 2 h. The reaction mixture was adjusted to pH 6 with 2N HCl. The mixture was purified directly by C18-flash chromatography (eluting with 0-100% MeCN in water (0.1% $NH_4OH$)) to afford 6-methoxy-2-(1-methyl-2-oxo-4-oxa-1-azaspiro[5.5]undecan-9-yl)-2H-indazole-5-carboxylic acid (50 mg, 80%) as a yellow solid. MS ESI, m/z=374 $[M+H]^+$.

6-Methoxy-2-(1-methyl-2-oxo-4-oxa-1-azaspiro[5.5] undecan-9-yl)-N-(pyrazolo[1,5-a]pyrimidin-3-yl)-2H-indazole-5-carboxamide—Isomer 1 (Example 118) & Isomer 2 (Example 119)

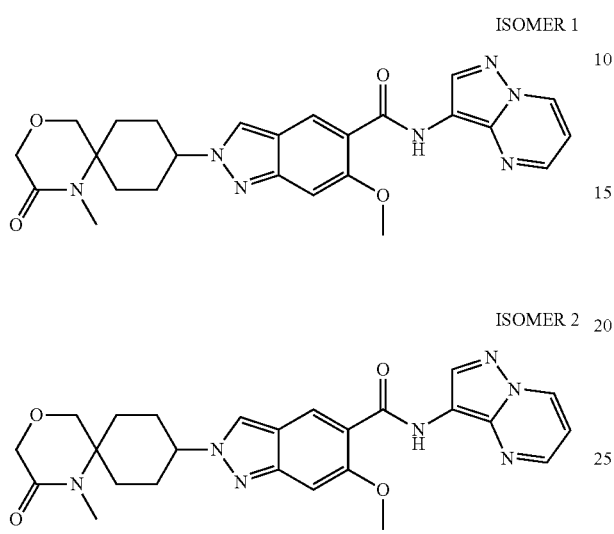

The HCl salt of pyrazolo[1,5-a]pyrimidin-3-amine (23 mg, 0.1 mmol) was added to a solution of 6-methoxy-2-(1-methyl-2-oxo-4-oxa-1-azaspiro[5.5]undecan-9-yl)-2H-indazole-5-carboxylic acid (45 mg, 0.1 mmol), HATU (55 mg, 0.1 mmol) and DIPEA (634, 0.4 mmol) in DMF (3 mL). The resulting mixture was stirred at 25° C. for 2 h. The reaction mixture was concentrated under reduced pressure and purified by C18-flash chromatography (eluting with 0-100% MeCN in water (0.1% NH$_4$OH)) to give a mixture of isomers of 6-methoxy-2-(1-methyl-2-oxo-4-oxa-1-azaspiro[5.5]undecan-9-yl)-N-(pyrazolo[1,5-c]pyrimidin-3-yl)-2H-indazole-5-carboxamide as a yellow solid. This mixture was separated by prep. chiral HPLC (Chiralpak® IA 5 µm 20 mm×250 mm; isocratic with 50% MTBE (0.5% 2N NH$_3$-MeOH) in MeOH; over 24 min, 20 mL/min) to afford as first eluting isomer 6-methoxy-2-(1-methyl-2-oxo-4-oxa-1-azaspiro[5.5]undecan-9-yl)-N-(pyrazolo[1,5-a]pyrimidin-3-yl)-2H-indazole-5-carboxamide—Isomer 1, (19 mg, 32%, 100% ee) and as second eluting isomer 6-methoxy-2-(1-methyl-2-oxo-4-oxa-1-azaspiro[5.5]undecan-9-yl)-N-(pyrazolo[1,5-a]pyrimidin-3-yl)-2H-indazole-5-carboxamide—Isomer 2, (3 mg, 5%, 99.5% ee), both as colorless solids. Isomer 1: $^1$H NMR (400 MHz, DMSO-d$_6$) δ 10.35 (s, 1H), 9.07 (dd, 1H), 8.73 (s, 1H), 8.70 (s, 1H), 8.54 (dd, 1H), 8.49 (s, 1H), 7.26 (s, 1H), 7.05 (dd, 1H), 4.75-4.68 (m, 1H), 4.07 (s, 3H), 4.07 (s, 2H), 3.91 (s, 2H), 2.71 (s, 3H), 2.41-2.34 (m, 2H), 2.22-2.04 (m, 4H), 1.63-1.55 (m, 2H). MS ESI, m/z=490 [M+H]$^+$. Isomer 2: $^1$H NMR (400 MHz, DMSO-d$_6$) δ 10.34 (s, 1H), 9.07 (dd, 1H), 8.73 (s, 1H), 8.61 (s, 1H), 8.54 (dd, 1H), 8.47 (s, 1H), 7.22 (s, 1H), 7.05 (dd, 1H), 4.68-4.56 (m, 1H), 4.08 (s, 2H), 4.06 (s, 3H), 3.98 (s, 2H), 2.88 (s, 3H), 2.20-1.94 (m, 6H), 1.81 (br. d, 2H). MS ESI, m/z=490 [M+H]$^+$.

rel-2-(5R,7R,8R)-1,7-Dimethyl-2-oxo-1-azaspiro [4.5]decan-8-yl)-N-(imidazo[1,2-b]pyridazin-3-yl)-6-methoxy-2H-indazole-5-carboxamide—Isomer 1 (Example 120) & Isomer 2 (Example 121)

rel-2-(5S,7R,8R)-1,7-Dimethyl-2-oxo-1-azaspiro [4.5]decan-8-yl)-N-(imidazo[1,2-b]pyridazin-3-yl)-6-methoxy-2H-indazole-5-carboxamide—Isomer 1 (Example 122) & Isomer 2 (Example 123)

rac-3-Bromo-N-((3R,4R)-4-(5-bromo-6-methoxy-2H-indazol-2-yl)-3-methylcyclohex-1-en-1-yl)-N-methylpropanamide

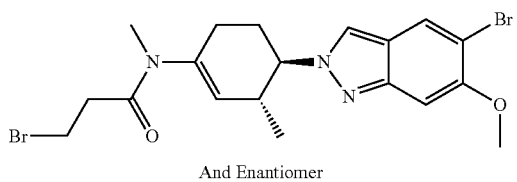 [SMILES: COc1cc2nn([C@@H]3CCC(N(C)C(=O)CCBr)=C[C@H]3C)cc2cc1Br]

And Enantiomer

Methanamine in THF (2 M) (34.1 mL, 68.2 mmol) was added over 5 min to a solution of rac-(3R,4R)-4-(5-bromo-6-methoxy-2H-indazol-2-yl)-3-methylcyclohexan-1-one (synthesis as described in the synthesis of Int V-1) (2.3 g, 6.8 mmol) in toluene (100 mL) at −78° C. in a sealed vessel. The resulting solution was warmed to rt and heated at 110° C. for 2.5 h. The mixture was concentrated under reduced pressure. The residue was dissolved in THF (100 mL) and cooled to at 0° C. Sodium bicarbonate (859 mg, 10.2 mmol) and 3-bromopropanoyl chloride (1.2 g, 6.8 mmol) were added to the reaction mixture, which was stirred at 25° C. for 30 min. The reaction mixture was quenched with aq. saturated NH$_4$Cl (25 mL) and extracted with EtOAc (150 mL×2). The organic layer was dried over Na$_2$SO$_4$, filtered and concentrated under reduced pressure to yield a colourless oil. The crude was purified by silica gel chromatography (eluting with 0-60% EtOAc in PE to afford rac-3-bromo-N-((3R, 4R)-4-(5-bromo-6-methoxy-2H-indazol-2-yl)-3-methylcyclohex-1-en-1-yl)-N-methylpropanamide (850 mg, 26%) as a red solid. MS ESI, m/z=484/486/485 (1:2:1) [M+H]$^+$.

rac-(5R,7R,8R)-8-(5-Bromo-6-methoxy-2H-indazol-2-yl)-1,7-dimethyl-1-azaspiro[4.5]decan-2-one and rac-(5S,7R,8R)-8-(5-Bromo-6-methoxy-2H-indazol-2-yl)-1,7-dimethyl-1-azaspiro[4.5]decan-2-one

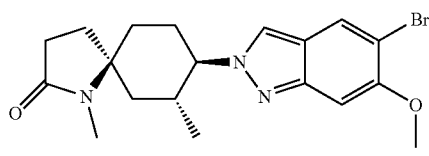

And Enantiomer

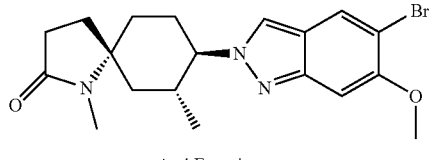

And Enantiomer

To a solution of rac-3-bromo-N-((3R,4R)-4-(5-bromo-6-methoxy-2H-indazol-2-yl)-3-methylcyclohex-1-en-1-yl)-N-methylpropanamide (450 mg, 0.9 mmol) in toluene (60 mL) was added dropwise a solution of tributylstannane (810 mg, 2.8 mmol) and AIBN (76 mg, 0.5 mmol) in MeCN (1 mL) and toluene (15 mL) over 20 min. The resulting solution was heated at 80° C. for 6 h. The reaction mixture was concentrated under reduced pressure. The residue was purified by C18 flash chromatography (eluting with 0-100% MeCN in water (0.05% FA)) followed by prep. HPLC (XBridge Prep OBD C18, 30×150 mm 5 μm; mobile phase A: water (10 mM NH$_4$HCO$_3$+0.1% NH$_4$OH); mobile Phase B: MeCN; gradient: 34% B to 44% B in 10 min, then isocratic at 44% B for 10 min; flow rate: 60 mL/min) to afford as first eluting mixture rac-(5R,7R,8R)-8-(5-bromo-6-methoxy-2H-indazol-2-yl)-1,7-dimethyl-1-azaspiro[4.5]decan-2-one (26 mg, 7%) and as second eluting mixture rac-(5S,7R,8R)-8-(5-bromo-6-methoxy-2H-indazol-2-yl)-1,7-dimethyl-1-azaspiro[4.5]decan-2-one (26 mg, 7%), both as pale-yellow solids. rac-(5R,7R,8R)-8-(5-bromo-6-methoxy-2H-indazol-2-yl)-1,7-dimethyl-1-azaspiro[4.5]decan-2-one: $^1$H NMR (300 MHz, CDCl$_3$) δ 7.84 (s, 1H), 7.78 (d, 1H), 7.05 (s, 1H), 3.91 (s, 3H), 3.79 (td, 1H), 2.77 (s, 3H), 2.48-2.23 (m, 4H), 2.15-2.03 (m, 3H), 1.88 (td, 1H), 1.70-1.57 (m, 3H), 0.67 (d, 3H). MS ESI, m/z=406/408 [M+H]$^+$. rac-(5S,7R,8R)-8-(5-bromo-6-methoxy-2H-indazol-2-yl)-1,7-dimethyl-1-azaspiro[4.5]decan-2-one. $^1$H NMR (300 MHz, CDCl$_3$) δ 7.85 (s, 1H), 7.80 (d, 1H), 7.05 (s, 1H), 4.00-3.84 (m, 5H), 3.21 (s, 3H), 2.80-2.64 (m, 1H), 2.63-2.47 (m, 2H), 2.42 (t, 2H), 2.26-2.04 (m, 3H), 1.96-1.71 (m, 3H), 1.49 (dd, 1H), 0.71 (d, 3H). MS ESI, m/z=406/408 [M+H]$^+$.

rel-2-(5R,7R,8R)-1,7-Dimethyl-2-oxo-1-azaspiro [4.5]decan-8-yl)-N-(imidazo[1,2-b]pyridazin-3-yl)-6-methoxy-2H-indazole-5-carboxamide—Isomer 1 (Example 120) & Isomer 2 (Example 121)

ISOMER 1

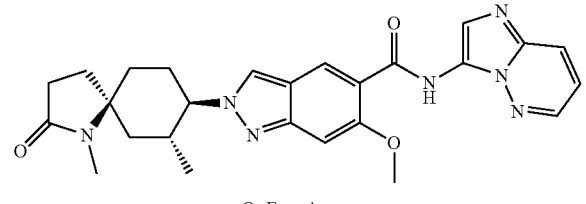

Or Enantiomer

ISOMER 2

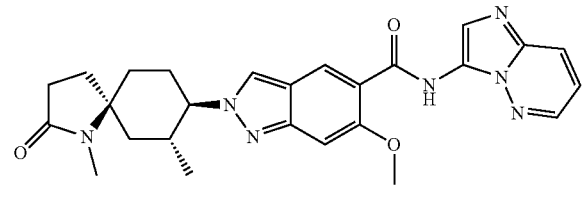

Or Enantiomer rel-2-(5S,7R,8R)-1,7-Dimethyl-2-oxo-1-azaspiro [4.5]decan-8-yl)-N-(imidazo[1,2-b]pyridazin-3-yl)-6-methoxy-2H-indazole-5-carboxamide—Isomer 1 (Example 122) & Isomer 2 (Example 123)

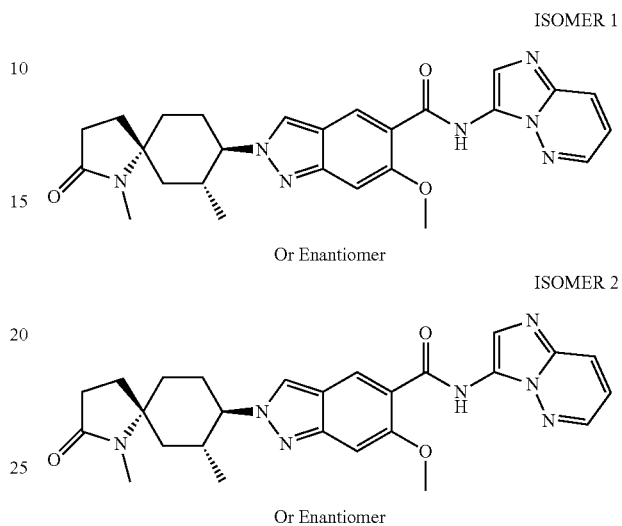

A suspension of rac-(5R,7R,8R)-8-(5-bromo-6-methoxy-2H-indazol-2-yl)-1,7-dimethyl-1-azaspiro[4.5]decan-2-one (26 mg, 0.1 mmol), Pd(OAc)$_2$ (29 mg, 0.1 mmol), 1,3-bis(diphenylphosphino)propane (26 mg, 0.1 mmol) and TEA (89 μL, 0.6 mmol) in MeCN (10 mL) was heated in a sealed vessel at 100° C. for 15 h under CO atmosphere at 15 atm. After cooling to rt, additional Pd(OAc)$_2$ (29 mg, 0.1 mmol), 1,3-bis(diphenylphosphino)propane (26 mg, 0.1 mmol) and TEA (894, 0.6 mmol) were added into the above reaction mixture. The resulting suspension was heated again at 100° C. in a sealed vessel under CO atmosphere at 15 atm for additional 15 h. The mixture was concentrated under reduced pressure. The residue was purified by C18-flash chromatography (eluting with 0-100% acetonitrile in water (0.1% NH$_4$OH)) followed by prep. chiral HPLC (Chiralpak® IA 5 μm 20 mm×250 mm; isocratic with 50% MTBE (0.5% 2 M NH$_3$-MeOH) in MeOH/DCM (1/1) over 10 min; 20 mL/min) to afford rel-2-((5R,7R,8R)-1,7-dimethyl-2-oxo-1-azaspiro[4.5]decan-8-yl)-N-(imidazo[1,2-b] pyridazin-3-yl)-6-methoxy-2H-indazole-5-carboxamide—Isomer 1 (5 mg, 16%; 97.2% ee) and rel-2-((5R,7R,8R)-1, 7-dimethyl-2-oxo-1-azaspiro[4.5]decan-8-yl)-N-(imidazo [1,2-b]pyridazin-3-yl)-6-methoxy-2H-indazole-5-carboxamide—Isomer 2 (4 mg, 13%; 99.5% ee), both as yellow solids. Isomer 1 and 2 are enantiomers to each other, the LCMS/$^1$H NMR obtained for both isomers are identical. $^1$H NMR (400 MHz, DMSO-d$_6$) δ 11.05 (s, 1H), 8.64 (dd, 1H), 8.62 (s, 1H), 8.59 (s, 1H), 8.15 (dd, 1H), 8.05 (s, 1H), 7.31 (s, 1H), 7.22 (dd, 1H), 4.21-4.13 (m, 1H), 4.12 (s, 3H), 2.68 (s, 3H), 2.41-2.26 (m, 3H), 2.26-2.14 (m, 1H), 2.09-1.89 (m, 4H), 1.71 (t, 1H), 1.61-1.50 (m, 2H), 0.59 (d, 3H). MS ESI, m/z=488 [M+H]$^+$.

rac-(5S,7R,8R)-8-(5-Bromo-6-methoxy-2H-indazol-2-yl)-1,7-dimethyl-1-azaspiro[4.5]decan-2-one (26 mg, 0.1 mmol) was subjected to the reaction conditions described above. The mixture was concentrated under reduced pressure. The residue was purified by C18-flash chromatography (eluting with 0-100% acetonitrile in water (0.1% NH$_4$OH))

followed by prep. chiral HPLC (YMC Chiral ART Cellulose-SB 5 μm 20 mm×250 mm; isocratic with 50% MTBE (0.5% 2 M NH₃-MeOH) in ethanol over 18 min; 20 mL/min) to afford rel-2-((5S,7R,8R)-1,7-dimethyl-2-oxo-1-azaspiro [4.5]decan-8-yl)-N-(imidazo[1,2-b]pyridazin-3-yl)-6-methoxy-2H-indazole-5-carboxamide—Isomer 1 (4 mg, 13%, 99.9% ee) and rel-2-((5S,7R,8R)-1,7-dimethyl-2-oxo-1-azaspiro[4.5]decan-8-yl)-N-(imidazo[1,2-b]pyridazin-3-yl)-6-methoxy-2H-indazole-5-carboxamide—Isomer 2 (4 mg, 13%, 98.6% ee), both as yellow solids. Isomer 1 and 2 are enantiomers to each other, the LCMS/$^1$H NMR obtained for both isomers are identical. $^1$H NMR (300 MHz, DMSO-$d_6$) δ 11.05 (s, 1H), 8.67-8.61 (m, 2H), 8.59 (s, 1H), 8.15 (dd, 1H), 8.05 (s, 1H), 7.32 (s, 1H), 7.22 (dd, 1H), 4.26 (dt, 1H), 4.12 (s, 3H), 3.08 (s, 3H), 2.75-2.54 (m, 1H), 2.53-2.36 (m, 1H), 2.27 (t, 2H), 2.16-1.92 (m, 3H), 1.89-1.70 (m, 3H), 1.53 (t, 1H), 0.62 (d, 3H). MS ESI, m/z=488 [M+H]⁺.

Potency of IRAK4 Inhibitor Compounds in IRAK4 Enzyme Assay

The inhibitory activity of compounds against IRAK4 were determined in an enzymatic assay using mass spectrometry readout. Ten point half-log compound concentration response curves, with a top concentration of 1 μM or 10 μM, were generated from 10 mM stocks of compound solubilized in DMSO using an Echo 655 (Labcyte Inc) and added to 384 well assay plates (Greiner #781280). To the assay plates, 10 μL of human recombinant IRAK4 protein (Life Technologies #PV4002) diluted to a final concentration of 0.2 nM in assay buffer (50 mM Tris-HCl pH 7.4, 10 mM MgCl, 5 mM glutathione, 0.01% BSA, 3 mM ATP) was added. The enzyme was incubated with the compounds at room temperature for 15 minutes before a peptide substrate (KKARFSRFAGSSPSQSSMVAR, Innovagen custom synthesis, 10 mM in DMSO) was added to each well to a final concentration of 10 μM using an Echo 655 (Labcyte Inc). After two hours at room temperature, the reaction was stopped with 90 μL of 0.4% formic acid (Merck #33015). The unphosphorylated and phosphorylated peptide were measured by LC-MS/MS on a Waters TQ-S mass spectrometer. Peaks were integrated using the TargetLynx software and the ratios between phosphorylated and unphosphorylated peptides were calculated. Curves were fitted and compound potencies determined in Genedata Screener 15 (Genedata AG). Data presented are the geometric mean of at least n=2, or as denoted by an * are obtained from a single experiment.

IRAK4 Phosphorylation Cell Assay

The activation of IRAK4 by TLR or IL-1R ligands leads to IRAK4 auto-phosphorylation, which can be prevented by IRAK4 kinase inhibitors. The effect of IRAK4 inhibitor compounds on IRAK4 auto-phosphorylation was assessed in IL-1β-stimulated Karpas-299 cells as a measurement of cellular potency. Karpas-299 cells were cultured in RPMI 1640 (Gibco 61870-010) containing 10% FBS (Gibco #10270). Cells were plated at 2×10⁴ cells per well in poly-D-lysine coated 384 well plates (Corning #356663) to which compounds had been added at various concentrations (10 point half log dose response with a final top concentration of 30 μM) using an Echo 655 (Labcyte Inc). Cells were centrifuged (250 g, 4 mins), incubated at 37° C. for 1 h, then stimulated with 22.7 ng/mL recombinant IL-1β (R&D Systems, #201-LB-025) at 37° C. for 10 mins, followed by fixation in 4% paraformaldehyde for 10 mins and permeabilization in ice-cold 70% MeOH for 30 mins. Cells were washed twice with phosphate-buffered saline (PBS) on a BlueWasher (BlueCatBio) then blocked with PBS containing 10% FBS for 20 mins. Blocking solution was removed with a BlueWasher and cells were stained with anti-pIRAK4 (Thr345/Ser346) (CST, #11927, 1:400) in blocking buffer with 0.05% Tween-20 for 1 h, then washed twice with PBS containing 0.05% Tween-20 on a BlueWasher, followed by staining with a Alexa 647-conjugated secondary anti-rabbit IgG antibody (CST, #4414, 1:2,000) and Hoechst 33342 (Sigma, 1:2,000) in blocking buffer with 0.05% Tween-20 for 30 mins. Finally, the cells were washed twice with PBS containing 0.05% Tween-20 and imaged on an ImageXpress Micro (Molecular Devices) with a 10× air objective using the appropriate filters. Images were analysed in Columbus (PerkinElmer) and the fluorescence intensity per cell from the secondary antibody was quantified. The quantified data were analysed in Genedata Screener 15 (Genedata AG). Results obtained in this assay are presented in Table 1 and demonstrate the ability of the compounds of the present specification to inhibit IRAK4 in cells. IC$_{50}$ values are the geometric mean of at least 2 experiments.

TABLE 1

Activity of Compounds in IRAK4 enzyme inhibition assay and IRAK4 phosphorylation cell assay

| Example | IRAK4 Enzyme IC$_{50}$ (nM) | IRAK4 Cell IC$_{50}$ (nM) | Example | IRAK4 Enzyme IC$_{50}$ (nM) | IRAK4 Cell IC$_{50}$ (nM) |
| --- | --- | --- | --- | --- | --- |
| 1 | 0.1 | 5 | 64 | <0.5 | 38 |
| 2 | 3.4 | 124 | 65 | 1.1 | 44 |
| 3 | 8.5 | 272 | 66 | <0.5 | 23 |
| 4 | <0.3* | 17 | 67 | 4.3 | 144 |
| 5 | 0.5 | 31 | 68 | 1.6 | 53 |
| 6 | 0.7 | 44 | 69 | 0.5 | 22 |
| 7 | 6.0 | 111 | 70 | 0.4 | 9 |
| 8 | 2.8 | 58 | 71 | 1.9 | 30 |
| 9 | 1.6 | 57 | 72 | 0.4 | 7 |
| 10 | 1.2 | 19 | 73 | 3.2 | 57 |
| 11 | >1010 | >30000 | 74 | 2.7 | 79 |
| 12 | 1.0 | 33 | 75 | 0.3 | 12 |
| 13 | 6.5 | 816 | 76 | 2.3 | — |
| 14 | 17.7 | 171 | 77 | 0.7 | 14 |
| 15 | 0.5 | 91 | 78 | 2.5 | 52 |
| 16 | 0.6 | 77 | 79 | 1.0 | 21 |
| 17 | 1.0 | 50 | 80 | 1.5 | 28 |
| 18 | <0.6 | 19 | 81 | 5.1 | 82 |
| 19 | 1.0 | 47 | 82 | 2.4 | 27 |
| 20 | 0.7 | 35 | 83 | 2.1 | 34 |
| 21 | 0.7 | 36 | 84 | 0.4* | 40 |
| 22 | 5.1 | 268 | 85 | 0.8 | 50 |
| 23 | 0.2 | 5 | 86 | 1.9 | 36 |
| 24 | 83.1 | 668 | 87 | 0.2 | 26 |
| 25 | 1.4 | 19 | 88 | 1.3 | 44 |
| 26 | 1.6 | 26 | 89 | 1.1 | 36 |
| 27 | 4.4 | 67 | 90 | 5.2 | 101 |
| 28 | 3.0 | 161 | 91 | 2.3 | 88 |
| 29 | 0.5 | 31 | 92 | 1.6 | 30 |
| 30 | <0.3 | 46 | 93 | 0.4 | 8 |
| 31 | 0.8 | 71 | 94 | 0.3 | 10 |
| 32 | 10.6 | 257 | 95 | 0.2 | 7 |
| 33 | 1.0 | 45 | 96 | 0.5 | 15 |
| 34 | 2.0 | 31 | 97 | 0.7 | 15 |
| 35 | 7.2 | 115 | 98 | 0.6 | 20 |
| 36 | 3.8 | 56 | 99 | 1.2 | 35 |
| 37 | 0.3 | 6 | 100 | <0.03 | 6 |
| 38 | 4.6 | 186 | 101 | <0.4 | 31 |
| 39 | 10.0 | 160 | 102 | 0.7 | 19 |
| 40 | 6.3 | 158 | 103 | 0.6 | 17 |
| 41 | 14.3 | 331 | 104 | 1.1 | 25 |
| 42 | 1.4 | 89 | 105 | 6.5 | 96 |
| 43 | 1.8 | 101 | 106 | 0.6 | 15 |
| 44 | 0.8 | 42 | 107 | 0.9 | 24 |
| 45 | 1.2 | 70 | 108 | 0.4 | 16 |
| 46 | 0.6 | 56 | 109 | 0.6 | 15 |
| 47 | 0.5 | 64 | 110 | 0.9 | 16 |
| 48 | 0.7 | 17 | 111 | 0.9 | 27 |
| 49 | 6.1 | 46 | 112 | 0.7 | 21 |

TABLE 1-continued

| | | | | | |
|---|---|---|---|---|---|
| 50 | 3.4 | 84 | 113 | 0.7 | 23 |
| 51 | 2.8 | 46 | 114 | 0.7 | 16 |
| 52 | 5.5 | 96 | 115 | 0.8 | 20 |
| 53 | 3.5 | 49 | 116 | 0.3 | 13 |
| 54 | 0.6 | 25 | 117 | 0.3 | 22 |
| 55 | 0.7 | 51 | 118 | 13.9 | 199 |
| 56 | 1.2 | 79 | 119 | 0.5 | 16 |
| 57 | 0.8 | 60 | 120 | 0.3 | 13 |
| 58 | 0.9 | 16 | 121 | 3.4 | 68 |
| 59 | 1.3 | 40 | 122 | 0.7 | 18 |
| 60 | 0.8 | 21 | 123 | 3.0 | 76 |
| 61 | 24.2 | 238 | | | |
| 62 | 16.0 | 185 | | | |
| 63 | 46.8 | 338 | | | |

Effect of IRAK4 Inhibitors on IL-1β-Induced Cytokine Release in Human THP-1 Monocyte Cell Line THP-1 cells were cultured in RPMI 1640 (Gibco 72400-021) containing 10% FBS (Gibco 10270-106), 1 mM Na-pyruvate (Gibco 11360-070) and 100 U/mL Penicillin-Streptomycin (Gibco 15140-122). Cells were plated at $5\times10^4$ cells per well in 384 well Echo certified plates (Labcyte PPT-0200) to which compounds had been added at various concentrations (10 point half log dose response with a final top concentration of 10 μM) using an Echo 655 (Labcyte Inc). The plate was incubated for 1 h at 37° C., then recombinant IL-1β (R&D Systems 201-LB-025/CF) was added to a final concentration of 1.8 ng/mL. The plates were incubated at 37° C. for 18h. The plates were centrifuged at 250×g for four minutes, then 1.6 μL of the cell supernatant was transferred to a white low volume 384 well plate (Greiner #784075) using acoustic dispensing on an Echo 655. Next, 200 nL of acceptor bead (5 mg/mL) and biotinylated anti-IL-8 antibody (500 nM) was added using acoustic dispensing (beads and antibody were from a PerkinElmer 18 Alpha LISA detection kit, AL224C). The plate was sealed, briefly centrifuged, then incubated at room temperature for 1 h. Afterwards, 200 nL of donor bead solution (5 mg/mL) was added, the plate sealed and briefly centrifuged, then incubated for 1 h before being read on an Envision plate reader to allow determination the concentration of IRAK4 inhibitor required to effect a 50% reduction in the amount of IL-8 released following IL-1β stimulation in THP1 cells (Table 2). The quantified data were analysed in Genedata Screener 15 (Genedata AG). Data presented are the geometric mean of at least n=2, or as denoted by an * are obtained from a single experiment.

In Vitro Effect of IRAK4 Inhibitors on LPS- and IL-1β-Induced Cytokine Release in Human PBMCs To evaluate the effect and potency of IRAK4 inhibitors on blocking disease-relevant pathways in human primary immune cells, we stimulated human PBMCs (peripheral blood mononuclear cells) with LPS (TLR4 agonist) or IL-1β (IL-1R ligand) and measured the release of the proinflammatory cytokines IL-6 and TNF-α. Briefly, PBMCs were isolated from human blood, donated from healthy individuals, using LymphoPrep density gradient and plated at a cell density of 200 000 cells/well (for LPS assay) or 300 000 cells/well (for IL-1β assay) in 96-well culture plates. Cells were incubated for 1 h with serial dilutions of IRAK4 inhibitor or vehicle (DMSO) prior to stimulation of cells with 0.11 ng/mL LPS (derived from E. coli) or 1 ng/mL recombinant human IL-1β. After 4 h of LPS stimulation or 20 h of IL-1β stimulation, the supernatant was collected and the levels of the proinflammatory cytokines TNF-α, IL-8 and IL-6 were measured by Mesoscale Discovery (MSD) multiplex assay. Dose-response curves were plotted and $IC_{50}$ values were calculated with 4-parameter curve fit using GraphPad Prism 8 (see Table 3). IRAK4 inhibitors according to the present specification proved to be highly active in inhibiting proinflammatory cytokine release and TNF-α.

In Vivo Effect of IRAK4 Inhibition in a Mouse Model of LPS-Induced Airway Inflammation TLRs act as a first sensor of microbes and allergens in the airways and can mediate a rapid inflammatory response. A mouse model of inhaled LPS challenge was used to study the effect of IRAK4 inhibition on the processes of an acute TLR4-driven airway inflammation. Briefly, 9-week old C57Bl/6NCrl female mice were dosed with 5, 15 and 50 mg/kg of test compound (Example 89) or vehicle alone (5% DMSO, 95% SBE-B-CD (30% w/v) in water) by oral administration. After 0.5 h, the animals were challenged by whole body exposure to an aerosol of 1 mg/mL LPS (E. coli 0111:B4 from Sigma L2630) in saline, or saline only, for 0.5 h at a 6 L/min compressed air flow. Following exposure, the boxes were ventilated and the animals returned to their housing cages. After 4 h, animals were euthanized with a single intraperitoneal injection of 0.3 mL pentobarbital (100 mg/mL) and manual bronchoalveolar lavage (BAL) was performed from the whole lung using 1 mL of PBS. The collected BAL fluid (BALF) was centrifuged at 300×g for 10 min at 4° C. and the supernatant was collected and stored at −80° C. The levels of proinflammatory cytokines were measured in the BALF supernatant using MSD multiplex assay 8 mice per treatment group were used, except for the LPS/vehicle group where 20 mice were used. The levels of IL-6 and TNF-α in the BALF supernatant in the different treatment groups are represented in FIG. 1. Example 89 reduced the levels of IL-6 and TNF-α upon inhaled LPS challenge, in a dose-dependent manner.

TABLE 2

$IC_{50}$ values for compounds of specification against IL-1β stimulated IL-8 release in hTHP1 cells

| Example | hTHP1, IL1β stim, IL8 release red. $IC_{50}$ (nM) | Example | hTHP1, IL1β stim, IL8 release red. $IC_{50}$ (nM) |
|---|---|---|---|
| 5 | 16 | 33 | 30* |
| 7 | 48 | 34 | 22* |
| 8 | 50 | 37 | 3* |
| 10 | 14* | 38 | 31* |
| 12 | 29 | 45 | 46 |
| 13 | 59 | 57 | 35 |
| 14 | 38 | 64 | 18 |
| 17 | 24 | 65 | 52 |
| 18 | 21 | 66 | 18 |
| 19 | 35* | 67 | 91 |
| 20 | 31 | 68 | 84 |
| 21 | 17 | 69 | 15 |
| 23 | 7* | 80 | 70* |
| 25 | 23* | 86 | 31 |
| 26 | 25* | 89 | 31 |
| 29 | 20 | 91 | 49 |
| 30 | 14 | 92 | 28* |
| 31 | 32 | 93 | 30* |

*n = 1

TABLE 3

$IC_{50}$ values (nM) for IRAK4 inhibitor compounds in human PBMCs stimulated with LPS and IL-1β

| Stimulation | Cytokine read-out | Example 89 ($IC_{50}$, nM) |
|---|---|---|
| IL-1β | IL-6 | 22 |
| | IL-8 | 30 |
| LP5 | IL-6 | 32 |
| | TNF-α | 39 |

The invention claimed is:
1. A compound of Formula (A):

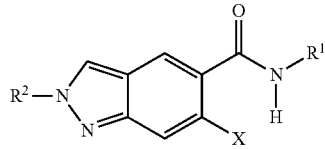

or a pharmaceutically acceptable salt or stereoisomer thereof,
wherein:
R¹ is

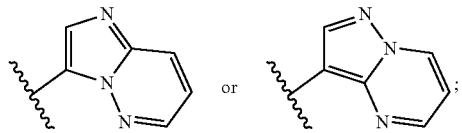 [SMILES: *c1cnc2cccnn12 ; *c1cnn2cccnc12]

R² is

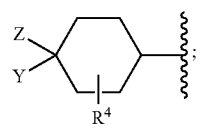

R⁴ is H, CH₃, or CH₂CH₃;
Y is C(O)N(CH₃)₂ or N(R⁵)C(O)R⁶;
Z is H;
R⁵ is H, C₁-C₆ alkyl, or C₃-C₆ cycloalkyl;
R⁶ is C₁-C₆ alkyl or C₃-C₆ cycloalkyl;
  wherein the C₁-C₆ alkyl is optionally substituted with one or more substituents independently selected from the group consisting of F, Cl, C(O)CH₃, NH₂, NHCH₃, N(CH₃)₂, OH, and OC₁-C₃ alkyl; and
  wherein the C₃-C₆ cycloalkyl is optionally substituted with one or more substituents independently selected from the group consisting of F, Cl, C₁-C₃ alkyl, C(O)CH₃, NH₂, NHCH₃, N(CH₃)₂, OH, and OC₁-C₃ alkyl;
X is NR⁸R⁹ or OR⁷;
R⁷ is CH₃, CH₂CH₃, CH₂CH₂CH₃, CH(CH₃)₂, or C₃-C₆ cycloalkyl;
R⁸ is H or C₁-C₆ alkyl; and
R⁹ is H or C₁-C₆ alkyl.

2. The compound according to claim 1, or a pharmaceutically acceptable salt or stereoisomer thereof, wherein R¹ is

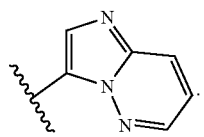 [SMILES: *c1cnc2cccnn12]

3. The compound according to claim 1, or a pharmaceutically acceptable salt or stereoisomer thereof, wherein X is OR⁷.

4. The compound according to claim 1, or a pharmaceutically acceptable salt or stereoisomer thereof, wherein X is OCH₃.

5. The compound according to claim 1, or a stereoisomer thereof, wherein the compound, or stereoisomer thereof, is N-(Imidazo[1,2-b]pyridazin-3-yl)-6-methoxy-2-((1r,4r)-4-(N-methylacetamido)cyclohexyl)-2H-indazole-5-carboxamide:

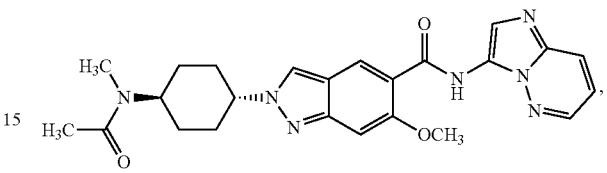

or a pharmaceutically acceptable salt thereof.

6. The compound according to claim 1, or a stereoisomer thereof, wherein the compound, or stereoisomer thereof, is N-(Imidazo[1,2-b]pyridazin-3-yl)-6-methoxy-2-((1r,4r)-4-(N-methylacetamido)cyclohexyl)-2H-indazole-5-carboxamide:

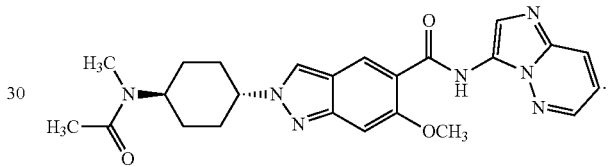

7. The compound according to claim 1, or a stereoisomer thereof, wherein the compound, or stereoisomer thereof, is N-(Imidazo[1,2-b]pyridazin-3-yl)-6-methoxy-2-((1R,2R,4R*)-2-methyl-4-(N-methylacetamido) cyclohexyl)-2H-indazole-5-carboxamide:

Isomer 2

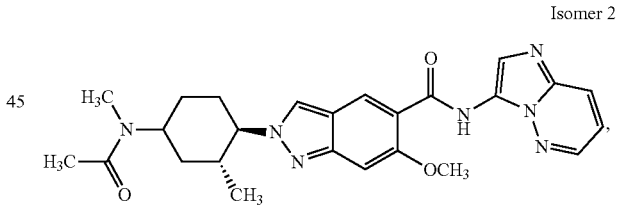

or a pharmaceutically acceptable salt thereof.

8. The compound according to claim 1, or a stereoisomer thereof, wherein the compound, or stereoisomer thereof, is N-(Imidazo[1,2-b]pyridazin-3-yl)-6-methoxy-2-((1R,2R,4R*)-2-methyl-4-(N-methylacetamido) cyclohexyl)-2H-indazole-5-carboxamide:

Isomer 2

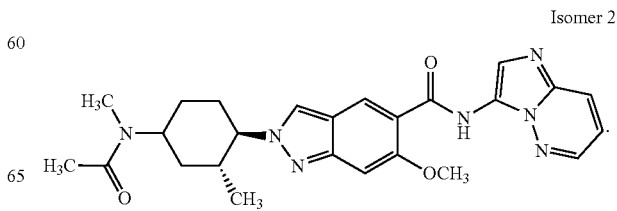

9. The compound according to claim 1, or a stereoisomer thereof, wherein the compound, or stereoisomer thereof, is 2-((1R,4r)-4-((R)-2-Hydroxy-N-methylpropanamido)cyclohexyl)-N-(imidazo[1,2-b]pyridazin-3-yl)-6-methoxy-2H-indazole-5-carboxamide:

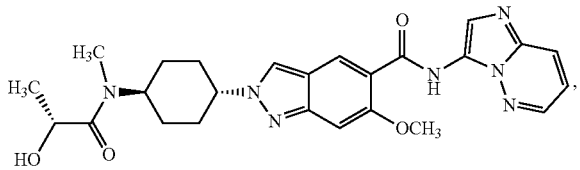 [SMILES: COc1cc2nn([C@H]3CC[C@H](N(C)C(=O)[C@@H](C)O)CC3)cc2cc1C(=O)Nc1cnc2cccnn12], or a pharmaceutically acceptable salt thereof.

10. The compound according to claim 1, or a stereoisomer thereof, wherein the compound, or stereoisomer thereof, is 2-((1R,4r)-4-((R)-2-Hydroxy-N-methylpropanamido)cyclohexyl)-N-(imidazo[1,2-b]pyridazin-3-yl)-6-methoxy-2H-indazole-5-carboxamide:

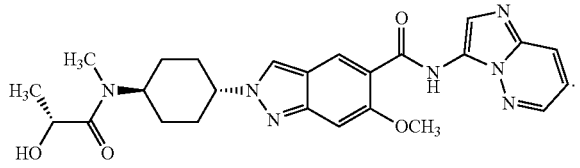 [SMILES: COc1cc2nn([C@H]3CC[C@H](N(C)C(=O)[C@@H](C)O)CC3)cc2cc1C(=O)Nc1cnc2cccnn12].

11. The compound according to claim 1, or a stereoisomer thereof, wherein the compound, or stereoisomer thereof, is:

2-((1s,4s)-4-(Dimethylcarbamoyl)cyclohexyl)-N-(imidazo[1,2-b]pyridazin-3-yl)-6-methoxy-2H-indazole-5-carboxamide

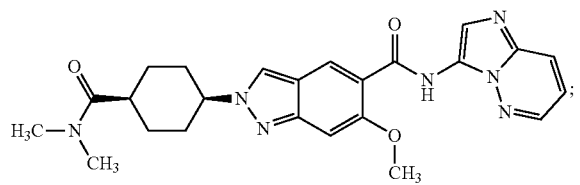 [SMILES: COc1cc2nn([C@H]3CC[C@@H](C(=O)N(C)C)CC3)cc2cc1C(=O)Nc1cnc2cccnn12];

2-((1r,4r)-4-(Dimethylcarbamoyl)cyclohexyl)-N-(imidazo[1,2-b]pyridazin-3-yl)-6-methoxy-2H-indazole-5-carboxamide

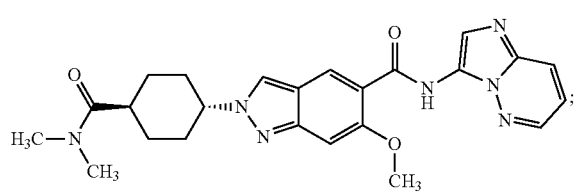 [SMILES: COc1cc2nn([C@H]3CC[C@H](C(=O)N(C)C)CC3)cc2cc1C(=O)Nc1cnc2cccnn12];

N-(Imidazo[1,2-b]pyridazin-3-yl)-6-methoxy-2-((1s,4s)-4-(N-methylacetamido)cyclo 1)-2H-indazole-5-carboxamide

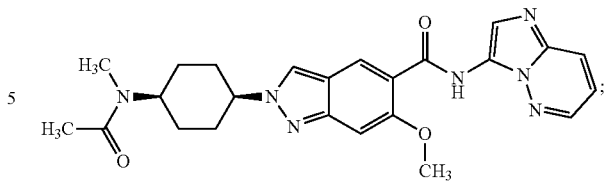;

N-(Imidazo[1,2-b]pyridazin-3-yl)-6-methoxy-2-((1 r,4r)-4-(N-methylacetamido)cyclohexyl)-2H-indazole-5-carboxamide

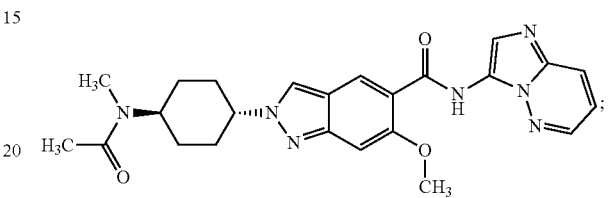;

6-Methoxy-2-((1s,4s)-4-(N-methylacetamido)cyclohexyl)-N-(pyrazolo[1,5-a]pyrimidin-3-yl)-2H-indazole-5-carboxamide

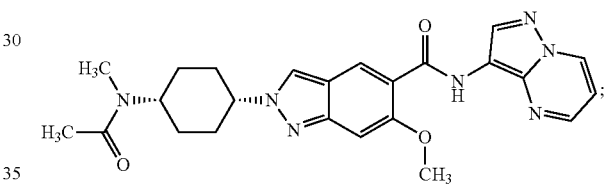;

6-Methoxy-2-((1r,4r)-4-(N-methylacetamido)cyclohexyl)-N-(pyrazolo[1,5-a]pyrimidin-3-yl)-2H-indazole-5-carboxamide

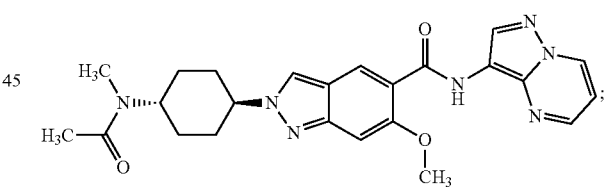;

2-((1r,4r)-4-(Cyclopropanecarboxamido)cyclohexyl)-6-methoxy-N-(pyrazolo[1,5-a]pyrimidin-3-yl)-2H-indazole-5-carboxamide

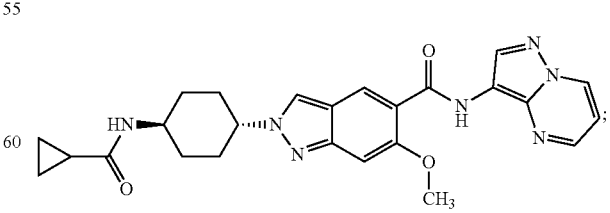;

2-((1s,4s)-4-(Cyclopropanecarboxamido)cyclohexyl)-6-methoxy-N-(pyrazolo[1,5-a]pyrimidin-3-yl)-2H-indazole-5-carboxamide

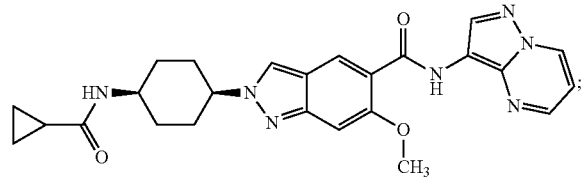 [SMILES: COc1cc2nn([C@H]3CC[C@@H](NC(=O)C4CC4)CC3)cc2cc1C(=O)Nc1cnn2cccnc12]

6-Cyclopropoxy-2-((1s,4s)-4-(N-methylacetamido)cyclohexyl)-N-(pyrazolo[1,5-a]pyrimidin-3-yl)-2H-indazole-5-carboxamide

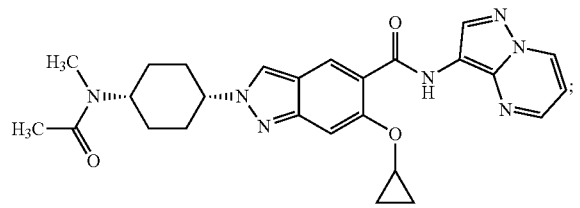 [SMILES: CC(=O)N(C)[C@H]1CC[C@@H](n2cc3cc(C(=O)Nc4cnn5cccnc45)c(OC4CC4)cc3n2)CC1]

6-Cyclopropoxy-2-((1r,4r)-4-(N-methylacetamido)cyclohexyl)-N-(pyrazolo[1,5-a]pyrimidin-3-yl)-2H-indazole-5-carboxamide

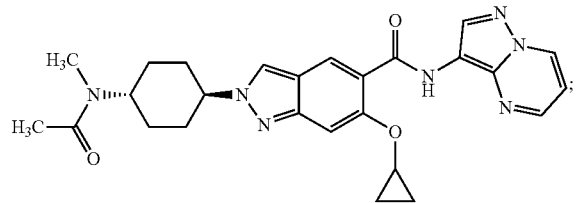 [SMILES: CC(=O)N(C)[C@H]1CC[C@H](n2cc3cc(C(=O)Nc4cnn5cccnc45)c(OC4CC4)cc3n2)CC1]

N-(Imidazo[1,2-b]pyridazin-3-yl)-6-methoxy-2-((1S,2S,4R*)-2-methyl-4-(N-methylacetamido) cyclohexyl)-2H-indazole-5-carboxamide (Isomer 1 or Isomer 2)

ISOMER 1

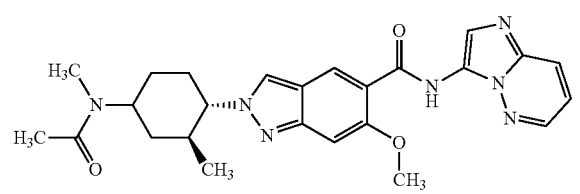

ISOMER 2

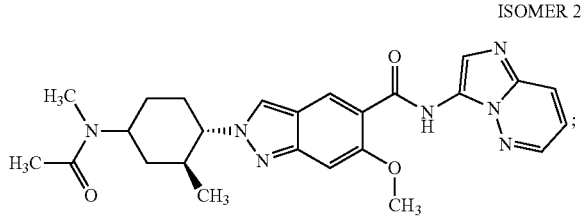

N-(Imidazo[1,2-b]pyridazin-3-yl)-6-methoxy-2-((1R,2R,4R*)-2-methyl-4-(N-methylacetamido) cyclohexyl)-2H-indazole-5-carboxamide (Isomer 1 or Isomer 2

ISOMER 1

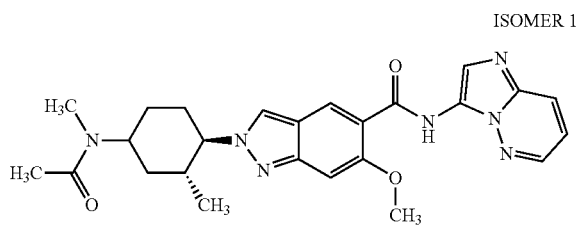

ISOMER 2

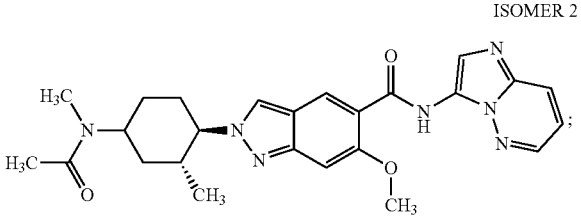

2-((1R,4r)-4-((R)-2-Hydroxy-N-methylpropanamido)cyclohexyl)-6-methoxy-N-(pyrazolo[1,5-a]pyrimidin-3-yl)-2H-indazole-5-carboxamide

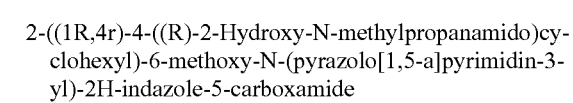

2-((1S,4r)-4-((S)-2-Hydroxy-N-methylpropanamido)cyclohexyl)-6-methoxy-N-(pyrazolo[1,5-a]pyrimidin-3-yl)-2H-indazole-5-carboxamide

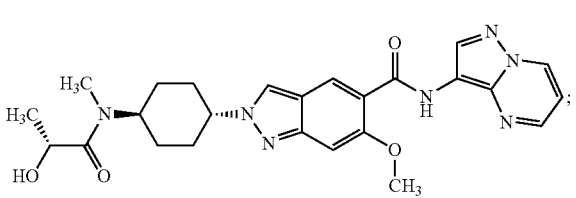 [SMILES: COc1cc2nn([C@H]3CC[C@H](N(C)C(=O)[C@@H](C)O)CC3)cc2cc1C(=O)Nc1cnn2cccnc12]

6-Methoxy-2-((1R,2R,4R*)-2-methyl-4-(N-methylacetamido)cyclohexyl)-N-(pyrazolo[1,5-a]pyrimidin-3-yl)-2H-indazole-5-carboxamide (Isomer 1 or Isomer 2)

ISOMER 1

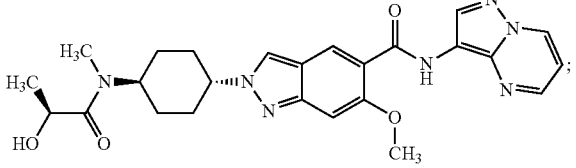

ISOMER 2

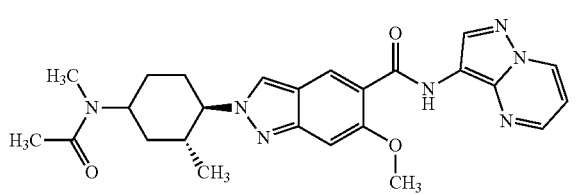

6-Methoxy-2-((1S,2S,4R*)-2-methyl-4-(N-methylacet-
amido)cyclohexyl)-N-(pyrazolo[1,5-a]pyrimidin-3-
yl)-2H-indazole-5-carboxamide (Isomer 1 or Isomer 2)

ISOMER 1

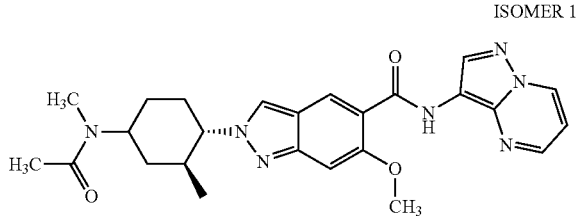

ISOMER 2

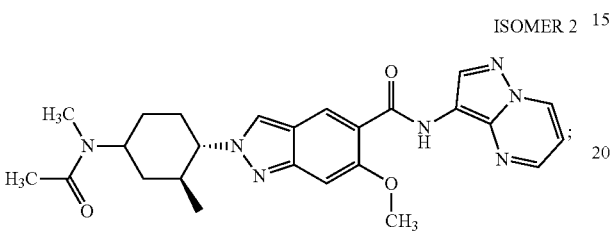

2-((1S,4r)-4-((S)-2-Hydroxy-N-methylpropanamido)cy-
clohexyl)-N-(imidazo[1,2-b]pyridazin-3-yl)-6-
methoxy-2H-indazole-5-carboxamide

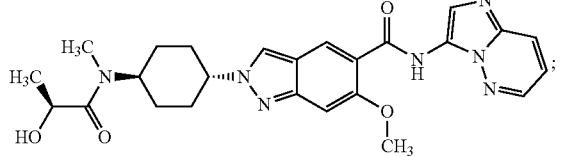

2-((1R,4r)-4-((R)-2-Hydroxy-N-methylpropanamido)cy-
clohexyl)-N-(imidazo[1,2-b]pyridazin-3-yl)-6-
methoxy-2H-indazole-5-carboxamide

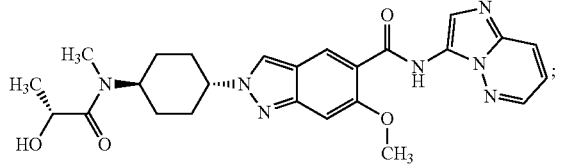

6-Methoxy-2-((1r,4r)-4-(N-methylcyclopropanecarbox-
amido)cyclohexyl)-N-(pyrazolo[1,5-a]pyrimidin-3-
yl)-2H-indazole-5-carboxamide

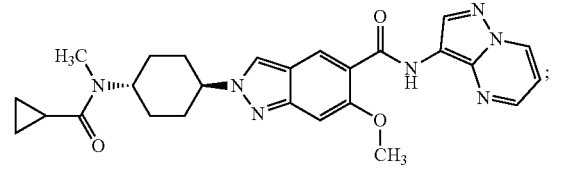 [SMILES: COc1cc2nn([C@H]3CC[C@H](N(C)C(=O)C4CC4)CC3)cc2cc1C(=O)Nc1cnn2cccnc12]

2-((1R,4r)-4-((1r,3R)-3-Hydroxy-N-methylcyclobutane-
1-carboxamido)cyclohexyl)-6-methoxy-N-(pyrazolo
[1,5-a]pyrimidin-3-yl)-2H-indazole-5-carboxamide

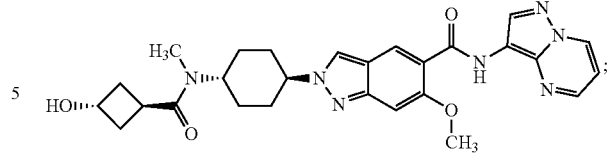

2-((1R,4r)-4-((1s,3S)-3-Hydroxy-N-methylcyclobutane-
1-carboxamido)cyclohexyl)-6-methoxy-N-(pyrazolo
[1,5-a]pyrimidin-3-yl)-2H-indazole-5-carboxamide

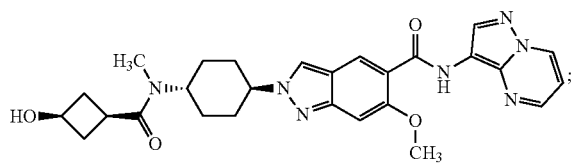 [SMILES: COc1cc2nn([C@H]3CC[C@H](N(C)C(=O)[C@H]4C[C@@H](O)C4)CC3)cc2cc1C(=O)Nc1cnn2cccnc12]

2-((1r,4r)-4-(2-Hydroxy-N,2-dimethylpropanamido)cy-
clohexyl)-6-methoxy-N-(pyrazolo[1,5-a]pyrimidin-3-
yl)-2H-indazole-5-carboxamide

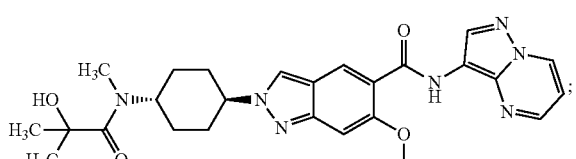

or a pharmaceutically acceptable salt thereof.

12. The compound according to claim 1, or a stereoisomer thereof, wherein the compound, or stereoisomer thereof, is:

2-((1s,4s)-4-(Dimethylcarbamoyl)cyclohexyl)-N-(imi-
dazo[1,2-b]pyridazin-3-yl)-6-methoxy-2H-indazole-5-
carboxamide

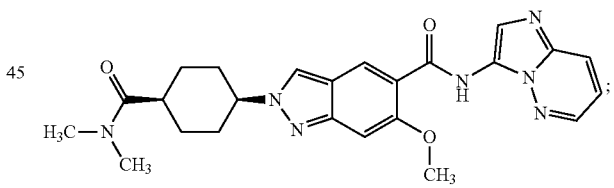

2-((1r,4r)-4-(Dimethylcarbamoyl)cyclohexyl)-N-(imi-
dazo[1,2-b]pyridazin-3-yl)-6-methoxy-2H-indazole-5-
carboxamide

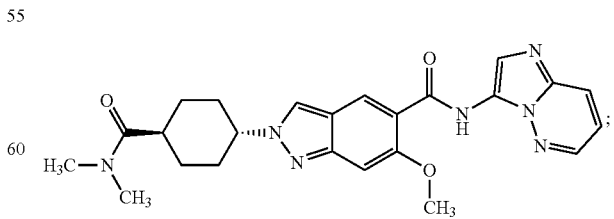

N-(Imidazo[1,2-b]pyridazin-3-yl)-6-methoxy-2-((1s,4s)-
4-(N-methylacetamido)cyclohexyl)-2H-indazole-5-
carboxamide

191

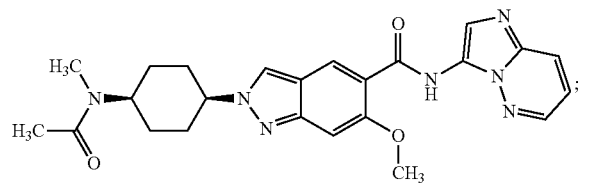 [SMILES: COc1cc2nn([C@H]3CC[C@@H](N(C)C(C)=O)CC3)cc2cc1C(=O)Nc1cnc2cccnn12]

N-(Imidazo[1,2-b]pyridazin-3-yl)-6-methoxy-2-((1r,4r)-4-(N-methylacetamido)cyclohexyl)-2H-indazole-5-carboxamide

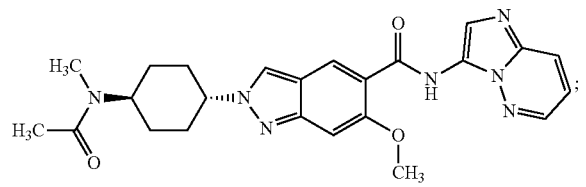 [SMILES: COc1cc2nn([C@H]3CC[C@H](N(C)C(C)=O)CC3)cc2cc1C(=O)Nc1cnc2cccnn12]

6-Methoxy-2-((1s,4s)-4-(N-methylacetamido)cyclohexyl)-N-(pyrazolo[1,5-a]pyrimidin-3-yl)-2H-indazole-5-carboxamide

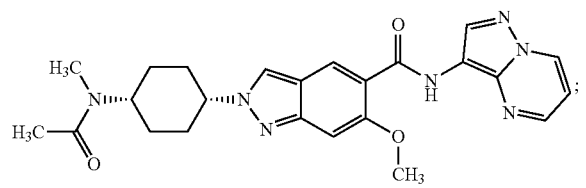 [SMILES: COc1cc2nn([C@H]3CC[C@@H](N(C)C(C)=O)CC3)cc2cc1C(=O)Nc1cnn2cccnc12]

6-Methoxy-2-((1r,4r)-4-(N-methylacetamido)cyclohexyl)-N-(pyrazolo[1,5-a]pyrimidin-3-yl)-2H-indazole-5-carboxamide

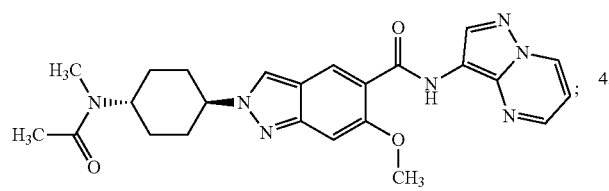

2-((1r,4r)-4-(Cyclopropanecarboxamido)cyclohexyl)-6-methoxy-N-(pyrazolo[1,5-a]pyrimidin-3-yl)-2H-indazole-5-carboxamide

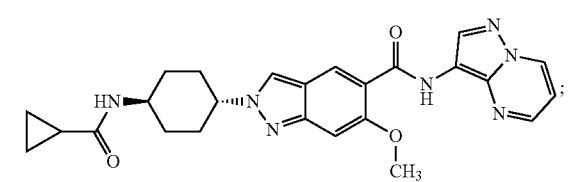 [SMILES: COc1cc2nn([C@H]3CC[C@H](NC(=O)C4CC4)CC3)cc2cc1C(=O)Nc1cnn2cccnc12]

2-((1s,4s)-4-(Cyclopropanecarboxamido)cyclohexyl)-6-methoxy-N-(pyrazolo[1,5-a]pyrimidin-3-yl)-2H-indazole-5-carboxamide

192

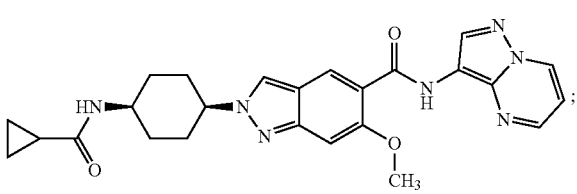 [SMILES: COc1cc2nn([C@H]3CC[C@@H](NC(=O)C4CC4)CC3)cc2cc1C(=O)Nc1cnn2cccnc12]

6-Cyclopropoxy-2-((1s,4s)-4-(N-methylacetamido)cyclohexyl)-N-(pyrazolo[1,5-a]pyrimidin-3-yl)-2H-indazole-5-carboxamide

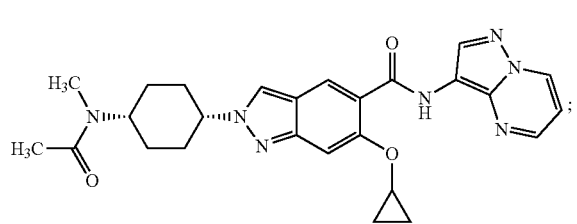 [SMILES: CC(=O)N(C)[C@H]1CC[C@@H](n2cc3cc(C(=O)Nc4cnn5cccnc45)c(OC4CC4)cc3n2)CC1]

6-Cyclopropoxy-2-((1r,4r)-4-(N-methylacetamido)cyclohexyl)-N-(pyrazolo[1,5-a]pyrimidin-3-yl)-2H-indazole-5-carboxamide

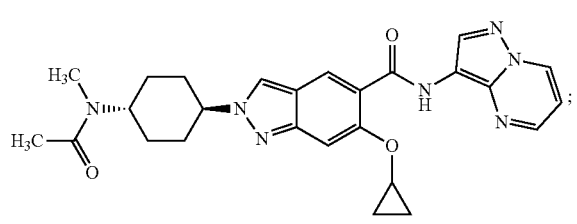 [SMILES: CC(=O)N(C)[C@H]1CC[C@H](n2cc3cc(C(=O)Nc4cnn5cccnc45)c(OC4CC4)cc3n2)CC1]

N-(Imidazo[1,2-b]pyridazin-3-yl)-6-methoxy-2-((1S,2S,4R*)-2-methyl-4-(N methylacetamido) cyclohexyl)-2H-indazole-5-carboxamide (Isomer 1 or Isomer 2)

ISOMER 1

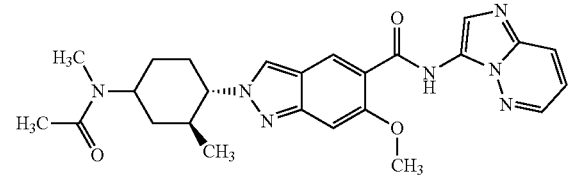

ISOMER 2

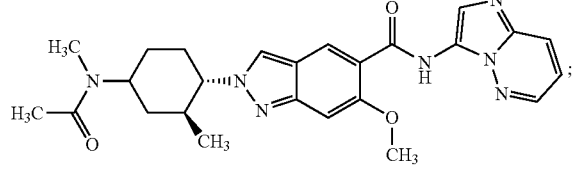

N-(Imidazo[1,2-b]pyridazin-3-yl)-6-methoxy-2-((1R,2R,4R*)-2-methyl-4-(N-methylacetamido) cyclohexyl)-2H-indazole-5-carboxamide (Isomer 1 or Isomer 2)

ISOMER 1

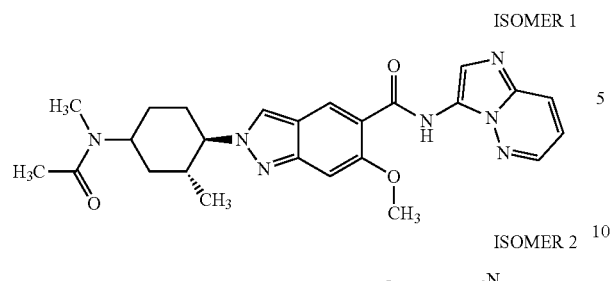

ISOMER 2

2-((1R,4r)-4-((R)-2-Hydroxy-N-methylpropanamido)cy-clohexyl)-6-methoxy-N-(pyrazolo[1,5-a]pyrimidin-3-yl)-2H-indazole-5-carboxamide

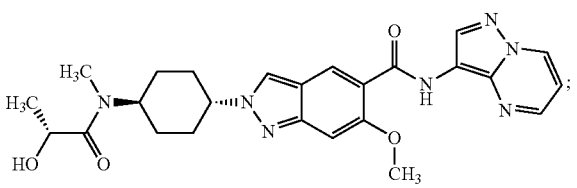 [SMILES: COc1cc2nn([C@H]3CC[C@H](N(C)C(=O)[C@@H](C)O)CC3)cc2cc1C(=O)Nc1cnn2cccnc12]

2-((1S,4r)-4-((S)-2-Hydroxy-N-methylpropanamido)cy-clohexyl)-6-methoxy-N-(pyrazolo[1,5-a]pyrimidin-3-yl)-2H-indazole-5-carboxamide

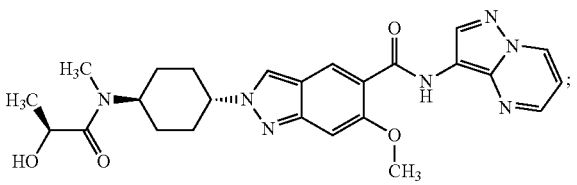 [SMILES: COc1cc2nn([C@H]3CC[C@H](N(C)C(=O)[C@H](C)O)CC3)cc2cc1C(=O)Nc1cnn2cccnc12]

6-Methoxy-2-((1R,2R,4R*)-2-methyl-4-(N-methylacet-amido)cyclohexyl)-N-(pyrazolo[1,5-a]pyrimidin-3-yl)-2H-indazole-5-carboxamide (Isomer 1 or Isomer 2)

ISOMER 1

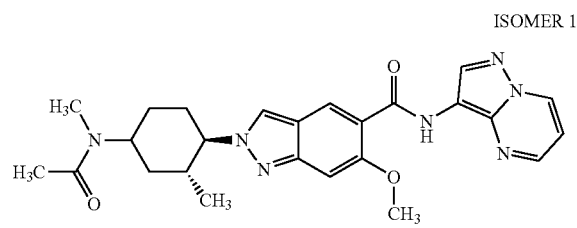

ISOMER 2

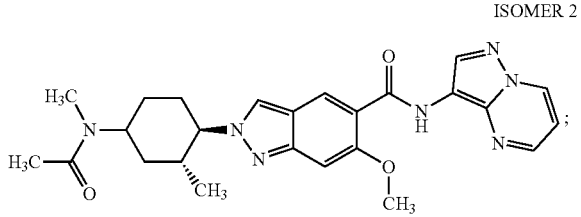

6-Methoxy-2-((1S,2S,4R*)-2-methyl-4-(N-methylacet-amido)cyclohexyl)-N-(pyrazolo[1,5-a]pyrimidin-3-yl)-2H-indazole-5-carboxamide (Isomer 1 or Isomer 2)

ISOMER 1

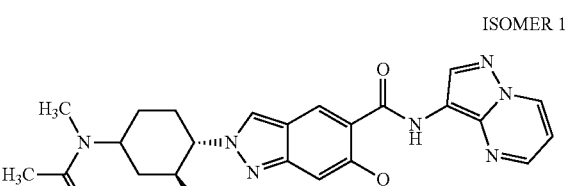

ISOMER 2

2-((1S,4r)-4-((S)-2-Hydroxy-N-methylpropanamido)cy-clohexyl)-N-(imidazo[1,2-b]pyridazin-3-yl)-6-methoxy-2H-indazole-5-carboxamide

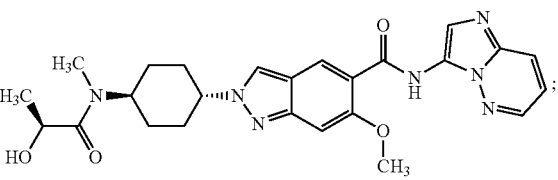 [SMILES: COc1cc2nn([C@H]3CC[C@H](N(C)C(=O)[C@H](C)O)CC3)cc2cc1C(=O)Nc1cnc2cccnn12]

2-((1R,4r)-4-((R)-2-Hydroxy-N-methylpropanamido)cy-clohexyl)-N-(imidazo[1,2-b]pyridazin-3-yl)-6-methoxy-2H-indazole-5-carboxamide

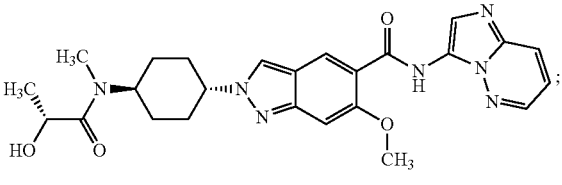 [SMILES: COc1cc2nn([C@H]3CC[C@H](N(C)C(=O)[C@@H](C)O)CC3)cc2cc1C(=O)Nc1cnc2cccnn12]

6-Methoxy-2-((1r,4r)-4-(N-methylcyclopropanecarbox-amido)cyclohexyl)-N-(pyrazolo[1,5-a]pyrimidin-3-yl)-2H-indazole-5-carboxamide

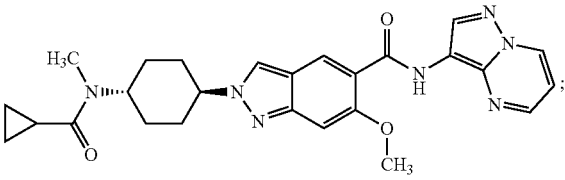 [SMILES: COc1cc2nn([C@H]3CC[C@H](N(C)C(=O)C4CC4)CC3)cc2cc1C(=O)Nc1cnn2cccnc12]

2-((1R,4r)-4-((1r,3R)-3-Hydroxy-N-methylcyclobutane-1-carboxamido)cyclohexyl)-6-methoxy-N-(pyrazolo[1,5-a]pyrimidin-3-yl)-2H-indazole-5-carboxamide

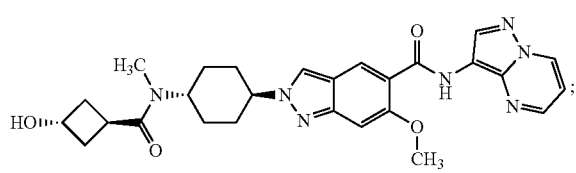 [SMILES: COc1cc2nn([C@H]3CC[C@H](N(C)C(=O)[C@H]4C[C@H](O)C4)CC3)cc2cc1C(=O)Nc1cnn2cccnc12]

2-((1R,4r)-4-((1s,3S)-3-Hydroxy-N-methylcyclobutane-1-carboxamido)cyclohexyl)-6-methoxy-N-(pyrazolo[1,5-a]pyrimidin-3-yl)-2H-indazole-5-carboxamide

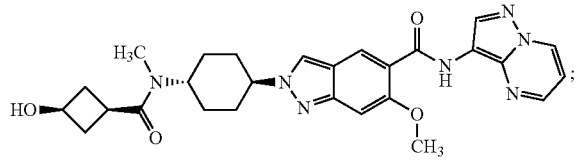 [SMILES: COc1cc2nn([C@H]3CC[C@H](N(C)C(=O)[C@H]4C[C@@H](O)C4)CC3)cc2cc1C(=O)Nc1cnn2cccnc12]

2-((1r,4r)-4-(2-Hydroxy-N,2-dimethylpropanamido)cyclohexyl)-6-methoxy-N-(pyrazolo[1,5-a]pyrimidin-3-yl)-2H-indazole-5-carboxamide

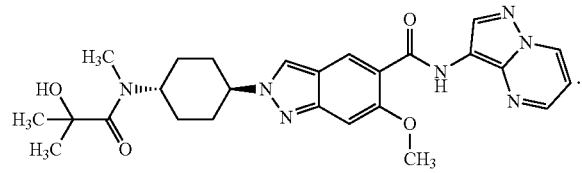 [SMILES: COc1cc2nn([C@H]3CC[C@H](N(C)C(=O)C(C)(C)O)CC3)cc2cc1C(=O)Nc1cnn2cccnc12]

13. A pharmaceutical composition comprising at least one pharmaceutically acceptable excipient and a compound according to claim 1, or a pharmaceutically acceptable salt or stereoisomer thereof.

14. A pharmaceutical composition comprising at least one pharmaceutically acceptable excipient and a compound according to claim 5, or a pharmaceutically acceptable salt thereof.

15. A pharmaceutical composition comprising at least one pharmaceutically acceptable excipient and a compound according to claim 6.

16. A pharmaceutical composition comprising at least one pharmaceutically acceptable excipient and a compound according to claim 7, or a pharmaceutically acceptable salt thereof.

17. A pharmaceutical composition comprising at least one pharmaceutically acceptable excipient and a compound according to claim 8.

* * * * *